US012466827B2

(12) United States Patent
Lee et al.

(10) Patent No.: US 12,466,827 B2
(45) Date of Patent: Nov. 11, 2025

(54) 1,3,4-OXADIAZOLE DERIVATIVE COMPOUNDS AS HISTONE DEACETYLASE 6 INHIBITOR, AND THE PHARMACEUTICAL COMPOSITION COMPRISING THE SAME

(71) Applicant: CHONG KUN DANG PHARMACEUTICAL CORP., Seoul (KR)

(72) Inventors: Chang Kon Lee, Yongin-si (KR); Moo Sung Ko, Yongin-si (KR); Dal-Yong Gwak, Yongin-si (KR); Seok Hyoun Yun, Yongin-si (KR); Seo Young Lee, Yongin-si (KR); Hyunjin Michael Kim, Yongin-si (KR)

(73) Assignee: CHONG KUN DANG PHARMACEUTICAL CORP., Seoul (KR)

( * ) Notice: Subject to any disclaimer, the term of this patent is extended or adjusted under 35 U.S.C. 154(b) by 604 days.

(21) Appl. No.: 17/904,806

(22) PCT Filed: Feb. 25, 2021

(86) PCT No.: PCT/KR2021/002362
§ 371 (c)(1),
(2) Date: Aug. 23, 2022

(87) PCT Pub. No.: WO2021/172886
PCT Pub. Date: Sep. 2, 2021

(65) Prior Publication Data

US 2023/0147859 A1 May 11, 2023

(30) Foreign Application Priority Data

Feb. 25, 2020 (KR) ........................ 10-2020-0023249

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ............................ C07D 471/04; C07D 519/00
See application file for complete search history.

(56) References Cited

U.S. PATENT DOCUMENTS

| | | | |
|---|---|---|---|
| 2010/0120761 | A1 | 5/2010 | Berdini et al. |
| 2012/0041000 | A1 | 2/2012 | Saxty et al. |
| 2018/0023114 | A1 | 1/2018 | Morin et al. |
| 2018/0215743 | A1 | 8/2018 | Lee et al. |
| 2018/0230113 | A1 | 8/2018 | Lee et al. |
| 2018/0230114 | A1 | 8/2018 | Lee et al. |

FOREIGN PATENT DOCUMENTS

| | | | |
|---|---|---|---|
| AU | 2016299484 | B2 | 8/2019 |
| KR | 20120034635 | A | 4/2012 |
| RU | 2695227 | C1 | 7/2019 |
| RU | 2700696 | C2 | 9/2019 |
| RU | 2709207 | C2 | 12/2019 |
| TW | 201712007 | A | 4/2017 |
| TW | 202146409 | A | 12/2021 |
| WO | 2009002534 | A1 | 12/2008 |
| WO | 2011011186 | A2 | 1/2011 |
| WO | 2011038086 | A2 | 3/2011 |
| WO | 2011091213 | A2 | 7/2011 |
| WO | 2013008162 | A1 | 1/2013 |
| WO | 2013041407 | A1 | 3/2013 |
| WO | 2013052110 | A1 | 4/2013 |
| WO | 2013066833 | A1 | 5/2013 |
| WO | 2013066835 | A2 | 5/2013 |
| WO | 2013066838 | A1 | 5/2013 |
| WO | 2013066839 | A2 | 5/2013 |
| WO | 2013080120 | A1 | 6/2013 |
| WO | 2013134467 | A1 | 9/2013 |
| WO | 2017018804 | A1 | 2/2017 |
| WO | 2017030938 | A1 | 2/2017 |
| WO | 2017222950 | A1 | 12/2017 |
| WO | 2017222951 | A1 | 12/2017 |
| WO | 2019110663 | A1 | 6/2019 |
| WO | 2021127643 | A1 | 6/2021 |

(Continued)

OTHER PUBLICATIONS

Alzheimer's disease [online] retrieved from the internet on Mar. 25, 2022 URLhttps:/Avww.mayoclinic.org/diseases-conditions/alzheimers-disease/symptoms-causes/syc-.*
Chen, et al. Amyloid beta: structure, biology and structure-based therapeutic development. Acta Pharmacologica Sinica 2017:1205-1235.*
U.S. Appl. No. 17/904,809, filed Aug. 23, 2022, Lee et al.
Extended European Search Report corresponding to European Patent Application No. 21760387.7 (5 pages) (dated Jun. 5, 2023).
Bolden et al. "Anticancer activities of histone deacetylase inhibitors" Nature Reviews Drug Discovery, 5:769-784 (2006).
Chen et al. "Computational Exploration of Zinc Binding Groups for HDAC Inhibition" The Journal of Organic Chemistry, 78(10):5051-5055 (2013).

(Continued)

*Primary Examiner* — Shawquia Jackson
(74) *Attorney, Agent, or Firm* — Myers Bigel, P.A.

(57) ABSTRACT

The present invention relates to a novel compound having a histone deacetylase 6 (HDAC6) inhibitory activity, an isomer thereof or a pharmaceutically acceptable salt thereof, the use thereof for preparing a therapeutic medicament; a pharmaceutical composition containing the same, and a treatment method using the composition; and a preparation method thereof. The novel compound, the isomer thereof, or the pharmaceutically acceptable salt thereof according to the present invention has the HDAC6 inhibitory activity, which is effective in the prevention or treatment of HDAC6-mediated diseases including cancer, inflammatory diseases, autoimmune diseases, neurological or neurodegenerative diseases.

12 Claims, No Drawings

(56) References Cited

FOREIGN PATENT DOCUMENTS

WO 2021172887 A1 9/2021

OTHER PUBLICATIONS

Hassig et al. "Nuclear histone acetylases and deacetylases and transcriptional regulation: HATs off to HDACs" Current Opinion in Chemical Biology, 1:300-308 (1997).
International Search Report and the Written Opinion of the International Searching Authority corresponding to International Patent Application No. PCT/KR2021/002362 (11 pages) (mailed Jun. 11, 2021).
Kovacs et al. "HDAC6 Regulates Hsp90 Acetylation and Chaperone-Dependent Activation of Glucocorticoid Receptor" Molecular Cell, 18:601-607 (2005).
Li et al. "Discovery of a new class of histone deacetylase inhibitors with a novel zinc binding group" MedChemComm, 6:613-618 (2015).
Li et al. "HDAC6 α-tubulin deacetylase: A potential therapeutic target in neurodegenerative diseases" Journal of the Neurological Sciences, 304:1-8 (2011).
Methot et al. "Exploration of the internal cavity of histone deacetylase (HDAC) with selective HDAC1/HDAC2 Inhibitors (SHI-1:2)" Bioorganic & Medicinal Chemistry Letters, 18:973-978 (2008).
Santo et al. "Preclinical activity, pharmacodynamic, and pharmacokinetic properties of a selective HDAC6 inhibitor, ACY-1215, in combination with bortezomib in multiple myeloma" Blood, 119(11):2579-2589 (2012).
Subramanian et al. "Clinical Toxicities of Histone Deacetylase Inhibitors" Pharmaceuticals, 3:2751-2767 (2010).
Vishwakarma et al. "Tubastatin, a selective histone deacetylase 6 inhibitor shows anti-inflammatory and anti-rheumatic effects" International Immunopharmacology, 16:72-78 (2013).
Warrell et al. "Therapeutic Targeting of Transcription in Acute Promyelocytic Leukemia by Use of an Inhibitor of Histone Deacetylase" Journal of the National Cancer Institute, 90(21):1621-1625 (1998).
Witt et al. "HDAC family: What are the cancer relevant targets?" Cancer Letters, 277:8-21 (2009).
Yu et al. "Design, Synthesis, and Biological Evaluation of Imidazo[1,2-alpha]pyridine Derivatives as Novel PI3K/mTOR Dual Inhibitors" Journal of Medicinal Chemistry, 63:3028-3046 (2020).
Zhang et al. "Mice Lacking Histone Deacetylase 6 Have Hyperacetylated Tubulin but are Viable and Develop Normally" Molecular and Cellular Biology, 28(5):1688-1701 (2008).

* cited by examiner

1,3,4-OXADIAZOLE DERIVATIVE COMPOUNDS AS HISTONE DEACETYLASE 6 INHIBITOR, AND THE PHARMACEUTICAL COMPOSITION COMPRISING THE SAME

TECHNICAL FIELD

The present invention relates to a 1, 3,4-oxadiazole derivative compound having a histone deacetylase 6 (HDAC6) inhibitory activity, an optical isomer thereof, a pharmaceutically acceptable salt thereof; the use for preparing a therapeutic medicament; a treatment method using the same; a pharmaceutical composition containing the same; and a preparation method thereof.

BACKGROUND ART

Post-translational modifications such as acetylation in cells are very important regulatory modules at the center of biological processes and are strictly controlled by a number of enzymes. Histones are core proteins that make up the chromatin, acting as spools around which DNA winds to help condensation of DNA. In addition, the balance between acetylation and deacetylation of histones plays a very important role in gene expression.

Histone deacetylases (HDACs) are enzymes that remove the acetyl group of the histone protein lysine residues constituting the chromatin, which are known to be associated with gene silencing and to induce cell cycle arrest, angiogenesis inhibition, immune regulation, cell death, and the like (Hassig et al., Curr. Opin. Chem. Biol. 1997, 1, 300-308). Further, it has been reported that inhibition of HDAC enzyme function induces cancer cell death by reducing the activity of cancer cell survival-related factors and activating cancer cell death-related factors in vivo (Warrell et al, J. Natl. Cancer Inst. 1998, 90, 1621-1625).

In humans, 18 HDACs are known and are classified into 4 groups depending on their homology with yeast HDACs. Here, 11 HDACs using zinc as a cofactor can be divided into three groups of Class I (HDACs 1,2, 3, and 8), Class II (IIa: HDACs 4, 5, 7, and 9; IIb: HDACs 6 and 10) and Class IV (HDAC11). Further, 7 HDACs of Class III (SIRT 1-7) employ $NAD^+$as a cofactor instead of zinc (Bolden et al., Nat. Rev. Drug. Discov. 2006, 5 (9), 769-784).

Various HDAC inhibitors are in the preclinical or clinical development stage. However, until now, only non-selective HDAC inhibitors are known as anticancer agents, wherein vorinostat (SAHA) and romidepsin (FK228) have been approved as treatments for cutaneous T-cell lymphoma, and panobinostat (LBH-589) has been approved as a treatment for multiple myeloma. However, non-selective HDACs inhibitors are generally known to cause side effects such as fatigue and nausea, and the like, at high doses (Piekarz et al., Pharmaceuticals 2010, 3, 2751-2767). These side effects are reported to be caused by inhibition of Class I HDACs, and due to these side effects, non-selective HDACs inhibitors have been limited in drug development in fields other than anticancer agents (Witt et al., Cancer Letters 277 (2009) 8.21).

Meanwhile, it has been reported that selective Class II HDAC inhibition may not show the toxicity seen in Class I HDAC inhibition, and if a selective Class II HDAC inhibitor is developed, side effects such as toxicity caused by the non-selective HDAC inhibition may be solved, and thus the selective HDAC inhibitor has the potential to be developed as effective therapeutic agent for various diseases (Matthias et al., Mol. Cell. Biol. 2008, 28, 1688-1701).

HDAC6, one of the Class IIb HDACs, is mainly present in the cytoplasm and is known to be involved in deacetylation of a number of non-histone substrates (HSP90, cortactin, and the like) including tubulin proteins (Yao et al., Mol. Cell 2005, 18, 601-607). The HDAC6 has two catalytic domains, and the C-terminal of zinc-finger domain may bind to ubiquitinated proteins. Since the HDAC6 has a large number of non-histone proteins as substrates, it is known to play an important role in various diseases such as cancer, inflammatory diseases, autoimmune diseases, neurological diseases, and neurodegenerative disorders, and the like (Santo et al., Blood 2012 119:2579-258; Vishwakarma et al., International Immunopharmacology 2013, 16, 72-78; Hu et al., J. Neurol. Sci. 2011, 304, 1-8).

A common structural feature of various HDAC inhibitors is that they consist of a cap group, a linker group, and a zinc-binding group (ZBG), as shown in the structure of vorinostat below. Many researchers have studied the inhibitory activity and selectivity for enzymes through structural modifications of the cap group and linker group. Among the groups, the zinc-binding group is known to play a more important role in the enzyme inhibitory activity and selectivity (Wiest et al., J. Org. Chem. 2013 78:5051-5065; Methot et al., Bioorg. Med. Chem. Lett. 2008, 18, 973-978).

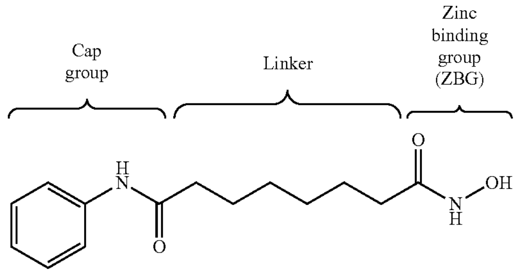 [SMILES: O=C(CCCCCCC(=O)Nc1ccccc1)NO]

Most of the zinc-binding groups are hydroxamic acid or benzamide, and among them, hydroxamic acid derivatives exhibit a strong HDAC inhibitory effect, but have problems such as low bioavailability and severe off-target activity. Since benzamide contains aniline, there is a problem that toxic metabolites may be caused in vivo (Woster et al., Med. Chem. Commun. 2015, online publication).

Therefore, for the treatment of cancer, inflammatory diseases, autoimmune diseases, neurological diseases, and neurodegenerative disorders, and the like, there is a need to develop a selective HDAC6 inhibitor having a zinc-binding group with improved bioavailability without side effects, unlike non-selective inhibitors with side effects.

DISCLOSURE

Technical Problem

An object of the present invention is to provide a 1,3,4-oxadiazole derivative compound having y a selective histone deacetylase 6 (HDAC6) inhibitory activity, an optical isomer thereof, or a pharmaceutically acceptable salt thereof.

Another object of the present invention is to provide a pharmaceutical composition including a 1, 3,4-oxadiazole derivative compound having a selective HDAC6 inhibitory activity, an optical isomer thereof, or a pharmaceutically acceptable salt thereof.

Still another object of the present invention is to provide a preparation method thereof.

Still another object of the present invention is to provide a pharmaceutical composition including the compounds for preventing or treating histone deacetylase 6 (HDAC6)-mediated diseases including infectious diseases; neoplasm; endocrine, nutritional and metabolic diseases; mental and behavioral disorders; neurological diseases; diseases of eyes and adnexa; circulatory diseases; respiratory diseases; digestive diseases; skin and subcutaneous tissue diseases; musculoskeletal and connective tissue diseases; or congenital malformations, alterations, or chromosomal abnormalities.

Still another object of the present invention is to provide the use of the compounds for preparing a medicament t for preventing or treating HDAC6-mediated diseases.

Still another object of the present invention is to provide a method for preventing or treating HDAC6-mediated diseases including administering a therapeutically effective amount of the composition including the compounds as described above.

Technical Solution

The present inventors found a 1, 3,4-oxadiazole derivative compound having a histone deacetylase 6 (HDAC6) inhibitory activity to inhibit or treat HDAC6-mediated diseases, and completed the present invention.

1, 3,4-Oxadiazole Derivative Compound

In one general aspect, the present invention provides a 1, 3,4-oxadiazole derivative compound represented by Chemical Formula I below, an optical isomer thereof, or a pharmaceutically acceptable salt thereof:

[Chemical Formula I]

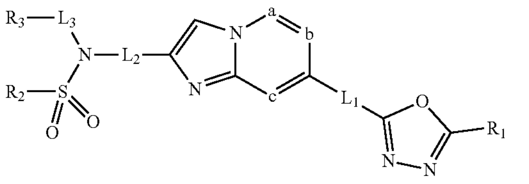

in the Chemical Formula I above, $L_1$, $L_2$ and $L_3$ are each independently —($C_0$-$C_2$alkyl)-;

a, b and c are each independently N or $CR^4$, wherein a, b and c cannot be N at the same time, and $R^4$ is —H, —X or —O($C_1$-$C_4$alkyl);

$R_1$ is —$CX_2H$ or —$CX_3$;

$R_2$ is —($C_1$-$C_4$alkyl), —($C_1$-$C_4$alkyl)-O—($C_1$-$C_4$alkyl), —$NR^AR^B$, aryl, heteroaryl,

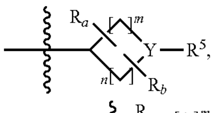 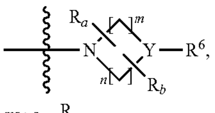

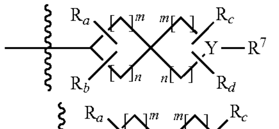 or

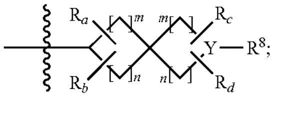

Y is —N—, —CH—, —O— or —S(═O)$_2$—;

when Y is —N— or —CH—, $R_5$, $R_6$, $R_7$ and $R_8$ are each independently —H, —X, —OH, —($C_1$-$C_4$alkyl), —($C_1$-$C_4$alkyl)-O($C_1$-$C_4$alkyl), —($C_3$-$C_7$cycloalkyl), —($C_2$-$C_6$heterocycloalkyl), —O($C_1$-$C_4$alkyl), —$NR^CR^D$, —$CF_3$, —$CF_2H$, —CN, —C(═O)—($C_1$-$C_4$alkyl), —C(═O)—($C_3$-$C_7$cycloalkyl), —C(═O)—($C_2$-$C_6$heterocycloalkyl), —C(═O)—O($C_1$-$C_4$alkyl), —($C_1$-$C_4$alkyl)-C(═O)—O($C_1$-$C_4$alkyl), —C(═O)—$NR^CR^D$, —C(═O)—($C_1$-$C_4$alkyl)-$NR^CR^D$, —S(═O)$_2$—($C_1$-$C_4$alkyl), -aryl, -heteroaryl, —($C_1$-$C_4$alkyl)-aryl, —($C_1$-$C_4$alkyl) heteroaryl, an amine protecting group or

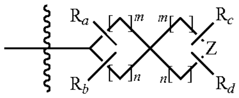

wherein at least one H of —($C_1$-$C_4$alkyl), —(C═O)—($C_1$-$C_4$alkyl), —($C_3$-$C_7$cycloalkyl) and —C(═O)—($C_3$-$C_7$cycloalkyl) may be substituted with —X, —OH, —O($C_1$-$C_4$alkyl), —C(═O)—($C_1$-$C_4$alkyl), —C(═O)—O($C_1$-$C_4$alkyl), —$CF_3$ or —$CF_2$H; at least one H of -aryl, -heteroaryl, —($C_1$-$C_4$alkyl)-aryl and —($C_1$-$C_4$alkyl) heteroaryl may be substituted with —X, —OH, —($C_1$-$C_4$alkyl), —O($C_1$-$C_4$alkyl), —C(═O)—($C_1$-$C_4$alkyl), —C(═O)—O($C_1$-$C_4$alkyl), or —CF 3—$CF_2$H; —($C_2$-$C_6$heterocycloalkyl), -heteroaryl or —($C_1$-$C_4$alkyl) heteroaryl may contain N, O or S atom in the ring; and Z is —NH—, —$CH_2$— or —O—;

when Y is —O— or —S(═O)$_2$—, $R_5$, $R_6$, $R_7$ and $R_8$ are nothing (null);

$R^A$ to $R^D$ are each independently —H, —($C_1$-$C_4$alkyl), —($C_3$-$C_7$cycloalkyl), —($C_2$-$C_6$heterocycloalkyl), —($C_1$-$C_4$alkyl)-($C_2$-$C_6$heterocycloalkyl), aryl, heteroaryl or —($C_1$-$C_4$alkyl)-aryl, wherein at least one H of —($C_3$-$C_7$cycloalkyl), —($C_2$-$C_6$heterocycloalkyl), —($C_1$-$C_4$alkyl)-($C_2$-$C_6$heterocycloalkyl), aryl, heteroaryl and —($C_1$-$C_4$alkyl)-aryl may be substituted with —($C_1$-$C_4$alkyl), —C(═O)—($C_1$-$C_4$alkyl), —S(═O)$_2$—($C_1$-$C_4$alkyl) or —($C_2$-$C_6$heterocycloalkyl);

m and n are each independently an integer of 1,2 or 3;

$R_a$ to $R_d$ are each independently —H or —($C_1$-$C_4$alkyl);

$R_3$ is —H, —($C_1$-$C_4$alkyl), —($C_1$-$C_4$alkyl)-O($C_1$-$C_4$alkyl), —($C_1$-$C_4$alkyl)-C(═O)—O($C_1$-$C_4$alkyl), —C(═O)—O($C_1$-$C_4$alkyl), —($C_3$-$C_7$cycloalkyl), —($C_2$-$C_6$heterocycloalkyl), -aryl or -heteroaryl, wherein at least one H of —($C_1$-$C_4$alkyl), —($C_3$-$C_7$cycloalkyl), —($C_2$-$C_6$heterocycloalkyl), -aryl and -heteroaryl may each independently be substituted with —X, —OH, —O($C_1$-$C_4$alkyl), —C(═O)—O($C_1$-$C_4$alkyl), —C(═O)—($C_1$-$C_4$alkyl), —$CF_3$, —$CF_2$H, —$OCF_3$, —S(═O)$_2$—($C_1$-$C_4$alkyl), -aryl, —O-aryl, -heteroaryl or —$NR^ER^F$, and the $R^E$ and $R^F$ are each independently —H or —($C_1$-$C_4$alkyl); and X is F, Cl, Br or I.

According to an embodiment of the present invention, in the Chemical Formula I above, $L_1$ to $L_3$ are each independently —($C_0$-$C_1$alkyl)-;

a, b and c are each independently N or $CR^4$, wherein a, b and c cannot be N at the same time, and $R^4$ is —H or —X;

$R_1$ is —$CX_2H$ or —$CX_3$;

$R_2$ is —($C_1$-$C_4$alkyl), —$NR^AR^B$,

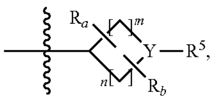, 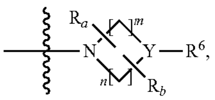,

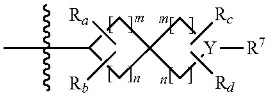 or

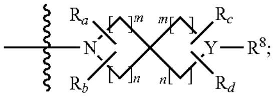;

m and n are each independently an integer of 1 or 2;

$R_a$ to $R_d$ are each independently —H or —($C_1$-$C_4$alkyl);

Y is —N—, —O—or —S(═O)$_2$—;

when Y is —N—, $R_5$, $R_6$, $R_7$ and $R_8$ are each independently —H, —($C_1$-$C_4$alkyl), —($C_3$-$C_7$cycloalkyl), —($C_2$-$C_6$heterocycloalkyl), —C(═O)—($C_1$-$C_4$alkyl), —C(═O)—($C_3$-$C_7$cycloalkyl), —C(═O)—($C_2$-$C_6$heterocycloalkyl), —C(═O)—O($C_1$-$C_4$alkyl), —C(═O)—NR$^C$R$^D$, —S(═O)$_2$—($C_1$-$C_4$alkyl), -heteroaryl or

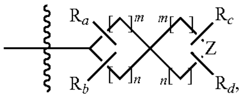, wherein at least one-H of —($C_1$-$C_4$alkyl), —(C═O)—($C_1$-$C_4$alkyl) and —($C_3$-$C_7$cycloalkyl) may be substituted with —X or —OH; —($C_2$-$C_6$heterocycloalkyl) or -heteroaryl may contain N, O or S atoms in the ring; and Z is —NH—, —CH$_2$—or —O—;

when Y is —O—or —S(═O)$_2$—, $R_5$, $R_6$, $R_7$ and $R_8$ are nothing (null);

$R^A$ to $R^D$ are each independently —H or —($C_1$-$C_4$alkyl);

$R^3$ is -aryl or -heteroaryl, wherein at least one H of -aryl and -heteroaryl may each independently be substituted with —X; and X may be F, $C_1$ or Br.

Further, according to another embodiment of the present invention, in the Chemical Formula I above, $L_1$ and $L_3$ are each independently —($C_0$alkyl)-;

$L_2$ is —($C_1$alkyl)-;

a, b and c are each independently CR$^4$, wherein $R_4$ is —H or —X;

$R_1$ is —CX$_2$H or —CX$_3$;

$R_2$ is

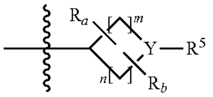 or 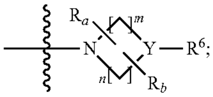;

m and n are each independently an integer of 1 or 2;

$R_a$ and $R_b$ are each independently —H or —($C_1$-$C_4$alkyl);

Y is —N—, $R_5$ and $R_6$ are each independently —H, —($C_1$-$C_4$alkyl), —($C_3$-$C_7$cycloalkyl), —($C_2$-$C_6$heterocycloalkyl), —C(═O)—($C_1$-$C_4$alkyl), —C(═O)—($C_3$-$C_7$cycloalkyl), —C(═O)—($C_2$-$C_6$heterocycloalkyl), —C(═O)—O($C_1$-$C_4$alkyl), —C(═O)—NR$^C$R$^D$, —S(═O)$_2$—($C_1$-$C_4$alkyl), -heteroaryl or

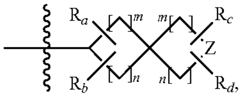, wherein at least one-H of —($C_1$-$C_4$alkyl), —(C═O)—($C_1$-$C_4$alkyl) and —($C_3$-$C_7$cycloalkyl) may be substituted with —X or —OH; —($C_2$-$C_6$heterocycloalkyl) or -heteroaryl may contain N, O or S atoms in the ring; and Z is —CH$_2$—or —O—;

$R^C$ and $R^D$ are each independently —H or —($C_1$-$C_4$alkyl);

$R^3$ is -aryl, wherein at least one H of -aryl may each independently be substituted with —X; and X may be F or $C_1$.

Further, according to still another embodiment of the present invention, in the Chemical Formula I above, $L_1$ to $L_3$ are each independently —($C_0$-$C_1$alkyl)-;

a, b and c are each independently N or CR$^4$, wherein a, b and c cannot be N at the same time, and $R^4$ is —H or —X;

$R_1$ is —CX$_2$H or —CX$_3$;

$R_2$ is —($C_1$-$C_4$alkyl),

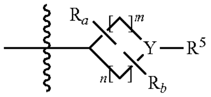 or 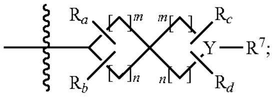;

m and n are each independently an integer of 1 or 2;

$R_a$ to $R_d$ are each independently —H or —($C_1$-$C_4$alkyl);

Y is —N—, —O—or —S(═O)$_2$—;

when Y is —N—, $R_5$, $R_6$, $R_7$ and $R_8$ are each independently —H, —($C_1$-$C_4$alkyl), —($C_3$-$C_7$cycloalkyl), —($C_2$-$C_6$heterocycloalkyl), —C(═O)—($C_1$-$C_4$alkyl), —C(═O)—($C_3$-$C_7$cycloalkyl), —C(═O)—($C_2$-$C_6$heterocycloalkyl), —C(═O)—O($C_1$-$C_4$alkyl), —C(═O)—NR$^C$R$^D$, —S(═O)$_2$—($C_1$-$C_4$alkyl), -heteroaryl or

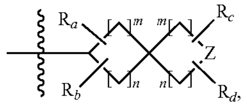, wherein at least one-H of —($C_1$-$C_4$alkyl), —(C═O)—($C_1$-$C_4$alkyl) and —($C_3$-$C_7$cycloalkyl) may be substituted with —X or —OH; —($C_2$-$C_6$heterocycloalkyl) or -heteroaryl may contain N, O or S atoms in the ring; and Z is —NH—, —CH$_2$—or —O—;

when Y is —O—or —S(═O)$_2$—, $R_5$, $R_6$, $R_7$ and $R_8$ are nothing (null);

$R^C$ and $R^D$ are each independently —H or —($C_1$-$C_4$alkyl);

$R^3$ is -aryl or -heteroaryl, wherein at least one H of -aryl or -heteroaryl may each independently be substituted with —X; and X may be F, $C_1$ or Br.

Further, according to still another embodiment of the present invention, in the Chemical Formula I above, $L_1$ to $L_3$ are each independently —($C_0$-$C_1$alkyl)-;

a, b and c are each independently N or $CR^4$, wherein a, b and c cannot be N at the same time, and $R^4$ is —H or —X;

$R_1$ is —$CX_2H$ or —$CX_3$;

$R_2$ is —$NR^AR^B$,

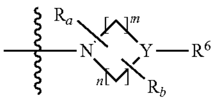

or

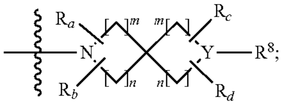

m and n are each independently an integer of 1 or 2;

$R_a$ to $R_d$ are each independently —H or —($C_1$-$C_4$alkyl);

Y is —N—, —O—or —S(═O)$_2$—;

when Y is —N—, $R_5$, $R_6$, $R_7$ and $R_8$ are each independently —H, —($C_1$-$C_4$alkyl), —($C_3$-$C_7$cycloalkyl), —($C_2$-$C_6$heterocycloalkyl), —C(═O)—($C_1$-$C_4$alkyl), —C(═O)—($C_3$-$C_7$cycloalkyl), —C(═O)—($C_2$-$C_6$heterocycloalkyl), —C(═O)—O($C_1$-$C_4$alkyl), —C(═O)—$NR^CR^D$, —S(═O)$_2$—($C_1$-$C_4$alkyl), -heteroaryl or

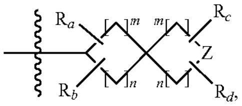

wherein at least one-H of —($C_1$-$C_4$alkyl), —(C═O)—($C_1$-$C_4$alkyl) and —($C_3$-$C_7$cycloalkyl) may be substituted with —X or —OH; —($C_2$-$C_6$heterocycloalkyl) or -heteroaryl may contain N, O or S atoms in the ring; and Z is —NH—, —$CH_2$—or —O—;

when Y is —O—or —S(═O)$_2$—, $R_5$, $R_6$, $R_7$ and $R_8$ are nothing (null);

$R^A$ to $R^D$ are each independently —H or —($C_1$-$C_4$alkyl);

$R^3$ is -aryl or -heteroaryl, wherein at least one H of -aryl and -heteroaryl may each independently be substituted with —X; and X may be F, $C_1$ or Br.

Specific compounds represented by Chemical Formula I of the present invention are shown in Table 1 below.

TABLE 1

| Ex | Comp | Structure |
|---|---|---|
| 1 | 3778 | 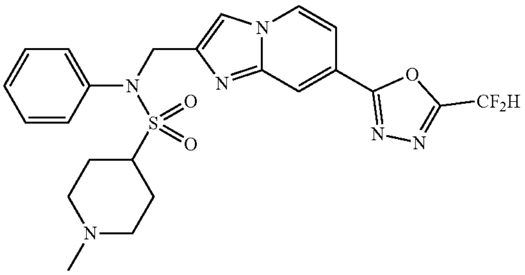 |
| 2 | 3779 | 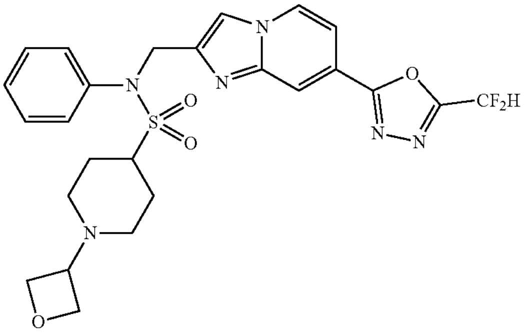 |
| 3 | 4214 | 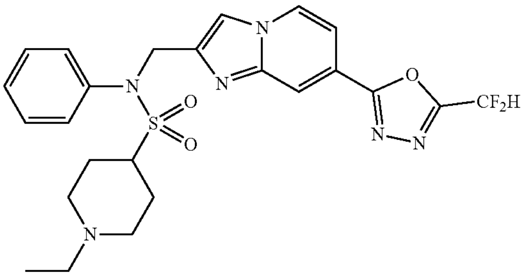 [SMILES: CCN1CCC(S(=O)(=O)N(Cc2cn3ccc(-c4nnc(C(F)F)o4)cc3n2)c2ccccc2)CC1] |

TABLE 1-continued
| Ex | Comp | Structure |
|---|---|---|
| 4 | 4215 | 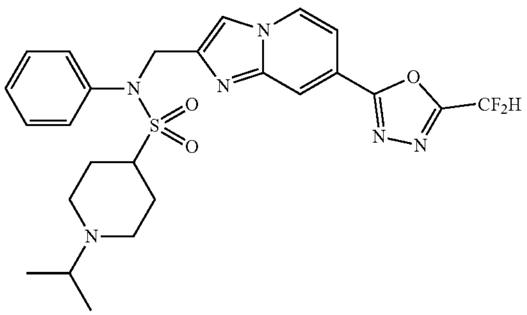 |
| 5 | 4216 | 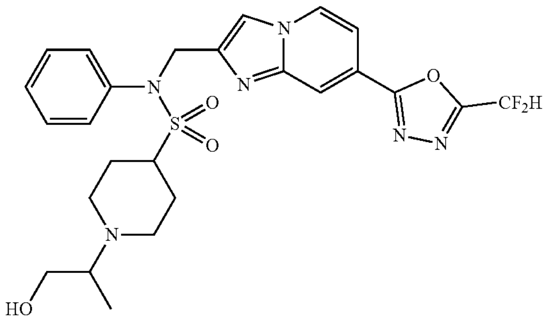 [SMILES: CC(CO)N1CCC(S(=O)(=O)N(Cc2cn3ccc(-c4nnc(C(F)F)o4)cc3n2)c2ccccc2)CC1] |
| 6 | 4217 | 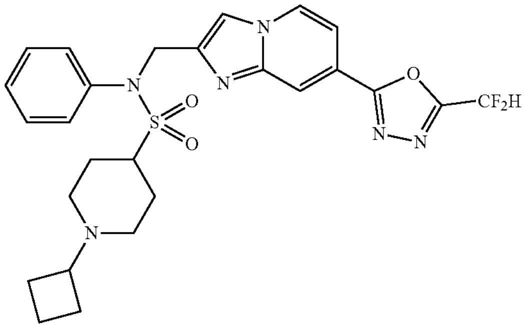 |
| 7 | 4218 | 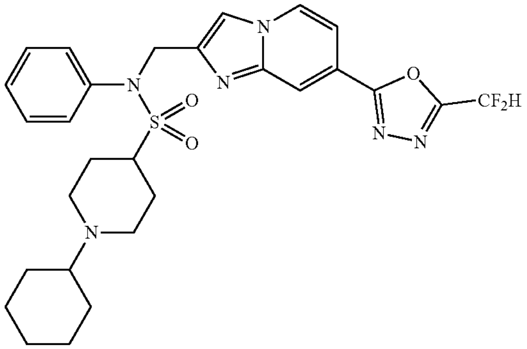 [SMILES: O=S(=O)(C1CCN(C2CCCCC2)CC1)N(Cc1cn2ccc(-c3nnc(C(F)F)o3)cc2n1)c1ccccc1] |

TABLE 1-continued
| Ex | Comp | Structure |
|---|---|---|
| 8 | 4219 | 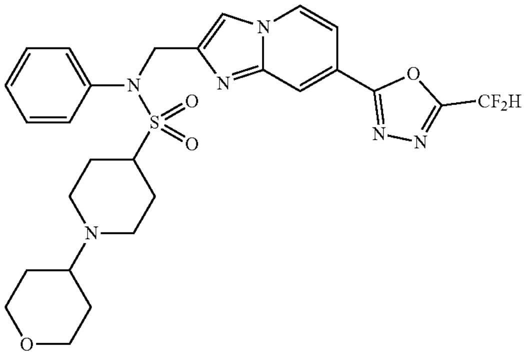 [SMILES: O=S(=O)(C1CCN(C2CCOCC2)CC1)N(Cc1cn2ccc(-c3nnc(C(F)F)o3)cc2n1)c1ccccc1] |
| 9 | 4220 | 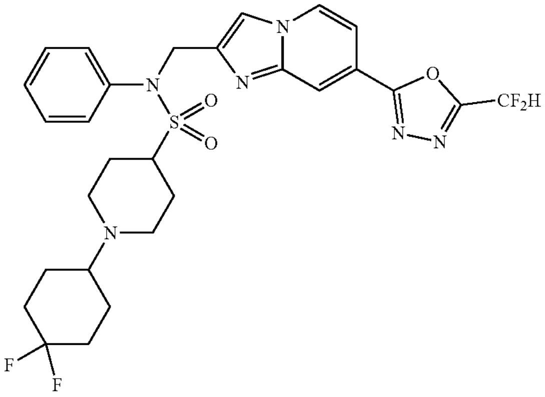 [SMILES: O=S(=O)(C1CCN(C2CCC(F)(F)CC2)CC1)N(Cc1cn2ccc(-c3nnc(C(F)F)o3)cc2n1)c1ccccc1] |
| 10 | 4221 | 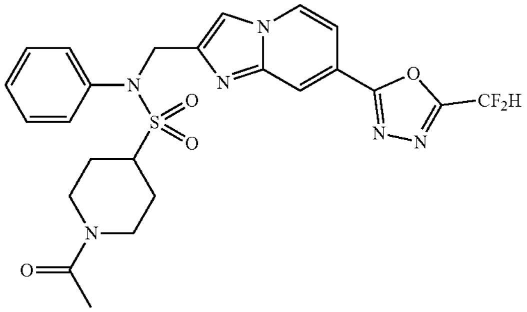 [SMILES: CC(=O)N1CCC(S(=O)(=O)N(Cc2cn3ccc(-c4nnc(C(F)F)o4)cc3n2)c2ccccc2)CC1] |
| 11 | 4222 | 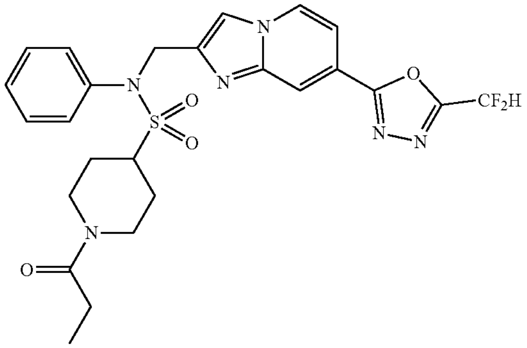 [SMILES: CCC(=O)N1CCC(S(=O)(=O)N(Cc2cn3ccc(-c4nnc(C(F)F)o4)cc3n2)c2ccccc2)CC1] |

TABLE 1-continued
| Ex | Comp | Structure |
|---|---|---|
| 12 | 4223 | 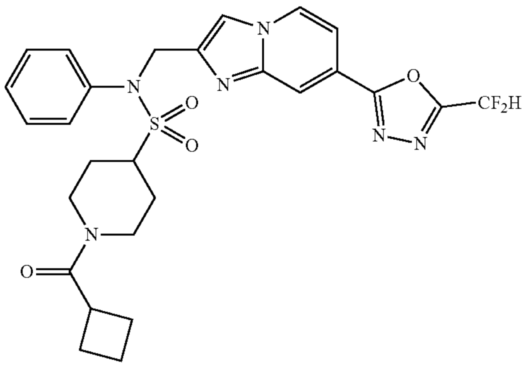 [SMILES: O=C(C1CCC1)N1CCC(S(=O)(=O)N(Cc2cn3ccc(-c4nnc(C(F)F)o4)cc3n2)c2ccccc2)CC1] |
| 13 | 4224 | 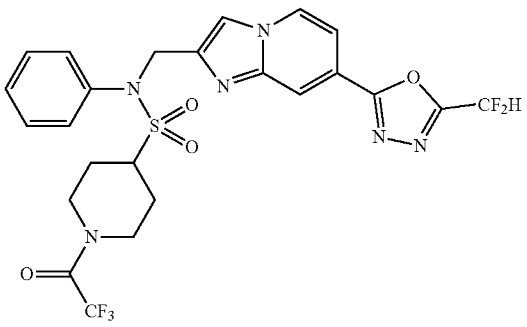 [SMILES: O=C(N1CCC(S(=O)(=O)N(Cc2cn3ccc(-c4nnc(C(F)F)o4)cc3n2)c2ccccc2)CC1)C(F)(F)F] |
| 14 | 4225 | 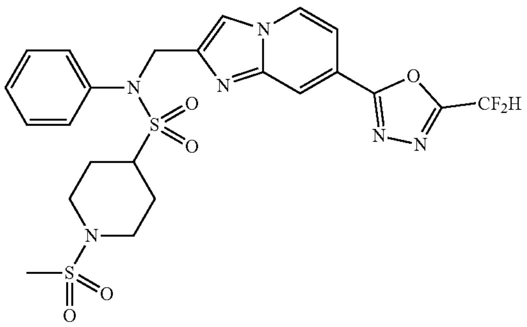 [SMILES: CS(=O)(=O)N1CCC(S(=O)(=O)N(Cc2cn3ccc(-c4nnc(C(F)F)o4)cc3n2)c2ccccc2)CC1] |
| 15 | 4226 | 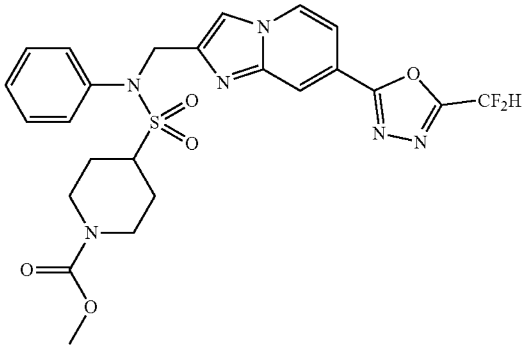 [SMILES: COC(=O)N1CCC(S(=O)(=O)N(Cc2cn3ccc(-c4nnc(C(F)F)o4)cc3n2)c2ccccc2)CC1] |

TABLE 1-continued
| Ex | Comp | Structure |
|---|---|---|
| 16 | 4227 | 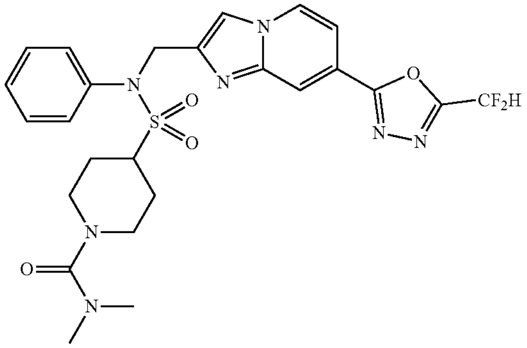 [SMILES: CN(C)C(=O)N1CCC(S(=O)(=O)N(Cc2cn3ccc(-c4nnc(C(F)F)o4)cc3n2)c2ccccc2)CC1] |
| 17 | 4228 | 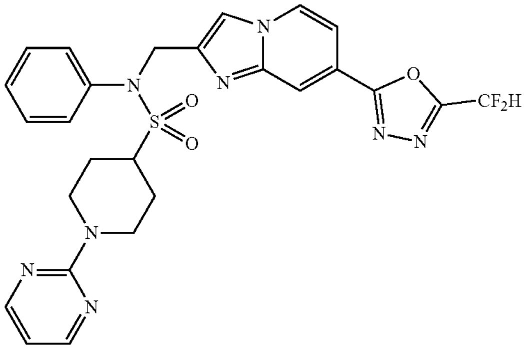 [SMILES: O=S(=O)(C1CCN(c2ncccn2)CC1)N(Cc1cn2ccc(-c3nnc(C(F)F)o3)cc2n1)c1ccccc1] |
| 18 | 4236 | 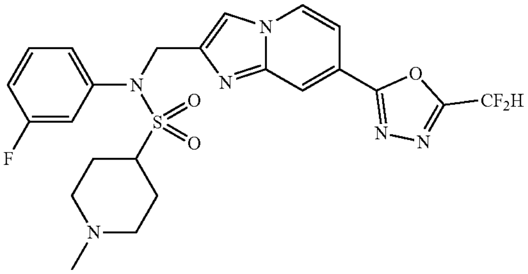 |
| 19 | 4237 | 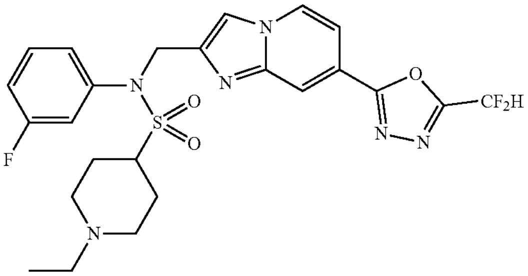 [SMILES: CCN1CCC(S(=O)(=O)N(Cc2cn3ccc(-c4nnc(C(F)F)o4)cc3n2)c2cccc(F)c2)CC1] |
| 20 | 4238 | 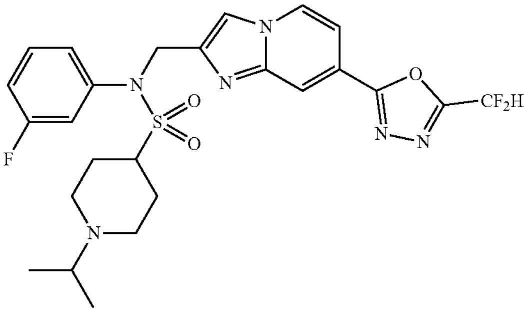 [SMILES: CC(C)N1CCC(S(=O)(=O)N(Cc2cn3ccc(-c4nnc(C(F)F)o4)cc3n2)c2cccc(F)c2)CC1] |

TABLE 1-continued
| Ex | Comp | Structure |
|---|---|---|
| 21 | 4239 | 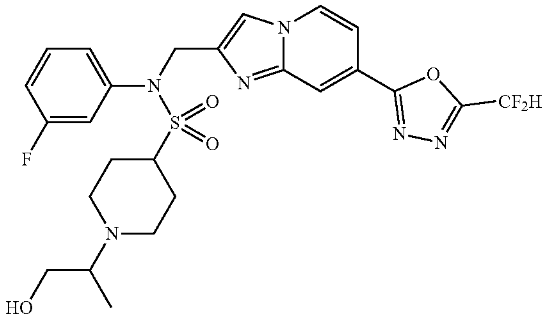 [SMILES: CC(CO)N1CCC(S(=O)(=O)N(Cc2cn3ccc(-c4nnc(C(F)F)o4)cc3n2)c2cccc(F)c2)CC1] |
| 22 | 4240 | 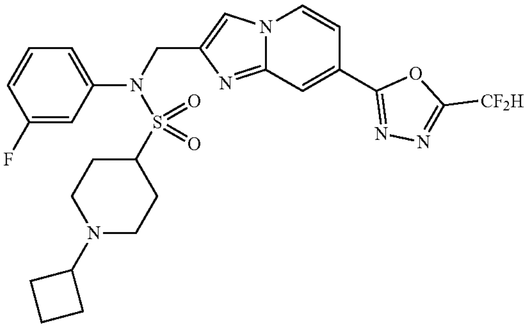 [SMILES: O=S(=O)(C1CCN(C2CCC2)CC1)N(Cc1cn2ccc(-c3nnc(C(F)F)o3)cc2n1)c1cccc(F)c1] |
| 23 | 4241 | 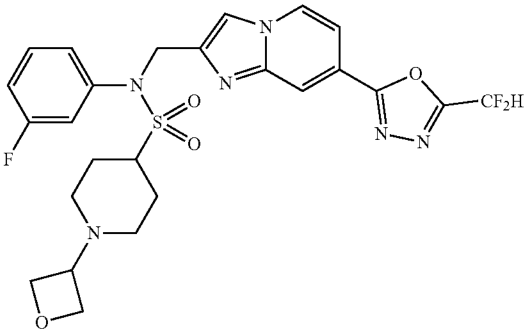 |
| 24 | 4242 | 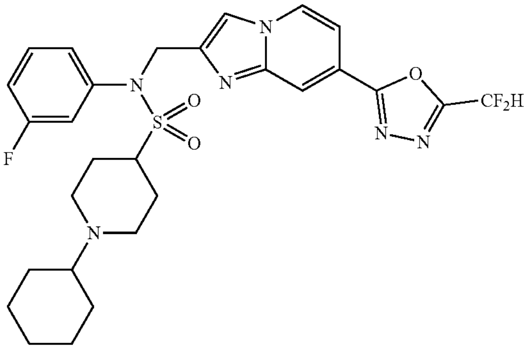 [SMILES: O=S(=O)(C1CCN(C2CCCCC2)CC1)N(Cc1cn2ccc(-c3nnc(C(F)F)o3)cc2n1)c1cccc(F)c1] |

TABLE 1-continued
| Ex | Comp | Structure |
|---|---|---|
| 25 | 4243 | 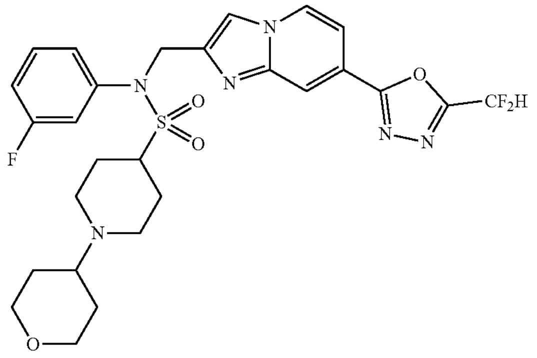 [SMILES: O=S(=O)(C1CCN(C2CCOCC2)CC1)N(Cc1cn2ccc(-c3nnc(C(F)F)o3)cc2n1)c1cccc(F)c1] |
| 26 | 4244 | 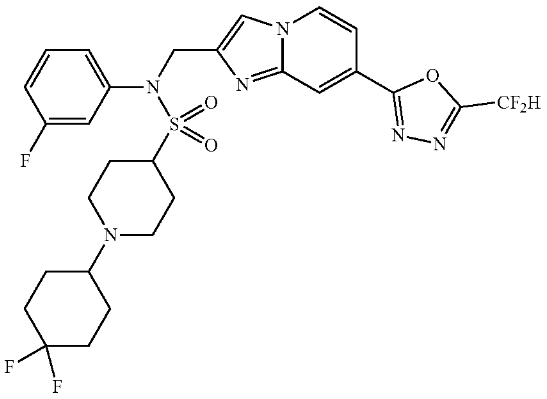 |
| 27 | 4245 | 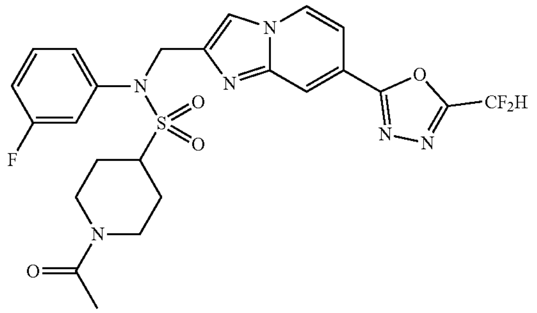 |
| 28 | 4246 | 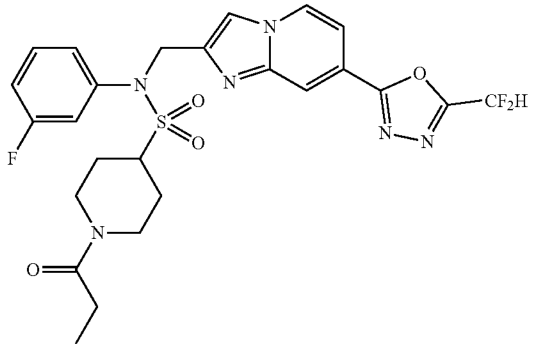 |

TABLE 1-continued
| Ex | Comp | Structure |
|---|---|---|
| 29 | 4247 | 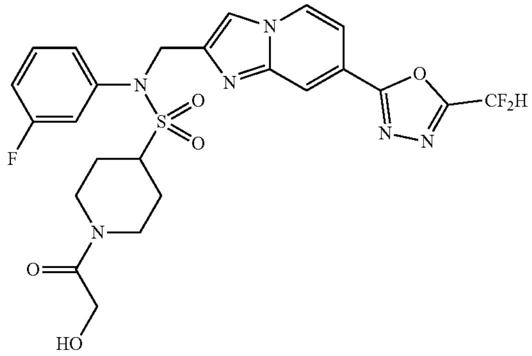 |
| 30 | 4248 | 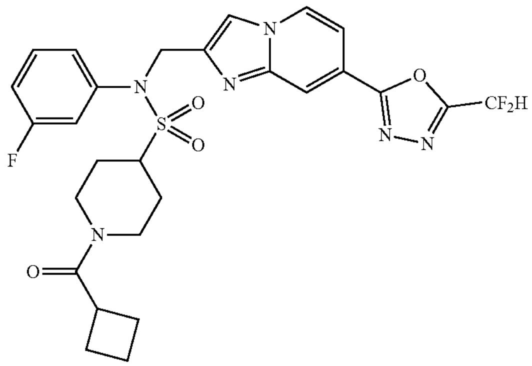 |
| 31 | 4249 | 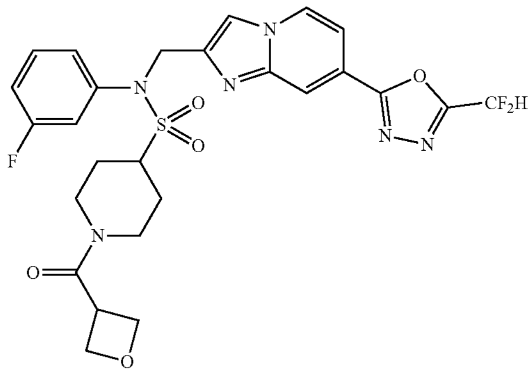 |
| 32 | 4250 | 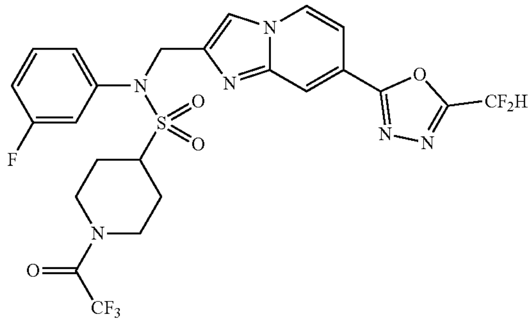 |

TABLE 1-continued
| Ex | Comp | Structure |
| --- | --- | --- |
| 33 | 4251 | 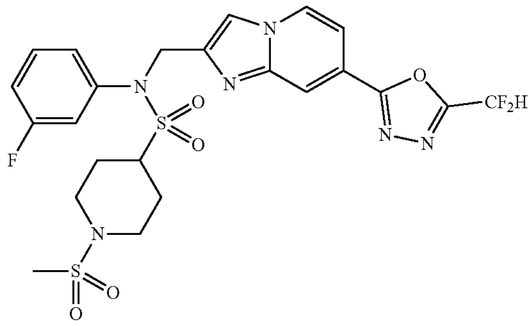 |
| 34 | 4252 | 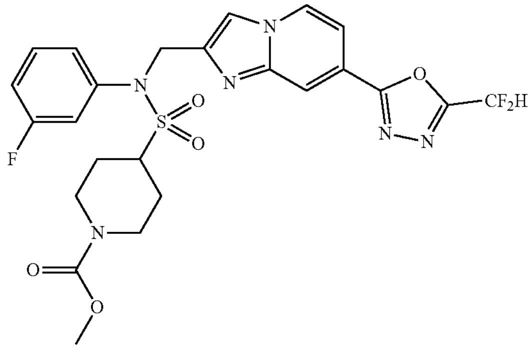 |
| 35 | 4253 | 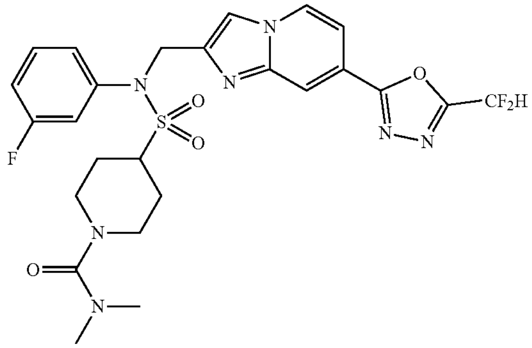 |
| 36 | 4254 | 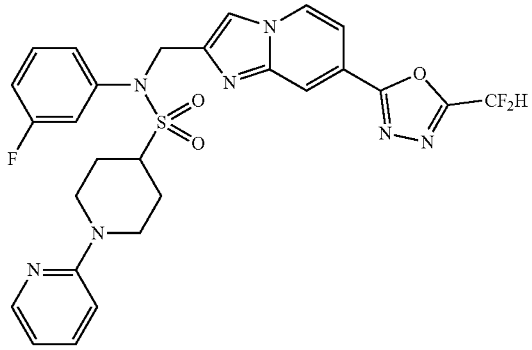 |

TABLE 1-continued
| Ex | Comp | Structure |
|---|---|---|
| 37 | 4255 | 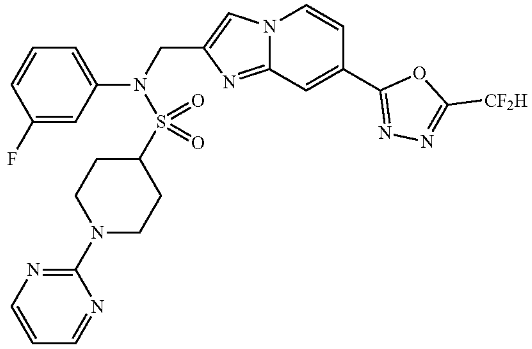 |
| 38 | 4256 | 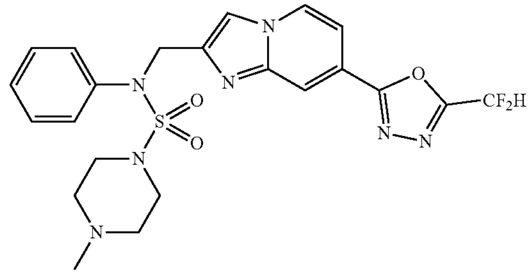 |
| 39 | 4257 | 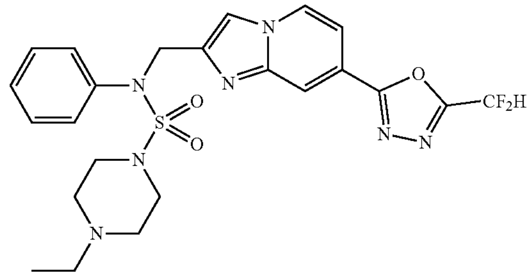 |
| 40 | 4258 | 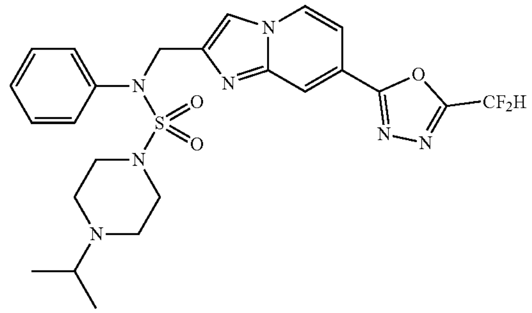 |
| 41 | 4259 | 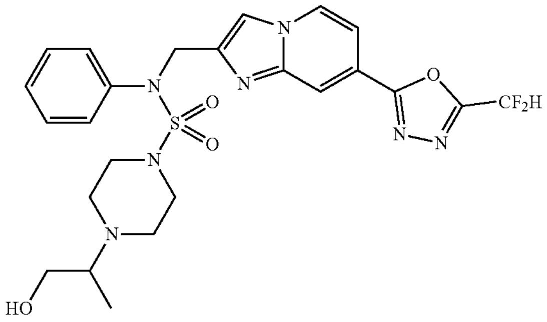 |

TABLE 1-continued
| Ex | Comp | Structure |
|---|---|---|
| 42 | 4260 | 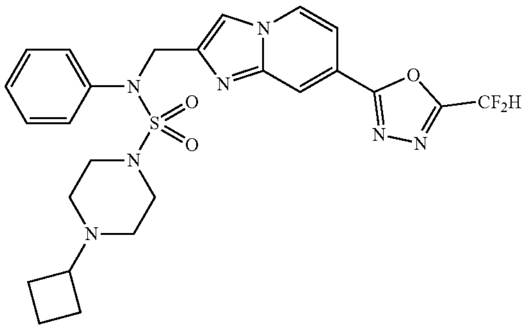 |
| 43 | 4261 | 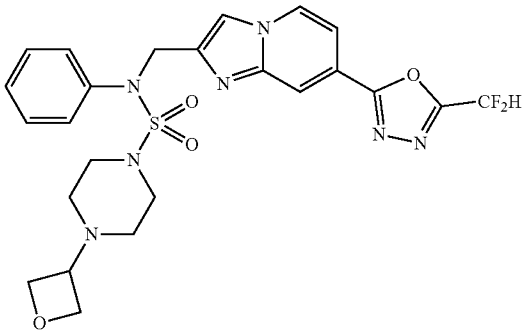 |
| 44 | 4262 | 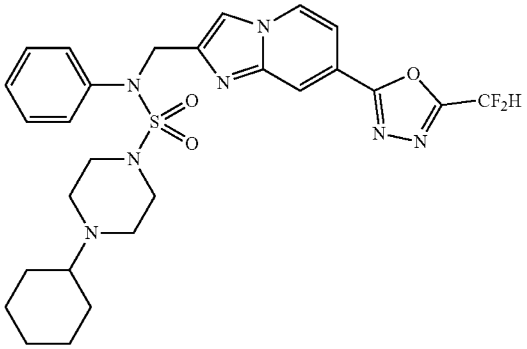 [SMILES: O=S(=O)(N1CCN(C2CCCCC2)CC1)N(Cc1cn2ccc(-c3nnc(C(F)F)o3)cc2n1)c1ccccc1] |
| 45 | 4263 | 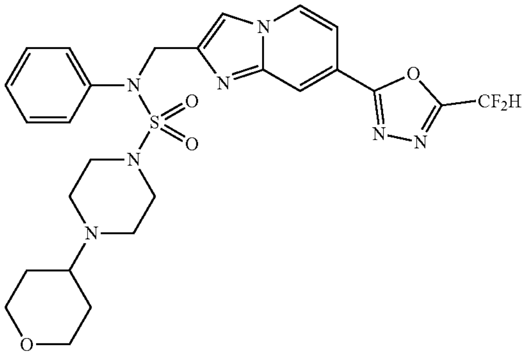 [SMILES: O=S(=O)(N1CCN(C2CCOCC2)CC1)N(Cc1cn2ccc(-c3nnc(C(F)F)o3)cc2n1)c1ccccc1] |

TABLE 1-continued
| Ex | Comp | Structure |
|---|---|---|
| 46 | 4264 | 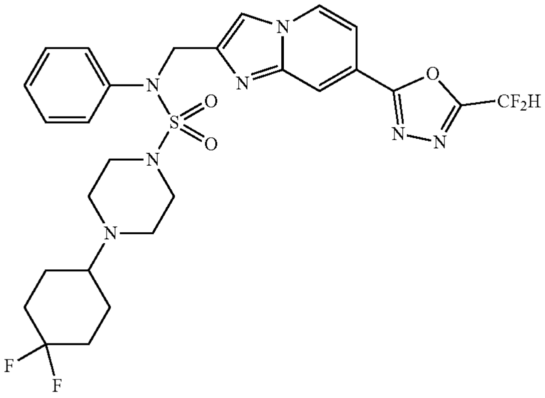 |
| 47 | 4265 | 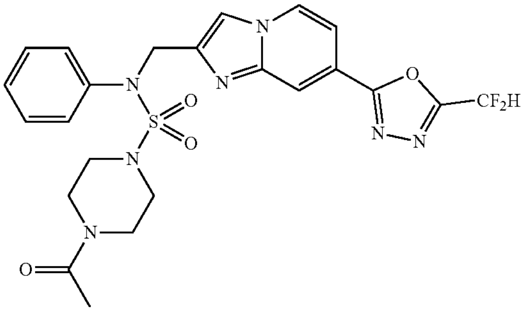 |
| 48 | 4266 | 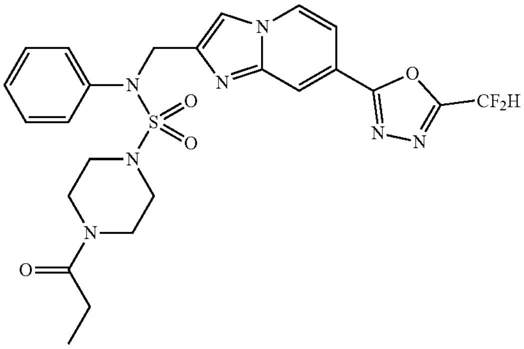 |
| 49 | 4267 | 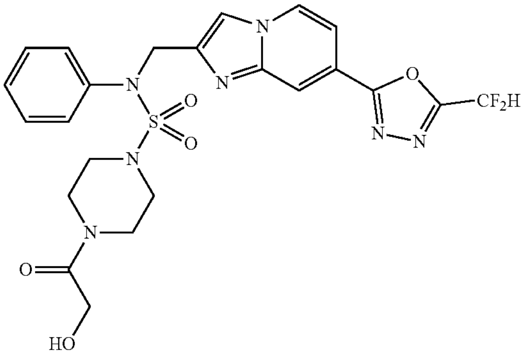 [SMILES: O=C(CO)N1CCN(S(=O)(=O)N(Cc2cn3ccc(-c4nnc(C(F)F)o4)cc3n2)c2ccccc2)CC1] |

TABLE 1-continued
| Ex | Comp | Structure |
| --- | --- | --- |
| 50 | 4268 | 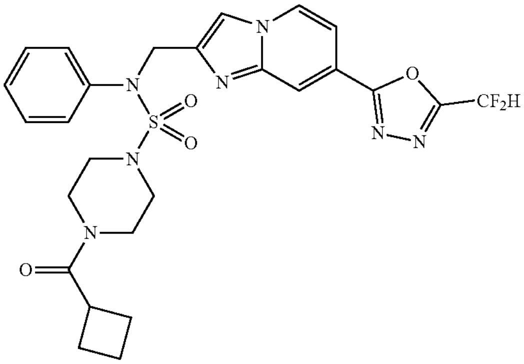 |
| 51 | 4269 | 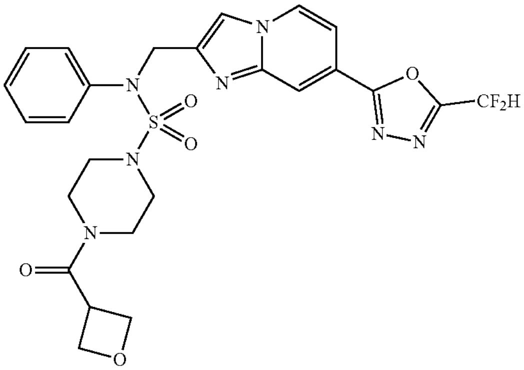 [SMILES: O=C(C1COC1)N1CCN(S(=O)(=O)N(Cc2cn3ccc(-c4nnc(C(F)F)o4)cc3n2)c2ccccc2)CC1] |
| 52 | 4270 | 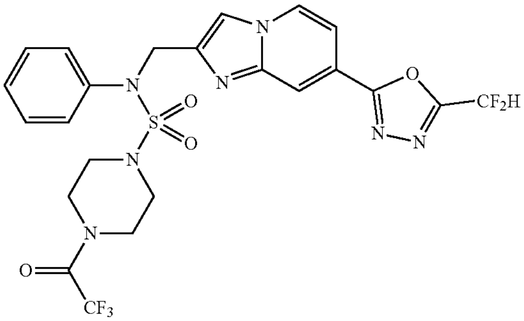 |
| 53 | 4271 | 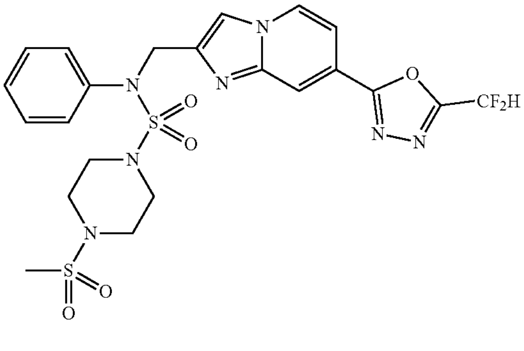 |

TABLE 1-continued
| Ex | Comp | Structure |
|---|---|---|
| 54 | 4272 | 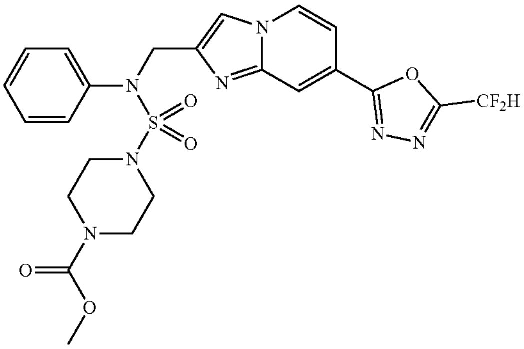 [SMILES: COC(=O)N1CCN(S(=O)(=O)N(Cc2cn3ccc(-c4nnc(C(F)F)o4)cc3n2)c2ccccc2)CC1] |
| 55 | 4273 | 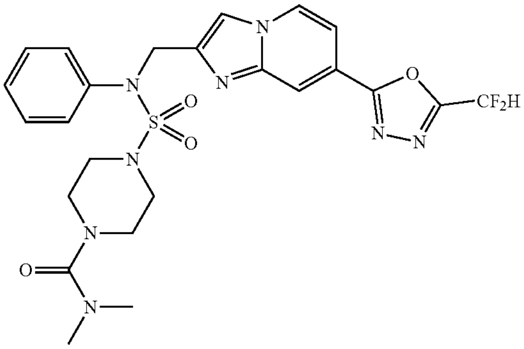 |
| 56 | 4274 | 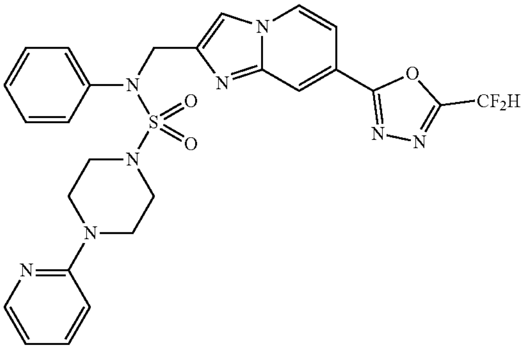 |
| 57 | 4275 | 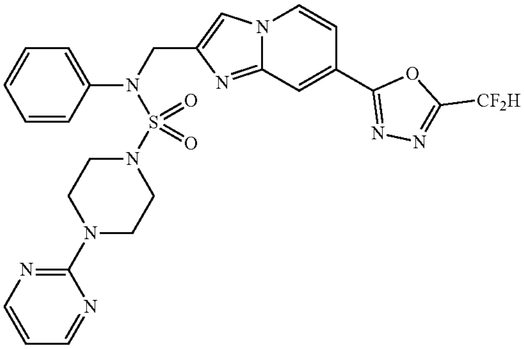 |

TABLE 1-continued
| Ex | Comp | Structure |
|---|---|---|
| 58 | 4297 | 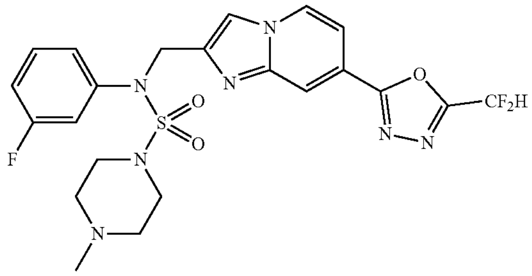 [SMILES: CN1CCN(S(=O)(=O)N(Cc2cn3ccc(-c4nnc(C(F)F)o4)cc3n2)c2cccc(F)c2)CC1] |
| 59 | 4298 | 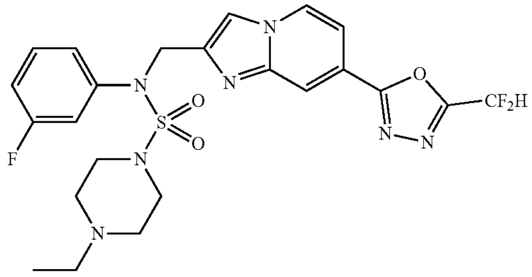 |
| 60 | 4299 | 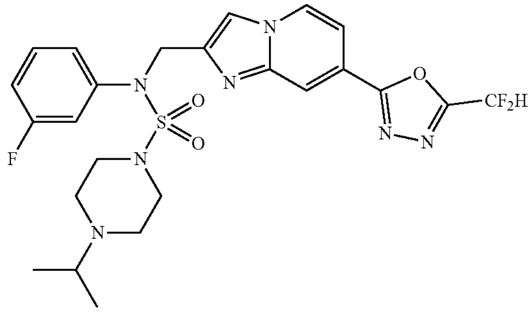 [SMILES: CC(C)N1CCN(S(=O)(=O)N(Cc2cn3ccc(-c4nnc(C(F)F)o4)cc3n2)c2cccc(F)c2)CC1] |
| 61 | 4300 | 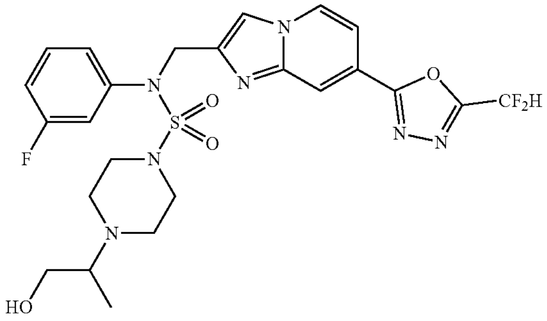 |
| 62 | 4301 | 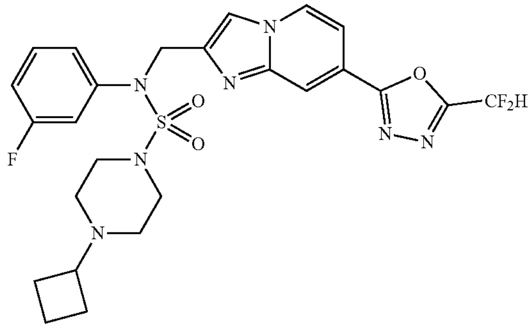 [SMILES: O=S(=O)(N1CCN(C2CCC2)CC1)N(Cc1cn2ccc(-c3nnc(C(F)F)o3)cc2n1)c1cccc(F)c1] |

TABLE 1-continued
| Ex | Comp | Structure |
|---|---|---|
| 63 | 4302 | 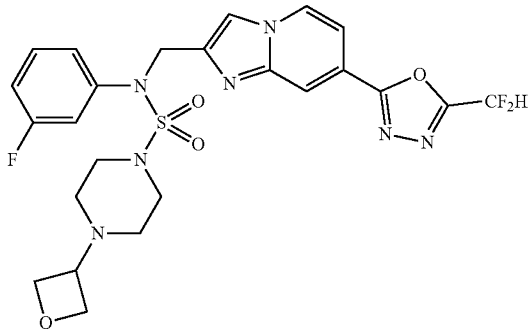 |
| 64 | 4303 | 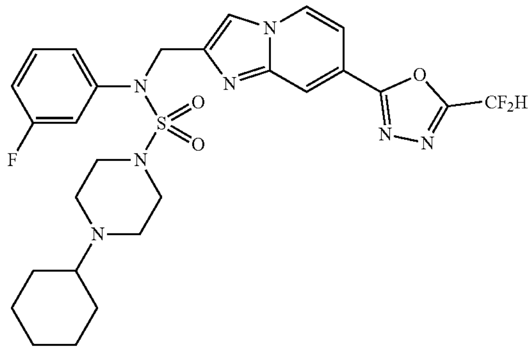 |
| 65 | 4304 | 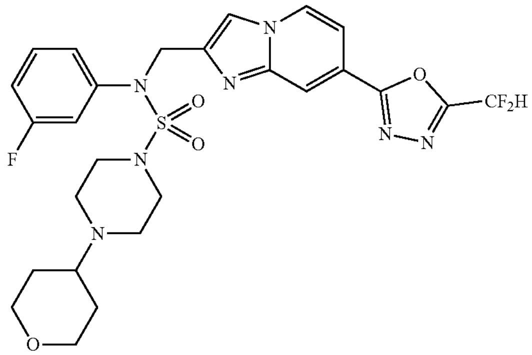 [SMILES: O=S(=O)(N1CCN(C2CCOCC2)CC1)N(Cc1cn2ccc(-c3nnc(C(F)F)o3)cc2n1)c1cccc(F)c1] |
| 66 | 4305 | 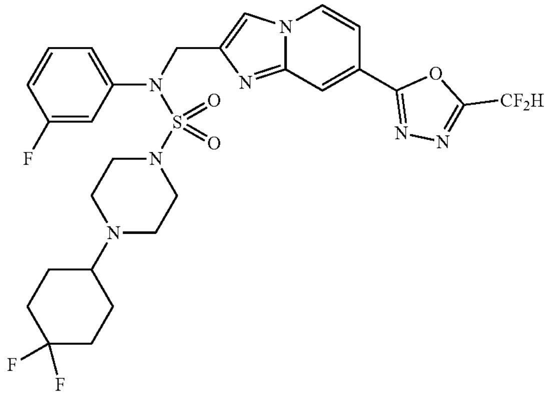 |

TABLE 1-continued
| Ex | Comp | Structure |
|---|---|---|
| 67 | 4306 | 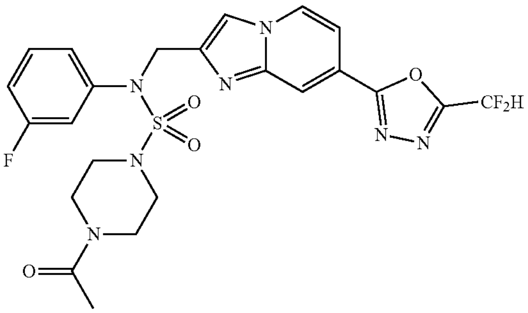 |
| 68 | 4307 | 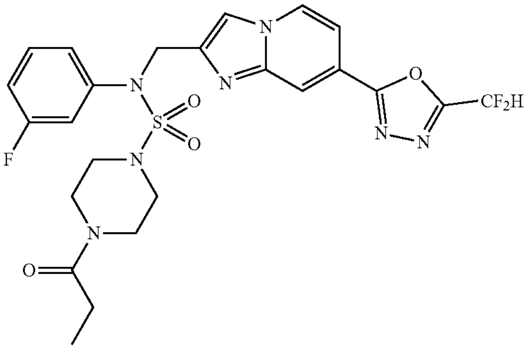 |
| 69 | 4308 | 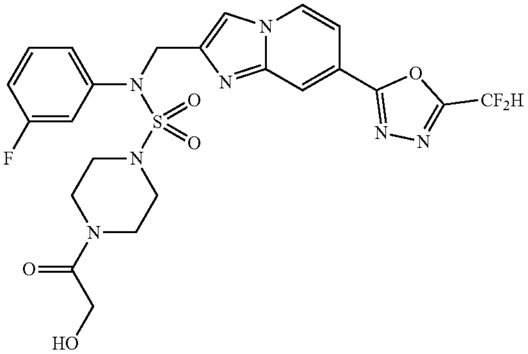 |
| 70 | 4309 | 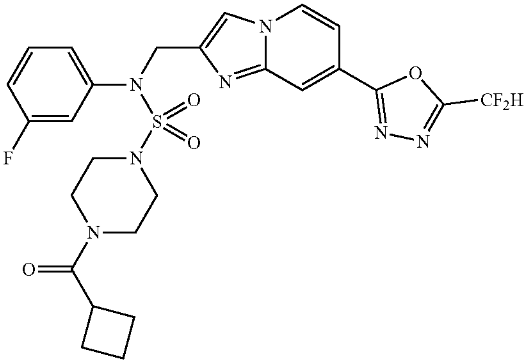 [SMILES: O=C(C1CCC1)N1CCN(S(=O)(=O)N(Cc2cn3ccc(-c4nnc(C(F)F)o4)cc3n2)c2cccc(F)c2)CC1] |

TABLE 1-continued
| Ex | Comp | Structure |
| --- | --- | --- |
| 71 | 4310 | 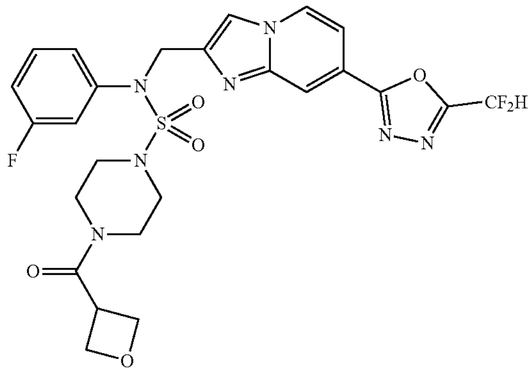 |
| 72 | 4311 | 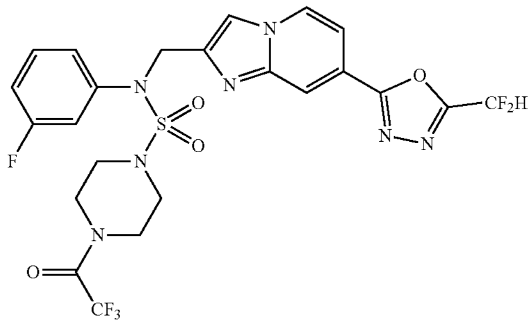 [SMILES: O=C(N1CCN(S(=O)(=O)N(Cc2cn3ccc(-c4nnc(C(F)F)o4)cc3n2)c2cccc(F)c2)CC1)C(F)(F)F] |
| 73 | 4312 | 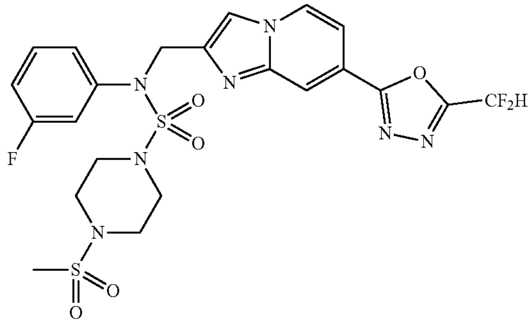 |
| 74 | 4313 | 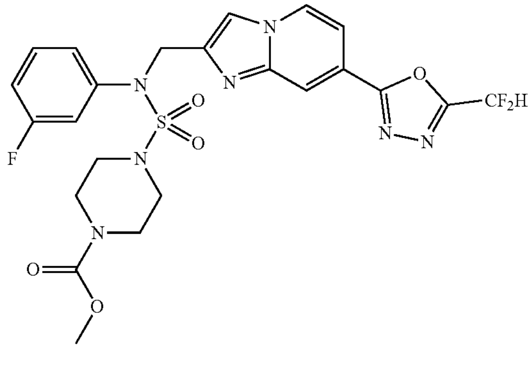 |

TABLE 1-continued
| Ex | Comp | Structure |
|---|---|---|
| 75 | 4314 | 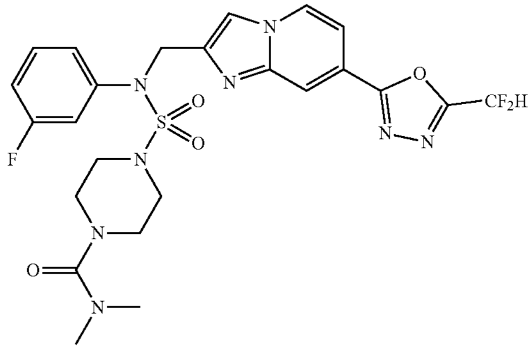 |
| 76 | 4315 | 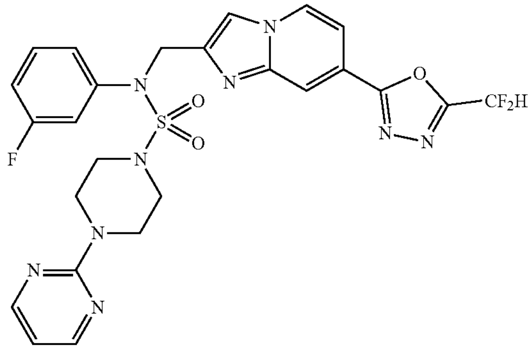 [SMILES: O=S(=O)(N1CCN(c2ncccn2)CC1)N(Cc1cn2ccc(-c3nnc(C(F)F)o3)cc2n1)c1cccc(F)c1] |
| 77 | 4616 | 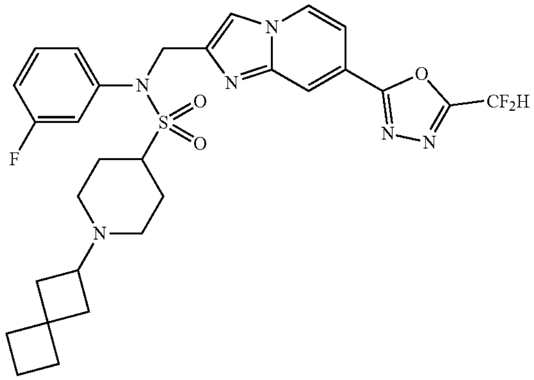 [SMILES: O=S(=O)(C1CCN(C2CC3(CCC3)C2)CC1)N(Cc1cn2ccc(-c3nnc(C(F)F)o3)cc2n1)c1cccc(F)c1] |
| 78 | 4617 | 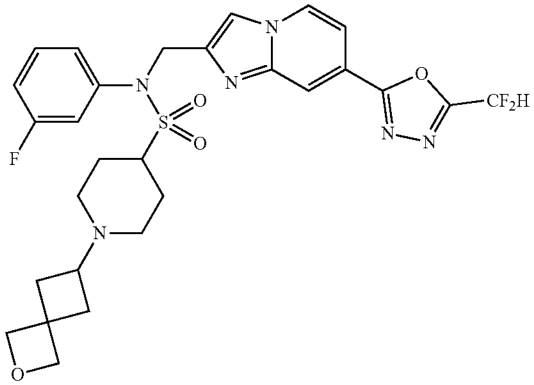 [SMILES: O=S(=O)(C1CCN(C2CC3(COC3)C2)CC1)N(Cc1cn2ccc(-c3nnc(C(F)F)o3)cc2n1)c1cccc(F)c1] |

TABLE 1-continued
| Ex | Comp | Structure |
|---|---|---|
| 79 | 4622 | 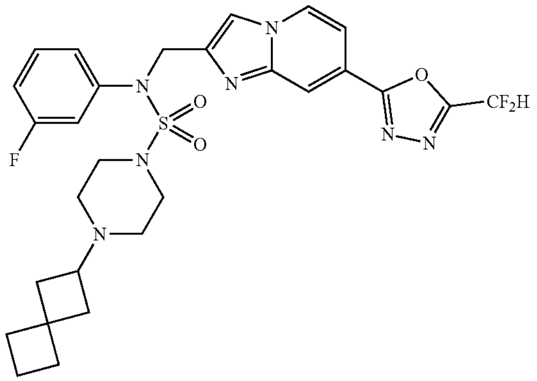 [SMILES: O=S(=O)(N1CCN(C2CC3(CCC3)C2)CC1)N(Cc1cn2ccc(-c3nnc(C(F)F)o3)cc2n1)c1cccc(F)c1] |
| 80 | 4623 | 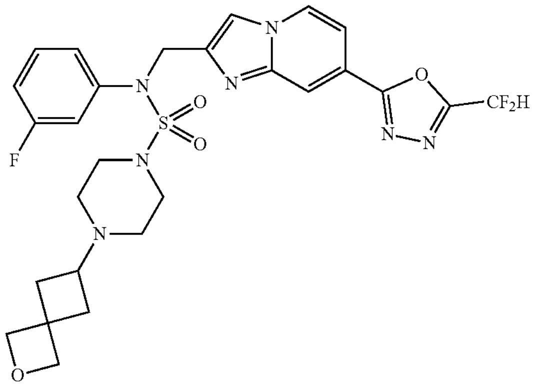 |
| 81 | 4624 | 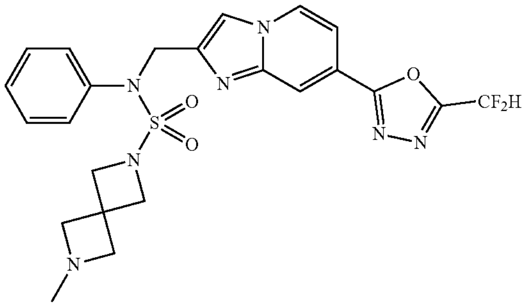 [SMILES: CN1CC2(C1)CN(S(=O)(=O)N(Cc1cn3ccc(-c4nnc(C(F)F)o4)cc3n1)c1ccccc1)C2] |
| 82 | 6893 | 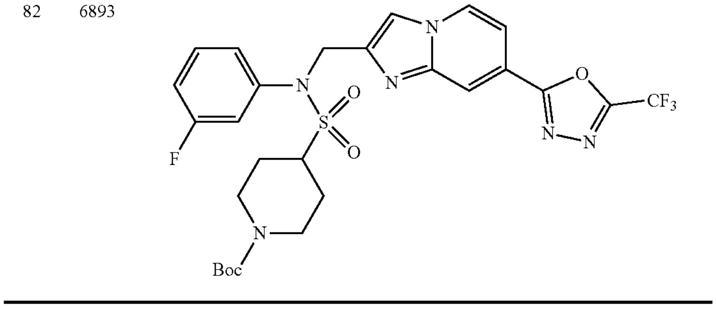 |

According to an embodiment of the present invention, it may be a specific compound represented by Chemical Formula I of the present invention:
TABLE 2
| Ex | Comp | Structure |
|---|---|---|
| 1 | 3778 | 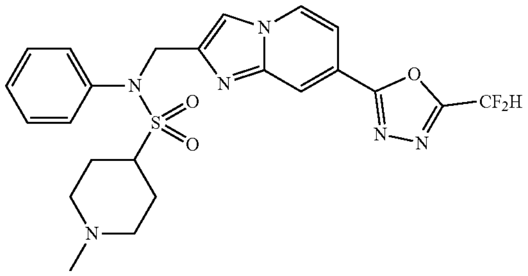 |
| 2 | 3779 | 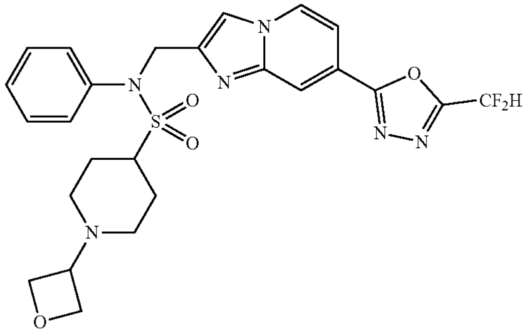 |
| 3 | 4214 | 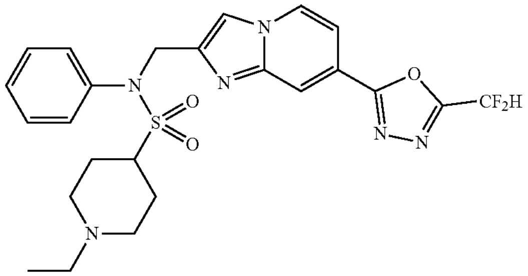 |
| 4 | 4215 | 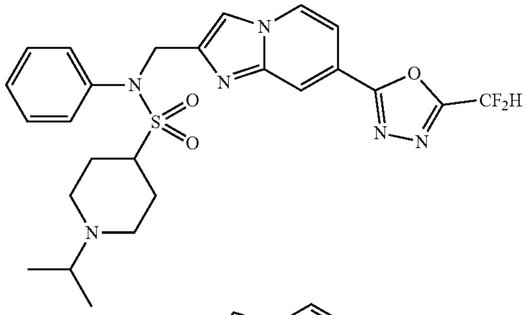 |
| 5 | 4216 | 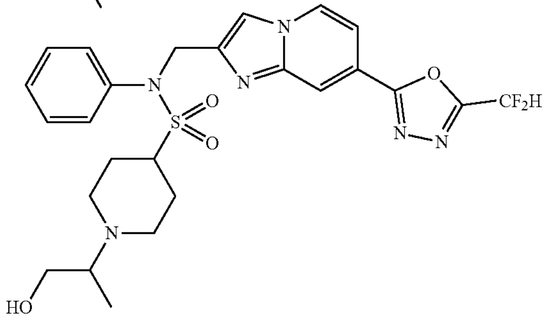 |

TABLE 2-continued
| Ex | Comp | Structure |
|---|---|---|
| 6 | 4217 | 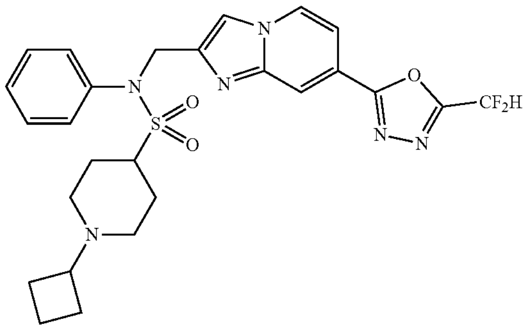 |
| 7 | 4218 | 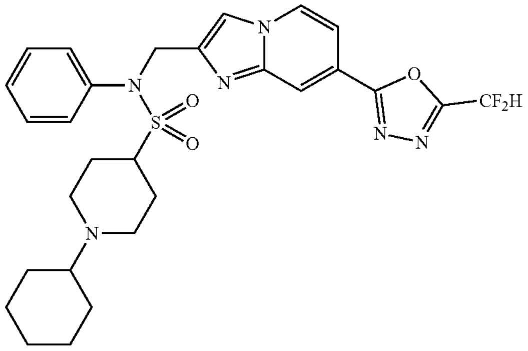 [SMILES: O=S(=O)(C1CCN(C2CCCCC2)CC1)N(Cc1cn2ccc(-c3nnc(C(F)F)o3)cc2n1)c1ccccc1] |
| 8 | 4219 | 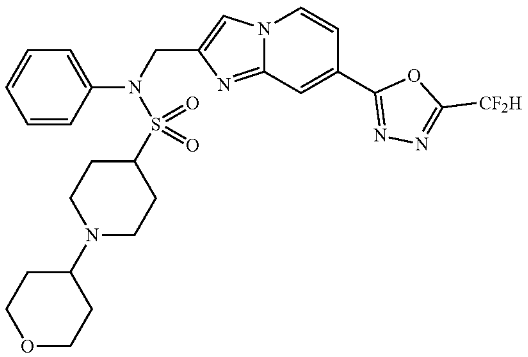 |
| 9 | 4220 | 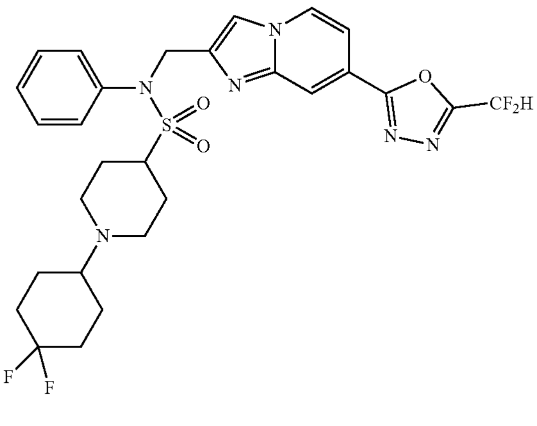 [SMILES: O=S(=O)(C1CCN(C2CCC(F)(F)CC2)CC1)N(Cc1cn2ccc(-c3nnc(C(F)F)o3)cc2n1)c1ccccc1] |

TABLE 2-continued
| Ex | Comp | Structure |
|---|---|---|
| 10 | 4221 | 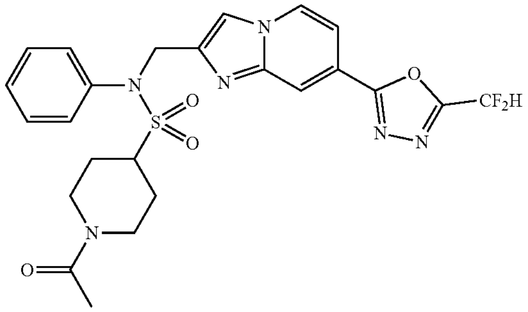 |
| 11 | 4222 | 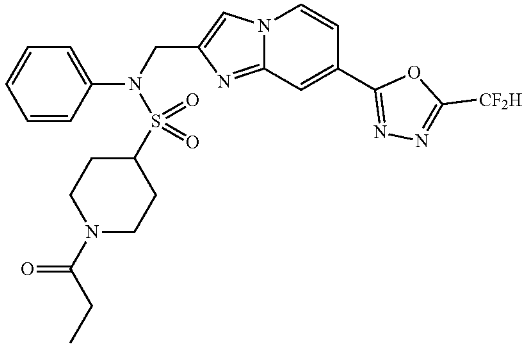 |
| 12 | 4223 | 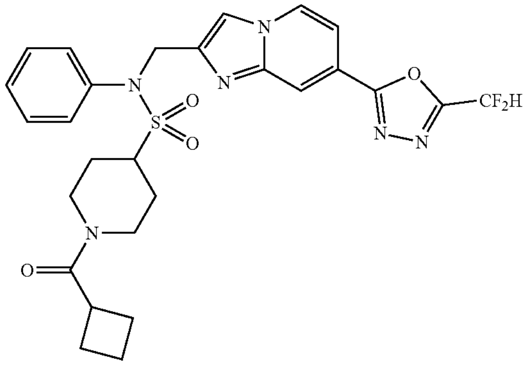 [SMILES: O=C(C1CCC1)N1CCC(S(=O)(=O)N(Cc2cn3ccc(-c4nnc(C(F)F)o4)cc3n2)c2ccccc2)CC1] |
| 13 | 4224 | 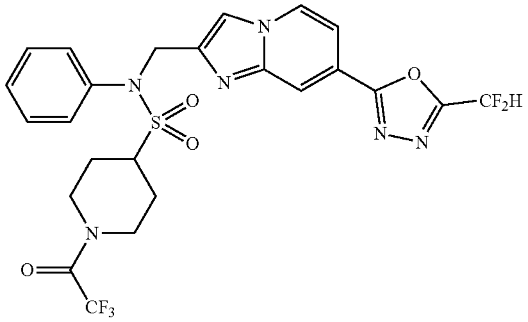 |

TABLE 2-continued
| Ex | Comp | Structure |
|---|---|---|
| 14 | 4225 | 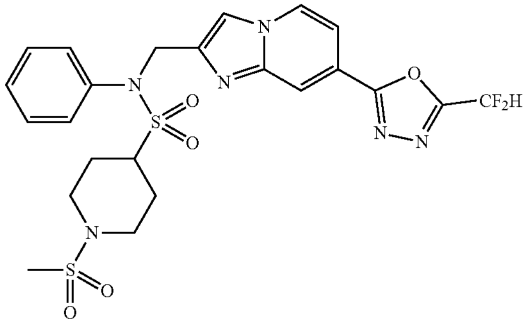 [SMILES: CS(=O)(=O)N1CCC(S(=O)(=O)N(Cc2cn3ccc(-c4nnc(C(F)F)o4)cc3n2)c2ccccc2)CC1] |
| 15 | 4226 | 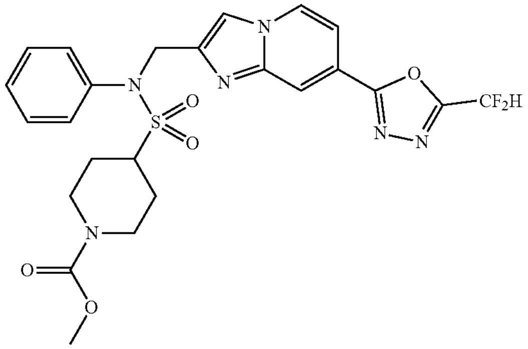 |
| 16 | 4227 | 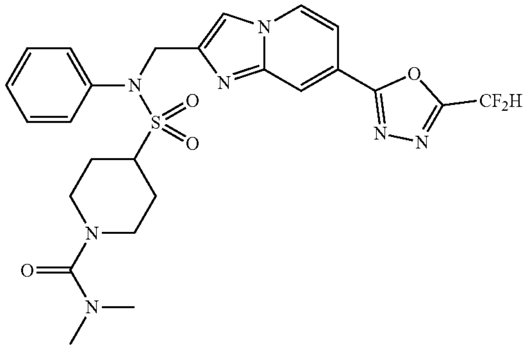 |
| 17 | 4228 | 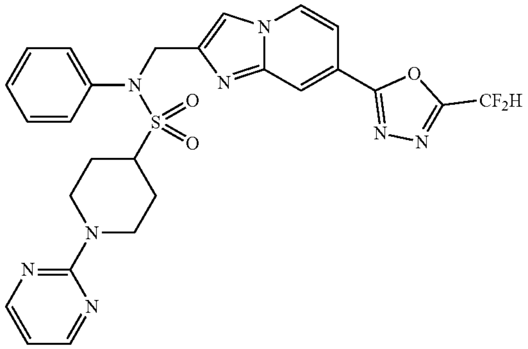 [SMILES: O=S(=O)(C1CCN(c2ncccn2)CC1)N(Cc1cn2ccc(-c3nnc(C(F)F)o3)cc2n1)c1ccccc1] |

TABLE 2-continued
| Ex | Comp | Structure |
| --- | --- | --- |
| 18 | 4236 | 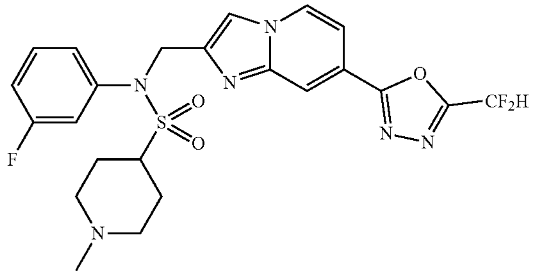 [SMILES: CN1CCC(S(=O)(=O)N(Cc2cn3ccc(-c4nnc(C(F)F)o4)cc3n2)c2cccc(F)c2)CC1] |
| 19 | 4237 | 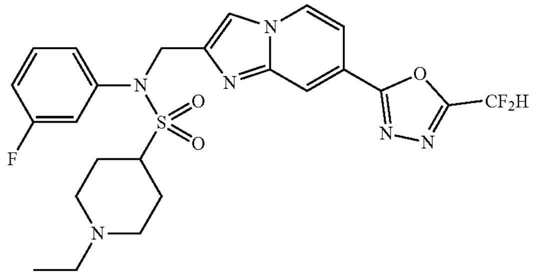 [SMILES: CCN1CCC(S(=O)(=O)N(Cc2cn3ccc(-c4nnc(C(F)F)o4)cc3n2)c2cccc(F)c2)CC1] |
| 20 | 4238 | 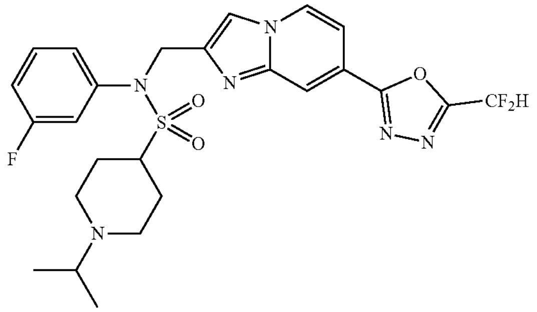 |
| 21 | 4239 | 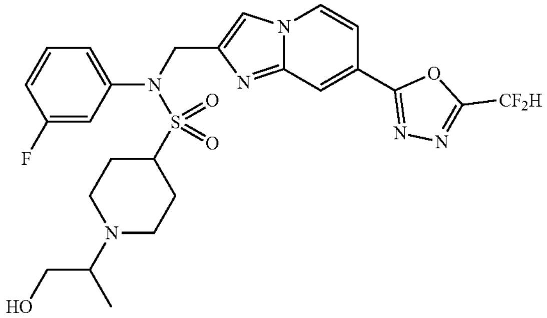 [SMILES: CC(CO)N1CCC(S(=O)(=O)N(Cc2cn3ccc(-c4nnc(C(F)F)o4)cc3n2)c2cccc(F)c2)CC1] |
| 22 | 4240 | 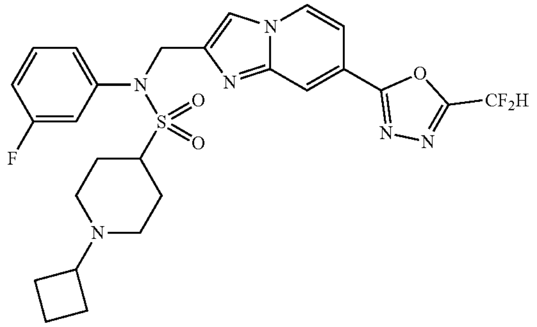 [SMILES: O=S(=O)(C1CCN(C2CCC2)CC1)N(Cc1cn2ccc(-c3nnc(C(F)F)o3)cc2n1)c1cccc(F)c1] |

TABLE 2-continued
| Ex | Comp | Structure |
| --- | --- | --- |
| 23 | 4241 | 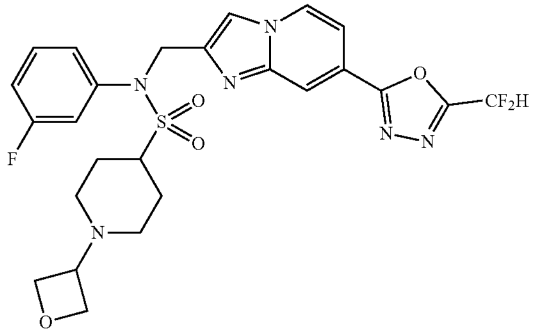 |
| 24 | 4242 | 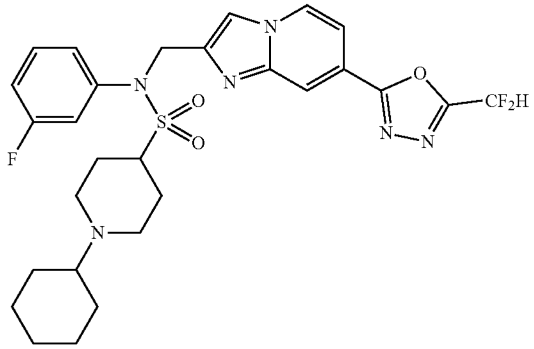 |
| 25 | 4243 | 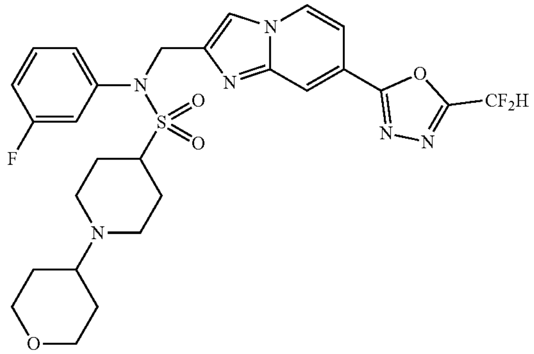 [SMILES: O=S(=O)(C1CCN(C2CCOCC2)CC1)N(Cc1cn2ccc(-c3nnc(C(F)F)o3)cc2n1)c1cccc(F)c1] |
| 26 | 4244 | 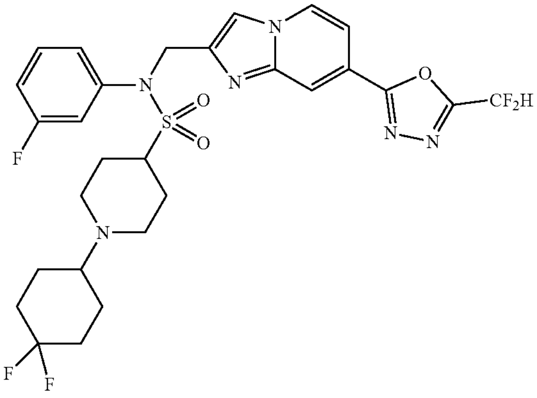 |

TABLE 2-continued
| Ex | Comp | Structure |
|---|---|---|
| 27 | 4245 | 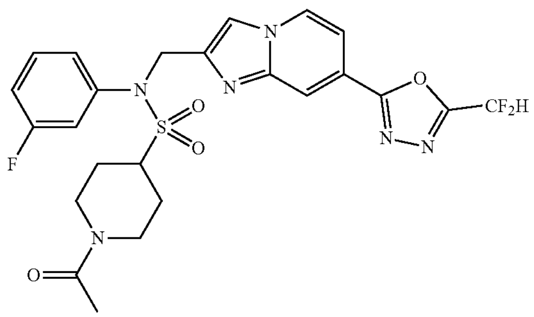 [SMILES: CC(=O)N1CCC(S(=O)(=O)N(Cc2cn3ccc(-c4nnc(C(F)F)o4)cc3n2)c2cccc(F)c2)CC1] |
| 28 | 4246 | 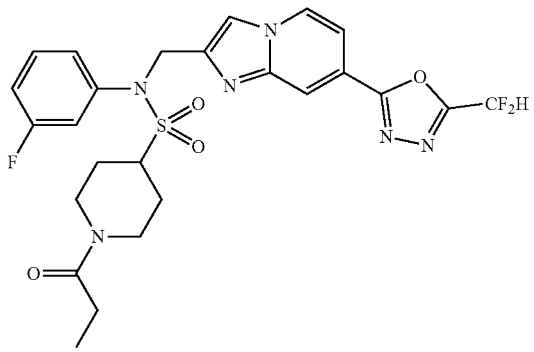 [SMILES: CCC(=O)N1CCC(S(=O)(=O)N(Cc2cn3ccc(-c4nnc(C(F)F)o4)cc3n2)c2cccc(F)c2)CC1] |
| 29 | 4247 | 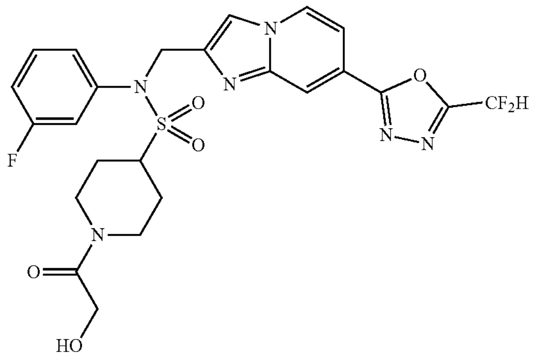 |
| 30 | 4248 | 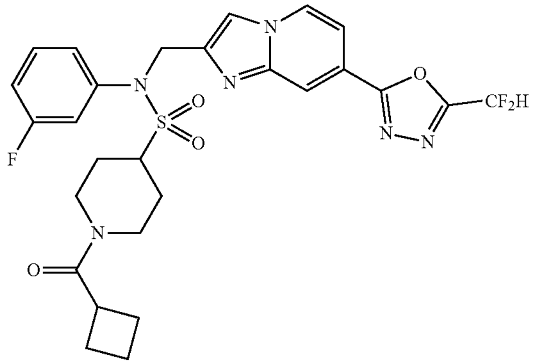 [SMILES: O=C(C1CCC1)N1CCC(S(=O)(=O)N(Cc2cn3ccc(-c4nnc(C(F)F)o4)cc3n2)c2cccc(F)c2)CC1] |

TABLE 2-continued
| Ex | Comp | Structure |
|---|---|---|
| 31 | 4249 | 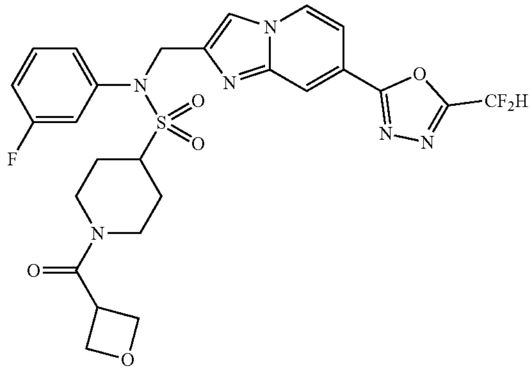 |
| 32 | 4250 | 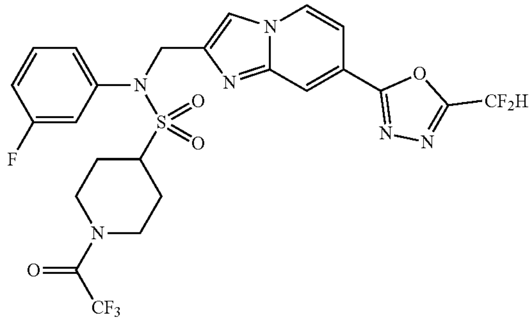 |
| 33 | 4251 | 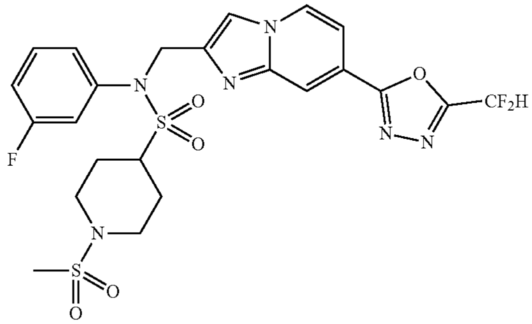 |
| 34 | 4252 | 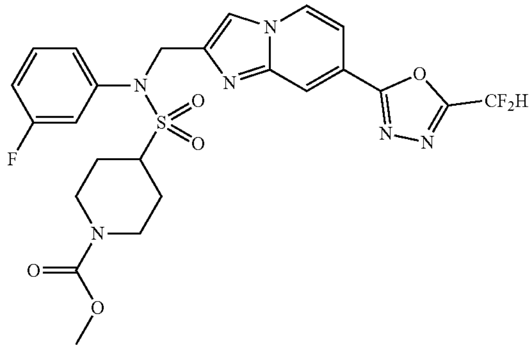 |

TABLE 2-continued
| Ex | Comp | Structure |
| --- | --- | --- |
| 35 | 4253 | 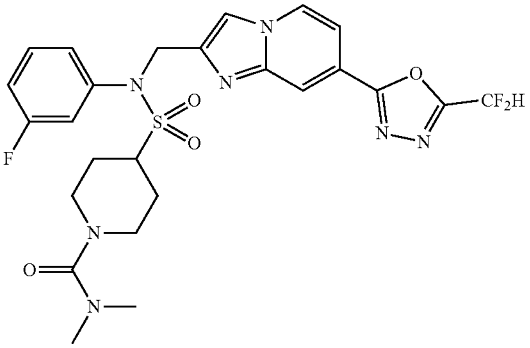 [SMILES: CN(C)C(=O)N1CCC(S(=O)(=O)N(Cc2cn3ccc(-c4nnc(C(F)F)o4)cc3n2)c2cccc(F)c2)CC1] |
| 36 | 4254 | 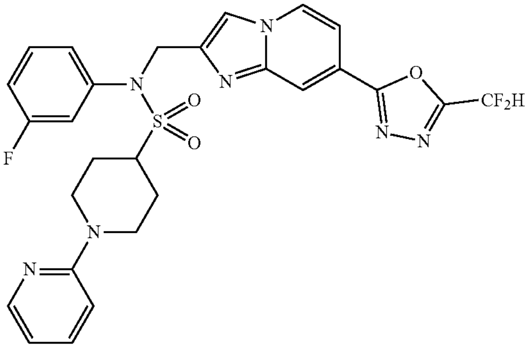 [SMILES: O=S(=O)(C1CCN(c2ccccn2)CC1)N(Cc1cn2ccc(-c3nnc(C(F)F)o3)cc2n1)c1cccc(F)c1] |
| 37 | 4255 | 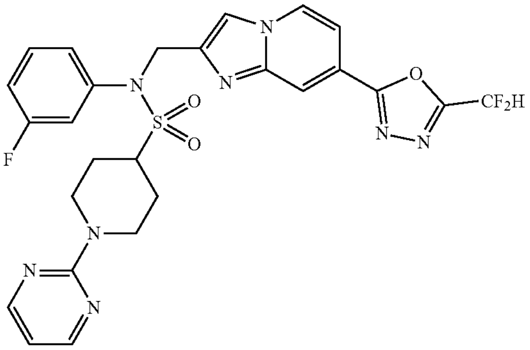 |
| 77 | 4616 | 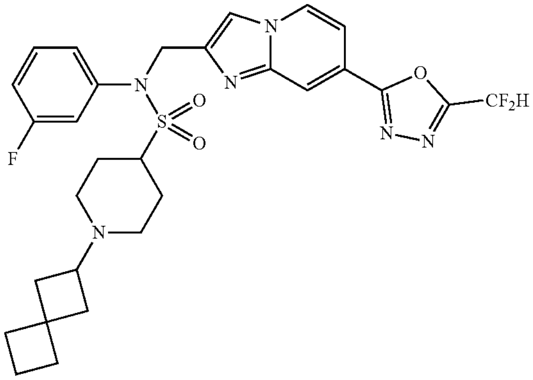 [SMILES: O=S(=O)(C1CCN(C2CC3(CCC3)C2)CC1)N(Cc1cn2ccc(-c3nnc(C(F)F)o3)cc2n1)c1cccc(F)c1] |

TABLE 2-continued
| Ex | Comp | Structure |
|---|---|---|
| 78 | 4617 | 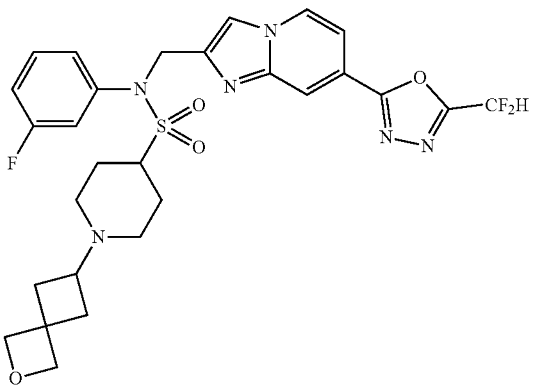 [SMILES: O=S(=O)(C1CCN(C2CC3(COC3)C2)CC1)N(Cc1cn2ccc(-c3nnc(C(F)F)o3)cc2n1)c1cccc(F)c1] |
| 82 | 6893 | 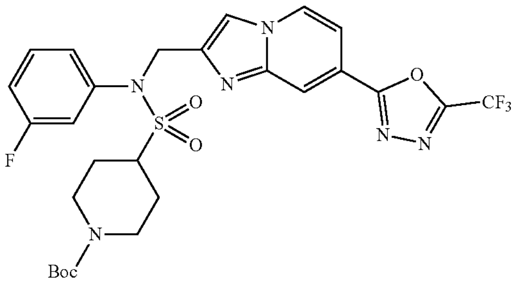 [SMILES: CC(C)(C)OC(=O)N1CCC(S(=O)(=O)N(Cc2cn3ccc(-c4nnc(C(F)(F)F)o4)cc3n2)c2cccc(F)c2)CC1] |
According to an embodiment of the present invention, it may be a specific compound represented by Chemical Formula I of the present invention:
TABLE 3
| Ex | Comp | Structure |
|---|---|---|
| 38 | 4256 | 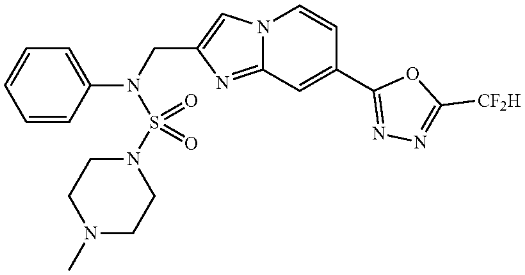 [SMILES: CN1CCN(S(=O)(=O)N(Cc2cn3ccc(-c4nnc(C(F)F)o4)cc3n2)c2ccccc2)CC1] |
| 39 | 4257 | 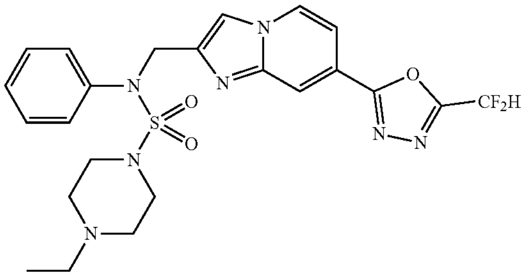 [SMILES: CCN1CCN(S(=O)(=O)N(Cc2cn3ccc(-c4nnc(C(F)F)o4)cc3n2)c2ccccc2)CC1] |

TABLE 3-continued
| Ex | Comp | Structure |
|---|---|---|
| 40 | 4258 | 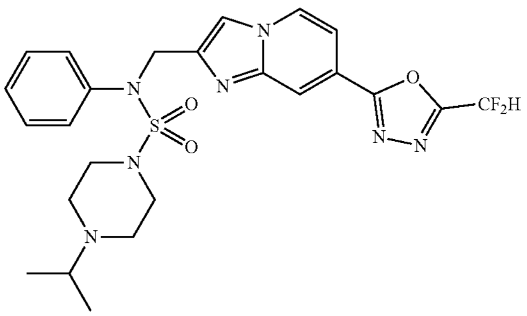 [SMILES: CC(C)N1CCN(S(=O)(=O)N(Cc2cn3ccc(-c4nnc(C(F)F)o4)cc3n2)c2ccccc2)CC1] |
| 41 | 459 | 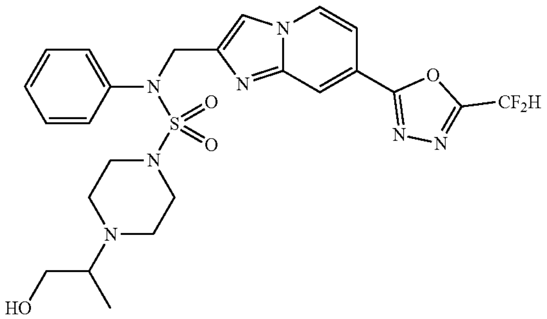 |
| 42 | 4260 | 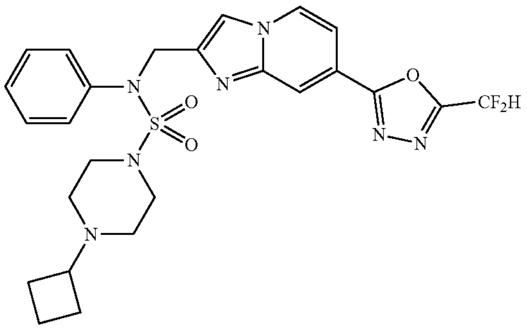 [SMILES: O=S(=O)(N1CCN(C2CCC2)CC1)N(Cc1cn2ccc(-c3nnc(C(F)F)o3)cc2n1)c1ccccc1] |
| 43 | 4261 | 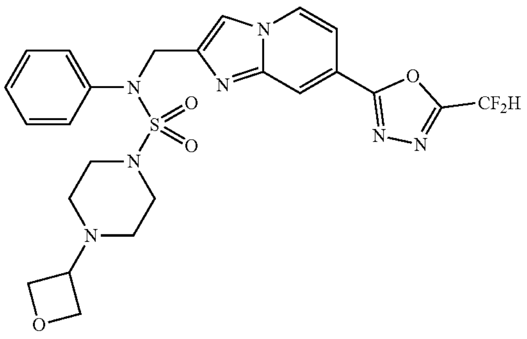 |

TABLE 3-continued
| Ex | Comp | Structure |
|---|---|---|
| 44 | 4262 | 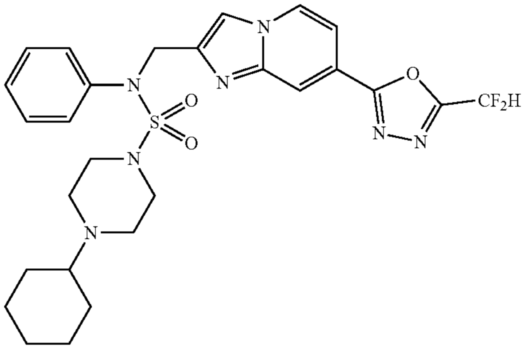 [SMILES: O=S(=O)(N1CCN(C2CCCCC2)CC1)N(Cc1cn2ccc(-c3nnc(C(F)F)o3)cc2n1)c1ccccc1] |
| 45 | 4263 | 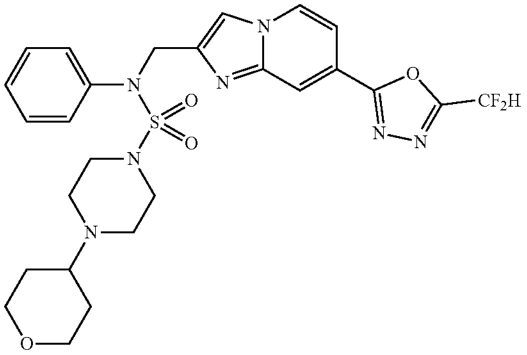 [SMILES: O=S(=O)(N1CCN(C2CCOCC2)CC1)N(Cc1cn2ccc(-c3nnc(C(F)F)o3)cc2n1)c1ccccc1] |
| 46 | 4264 | 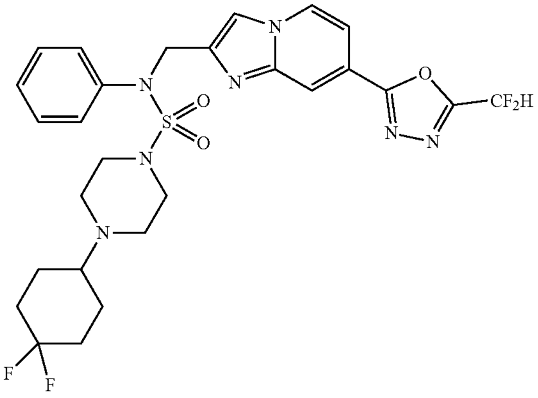 [SMILES: O=S(=O)(N1CCN(C2CCC(F)(F)CC2)CC1)N(Cc1cn2ccc(-c3nnc(C(F)F)o3)cc2n1)c1ccccc1] |
| 47 | 4265 | 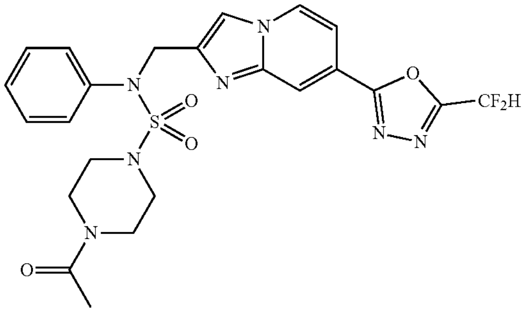 [SMILES: CC(=O)N1CCN(S(=O)(=O)N(Cc2cn3ccc(-c4nnc(C(F)F)o4)cc3n2)c2ccccc2)CC1] |

TABLE 3-continued
| Ex | Comp | Structure |
|---|---|---|
| 48 | 4266 | 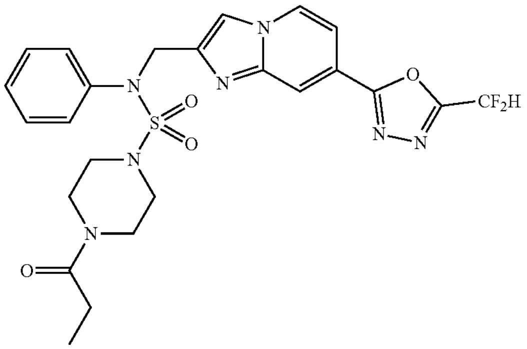 |
| 49 | 4267 | 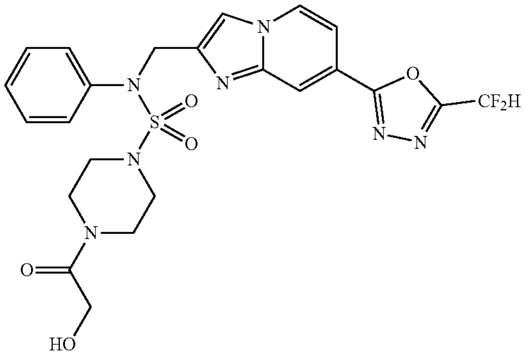 [SMILES: O=C(CO)N1CCN(S(=O)(=O)N(Cc2cn3ccc(-c4nnc(C(F)F)o4)cc3n2)c2ccccc2)CC1] |
| 50 | 4268 | 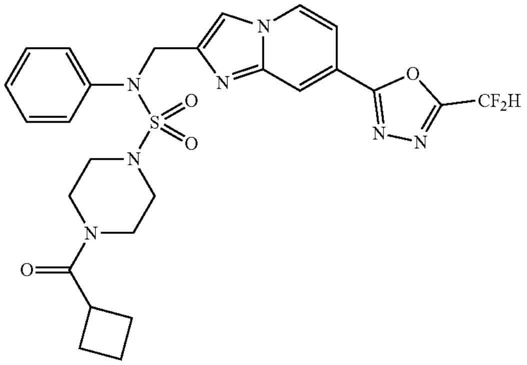 |
| 51 | 4269 | 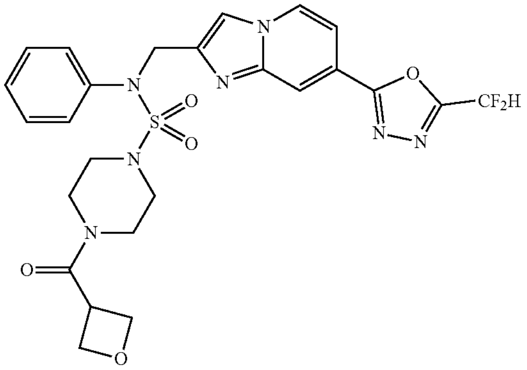 [SMILES: O=C(C1COC1)N1CCN(S(=O)(=O)N(Cc2cn3ccc(-c4nnc(C(F)F)o4)cc3n2)c2ccccc2)CC1] |

TABLE 3-continued
| Ex | Comp | Structure |
|---|---|---|
| 52 | 4270 | 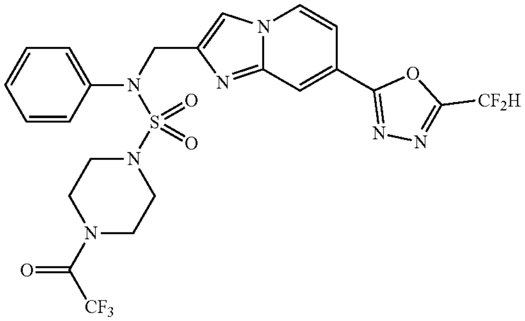 [SMILES: O=C(N1CCN(S(=O)(=O)N(Cc2cn3ccc(-c4nnc(C(F)F)o4)cc3n2)c2ccccc2)CC1)C(F)(F)F] |
| 53 | 4271 | 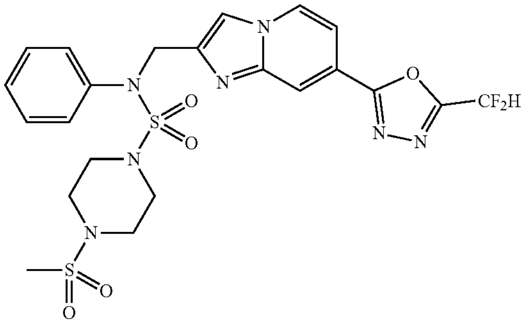 [SMILES: CS(=O)(=O)N1CCN(S(=O)(=O)N(Cc2cn3ccc(-c4nnc(C(F)F)o4)cc3n2)c2ccccc2)CC1] |
| 54 | 4272 | 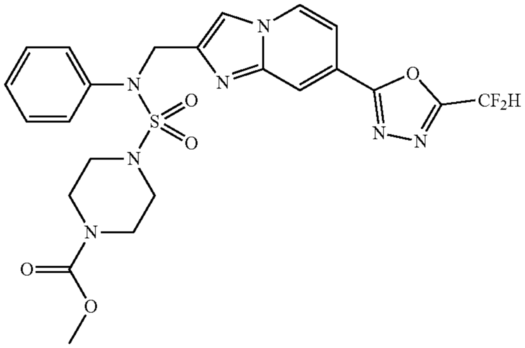 |
| 55 | 4273 | 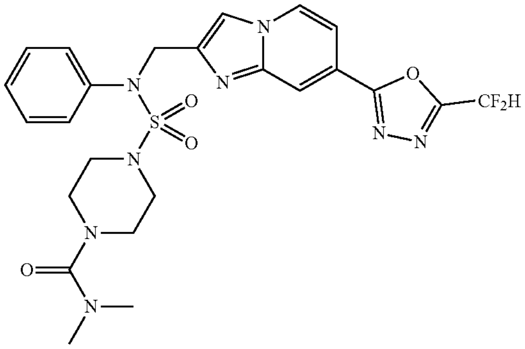 |

TABLE 3-continued
| Ex | Comp | Structure |
|---|---|---|
| 56 | 4274 | 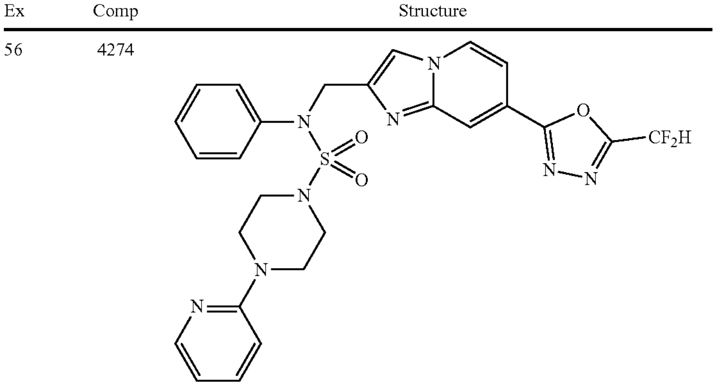 |
| 57 | 4275 | 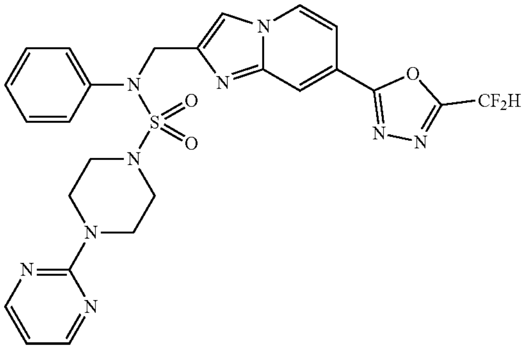 |
| 58 | 4297 | 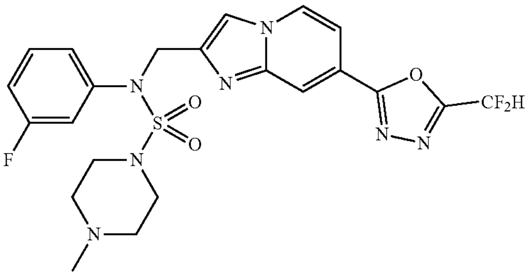 [SMILES: CN1CCN(S(=O)(=O)N(Cc2cn3ccc(-c4nnc(C(F)F)o4)cc3n2)c2cccc(F)c2)CC1] |
| 59 | 4298 | 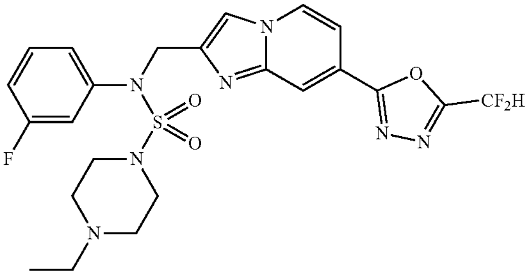 [SMILES: CCN1CCN(S(=O)(=O)N(Cc2cn3ccc(-c4nnc(C(F)F)o4)cc3n2)c2cccc(F)c2)CC1] |
| 60 | 4299 | 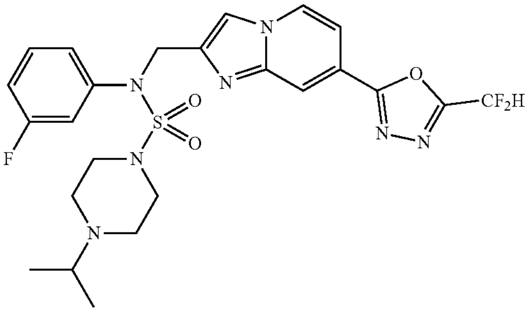 |

TABLE 3-continued
| Ex | Comp | Structure |
|---|---|---|
| 61 | 4300 | 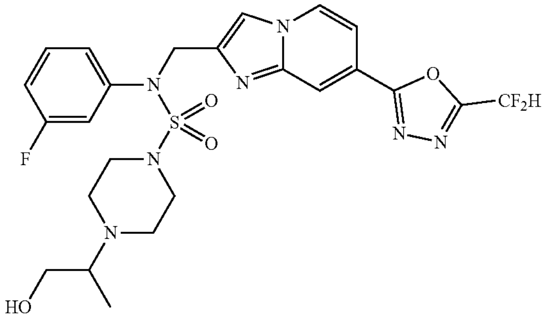 |
| 62 | 4301 | 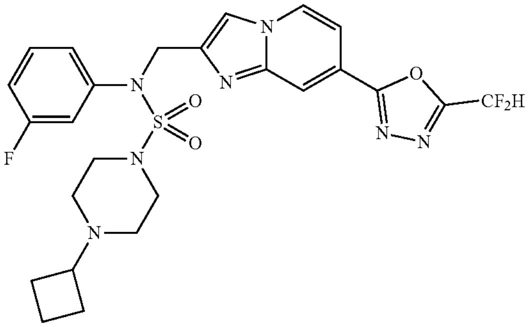 |
| 63 | 4302 | 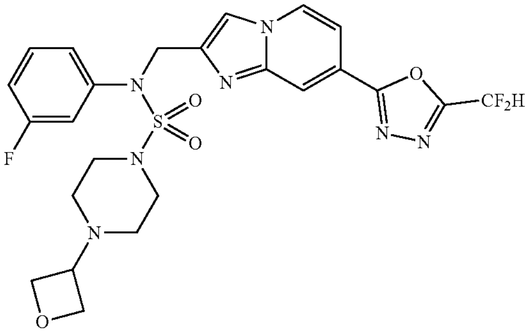 [SMILES: O=S(=O)(N1CCN(C2COC2)CC1)N(Cc1cn2ccc(-c3nnc(C(F)F)o3)cc2n1)c1cccc(F)c1] |
| 64 | 4303 | 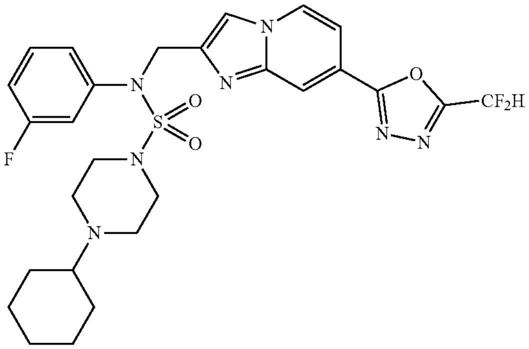 |

TABLE 3-continued
| Ex | Comp | Structure |
| --- | --- | --- |
| 65 | 4304 | 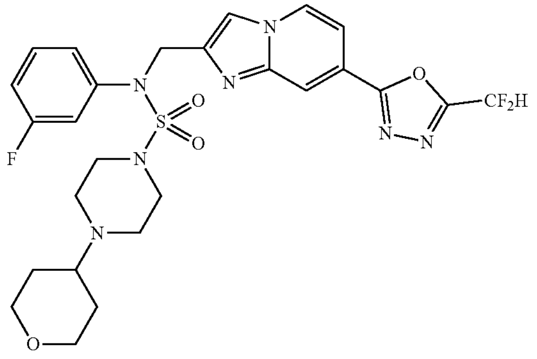 |
| 66 | 4305 | 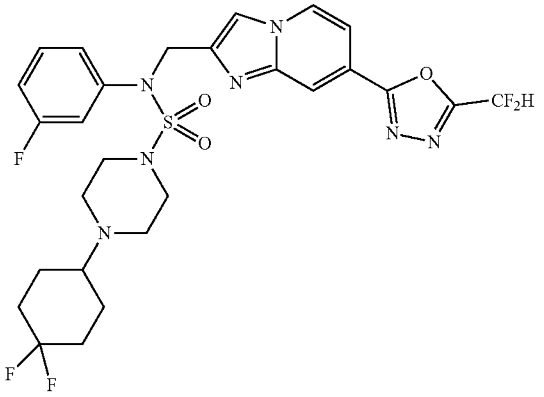 |
| 67 | 4306 | 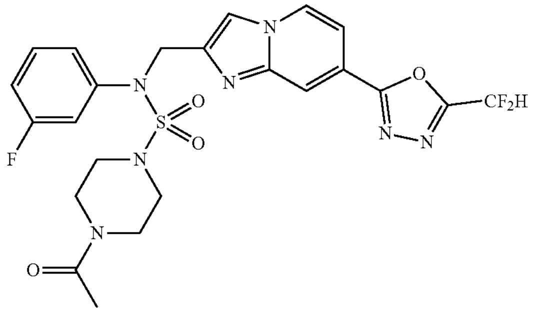 |
| 68 | 4307 | 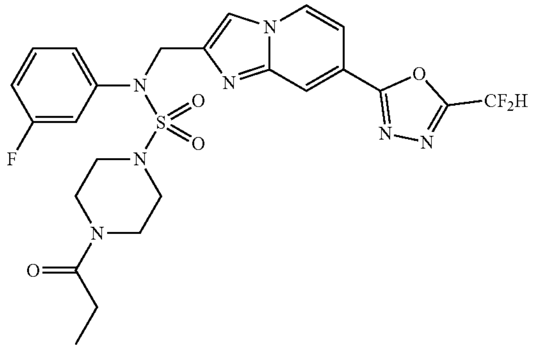 [SMILES: CCC(=O)N1CCN(S(=O)(=O)N(Cc2cn3ccc(-c4nnc(C(F)F)o4)cc3n2)c2cccc(F)c2)CC1] |

TABLE 3-continued
| Ex | Comp | Structure |
|---|---|---|
| 69 | 4308 | 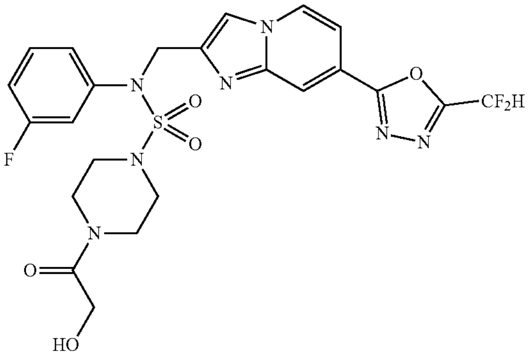 [SMILES: O=C(CO)N1CCN(S(=O)(=O)N(Cc2cn3ccc(-c4nnc(C(F)F)o4)cc3n2)c2cccc(F)c2)CC1] |
| 70 | 4309 | 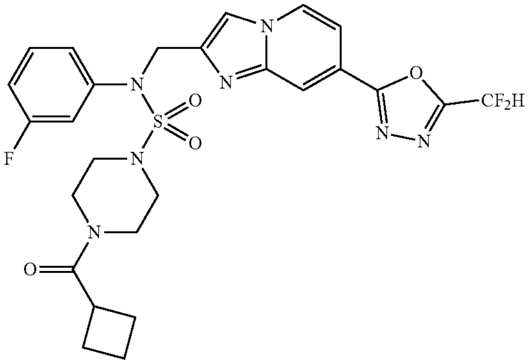 [SMILES: O=C(C1CCC1)N1CCN(S(=O)(=O)N(Cc2cn3ccc(-c4nnc(C(F)F)o4)cc3n2)c2cccc(F)c2)CC1] |
| 71 | 4310 | 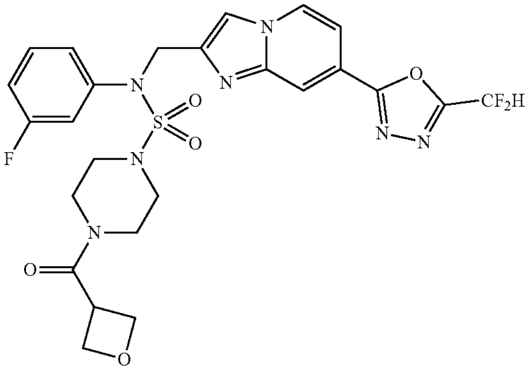 [SMILES: O=C(C1COC1)N1CCN(S(=O)(=O)N(Cc2cn3ccc(-c4nnc(C(F)F)o4)cc3n2)c2cccc(F)c2)CC1] |
| 72 | 4311 | 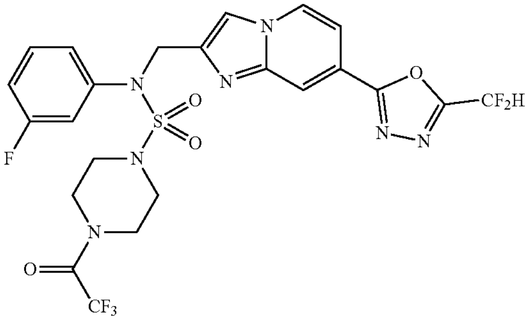 |

TABLE 3-continued
| Ex | Comp | Structure |
| --- | --- | --- |
| 73 | 4312 | 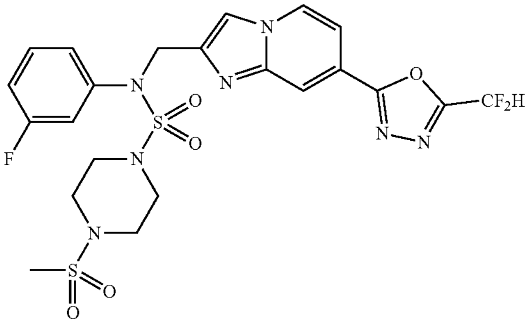 [SMILES: CS(=O)(=O)N1CCN(S(=O)(=O)N(Cc2cn3ccc(-c4nnc(C(F)F)o4)cc3n2)c2cccc(F)c2)CC1] |
| 74 | 4313 | 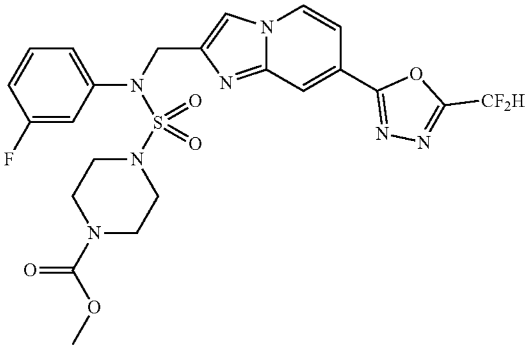 |
| 75 | 4314 | 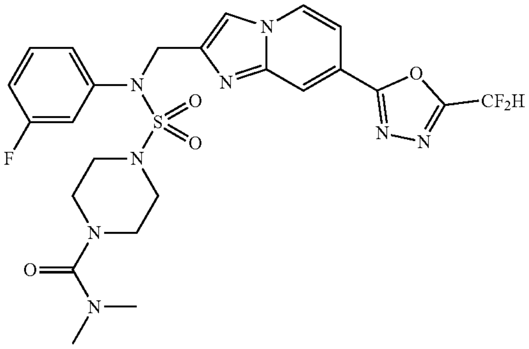 |
| 76 | 4315 | 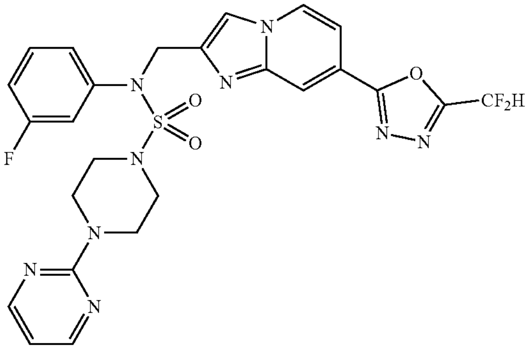 |

TABLE 3-continued

| Ex | Comp | Structure |
|---|---|---|
| 79 | 4622 | 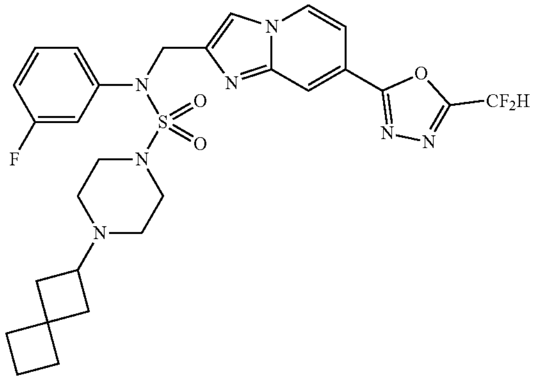 |
| 80 | 4623 | 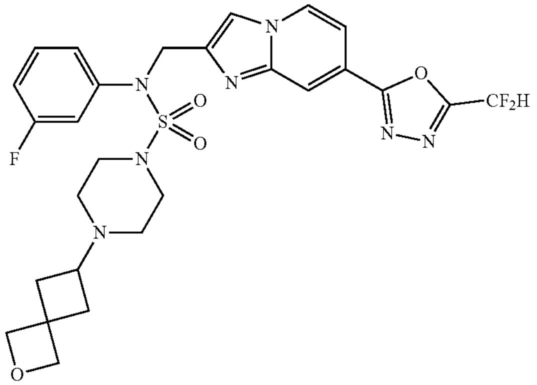 [SMILES: O=S(=O)(N1CCN(C2CC3(COC3)C2)CC1)N(Cc1cn2ccc(-c3nnc(C(F)F)o3)cc2n1)c1cccc(F)c1] |
| 81 | 4624 | 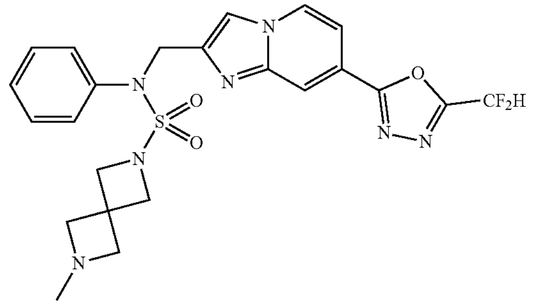 [SMILES: CN1CC2(C1)CN(S(=O)(=O)N(Cc1cn3ccc(-c4nnc(C(F)F)o4)cc3n1)c1ccccc1)C2] |

In the present invention, the pharmaceutically acceptable salt refers to a salt commonly used in the pharmaceutical industry, for example, may include inorganic ionic salts prepared from calcium, potassium, sodium, and magnesium, and the like, inorganic acid salts prepared from hydrochloric acid, nitric acid, phosphoric acid, bromic acid, iodic acid, perchloric acid, and sulfuric acid, and the like; organic acid salts prepared from acetic acid, trifluoroacetic acid, citric acid, maleic acid, succinic acid, oxalic acid, benzoic acid, tartaric acid, fumaric acid, manderic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, and the like; sulfonic acid salts prepared from methanesulfonic acid, ethanesulfonic acid, benzenesulfonic acid, p-toluenesulfonic acid, and naphthalenesulfonic acid, and the like; amino acid salts prepared from glycine, arginine, lysine, and the like; and amine salts prepared with trimethylamine, triethylamine, ammonia, pyridine, picoline, and the like, but types of salts referred to in the present invention are not limited by these salts listed above.

Preferred salts in the present invention include hydrochloride, phosphate, sulfate, trifluoroacetate, citrate, bromate, maleate, or tartrate.

The compound represented by Chemical Formula I of the present invention may contain one or more asymmetric carbons, thereby being able to exist as a racemate, a racemic mixture, a single enantiomer, a diastereomeric mixture, and each diastereomer. These isomers may be separated using conventional techniques, for example, by partitioning, such as by column chromatography, HPLC, or the like, the compound represented by Chemical Formula I. Alternatively, stereoisomers of each of the compounds represented by Chemical Formula I may be stereospecifically synthesized using optically pure starting materials and/or reagents with known arrangement.

Method for Preparing 1,3,4-Oxadiazole Derivative Compound

The present invention provides a method for preparing a 1, 3,4-oxadiazole derivative compound represented by Chemical Formula I, an optical isomer thereof, or a pharmaceutically acceptable salt thereof.

In the present invention, a preferred method for preparing the 1, 3,4-oxadiazole derivative compound represented by Chemical Formula I, the optical isomer thereof, or the pharmaceutically acceptable salt thereof is the same as Reaction Schemes 1 and 2 below, which also includes preparation methods that are modified to a level obvious to those skilled in the art.

[Reaction Scheme 1]

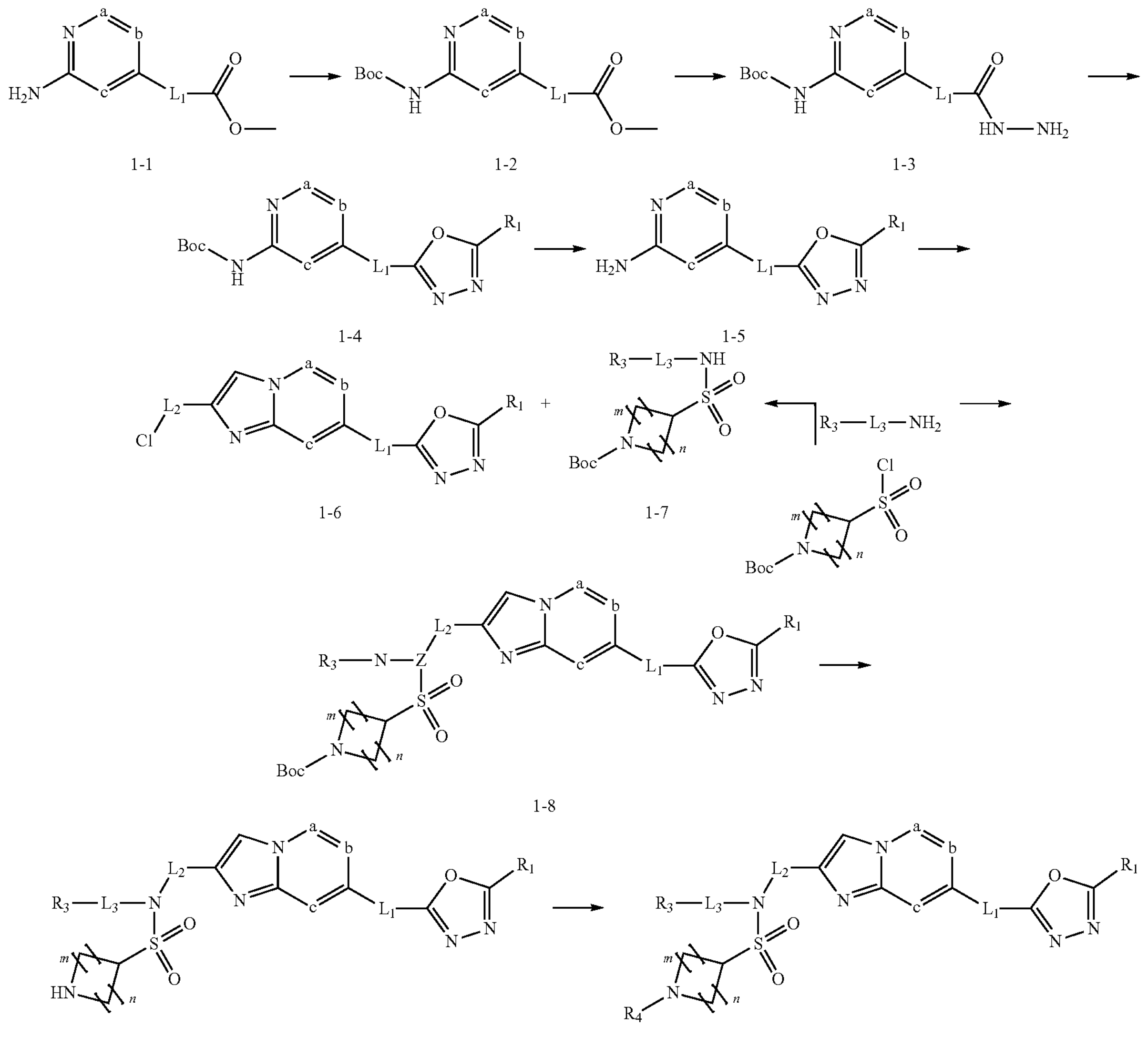

1-1 1-2 1-3 1-4 1-5 1-6 1-7 1-8 1-9 1-10

Reaction Scheme 1 shows a method for synthesizing a compound having a sulfonamide structure, wherein Compound 1-2 in which a protecting group is introduced into Compound 1-1 is synthesized, and then reacted with hydrazine to synthesize hydrazide Compounds 1-3. A cyclization reaction with difluoroacetic anhydride is performed to synthesize Compound 1-4, and then the protecting group is removed under an acidic condition to synthesize Compound 1-5. By reacting with 1,3-dichloropropan-2-one, bicyclic Compound 1-6 is synthesized and reacted with a sulfonamide functional group to synthesize Compound 1-8. Compound 1-9 from which the protecting group is removed under an acid condition is synthesized, and title Compound 1-10 is synthesized by introducing various functional groups.

Compounds prepared by the above Reaction Scheme are Compounds 3778, 3779, 4214, 4215, 4216, 4217, 4218, 4219, 4220, 4221, 4222, 4223,4224, 4225, 4226, 4227, 4228, 4236, 4237, 4238, 4239, 4240, 4241, 4242, 4243, 4244, 4245, 4246, 4247, 4248, 4249, 4250, 4251, 4252, 4253,4254, 4255, 4616, 4617 and 6893.

[Reaction Scheme 2]

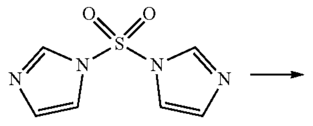

2-1

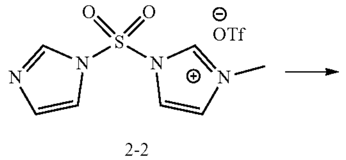

2-2

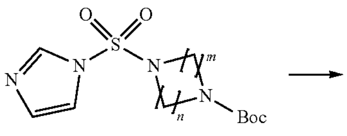

2-3

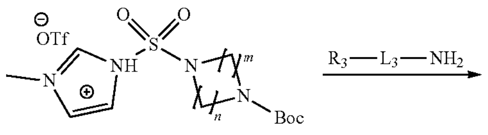

2-4

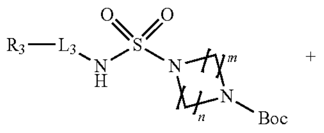

2-5

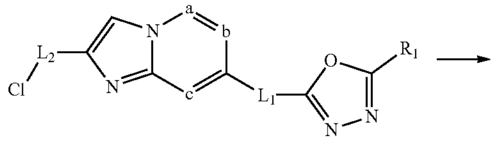

1-6

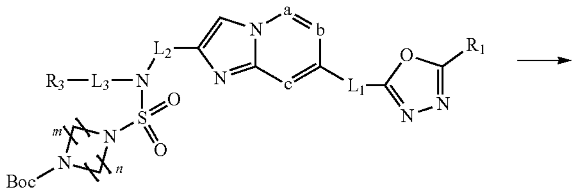

2-6

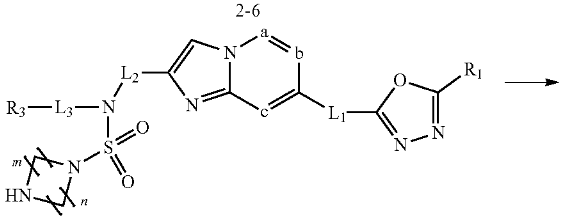

2-7

-continued

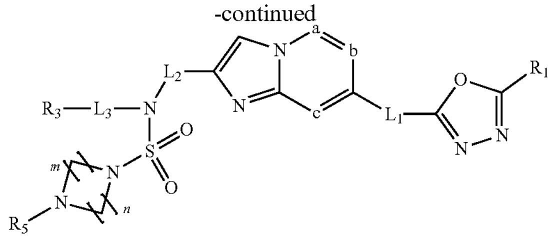

2-8

Reaction Scheme 2 shows a method for synthesizing a compound having a sulfamide structure, wherein Compound 2-2 in which a leaving group is introduced into 1,1'-sulfonylbis(1-H-imidazole) is synthesized. The synthesized Compound 2-2 is reacted with an amine compound to synthesize Compound 2-3, and the leaving group is introduced again to synthesize Compound 2-4. By reacting with an amine compound, Compound 2-5 is synthesized and reacted with Compound 1-6 synthesized in Reaction Scheme 1 to synthesize Sulfamide Compound 2-6. Compound 2-7 from which the protecting group is removed under an acid condition is synthesized, and title Compound 2-8 is synthesized by introducing various functional groups.

Compounds prepared by the above Reaction Scheme are Compounds 4256, 4257, 4258, 4259, 4260, 4261, 4262, 4263,4264, 4265, 4266, 4267, 4268, 4269, 4270, 4271, 4272, 4273,4274, 4275, 4297, 4298, 4299, 4300, 4301, 4302, 4303,4304, 4305, 4306, 4307, 4308, 4309, 4310, 4311, 4312, 4313,4314, 4315, 4622, 4623, and 4624.

Composition Comprising 1, 3,4-Oxadiazole Derivative Compounds, Use Thereof, and Treatment Method Using the Same The present invention provides a pharmaceutical composition for preventing or treating histone deacetylase 6-mediated diseases containing the compound represented by Chemical Formula I below, the optical isomer thereof, or the pharmaceutically acceptable salt thereof as an active ingredient:

[Chemical Formula I]

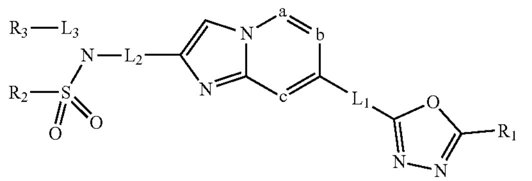

The Chemical Formula I is the same as defined above.

The pharmaceutical composition of the present invention exhibits a remarkable effect in the prevention or treatment of histone deacetylase 6-mediated diseases by selectively inhibiting a histone deacetylase 6.

The histone deacetylase 6-mediated diseases include infectious diseases such as prion disease; neoplasm such as benign tumors (e.g. myelodysplastic syndrome) or malignant tumors (e.g. multiple myeloma, lymphoma, leukemia, lung cancer, colorectal cancer, colon cancer, prostate cancer, urinary tract epithelial cell carcinoma, breast cancer, melanoma, skin cancer, liver cancer, brain cancer, stomach cancer, ovarian cancer, pancreatic cancer, head and neck cancer, oral cancer or glioma); endocrine, nutritional and metabolic diseases such as Wilson's disease, amyloidosis or diabetes; mental and behavioral disorders such as depression or Rett syndrome; neurological diseases such as central nervous system atrophy (e.g. Huntington's disease, spinal muscular atrophy (SMA), spinal cerebellar ataxia (SCA)), neurodegenerative diseases (e.g. Alzheimer's disease), movement disorders (e.g. Parkinson's disease), neuropathy (e.g. hereditary neuropathy (Charcot-Marie-Tooth disease), sporadic neuropathy, inflammatory neuropathy, drug-induced neuropathy), motor neuropathy (e.g. amyotrophic lateral sclerosis (ALS)), or central nervous system demyelination (e.g. multiple sclerosis (MS)); diseases of eyes and adnexa such as uveitis; circulatory diseases such as atrial fibrillation, stroke, and the like; respiratory diseases such as asthma; digestive diseases such as alcoholic liver disease, inflammatory bowel disease, Crohn's disease, ulcerative bowel disease, and the like; skin and subcutaneous tissue diseases such as psoriasis; musculoskeletal and connective tissue diseases such as rheumatoid arthritis, osteoarthritis, systemic lupus erythematosus (SLE), and the like; or congenital malformations, alterations, and chromosomal abnormalities such as autosomal dominant polycystic kidney disease, and also include symptoms or diseases related to abnormal functions of histone deacetylase.

The pharmaceutically acceptable salt is the same as described above in the pharmaceutically acceptable salt of the compound represented by Chemical Formula I of the present invention.

The pharmaceutical composition of the present invention may further include one or more pharmaceutically acceptable carriers for administration, in addition to the compound represented by Chemical Formula I, the optical isomer thereof, or the pharmaceutically acceptable salt thereof. The pharmaceutically acceptable carrier may be used by mixing saline, sterile water, Ringer's solution, buffered saline, dextrose solution, maltodextrin solution, glycerol, ethanol and one or more of these ingredients, and if necessary, other conventional additives such as antioxidants, buffers, bacteriostatic agents, and the like, may be added. Further, injectable formulations such as aqueous solutions, suspensions, emulsions, and the like, pills, capsules, granules or tablets may be formulated by further adding diluents, dispersants, surfactants, binders and lubricants. Accordingly, the composition of the present invention may be a patch, liquid, pill, capsule, granule, tablet, suppository, or the like. These formulations may be prepared by a conventional method used for formulation in the art or by a method disclosed in Remington's Pharmaceutical Science (latest edition), Mack Publishing Company, Easton PA, and formulated into various formulations depending on respective diseases or ingredients.

The composition of the present invention may be administered orally or parenterally (for example, intravenously, subcutaneously, intraperitoneally or topically) depending on the desired method, and the dosage range varies depending on the patient's weight, age, health sex, condition, diet, administration time, administration method, excretion rate, and severity of disease, and the like. The daily dose of the compound represented by Chemical Formula I of the present invention may be about 1 to 1000 mg/kg, preferably 5 to 100 mg/kg, and may be administered once a day or divided into several times a day.

The pharmaceutical composition of the present invention may further include one or more active ingredients exhibiting the same or similar medicinal effects in addition to the compound represented by Chemical Formula I above, the optical isomer thereof, or the pharmaceutically acceptable salt thereof.

The present invention provides a method for preventing or treating histone deacetylase 6-mediated diseases including administering a therapeutically effective amount of the compound represented by Chemical Formula I, the optical isomer thereof, or the pharmaceutically acceptable salt thereof.

The term "therapeutically effective amount" used in the present invention refers to an amount of the compound represented by Chemical Formula I that is effective for preventing or treating the histone deacetylase 6-mediated diseases.

In addition, the present invention provides a method for selectively inhibiting HDAC6 by administering the compound represented by Chemical Formula I, the optical isomer thereof, or the pharmaceutically acceptable salt thereof to a mammal including humans.

The method for preventing or treating the histone deacetylase 6-mediated diseases of the present invention also includes administering the compound represented by Chemical Formula I to treat the disease itself before the onset of the symptom, but also to inhibit or avoid the symptom thereof. In the management of the disease, prophylactic or therapeutic dose of a specific active ingredient will vary depending on the nature and severity of the disease or condition, and the route to which the active ingredient is administered. The dose and frequency of dose will vary depending on the age, weight and response of the individual patients. A suitable dosage regimen may be readily selected by a person having ordinary knowledge in the art considering these factors for granted. In addition, the method for preventing or treating histone deacetylase 6-mediated diseases of the present invention may further include administrating a therapeutically effective amount of an additional active agent useful for the treatment of the disease together with the compound represented by Chemical Formula I, wherein the additional active agent may exhibit synergistic or auxiliary effects together with the compound represented by Chemical Formula I.

The present invention also aims to provide the use of the compound represented by Chemical Formula I above, the optical isomer thereof, or the pharmaceutically acceptable salt thereof for preparing a medicament for treating histone deacetylase 6-mediated diseases. The compound represented by Chemical Formula I above for preparing the medicament may be mixed with acceptable adjuvants, diluents, carriers, and the like, and may be prepared as a complex formulation with other active agents to have a synergistic effect of active ingredients.

Matters mentioned in the uses, compositions and treatment methods of the present invention are applied equally as long as they are inconsistent with each other.

Advantageous Effects

The compound represented by Chemical Formula I above of the present invention, the optical isomer thereof, or the pharmaceutically acceptable salt thereof, is able to selectively inhibit histone deacetylase 6 (HDAC6), thereby having remarkably excellent preventive or therapeutic effects on HDAC6-mediated diseases.

BEST MODE

Hereinafter, the present invention will be described in more detail through Examples and Experimental Examples.

However, they are only examples of the present invention, and the scope of the present invention is not limited thereto.

Preparation of 1,3,4-Oxadiazole Derivative Compound of the Present Invention

A specific method for preparing the compounds represented by Chemical Formula I is the same as follows.

Example 1: Synthesis of Compound 3778, N-((7-(5-(difluoromethyl)-1,3,4-oxadiazol-2-yl)imidazo[1,2-a]pyridin-2-yl)methyl)-1-methyl-N-phenylpiperidine-4-sulfonamide

[Step 1] Synthesis of methyl 2-((tert-butoxycarbonyl)amino) isonicotinate

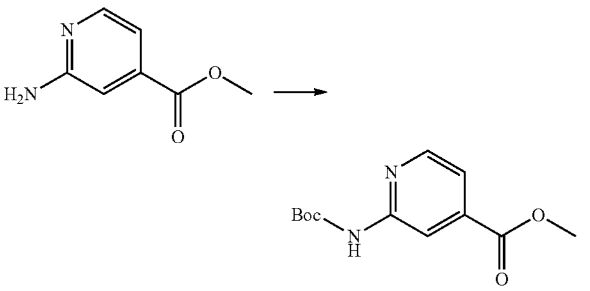

Methyl 2-aminoisonicotinate (20.000 g, 131.449 mmol) and di-tert-butyl dicarbonate (37.295 g, 170.884 mmol) were dissolved in tert-butanol (800 mL) at room temperature. The resulting solution was stirred at 60° C. for 16 hours, and then the temperature was lowered to room temperature to terminate the reaction. The precipitated solid was filtered, washed with ethanol, and dried to obtain the title compound (26.000 g, 78.4%) as a white solid.

[Step 2] Synthesis of tert-butyl (4-(hydrazinecarbonyl)pyridin-2-yl)carbamate

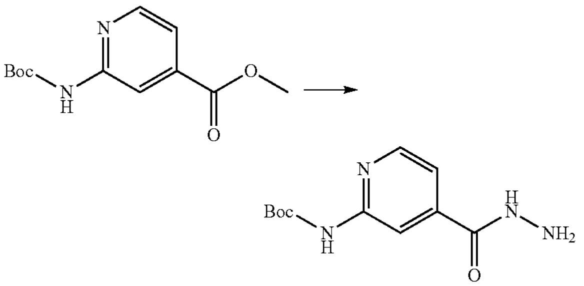

Methyl 2-((tert-butoxycarbonyl)amino) isonicotinate (26.000 g, 103.064 mmol) prepared in step 1 and hydrazine monohydrate (100.182 mL, 2.061 mol) were dissolved in methanol (800 mL) at room temperature. The resulting solution was stirred at the same temperature for 16 hours. Methanol (500 mL) was added to the obtained product, followed by filtration through a plastic filter to obtain an organic layer, and the organic layer was concentrated to obtain the title compound (25.000 g, 96.2%) as a white solid.

[Step 3] Synthesis of tert-butyl (4-(5-(difluoromethyl)-1, 3,4-oxadiazol-2-yl)pyridin-2-yl)carbamate

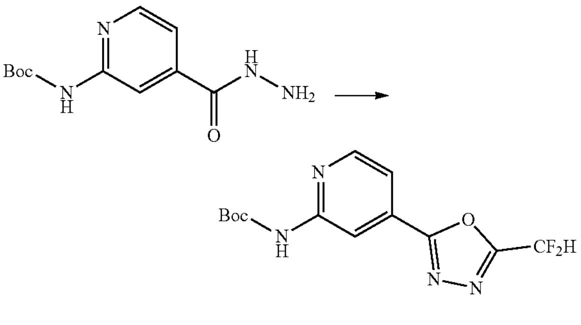

Tert-butyl (4-(hydrazinecarbonyl)pyridin-2-yl)carbamate (20.000 g, 79.280 mmol) prepared in step 2 and triethylamine (55.250 mL, 396.401 mmol) were dissolved in tetrahydrofuran (600 mL), and 2,2-difluoroacetic anhydride (49.281 mL, 396.401 mmol) was added at room temperature and heated to reflux for 16 hours, and then the temperature was lowered to room temperature to terminate the reaction. A saturated aqueous ammonium chloride solution was added to the reaction mixture, followed by extraction with ethyl acetate. The organic layer was washed with a saturated aqueous sodium chloride solution, dried over anhydrous magnesium sulfate, filtered, and concentrated under reduced pressure. Ethyl acetate (40 mL) and hexane (200 mL) were poured into the concentrate, suspended, and filtered to obtain a solid, and the obtained solid was washed with hexane and dried to obtain the title compound (11.500 g, 46.5%) as a white solid.

[Step 4] Synthesis of 4-(5-(difluoromethyl)-1,3,4-oxadiazol-2-yl)pyridin-2-amine

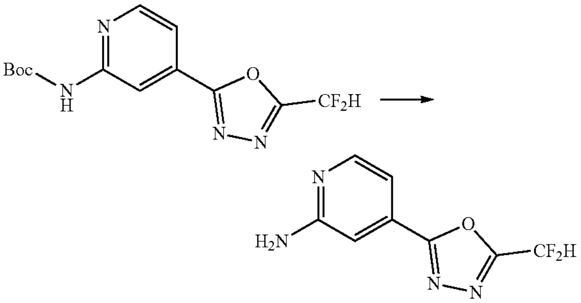

Tert-butyl (4-(5-(difluoromethyl)-1,3,4-oxadiazol-2-yl) pyridin-2-yl)carbamate (11.500 g, 36.826 mmol) prepared in step 3 was dissolved in dichloromethane (300 mL), and trifluoroacetic acid (28.199 mL, 368.259 mmol) was added at 0° C. The resulting solution was stirred at room temperature for 4 hours. After removing the solvent from the reaction mixture under reduced pressure, a saturated aqueous sodium hydrogen carbonate solution (150 mL) was poured into the concentrate and suspended, followed by filtration to obtain a solid. The obtained solid was washed with water and dried to obtain the title compound (7.500 g, 96.0%) as a white solid.

[Step 5] Synthesis of 2-(2-(chloromethyl)imidazo[1,2-a]pyridin-7-yl)-5-(difluoromethyl)-1,3,4-oxadiazole

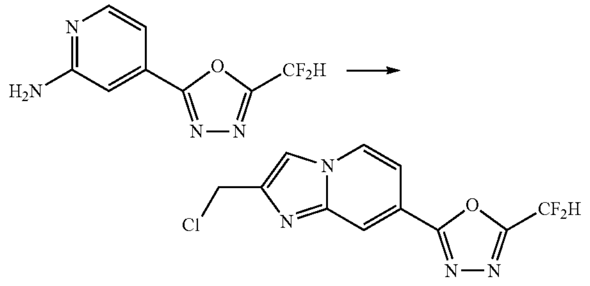

4-(5-(Difluoromethyl)-1,3,4-oxadiazol-2-yl)pyridin-2-amine (7.500 g, 35.351 mmol) prepared in step 4, 1,3-dichloropropan-2-one (6.732 g, 53.026 mmol), and sodium hydrogen carbonate (14.848 g, 176.753 mmol) were dissolved in 1,4-dioxane (250 mL) at room temperature. The resulting solution was heated to reflux for 16 hours, and then the temperature was lowered to room temperature to terminate the reaction. The reaction mixture was filtered through a plastic filter to remove solids, and the filtrate was purified by column chromatography ($SiO_2$, 80 g cartridge; ethyl acetate/hexane=10% to 90%) and concentrated to obtain the title compound (7.000 g, 69.6%) as a beige solid.

[Step 6] Synthesis of tert-butyl 4-(N-((7-(5-(difluoromethyl)-1,3,4-oxadiazol-2-yl)imidazo[1,2-a]pyridin-2-yl)methyl)-N-phenylsulfamoyl)piperidine-1-carboxylate

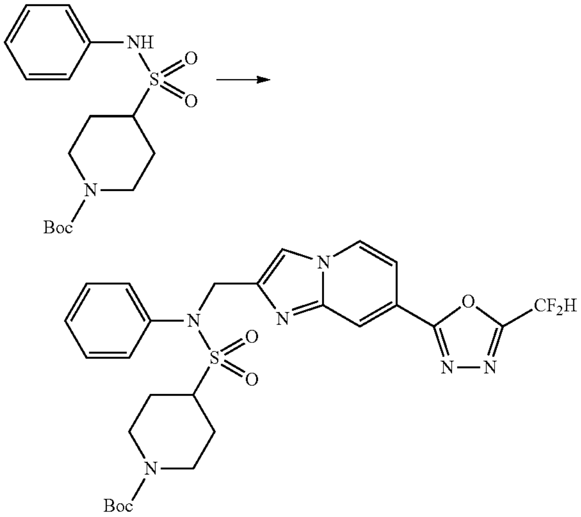

Tert-butyl 4-(N-phenylsulfamoyl)piperidine-1-carboxylate (0.050 0.147 mmol), 2-(2-(chloromethyl)imidazo[1,2-a]pyridin-7-yl)-5-(difluoromethyl)-1,3,4-oxadiazole (0.040 g, 0.140 mmol) prepared in step 5, potassium carbonate (0.041 g, 0.294 mmol), and potassium iodide (0.002 g, 0.015 mmol) were dissolved in N, N-dimethylformamide (3 mL) at room temperature, and the resulting solution was stirred at the same temperature for 16 hours. Water (5 mL) was added to the reaction mixture and stirred to precipitate a solid. The precipitated solid was filtered, washed with water, and dried to obtain the title compound (0.055 g, 63.6%) as a beige solid.

[Step 7] Synthesis of N-((7-(5-(difluoromethyl)-1,3,4-oxadiazol-2-yl)imidazo[1,2-a]pyridin-2-yl)methyl)-N-phenylpiperidine-4-sulfonamide

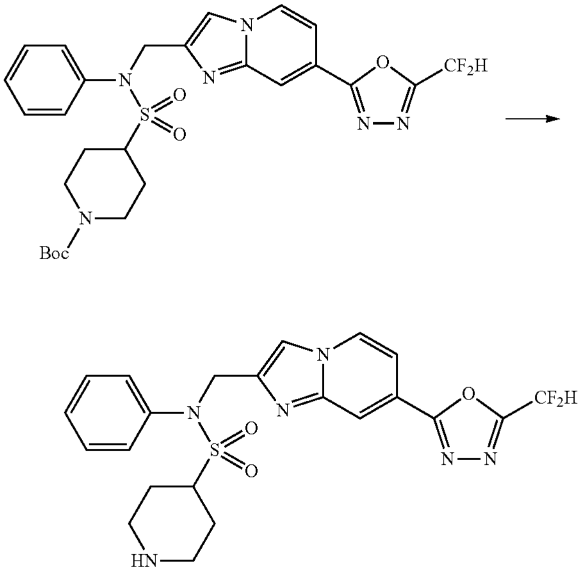

Tert-butyl 4-(N-((7-(5-(difluoromethyl)-1,3,4-oxadiazol-2-yl)imidazo[1,2-a]pyridin-2-yl)methyl)-N-phenylsulfamoyl)piperidine-1-carboxylate (0.100 g, 0.170 mmol) prepared in step 6 and trifluoroacetic acid (0.260 mL, 3.398 mmol) were dissolved in dichloromethane (3 mL) at room temperature, and the resulting solution was stirred at the same temperature for 3 hours. A saturated aqueous sodium hydrogen carbonate solution was poured into the reaction mixture, followed by extraction with dichloromethane. The organic layer was washed with a saturated aqueous water solution, dried over anhydrous magnesium sulfate, and filtered. After concentration under reduced pressure, the title compound (0.083 g, 100.0%) was obtained as a brown gel without further purification.

[Step 8] Synthesis of Compound 3778

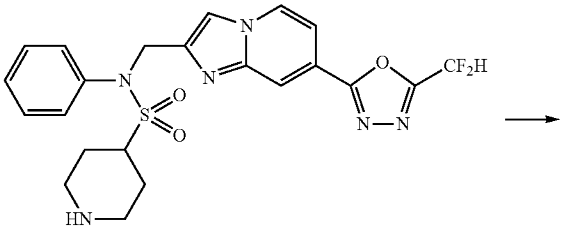

-continued

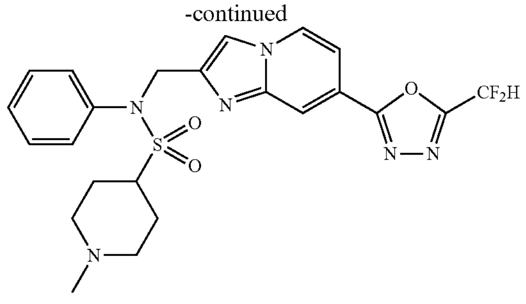

N-((7-(5-(difluoromethyl)-1,3,4-oxadiazol-2-yl)imidazo[1,2-a]pyridin-2-yl)methyl)-N-phenylpiperidine-4-sulfonamide (0.040 g, 0.082 mmol) prepared in step 7, formaldehyde (0.005 g, 0.164 mmol), acetic acid (0.005 mL, 0.082 mmol), and sodium triacetoxyborohydride (0.052 g, 0.246 mmol) were dissolved in dichloromethane (5 mL) at room temperature, and the resulting solution was stirred at the same temperature for 18 hours. A saturated aqueous sodium hydrogen carbonate solution was poured into the reaction mixture, followed by extraction with dichloromethane. The organic layer was washed with a saturated aqueous water solution, dried over anhydrous magnesium sulfate, filtered, and concentrated under reduced pressure. The concentrate was purified by chromatography ($SiO_2$ plate, 20×20×1 mm; dichloromethane/methanol=0% to 10%) and concentrated to obtain the title compound (0.016 g, 38.9%) as a white solid.

$^1$H NMR (400 MHZ, $CDCl_3$) δ 8.26 (s, 1H), 8.24-8.19 (m, 1H), 7.80 (s, 1H), 7.55-7.50 (m, 1H), 7.47 (d, J=7.8 Hz, 2H), 7.35 (d, J=9.2 Hz, 2H), 7.30 (d, J=5.1 Hz, 1H), 7.10-6.78 (m, 1H), 5.16 (d, J=3.0 Hz, 2H), 3.00 (d, J=10.2 Hz, 3H), 2.31 (s, 3H), 2.14 (s, 2H), 2.01 (s, 4H);

LRMS (ES) m/z 503.2 ($M^+$+1).

Example 2: Synthesis of Compound 3779, N-((7-(5-(difluoromethyl)-1,3,4-oxadiazol-2-yl)imidazo[1,2-a]pyridin-2-yl)methyl)-1-(oxetan-3-yl)-N-phenylpiperidine-4-sulfonamide

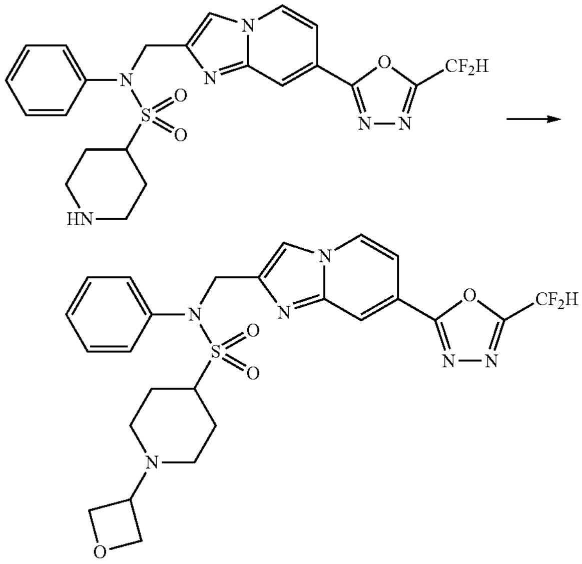

N-((7-(5-(difluoromethyl)-1,3,4-oxadiazol-2-yl)imidazo[1,2-a]pyridin-2-yl)methyl)-N-phenylpiperidine-4-sulfonamide (0.040 g, 0.082 mmol) prepared in step 7 of Example 1, oxetan-3-one (0.012 g, 0.164 mmol), acetic acid (0.005 mL, 0.082 mmol), and sodium triacetoxyborohydride (0.052 g, 0.246 mmol) were dissolved in dichloromethane (5 mL) at room temperature, and the resulting solution was stirred at the same temperature for 18 hours. A saturated aqueous sodium hydrogen carbonate solution was p poured into the reaction mixture, followed by extraction with dichloromethane. The organic layer was washed with a saturated aqueous water solution, dried over anhydrous magnesium sulfate, filtered, and concentrated under reduced pressure. The concentrate was purified by chromatography ($SiO_2$ plate, 20×20×1 mm; dichloromethane/methanol=0% to 10%) and concentrated to obtain the title compound (0.024 g, 53.8%) as a white solid.

$^1$H NMR (400 MHZ, $CDCl_3$) § 8.27 (s, 1H), 8.22 (d, J=6.9 Hz, 1H), 7.79 (s, 1H), 7.53 (d, J=7.2 Hz, 1H), 7.46 (d, J=7.8 Hz, 2H), 7.37 (t, J=7.9 Hz, 2H), 7.30 (s, 1H), 6.95 (td, J=52.7, 51.7, 2.5 Hz, 1H), 5.16 (s, 2H), 4.70-4.55 (m, 4H), 3.50 (s, 1H), 3.09 (s, 1H), 2.89 (s, 2H), 2.16 (s, 2H), 2.03 (s, 2H), 1.85 (s, 2H);

LRMS (ES) m/z 545.3 ($M^+$+1).

Example 3: Synthesis of Compound 4214, N-((7-(5-(difluoromethyl)-1,3,4-oxadiazol-2-yl)imidazo[1,2-a]pyridin-2-yl)methyl)-1-ethyl-N-phenylpiperidine-4-sulfonamide

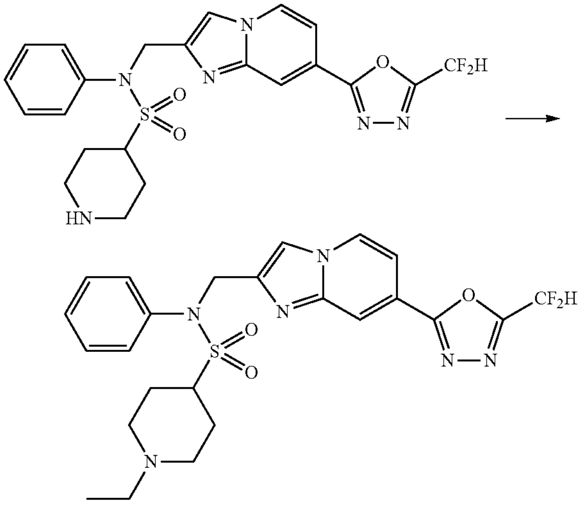

N-((7-(5-(difluoromethyl)-1,3,4-oxadiazol-2-yl)imidazo[1,2-a]pyridin-2-yl)methyl)-N-phenylpiperidine-4-sulfonamide (0.050 g, 0.102 mmol) prepared in step 7 of Example 1, acetaldehyde (0.009 9, 0.205 mmol) and sodium triacetoxyborohydride (0.065 g, 0.307 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 4 g cartridge; methanol/dichloromethane=0% to 3%) and concentrated to obtain the title compound (0.014 g, 26.5%) as an ivory solid.

$^1$H NMR (400 MHZ, $CDCl_3$) δ 8.25 (s, 1H), 8.22 (dd, 1H, J=7.1, 0.8 Hz), 7.80 (s, 1H), 7.52 (dd, 1H, J=7.1, 1.7 Hz), 7.49-7.45 (m, 2H), 7.38-7.34 (m, 2H), 7.30-7.26 (m, 1H), 6.95 (t, 1H, J=51.7 Hz), 5.17 (s, 2H), 3.06-2.96 (m, 3H), 2.29 (s, 3H), 2.15-2.08 (m, 2H), 2.05-1.89 (m, 4H);

LRMS (ES) m/z 517.4 ($M^+$+1).

Example 4: Synthesis of Compound 4215, N-((7-(5-(difluoromethyl)-1,3,4-oxadiazol-2-yl)imidazo[1,2-a]pyridin-2-yl)methyl)-1-isopropyl-N-phenylpiperidine-4-sulfonamide

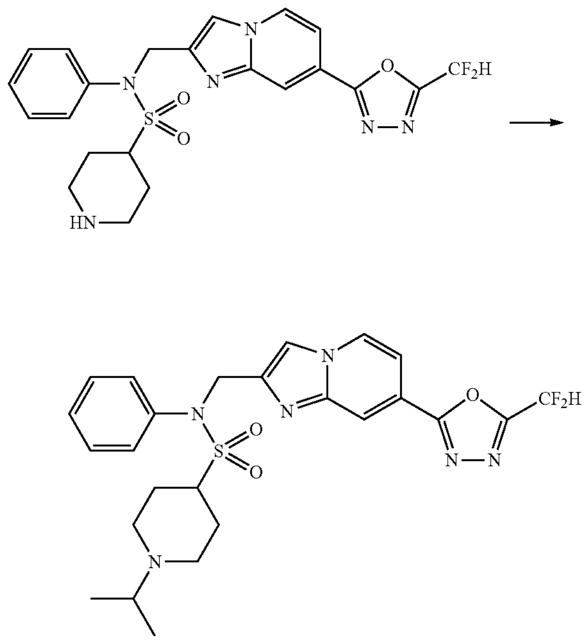

N-((7-(5-(difluoromethyl)-1,3,4-oxadiazol-2-yl)imidazo[1,2-a]pyridin-2-yl)methyl)-N-phenylpiperidine-4-sulfonamide (0.050 g, 0.102 mmol) prepared in step 7 of Example 1, propan-2-one (0.012 g, 0.205 mmol) and sodium triacetoxyborohydride (0.065 g, 0.307 mmol) in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 4 g cartridge; methanol/dichloromethane=0% to 3%) and concentrated to obtain the title compound (0.011 g, 20.3%) as an ivory solid.

$^1$H NMR (400 MHZ, $CDCl_3$) δ 8.26 (s, 1H), 8.22 (dd, 1H, J=7.1, 0.8 Hz), 7.81 (s, 1H), 7.52 (dd, 1H, J=7.1, 1.7 Hz), 7.49-7.45 (m, 2H), 7.38-7.34 (m, 2H), 7.30-7.26 (m, 1H), 6.95 (t, 1H, J=51.7 Hz), 5.17 (s, 2H), 3.09-2.99 (m, 3H), 2.45-2.39 (m, 1H), 2.15-2.04 (m, 3H), 2.04-1.88 (m, 3H), 1.05 (s, 3H), 1.03 (s, 3H);

LRMS (ES) m/z 531.4 ($M^+$+1).

Example 5: Synthesis of Compound 4216, N-((7-(5-(difluoromethyl)-1,3,4-oxadiazol-2-yl)imidazo[1,2-a]pyridin-2-yl)methyl)-1-(1-hydroxypropan-2-yl)-N-phenylpiperidine-4-sulfonamide

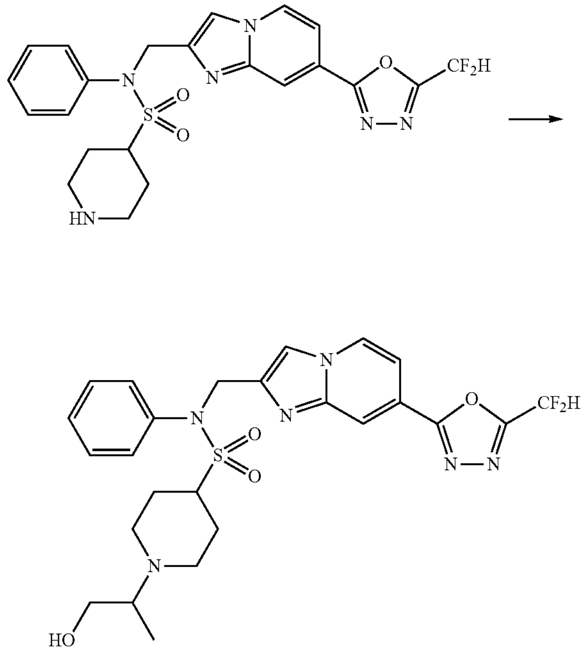 [SMILES: O=S(=O)(C1CCNCC1)N(Cc1cn2ccc(-c3nnc(C(F)F)o3)cc2n1)c1ccccc1 ; O=S(=O)(C1CCN(C2CCC2)CC1)N(Cc1cn2ccc(-c3nnc(C(F)F)o3)cc2n1)c1ccccc1]

N-((7-(5-(difluoromethyl)-1,3,4-oxadiazol-2-yl)imidazo[1,2-a]pyridin-2-yl)methyl)-N-phenylpiperidine-4-sulfonamide (0.050 g, 0.102 mmol) prepared in step 7 of Example 1, 1-hydroxypropan-2-one (0.015 g, 0.205 mmol), and sodium triacetoxyborohydride (0.065 g, 0.307 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 4 g cartridge; methanol/dichloromethane=0% to 3%) and concentrated to obtain the title compound (0.009 g, 16.1%) as an ivory solid.

$^1$H NMR (400 MHZ, $CDCl_3$) δ 8.26 (s, 1H), 8.22 (dd, 1H, J=7.1, 0.8 Hz), 7.78 (s, 1H), 7.53 (dd, 1H, J=7.1, 1.7 Hz), 7.48-7.44 (m, 2H), 7.38-7.34 (m, 2H), 7.30-7.26 (m, 1H), 6.95 (t, 1H, J=51.7 Hz), 5.16 (s, 2H), 3.43-3.39 (m, 1H), 3.33 (t, 1H, J=10.4 Hz), 3.12-3.04 (m, 1H), 2.84-2.30 (m, 3H), 2.58-2.52 (m, 1H), 2.20-2.15 (m, 2H), 2.11-1.83 (m, 4H), 0.89 (d, 3H, J=6.7 Hz);

LRMS (ES) m/z 547.0 ($M^+$+1).

Example 6: Synthesis of Compound 4217, 1-cyclobutyl-N-((7-(5-(difluoromethyl)-1,3,4-oxadiazol-2-yl)imidazo[1,2-a]pyridin-2-yl)methyl)-N-phenylpiperidine-4-sulfonamide

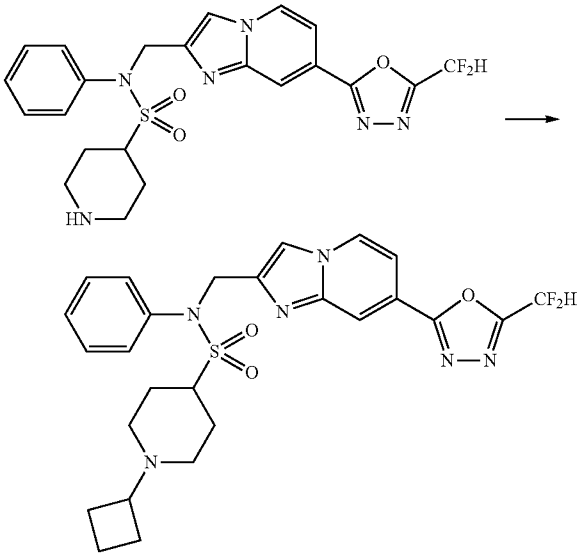

N-((7-(5-(difluoromethyl)-1,3,4-oxadiazol-2-yl)imidazo[1,2-a]pyridin-2-yl)methyl)-N-phenylpiperidine-4-sulfonamide (0.050 g, 0.102 mmol) prepared in step 7 of Example 1, cyclobutanone (0.014 g, 0.205 mmol), and sodium triacetoxyborohydride (0.065 g, 0.307 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 4 g cartridge; methanol/dichloromethane=0% to 3%) and concentrated to obtain the title compound (0.015 g, 27.0%) as an ivory solid.

$^1$H NMR (400 MHZ, $CDCl_3$) δ 8.25 (s, 1H), 8.21 (dd, 1H, J=7.1, 0.9 Hz), 7.80 (s, 1H), 7.52 (dd, 1H, J=7.1, 1.7 Hz), 7.48-7.44 (m, 2H), 7.38-7.33 (m, 2H), 7.30-7.26 (m, 1H), 6.95 (t, 1H, J=51.7 Hz), 5.16 (s, 2H), 3.08-2.98 (m, 3H), 2.74-2.66 (m, 1H), 2.15-2.11 (m, 2H), 2.06-1.83 (m, 8H), 1.74-1.53 (m, 2H);

LRMS (ES) m/z 543.4 ($M^+$+1).

Example 7: Synthesis of Compound 4218, 1-cyclohexyl-N-((7-(5-(difluoromethyl)-1,3,4-oxadiazol-2-yl)imidazo[1,2-a]pyridin-2-yl)methyl)-N-phenylpiperidine-4-sulfonamide

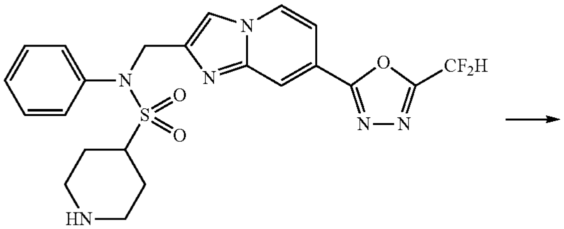

-continued

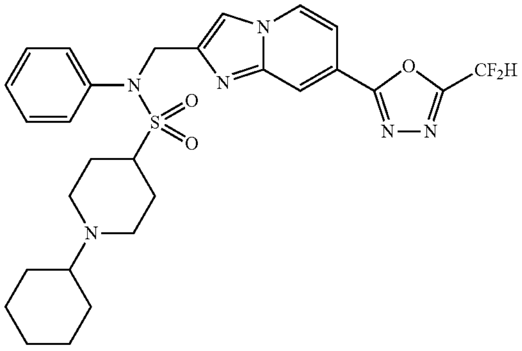

N-((7-(5-(difluoromethyl)-1,3,4-oxadiazol-2-yl)imidazo[1,2-a]pyridin-2-yl)methyl)-N-phenylpiperidine-4-sulfonamide (0.050 g, 0.102 mmol) prepared in step 7 of Example 1, cyclohexanone (0.020 g, 0.205 mmol), and sodium triacetoxyborohydride (0.065 g, 0.307 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 4 g cartridge; methanol/dichloromethane=0% to 3%) and concentrated to obtain the title compound (0.014 g, 24.0%) as an ivory solid.

$^1$H NMR (400 MHZ, $CDCl_3$) δ 8.25 (s, 1H), 8.21 (dd, 1H, J=7.1, 0.8 Hz), 7.81 (s, 1H), 7.52 (dd, 1H, J=7.1, 1.7 Hz), 7.48-7.46 (m, 2H), 7.38-7.34 (m, 2H), 7.30-7.26 (m, 1H), 6.95 (t, 1H, J=51.7 Hz), 5.17 (s, 2H), 3.05-3.02 (m, 3H), 2.32 (m, 1H), 2.23-2.10 (m, 4H), 1.99-1.91 (m, 2H), 1.81 (m, 3H), 1.66-1.62 (m, 1H), 1.29-1.07 (m, 6H);

LRMS (ES) m/z 571.4 ($M^+$+1).

Example 8: Synthesis of Compound 4219, N-((7-(5-(difluoromethyl)-1,3,4-oxadiazol-2-yl)imidazo[1,2-a]pyridin-2-yl)methyl)-N-phenyl-1-(tetrahydro-2H-pyran-4-yl)piperidine-4-sulfonamide

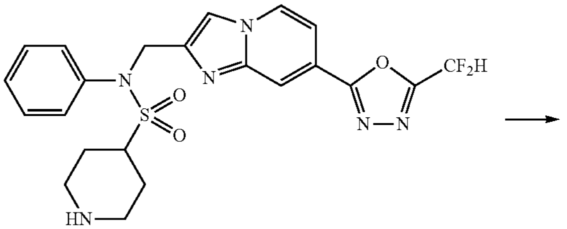

-continued

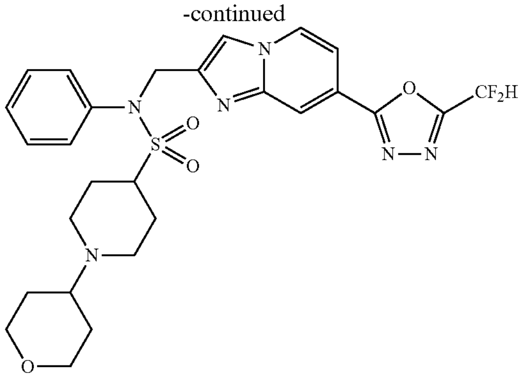

N-((7-(5-(difluoromethyl)-1,3,4-oxadiazol-2-yl)imidazo[1,2-a]pyridin-2-yl)methyl)-N-phenylpiperidine-4-sulfonamide (0.050 g, 0.102 mmol) prepared in step 7 of Example 1, tetrahydro-4H-pyran-4-one (0.020 g, 0.205 mmol), and sodium triacetoxyborohydride (0.065 g, 0.307 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 4 g cartridge; methanol/dichloromethane=0% to 3%) and concentrated to obtain the title compound (0.012 g, 20.5%) as an ivory solid.

$^1$H NMR (400 MHZ, $CDCl_3$) δ 8.26 (s, 1H), 8.21 (dd, 1H, J=7.1, 0.8 Hz), 7.80 (s, 1H), 7.52 (dd, 1H, J=7.1, 1.7 Hz), 7.48-7.45 (m, 2H), 7.38-7.34 (m, 2H), 7.30-7.25 (m, 1H), 6.95 (t, 1H, J=51.7 Hz), 5.17 (s, 2H), 4.04-3.99 (m, 2H), 3.41-3.34 (m, 2H), 3.09-3.02 (m, 3H), 2.53-2.48 (m, 1H), 2.19-2.13 (m, 4H), 2.01-1.92 (m, 2H), 1.72-1.69 (m, 2H), 1.63-1.54 (m, 2H);

LRMS (ES) m/z 573.4 ($M^+$+1).

Example 9: Synthesis of Compound 4220, 1-(4,4-difluorocyclohexyl)-N-((7-(5-(difluoromethyl)-1,3,4-oxadiazol-2-yl)imidazo[1,2-a]pyridin-2-yl)methyl)-N-phenylpiperidine-4-sulfonamide

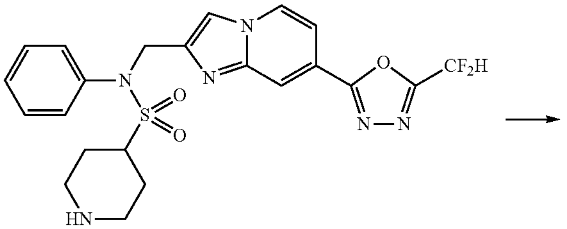

-continued

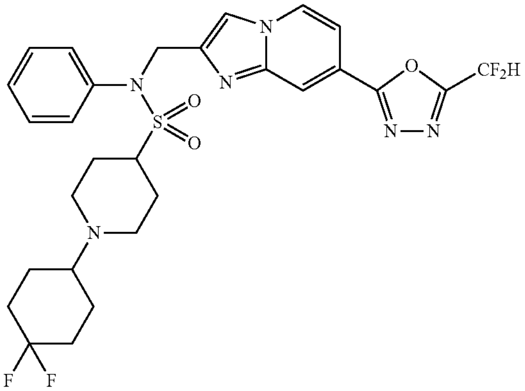

N-((7-(5-(difluoromethyl)-1,3,4-oxadiazol-2-yl)imidazo[1,2-a]pyridin-2-yl)methyl)-N-phenylpiperidine-4-sulfonamide (0.050 g, 0.102 mmol) prepared in step 7 of Example 1, 4,4-difluorocyclohexan-1-one (0.027 g, 0.205 mmol), and sodium triacetoxyborohydride (0.065 g, 0.307 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 4 g cartridge; methanol/dichloromethane=0% to 3%) and concentrated to obtain the title compound (0.009 g, 14.5%) as an ivory solid.

$^1$H NMR (400 MHZ, $CDCl_3$) δ 8.24 (s, 1H), 8.21 (dd, 1H, J=7.1, 0.9 Hz), 7.78 (s, 1H), 7.50 (dd, 1H, J=7.1, 1.7 Hz), 7.47-7.43 (m, 2H), 7.37-7.32 (m, 2H), 7.29-7.24 (m, 1H), 6.95 (t, 1H, J=51.7 Hz), 5.15 (s, 2H), 3.07-2.96 (m, 3H), 2.46-2.41 (m, 1H), 2.21-2.08 (m, 6H), 1.98-1.88 (m, 2H), 1.80-1.73 (m, 3H), 1.69-1.60 (m, 3H);

LRMS (ES) m/z 607.1 ($M^+$+1).

Example 10: Synthesis of Compound 4221, 1-acetyl-N-((7-(5-(difluoromethyl)-1,3,4-oxadiazol-2-yl)imidazo[1,2-a]pyridin-2-yl)methyl)-N-phenylpiperidine-4-sulfonamide

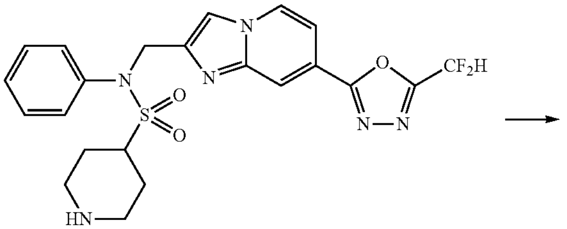

-continued

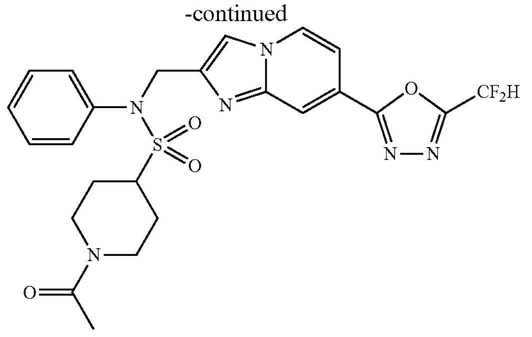

N-((7-(5-(difluoromethyl)-1,3,4-oxadiazol-2-yl)imidazo [1,2-a]pyridin-2-yl)methyl)-N-phenylpiperidine-4-sulfonamide (0.050 g, 0.102 mmol) prepared in step 7 of Example 1, acetyl chloride (0.015 mL, 0.205 mmol), and triethylamine (0.043 mL, 0.307 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=70% to 100%) and concentrated to obtain the title compound (0.014 g, 25.8%) as an ivory solid.

$^1H$ NMR (400 MHZ, $CDCl_3$) δ 8.26 (t, 1H, J=0.8 Hz), 8.22 (dd, 1H, J=7.1, 0.9 Hz), 7.73 (s, 1H), 7.53 (dd, 1H, J=7.1, 1.7 Hz), 7.46-7.42 (m, 2H), 7.38-7.34 (m, 2H), 7.34-7.27 (m, 1H), 6.95 (t, 1H, J=51.7 Hz), 5.13 (s, 2H), 4.72 (d, 1H, J=13.5 Hz), 3.95 (d, 1H, J=13.8 Hz), 3.67-3.29 (m, 1H), 3.11-3.03 (m, 1H), 2.58 (td, 1H, J=12.8, 2.5 Hz), 2.27-2.16 (m, 2H), 2.11 (s, 3H), 1.94-1.76 (m, 2H);

LRMS (ES) m/z 531.3 ($M^+$+1).

Example 11: Synthesis of Compound 4222, N-((7-(5-(difluoromethyl)-1,3,4-oxadiazol-2-yl)imidazo[1,2-a]pyridin-2-yl)methyl)-N-phenyl-1-propionylpiperidine-4-sulfonamide

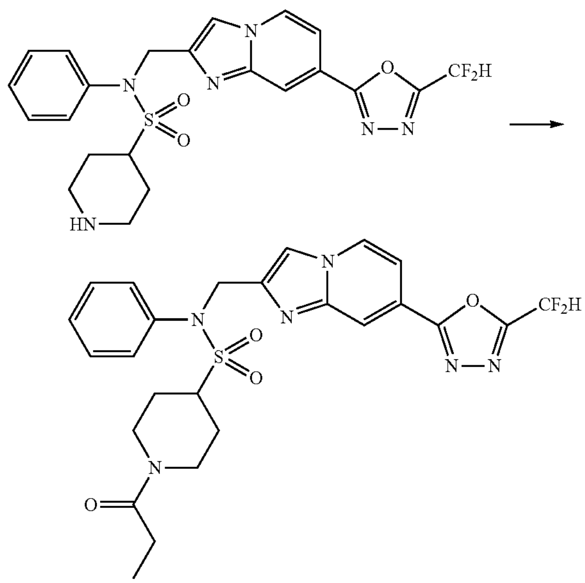

N-((7-(5-(difluoromethyl)-1,3,4-oxadiazol-2-yl)imidazo [1,2-a]pyridin-2-yl)methyl)-N-phenylpiperidine-4-sulfonamide (0.050 g, 0.102 mmol) prepared in step 7 of Example 1, propionyl chloride (0.019 g, 0.205 mmol), and triethylamine (0.043 mL, 0.307 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=70% to 100%) and concentrated to obtain the title compound (0.013 g, 23.3%) as an ivory solid.

$^1H$ NMR (400 MHZ, $CDCl_3$) 0 8.26 (s, 1H), 8.22 (dd, 1H, J=7.1, 0.9 Hz), 7.73 (s, 1H), 7.53 (dd, 1H, J=7.1, 1.7 Hz), 7.46-7.42 (m, 2H), 7.38-7.34 (m, 2H), 7.32-7.27 (m, 1H), 6.95 (t, 1H, J=51.7 Hz), 5.13 (s, 2H), 4.75 (d, 1H, J=13.4 Hz), 4.00 (d, 1H, J=13.5 Hz), 3.68-3.29 (m, 1H), 3.03 (t, 1H, J=12.1 Hz), 2.58 (t, 1H, J=11.9 Hz), 2.36 (q, 2H, J=7.4 Hz), 2.20 (t, 2H, J=15.4 Hz), 1.90-1.76 (m, 2H), 1.15 (t, 3H, J=7.4 Hz);

LRMS (ES) m/z 545.4 ($M^+$+1).

Example 12: Synthesis of Compound 4223, 1-(cyclobutanecarbonyl)-N-((7-(5-(difluoromethyl)-1,3,4-oxadiazol-2-yl)imidazo[1,2-a]pyridine-2-yl)methyl)-N-phenylpiperidine-4-sulfonamide

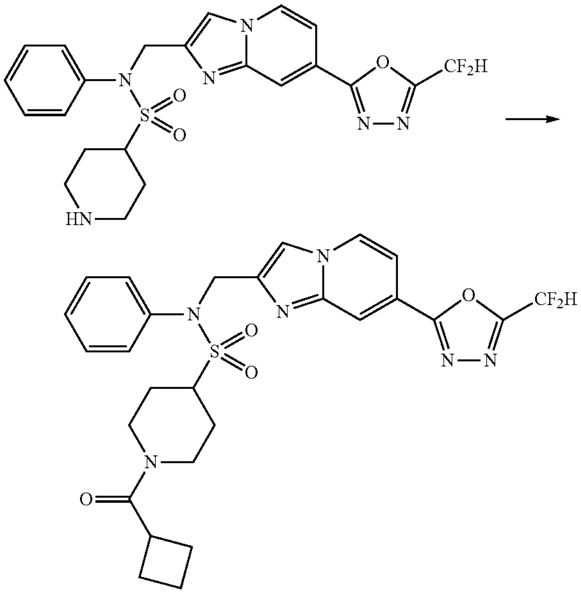

N-((7-(5-(difluoromethyl)-1,3,4-oxadiazol-2-yl)imidazo [1,2-a]pyridin-2-yl)methyl)-N-phenylpiperidine-4-sulfonamide (0.050 g, 0.102 mmol) prepared in step 7 of Example 1, cyclobutanecarbonyl chloride (0.024 g, 0.205 mmol), and triethylamine (0.043 mL, 0.307 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=70% to 100%) and concentrated to obtain the title compound (0.010 g, 17.1%) as an ivory solid.

$^1$H NMR (400 MHZ, $CDCl_3$) δ 8.27 (t, 1H, J=0.8 Hz), 8.22 (dd, 1H, J=7.1, 0.9 Hz), 7.74 (s, 1H), 7.54 (dd, 1H, J=7.1, 1.7 Hz), 7.46-7.42 (m, 2H), 7.38-7.34 (m, 2H), 7.32-7.27 (m, 1H), 6.95 (t, 1H, J=51.7 Hz), 5.13 (s, 2H), 4.78-4.76 (m, 1H), 3.84 (d, 1H, J=13.6 Hz), 3.50 (s, 1H), 3.33-3.24 (m, 2H), 3.23-2.90 (m, 1H), 2.61-2.54 (m, 1H), 2.40-2.33 (m, 2H), 2.19-2.12 (m, 4H), 2.06-1.74 (m, 3H);

LRMS (ES) m/z 571.0 ($M^+$+1).

Example 13: Synthesis of Compound 4224, N-((7-(5-(difluoromethyl)-1,3,4-oxadiazol-2-yl)imidazo[1,2-a]pyridin-2-yl)methyl)-N-phenyl-1-(2,2, 2-trifluoroacetyl)piperidine-4-sulfonamide

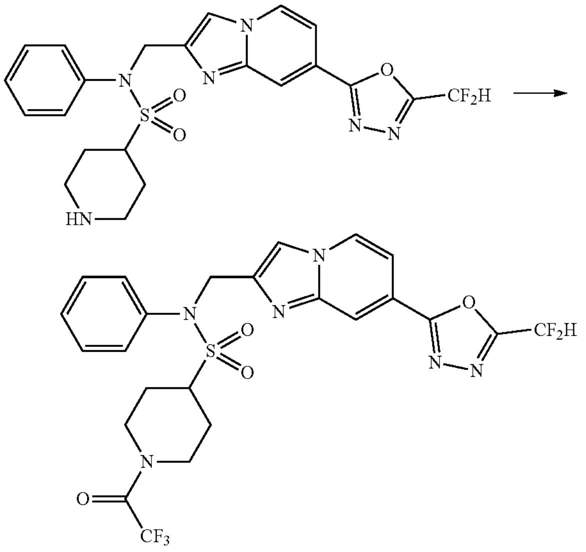

N-((7-(5-(difluoromethyl)-1,3,4-oxadiazol-2-yl)imidazo[1,2-a]pyridin-2-yl)methyl)-N-phenylpiperidine-4-sulfonamide (0.050 g, 0.102 mmol) prepared in step 7 of Example 1,2,2, 2-trifluoroacetic anhydride (0.043 g, 0.205 mmol), and triethylamine (0.043 mL, 0.307 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=70% to 100%) and concentrated to obtain the title compound (0.012 g, 20.1%) as an ivory solid.

$^1$H NMR (400 MHZ, $CDCl_3$) δ 8.28 (s, 1H), 8.22 (dd, 1H, J=7.1, 0.9 Hz), 7.70 (s, 1H), 7.55 (dd, 1H, J=7.1, 1.7 Hz), 7.45-7.41 (m, 2H), 7.39-7.34 (m, 2H), 7.33-7.29 (m, 1H), 6.95 (t, 1H, J=51.7 Hz), 5.12 (s, 2H), 4.60 (d, 1H, J=13.6 Hz), 4.16-4.12 (m, 1H), 3.48-3.40 (m, 1H), 3.23-3.16 (m, 1H), 2.93-2.86 (m, 1H), 2.33-2.27 (m, 2H), 2.21-1.91 (m, 2H);

LRMS (ES) m/z 585.1 ($M^+$+1).

Example 14: Synthesis of Compound 4225, N-((7-(5-(difluoromethyl)-1,3,4-oxadiazol-2-yl)imidazo[1,2-a]pyridin-2-yl)methyl)-1-(methylsulfonyl)-N-phenylpiperidine-4-sulfonamide

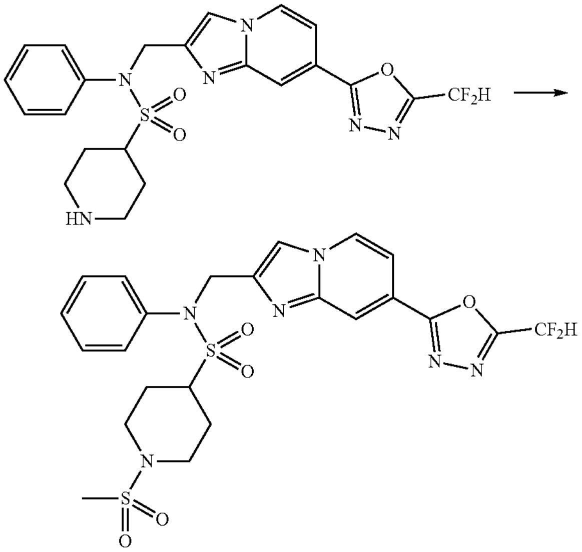

N-((7-(5-(difluoromethyl)-1,3,4-oxadiazol-2-yl)imidazo[1,2-a]pyridin-2-yl)methyl)-N-phenylpiperidine-4-sulfonamide (0.050 g, 0.102 mmol) prepared in step 7 of Example 1, methanesulfonyl chloride (0.016 mL, 0.205 mmol), and triethylamine (0.043 mL, 0.307 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=70% to 100%) and concentrated to obtain the title compound (0.012 g, 20.7%) as an ivory solid.

$^1$H NMR (400 MHZ, $CDCl_3$) δ 8.28 (s, 1H), 8.23 (dd, 1H, J=7.1, 0.9 Hz), 7.73 (s, 1H), 7.55 (dd, 1H, J=7.1, 1.7 Hz), 7.45-7.42 (m, 2H), 7.39-7.34 (m, 2H), 7.33-7.28 (m, 1H), 6.95 (t, 1H, J=51.7 Hz), 5.13 (s, 2H), 3.90 (dt, 2H, J=12.6, 3.5 Hz), 3.28-3.20 (m, 1H), 2.86-2.76 (m, 5H), 2.30-2.25 (m, 2H), 2.21-2.00 (m, 2H);

LRMS (ES) m/z 567.0 ($M^+$+1).

Example 15: Synthesis of Compound 4226, methyl 4-(N-((7-(5-(difluoromethyl)-1,3,4-oxadiazol-2-yl)imidazo[1,2-a]pyridin-2-yl)methyl)-N-phenylsulfamoyl)piperidine-1-carboxylate

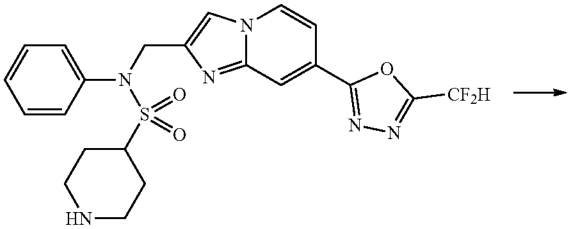

-continued

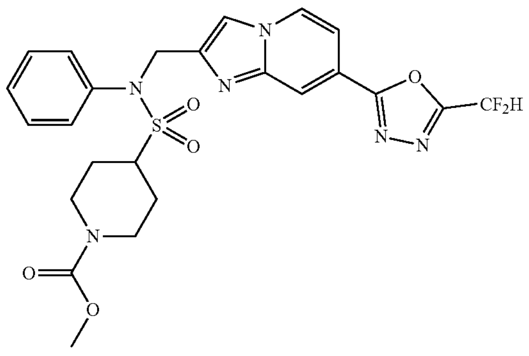

N-((7-(5-(difluoromethyl)-1,3,4-oxadiazol-2-yl)imidazo[1,2-a]pyridin-2-yl)methyl)-N-phenylpiperidine-4-sulfonamide (0.050 g, 0.102 mmol) prepared in step 7 of Example 1, methyl carbonochloridate (0.019 g, 0.205 mmol), and triethylamine (0.043 mL, 0.307 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=70% to 100%) and concentrated to obtain the title compound (0.015 g, 26.8%) as an ivory solid.

$^1$H NMR (400 MHZ, $CDCl_3$) δ 8.27 (s, 1H), 8.22 (dd, 1H, J=7.2, 0.9 Hz), 7.75 (s, 1H), 7.54 (dd, 1H, J=7.1, 1.7 Hz), 7.46-7.43 (m, 2H), 7.39-7.34 (m, 2H), 7.32-7.28 (m, 1H), 6.95 (t, 1H, J=51.7 Hz), 5.14 (s, 2H), 4.28 (s, 2H), 3.72 (s, 3H), 3.28-3.22 (m, 1H), 2.78 (m, 2H), 2.18-2.14 (m, 2H), 1.91-1.80 (m, 2H);

LRMS (ES) m/z 547.1 ($M^+$+1).

Example 16: Synthesis of Compound 4227, 4—(N-((7-(5-(difluoromethyl)-1,3,4-oxadiazol-2-yl)imidazo[1,2-a]pyridin-2-yl)methyl)-N-phenylsulfamoyl)-N, N-dimethylpiperidine-1-carboxamide -continued

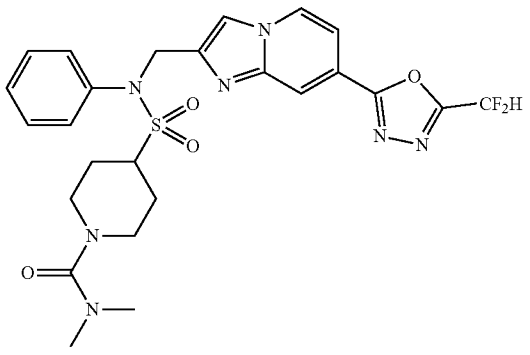

N-((7-(5-(difluoromethyl)-1,3,4-oxadiazol-2-yl)imidazo[1,2-a]pyridin-2-yl)methyl)-N-phenylpiperidine-4-sulfonamide (0.050 g, 0.102 mmol) prepared in step 7 of Example 1, dimethylcarbamic chloride (0.022 g, 0.205 mmol), and triethylamine (0.043 mL, 0.307 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=70% to 100%) and concentrated to obtain the title compound (0.013 g, 22.7%) as an ivory solid.

$^1$H NMR (400 MHZ, $CDCl_3$) δ 8.27 (s, 1H), 8.22 (dd, 1H, J=7.1, 0.9 Hz), 7.76 (s, 1H), 7.54 (dd, 1H, J=7.1, 1.7 Hz), 7.47-7.44 (m, 2H), 7.39-7.34 (m, 2H), 7.32-7.27 (m, 1H), 6.95 (t, 1H, J=51.7 Hz), 5.15 (s, 2H), 3.78 (d, 2H, J=13.3 Hz), 3.27-3.19 (m, 1H), 2.84-2.80 (m, 6H), 2.76-2.67 (m, 2H), 2.18-2.15 (m, 2H), 1.98-1.87 (m, 2H);

LRMS (ES) m/z 560.1 ($M^+$+1).

Example 17: Synthesis of Compound 4228, N-((7-(5-(difluoromethyl)-1,3,4-oxadiazol-2-yl)imidazo[1,2-a]pyridin-2-yl)methyl)-N-phenyl-1-(pyrimidin-2-yl)piperidine-4-sulfonamide

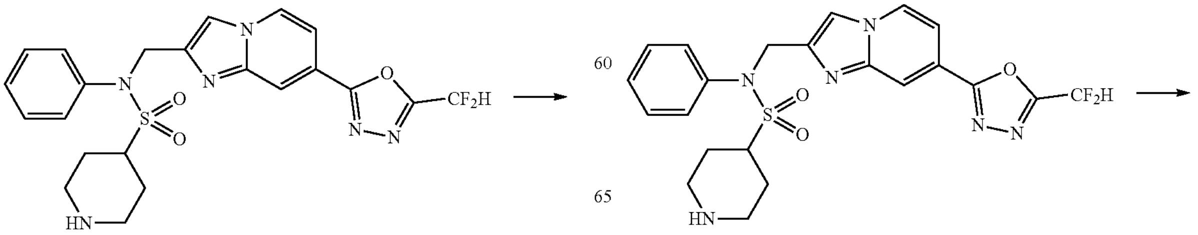

-continued

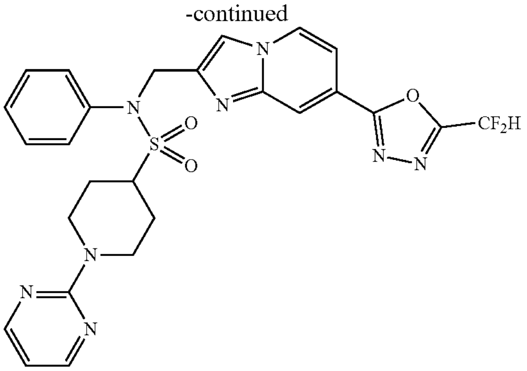

N-((7-(5-(difluoromethyl)-1,3,4-oxadiazol-2-yl)imidazo[1,2-a]pyridin-2-yl)methyl)-N-phenylpiperidine-4-sulfonamide (0.050 g, 0.102 mmol) prepared in step 7 of Example 1,2-chloropyrimidine (0.023 g, 0.205 mmol), and potassium carbonate (0.042 g, 0.307 mmol) were dissolved in acetonitrile (1 mL)/N, N-dimethylformamide (1 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=70% to 100%) and concentrated to obtain the title compound (0.014 g, 24.1%) as an ivory solid.

$^1H$ NMR (400 MHZ, $CDCl_3$) δ 8.33 (d, 2H, J=4.8 Hz), 8.26 (s, 1H), 8.22 (dd, 1H, J=7.1, 0.9 Hz), 7.77 (s, 1H), 7.54 (dd, 1H, J=7.1, 1.7 Hz), 7.48-7.45 (m, 2H), 7.39-7.35 (m, 2H), 7.31-7.29 (m, 1H), 6.95 (t, 1H, J=51.7 Hz), 6.53 (t, 1H, J=4.7 Hz), 5.17 (s, 2H), 4.94 (d, 2H, J=13.5 Hz), 3.41-3.34 (m, 1H), 2.89 (td, 2H, J=12.9, 4.3 Hz), 2.24-2.21 (m, 2H), 1.97-1.86 (m, 2H);

LRMS (ES) m/z 566.8 ($M^+$+1).

Example 18: Synthesis of Compound 4236, N-((7-(5-(difluoromethyl)-1,3,4-oxadiazol-2-yl)imidazo[1,2-a]pyridin-2-yl)methyl)-N-(3-fluorophenyl)-1-methylpiperidine-4-sulfonamide

[Step 1] Synthesis of tert-butyl 4-(N-(3-fluorophenyl)sulfamoyl)piperidine-1-carboxylate

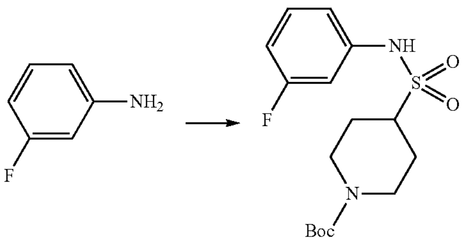 [SMILES: Nc1cccc(F)c1 ; CC(C)(C)OC(=O)N1CCC(S(=O)(=O)Nc2cccc(F)c2)CC1]

Ttert-butyl 4-(chlorosulfonyl)piperidine-1-carboxylate (5.000 g, 17.620 mmol), 3-fluoroaniline (2.937 g, 26.430 mmol), and triethylamine (2.947 mL, 21.144 mmol) were dissolved in dichloromethane (50 mL) at room temperature, and the resulting solution was stirred at the same temperature for 18 hours. Water was poured into the reaction mixture, followed by extraction with dichloromethane. The organic layer was washed with a saturated aqueous water solution, dried over anhydrous magnesium sulfate, filtered, and concentrated under reduced pressure. The concentrate was purified by column chromatography ($SiO_2$, 40 g cartridge; ethyl acetate/hexane=0% to 30%) and concentrated to obtain the title compound (3.200 g, 50.7%) as a white solid.

[Step 2] Synthesis of tert-butyl 4-(N-((7-(5-(difluoromethyl)-1,3,4-oxadiazol-2-yl)imidazo[1,2-a]pyridin-2-yl)methyl)-N-(3-fluorophenyl)sulfamoyl)piperidine-1-carboxylate

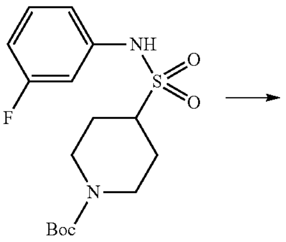

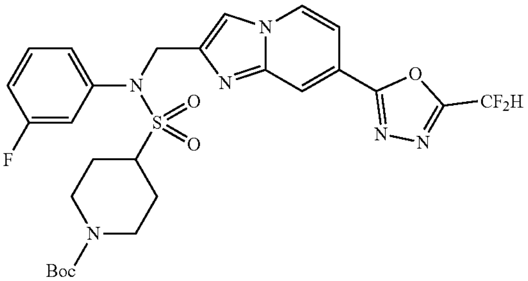

Tert-butyl 4-(N-(3-fluorophenyl)sulfamoyl)piperidine-1-carboxylate (2.680 g, 7.477 mmol) prepared in step 1,2-(2-(chloromethyl)imidazo[1,2-a]pyridin-7-yl)-5-(difluoromethyl)-1,3,4-oxadiazole (2.554 g, 8.972 mmol) prepared in step 5 of Example 1, potassium carbonate (1.550 g, 11.216 mmol), and potassium iodide (0.621 g, 3.739 mmol) were dissolved in N, N-dimethylformamide (5 mL) at room temperature, and the resulting solution was stirred at the same temperature for 3 hours. A saturated aqueous ammonium chloride solution was poured into the concentrate obtained by removing the solvent from the reaction mixture under reduced pressure, followed by extraction with dichloromethane. The organic layer was washed with a saturated aqueous water solution, dried over anhydrous magnesium sulfate, filtered, and concentrated under reduced pressure. The concentrate was purified by column chromatography ($SiO_2$, 40 g cartridge; ethyl acetate/hexane=0% to 90%) and concentrated to obtain the title compound (3.600 g, 79.4%) as a yellow solid.

[Step 3] Synthesis of N-((7-(5-(difluoromethyl)-1,3,4-oxadiazol-2-yl)imidazo[1,2-a]pyridin-2-yl)methyl)-N-(3-fluorophenyl)piperidine-4-sulfonamide

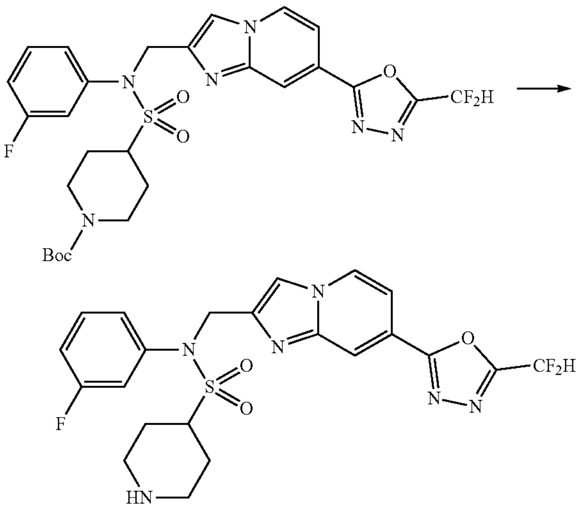

Tert-butyl 4-(N-((7-(5-(difluoromethyl)-1,3,4-oxadiazol-2-yl)imidazo[1,2-a]pyridin-2-yl)methyl)-N-(3-fluorophenyl)sulfamoyl)piperidine-1-carboxylate (1.200 g, 1.978 mmol) prepared in step 2 and trifluoroacetic acid (3.030 mL, 39.563 mmol) were dissolved in dichloromethane (18 mL) at 0° C., and the resulting solution was stirred at room temperature for 4 hours. A saturated aqueous sodium hydrogen carbonate solution was poured into the reaction mixture, extracted with dichloromethane, and then filtered through a plastic filter to remove a solid residue and an aqueous layer. After concentration under reduced pressure, the title compound (0.990 g, 100.1%) was obtained as a yellow solid without further purification.

[Step 4] Synthesis of Compound 4236

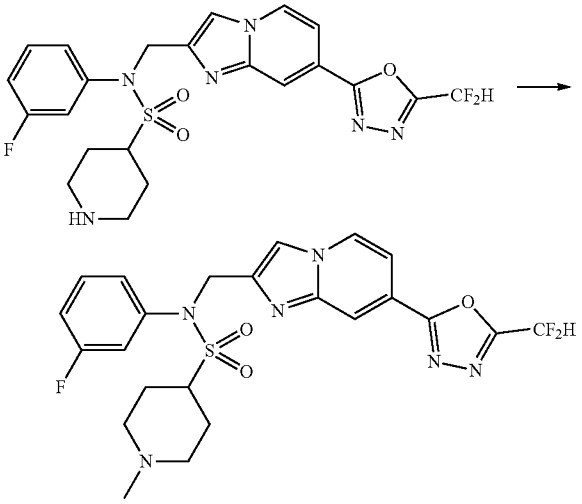

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3, formaldehyde (0.006 g, 0.197 mmol), acetic acid (0.006 mL, 0.099 mmol), sodium triacetoxyborohydride (0.063 g, 0.296 mmol), and triethylamine (0.014 mL, 0.099 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. Dichloromethane (3 mL) was added to the concentrate, followed by stirring, and the precipitated solid was filtered, washed with dichloromethane, and dried to obtain the title compound (0.028 g, 54.1%) as a white solid.

$^1$H NMR (400 MHZ, $CDCl_3$) δ 8.27 (p, J=0.7 Hz, 1H), 8.23 (dd, J=1.0, 7.1 Hz, 1H), 7.78 (s, 1H), 7.54 (dd, J=1.7, 7.1 Hz, 1H), 7.36-7.23 (m, 3H), 7.10-6.80 (m, 2H), 5.15 (s, 2H), 3.09-2.90 (m, 3H), 2.28 (s, 3H), 2.10 (d, J=11.3 Hz, 2H), 2.03-1.86 (m, 4H);

LRMS (ES) m/z 521.2 ($M^+$+1).

Example 19: Synthesis of Compound 4237, N-((7-(5-(difluoromethyl)-1,3,4-oxadiazol-2-yl)imidazo[1,2-a]pyridin-2-yl)methyl)-1-ethyl-N-(3-fluorophenyl)-piperidine-4-sulfonamide

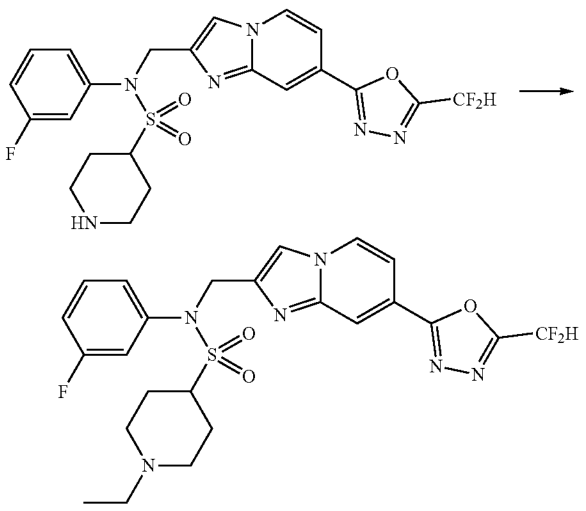

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, acetaldehyde (0.009 g, 0.197 mmol), acetic acid (0.006 mL, 0.099 mmol), sodium triacetoxyborohydride (0.063 g, 0.296 mmol) and triethylamine (0.014 mL, 0.099 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 10%) and concentrated to obtain the title compound (0.027 g, 51.9%) as a yellow solid.

$^1H$ NMR (400 MHZ, $CDCl_3$) δ 8.27 (s, 1H), 8.22 (d, J=7.1 Hz, 1H), 7.78 (s, 1H), 7.53 (dd, J=1.7, 7.1 Hz, 1H), 7.34-7.24 (m, 3H), 7.09-6.80 (m, 2H), 5.15 (s, 2H), 3.12-2.99 (m, 3H), 2.42 (q, J=7.2 Hz, 2H), 2.11 (d, J=11.7 Hz, 2H), 2.05-1.85 (m, 4H), 1.08 (t, J=7.2 Hz, 3H); LRMS (ES) m/z 535.1 ($M^+$+1).

Example 20: Synthesis of Compound 4238, N-((7-(5-(difluoromethyl)-1,3,4-oxadiazol-2-yl)imidazo[1,2-a]pyridin-2-yl)methyl)-N-(3-fluorophenyl)-1-isopropylpiperidine-4-sulfonamide

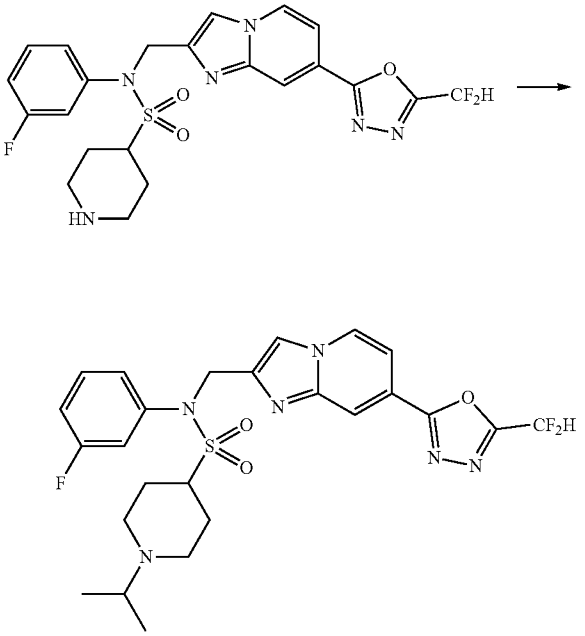 [SMILES: O=S(=O)(C1CCNCC1)N(Cc1cn2ccc(-c3nnc(C(F)F)o3)cc2n1)c1cccc(F)c1 ; CC(C)N1CCC(S(=O)(=O)N(Cc2cn3ccc(-c4nnc(C(F)F)o4)cc3n2)c2cccc(F)c2)CC1]

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, propan-2-one (0.011 g, 0.197 mmol), acetic (0.006 acid mL, 0.099 mmol), sodium triacetoxyborohydride (0.063 g, 0.296 mmol), and triethylamine (0.014 mL, 0.099 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 10%) and concentrated to obtain the title compound (0.018 g, 33.2%) as a white solid.

$^1H$ NMR (400 MHZ, $CDCl_3$) δ 8.27 (s, 1H), 8.23 (d, J=7.1 Hz, 1H), 7.79 (s, 1H), 7.53 (dd, J=1.8, 7.1 Hz, 1H), 7.36-7.24 (m, 3H), 7.09-6.81 (m, 2H), 5.15 (s, 2H), 3.01 (d, J=11.4 Hz, 3H), 2.85-2.72 (m, 1H), 2.12 (d, J=13.4 Hz, 4H), 2.02-1.87 (m, 2H), 1.04 (d, J=6.6 Hz, 6H);

LRMS (ES) m/z 549.4 ($M^+$+1).

Example 21: Synthesis of Compound 4239, N-((7-(5-(difluoromethyl)-1,3,4-oxadiazol-2-yl)imidazo[1,2-a]pyridin-2-yl)methyl)-N-(3-fluorophenyl)-1-(1-hydroxypropan-2-yl)piperidine-4-sulfonamide

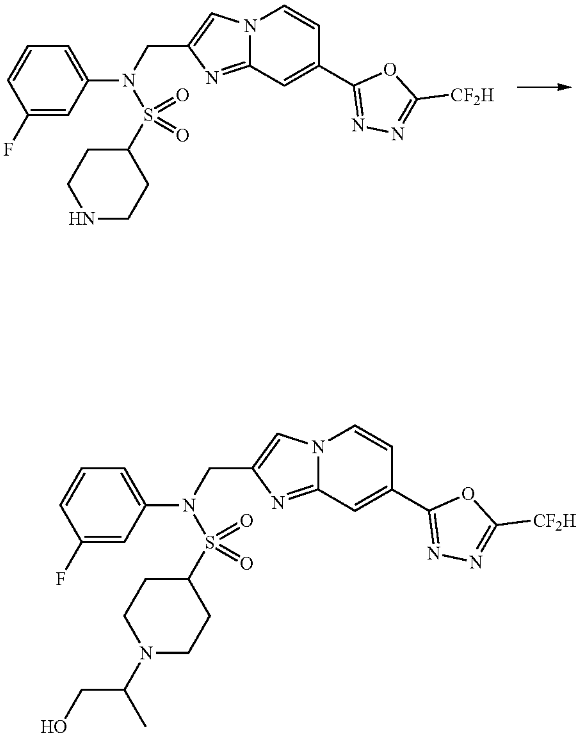

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, 1-hydroxypropan-2-one (0.015 g, 0.197 mmol), acetic acid (0.006 mL, 0.099 mmol), sodium triacetoxyborohydride (0.063 g, 0.296 mmol), and triethylamine (0.014 mL, 0.099 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 10%) and concentrated to obtain the title compound (0.019 g, 33.7%) as a yellow solid.

$^1H$ NMR (400 MHZ, $CDCl_3$) δ 8.28 (s, 1H), 8.23 (dd, J=7.1, 1.0 Hz, 1H), 7.77 (s, 1H), 7.54 (dd, J=7.1, 1.7 Hz, 1H), 7.37-7.22 (m, 3H), 7.11-6.80 (m, 2H), 5.15 (s, 2H), 3.42 (dd, J=10.8, 5.0 Hz, 1H), 3.33 (t, J=10.4 Hz, 1H), 3.09 (tt, J=11.9, 3.8 Hz, 1H), 2.96-2.80 (m, 3H), 2.55 (td, J=11.6, 2.4 Hz, 1H), 2.21-1.81 (m, 5H), 0.89 (d, J=6.7 Hz, 3H);

LRMS (ES) m/z 565.4 ($M^+$+1).

Example 22: Synthesis of Compound 4240, 1-cyclobutyl-N-((7-(5-(difluoromethyl)-1,3,4-oxadiazol-2-yl)imidazo[1,2-a]pyridin-2-yl)methyl)-N-(3-fluorophenyl)piperidine-4-sulfonamide

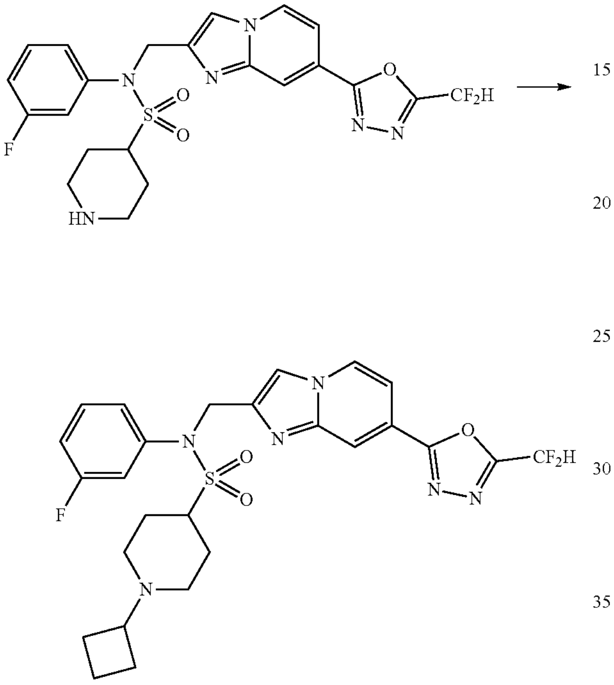

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, cyclobutanone (0.014 g, 0.197 mmol), acetic acid (0.006 mL, 0.099 mmol), sodium triacetoxyborohydride (0.063 g, 0.296 mmol), and triethylamine (0.014 mL, 0.099 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then was concentrated under reduced pressure. The concentrate purified by chromatography ($SiO_2$ plate, 20×20×1 mm; methanol/dichloromethane=0% to 10%) and concentrated to obtain the title compound (0.023 g, 41.9%) as a white solid.

$^1$H NMR (400 MHZ, $CDCl_3$) δ 8.27 (d, J=1.5 Hz, 1H), 8.22 (d, J=7.1 Hz, 1H), 7.78 (s, 1H), 7.53 (dd, J=1.7, 7.1 Hz, 1H), 7.36-7.23 (m, 3H), 7.10-6.80 (m, 2H), 5.14 (s, 2H), 3.03 (ddt, J=3.6, 12.1,26.5 Hz, 3H), 2.70 (p, J=7.8 Hz, 1H), 2.15-1.82 (m, 8H), 1.79-1.59 (m, 4H);

LRMS (ES) m/z 561.1 ($M^+$+1).

Example 23: Synthesis of Compound 4241, N-((7-(5-(difluoromethyl)-1,3,4-oxadiazol-2-yl)imidazo[1,2-a]pyridin-2-yl)methyl)-N-(3-fluorophenyl)-1-oxetan-3-yl)piperidine-4-sulfonamide

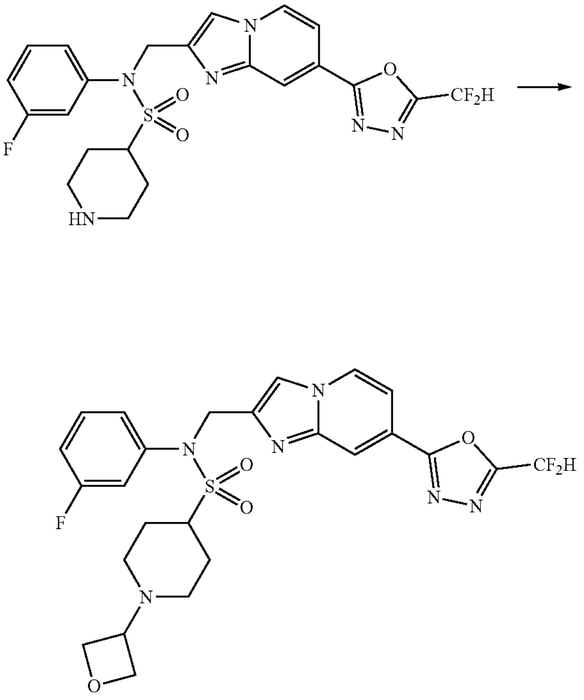

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, oxetan-3-one (0.014 g, 0.197 mmol), acetic acid (0.006 mL, 0.099 mmol), sodium triacetoxyborohydride (0.063 g, 0.296 mmol), and triethylamine (0.014 mL, 0.099 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 10%) and concentrated to obtain the title compound (0.027 g, 48.8%) as a white solid.

$^1$H NMR (400 MHZ, $CDCl_3$) § 8.27 (dt, J=0.8, 1.7 Hz, 1H), 8.23 (dd, J=1.0, 7.2 Hz, 1H), 7.76 (s, 1H), 7.53 (dd, J=1.7, 7.1 Hz, 1H), 7.36-7.23 (m, 3H), 7.10-6.81 (m, 2H), 5.14 (s, 2H), 4.62 (dt, J=6.4, 21.5 Hz, 4H), 3.53-3.43 (m, 1H), 3.09 (tt, J=3.9, 11.7 Hz, 1H), 2.87 (dt, J=3.4, 11.8 Hz, 2H), 2.17-2.09 (m, 2H), 1.99 (qd, J=3.8, 12.1 Hz, 2H), 1.88-1.78 (m, 2H);

LRMS (ES) m/z 563.1 ($M^+$+1).

Example 24: Synthesis of Compound 4242, 1-cyclohexyl-N-((7-(5-(difluoromethyl)-1,3,4-oxadiazol-2-yl)imidazo[1,2-a]pyridin-2-yl)methyl)-N-(3-fluorophenyl)piperidine-4-sulfonamide

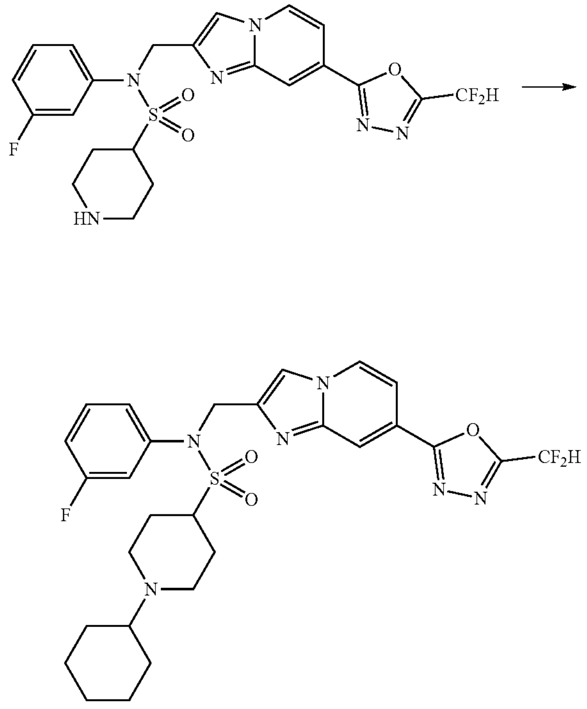

N-((7-(5-(difluoromethyl)-1,3,4-oxadiazol-2-yl)imidazo[1,2-a]pyridin-2-yl)methyl)-N-phenylpiperidine-4-sulfonamide (0.050 g, 0.099 mmol) prepared in step 3 of Example 18, cyclohexanone (0.019 g, 0.197 mmol), acetic acid (0.006 mL, 0.099 mmol), sodium triacetoxyborohydride (0.063 g, 0.296 mmol), and triethylamine (0.014 mL, 0.099 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 10%) and concentrated to obtain the title compound (0.030 g, 51.6%) as a white solid.

$^1$H NMR (400 MHZ, $CDCl_3$) δ 8.29-8.25 (m, 1H), 8.22 (dd, J=1.0, 7.1 Hz, 1H), 7.78 (s, 1H), 7.53 (dd, J=1.7, 7.1 Hz, 1H), 7.35-7.23 (m, 3H), 7.11-6.79 (m, 2H), 5.15 (s, 2H), 3.05 (dq, J=4.0, 11.9 Hz, 3H), 2.40-1.87 (m, 7H), 1.80 (dd, J=5.6, 10.2 Hz, 4H), 1.68-1.59 (m, 1H), 1.33-1.15 (m, 5H);

LRMS (ES) m/z 589.2 ($M^+$+1).

Example 25: Synthesis of Compound 4243, N-((7-(5-(difluoromethyl)-1,3,4-oxadiazol-2-yl)imidazo[1,2-a]pyridin-2-yl)methyl)-N-(3-fluorophenyl)-1-(tetrahydro-2H-pyran-4-yl)piperidine-4-sulfonamide

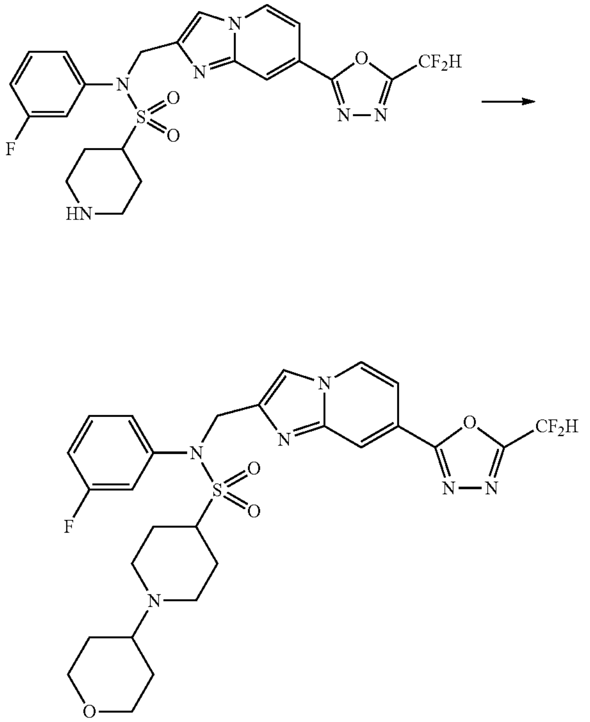 [SMILES: O=S(=O)(C1CCNCC1)N(Cc1cn2ccc(-c3nnc(C(F)F)o3)cc2n1)c1cccc(F)c1 ; O=S(=O)(C1CCN(C2CCOCC2)CC1)N(Cc1cn2ccc(-c3nnc(C(F)F)o3)cc2n1)c1cccc(F)c1]

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, tetrahydro-4H-pyran-4-one (0.020 g, 0.197 mmol), acetic acid (0.006 mL, 0.099 mmol), sodium triacetoxyborohydride (0.063 g, 0.296 mmol), and triethylamine (0.014 mL, 0.099 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 10%) and concentrated to obtain the title compound (0.023 g, 40.1%) as a yellow gel.

$^1$H NMR (400 MHZ, $CDCl_3$) δ 8.29-8.26 (m, 1H), 8.23 (dd, J=1.0, 7.1 Hz, 1H), 7.77 (s, 1H), 7.53 (dd, J=1.7, 7.1 Hz, 1H), 7.37-7.23 (m, 3H), 7.09-6.80 (m, 2H), 5.15 (s, 2H), 4.06-3.97 (m, 2H), 3.37 (td, J=2.0, 11.8 Hz, 2H), 3.12-3.02 (m, 3H), 2.56-2.46 (m, 1H), 2.20-2.06 (m, 4H), 2.00-1.89 (m, 2H), 1.71 (dd, J=3.5, 12.4 Hz, 2H), 1.64-1.52 (m, 2H);

LRMS (ES) m/z 591.1 ($M^+$+1).

Example 26: Synthesis of Compound 4244, 1-(4,4-difluorocyclohexyl)-N-((7-(5-(difluoromethyl)-1,3,4-oxadiazol-2-yl)imidazo[1,2-a]pyridin-2-yl)methyl)-N-(3-fluorophenyl)piperidine-4-sulfonamide

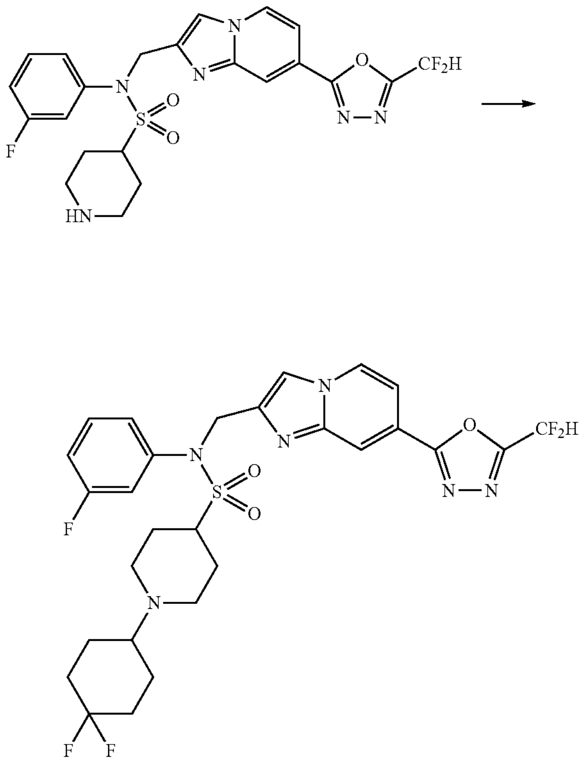 [SMILES: O=S(=O)(C1CCNCC1)N(Cc1cn2ccc(-c3nnc(C(F)F)o3)cc2n1)c1cccc(F)c1 ; O=S(=O)(C1CCN(C2CCC(F)(F)CC2)CC1)N(Cc1cn2ccc(-c3nnc(C(F)F)o3)cc2n1)c1cccc(F)c1]

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, 4, 4-difluorocyclohexan-1-one (0.026 g, 0.197 mmol), acetic acid (0.006 mL, 0.099 mmol), sodium triacetoxyborohydride (0.063 g, 0.296 mmol), and triethylamine (0.014 mL, 0.099 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 10%) and concentrated, and then the obtained product was again purified by chromatography ($SiO_2$ plate, 20×20×1 mm; methanol/1%-dichloromethane aqueous solution=0% to 7%) and concentrated to obtain the title compound (0.017 g, 27.9%) as a yellow gel.

$^1H$ NMR (400 MHZ, $CDCl_3$) § 8.28 (s, 1H), 8.23 (d, J=7.5 Hz, 1H), 7.77 (s, 1H), 7.54 (dd, J=1.7, 7.1 Hz, 1H), 7.36-7.23 (m, 3H), 7.09-6.79 (m, 2H), 5.15 (s, 2H), 3.03 (t, J=9.3 Hz, 2H), 2.45 (s, 1H), 2.16 (dt, J=11.7, 22.3 Hz, 6H), 2.00-1.56 (m, 9H);

LRMS (ES) m/z 625.2 ($M^+$+1).

Example 27: Synthesis of Compound 4245, 1-acetyl-N-((7-(5-(difluoromethyl)-1,3,4-oxadiazol-2-yl)imidazo[1,2-a]pyridin-2-yl)methyl)-N-(3-fluorophenyl)piperidine-4-sulfonamide

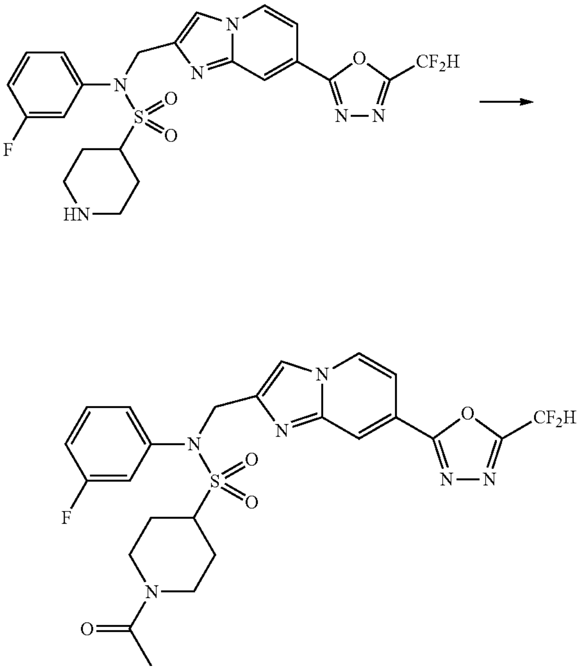 [SMILES: O=S(=O)(C1CCNCC1)N(Cc1cn2ccc(-c3nnc(C(F)F)o3)cc2n1)c1cccc(F)c1 ; CC(=O)N1CCC(S(=O)(=O)N(Cc2cn3ccc(-c4nnc(C(F)F)o4)cc3n2)c2cccc(F)c2)CC1]

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, acetyl chloride (0.014 mL, 0.197 mmol), and triethylamine (0.041 mL, 0.296 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.020 g, 37.7%) as a white gel.

$^1H$ NMR (400 MHZ, $CDCl_3$) 0 8.30-8.27 (m, 1H), 8.24 (dd, J=1.0, 7.1 Hz, 1H), 7.73 (s, 1H), 7.55 (dd, J=1.7, 7.1 Hz, 1H), 7.37-7.22 (m, 3H), 7.10-6.81 (m, 2H), 5.12 (s, 2H), 4.72 (d, J=13.3 Hz, 1H), 3.95 (d, J=13.6 Hz, 1H), 3.33 (tt, J=3.8, 11.7 Hz, 1H), 3.07 (ddd, J=2.8, 12.2, 14.0 Hz, 1H), 2.57 (td, J=2.9, 12.9 Hz, 1H), 2.22 (d, J=12.6 Hz, 1H), 2.11 (s, 3H), 1.83 (dtt, J=6.1, 12.3, 24.8 Hz, 3H);

LRMS (ES) m/z 548.9 ($M^+$+1).

Example 28: Synthesis of Compound 4246, N-((7-(5-(difluoromethyl)-1,3,4-oxadiazol-2-yl)imidazo[1,2-a]pyridin-2-yl)methyl)-N-(3-fluorophenyl)-1-propionylpiperidine-4-sulfonamide

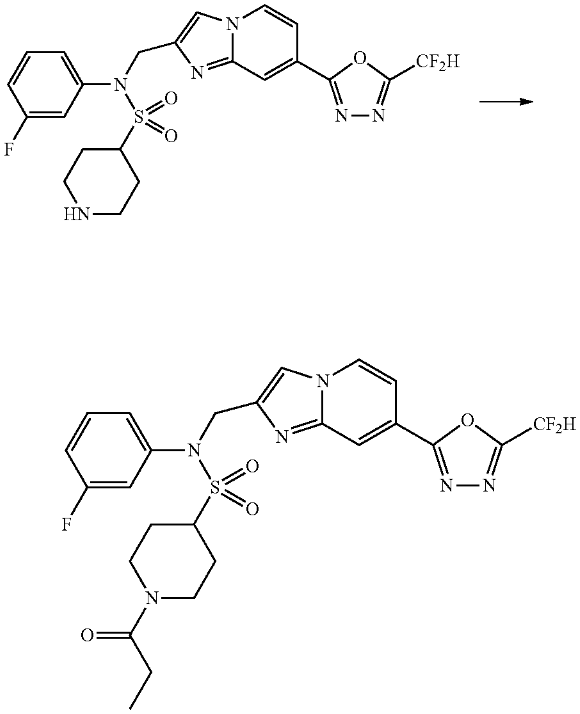 [SMILES: O=S(=O)(C1CCNCC1)N(Cc1cn2ccc(-c3nnc(C(F)F)o3)cc2n1)c1cccc(F)c1 ; CCC(=O)N1CCC(S(=O)(=O)N(Cc2cn3ccc(-c4nnc(C(F)F)o4)cc3n2)c2cccc(F)c2)CC1]

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050) g, 0.099 mmol) prepared in step 3 of Example 18, propionyl chloride (0.018 g, 0.197 mmol), and triethylamine (0.041 mL, 0.296 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.017 g, 29.9%) as a yellow solid.

$^1$H NMR (400 MHZ, $CDCl_3$) δ 8.30-8.28 (m, 1H), 8.24 (dd, J=1.0, 7.1 Hz, 1H), 7.76-7.71 (m, 1H), 7.56 (dd, J=1.7, 7.1 Hz, 1H), 7.38-7.22 (m, 3H), 7.11-6.82 (m, 2H), 5.13 (s, 2H), 4.75 (d, J=13.5 Hz, 1H), 4.00 (d, J=13.8 Hz, 1H), 3.33 (tt, J=3.8, 11.7 Hz, 1H), 3.03 (t, J=12.9 Hz, 1H), 2.57 (t, J=12.8 Hz, 1H), 2.36 (q, J=7.4 Hz, 2H), 2.18 (dd, J=13.1, 25.6 Hz, 2H), 1.90-1.70 (m, 2H), 1.16 (t, J=7.4 Hz, 3H);

LRMS (ES) m/z 563.0 ($M^+$+1).

Example 29: Synthesis of Compound 4247, N-((7-(5-(difluoromethyl)-1,3,4-oxadiazol-2-yl)imidazo[1,2-a]pyridin-2-yl)methyl)-N-(3-fluorophenyl)-1-(2-hydroxyacetyl)piperidine-4-sulfonamide

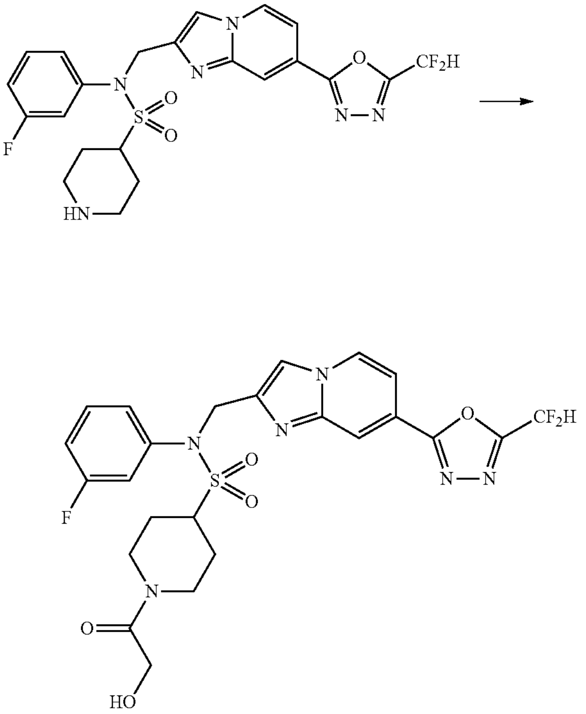 [SMILES: O=S(=O)(C1CCNCC1)N(Cc1cn2ccc(-c3nnc(C(F)F)o3)cc2n1)c1cccc(F)c1 ; O=C(CO)N1CCC(S(=O)(=O)N(Cc2cn3ccc(-c4nnc(C(F)F)o4)cc3n2)c2cccc(F)c2)CC1]

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, 2-hydroxyacetic acid (0.015 g, 0.197 mmol), triethylamine (0.028 mL, 0.197 mmol), and 1-[bis(dimethylamino)methylene]-1H-1,2, 3-triazolo[4, 5-b]pyridinium 3-oxide hexafluorophosphate (HATU, 0.056 g, 0.148 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated, and then the obtained product was again purified by chromatography ($SiO_2$ plate, 20×20×1 mm; methanol/1%-dichloromethane aqueous solution=5% to 7%) and concentrated to obtain the title compound (0.017 g, 31.2%) as a white gel.

$^1$H NMR (400 MHZ, $CDCl_3$) § 8.30 (dd, J=0.9, 1.7 Hz, 1H), 8.24 (dd, J=1.0, 7.2 Hz, 1H), 7.71 (s, 1H), 7.57 (dd, J=1.7, 7.1 Hz, 1H), 7.34 (td, J=6.2, 8.0 Hz, 1H), 7.30-7.22 (m, 2H), 7.10-6.81 (m, 2H), 5.11 (s, 2H), 4.68 (d, J=13.5 Hz, 1H), 4.18 (d, J=1.2 Hz, 2H), 3.65 (d, J=13.7 Hz, 1H), 3.39 (tt, J=3.8, 11.5 Hz, 1H), 3.07-2.96 (m, 1H), 2.77 (t, J=12.2 Hz, 1H), 2.23 (t, J=14.2 Hz, 2H), 1.87 (qd, J=4.3, 12.4 Hz, 2H);

LRMS (ES) m/z 565.0 ($M^+$+1).

Example 30: Synthesis of Compound 4248, 1-(cyclobutanecarbonyl)-N-((7-(5-(difluoromethyl)-1,3,4-oxadiazol-2-yl)imidazo[1,2-a]pyridine-2-yl)methyl)-N-(3-fluorophenyl)piperidine-4-sulfonamide

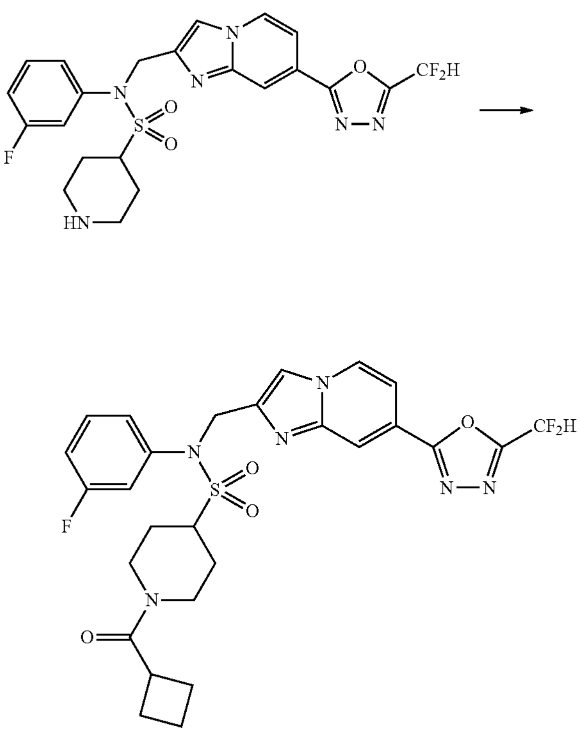 [SMILES: O=S(=O)(C1CCNCC1)N(Cc1cn2ccc(-c3nnc(C(F)F)o3)cc2n1)c1cccc(F)c1 ; O=C(C1COC1)N1CCC(S(=O)(=O)N(Cc2cn3ccc(-c4nnc(C(F)F)o4)cc3n2)c2cccc(F)c2)CC1]

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, cyclobutanecarbonyl chloride (0.023 g, 0.197 mmol), and triethylamine (0.041 mL, 0.296 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated, and then the obtained product was again purified by chromatography ($SiO_2$ plate, 20×20×1 mm; methanol/1%-dichloromethane aqueous solution=0% to 7%) and concentrated to obtain the title compound (0.010 g, 17.2%) as a white solid. $^{1}$H NMR (400 MHZ, $CDCl_3$) § 8.31-8.28 (m, 1H), 8.24 (dd, J=1.0, 7.1 Hz, 1H), 7.73 (s, 1H), 7.57 (dd, J=1.7, 7.1 Hz, 1H), 7.38-7.22 (m, 3H), 7.10-6.81 (m, 2H), 5.13 (s, 2H), 4.72 (d, J=13.4 Hz, 1H), 3.84 (d, J=13.7 Hz, 1H), 3.37-3.17 (m, 2H), 2.95 (t, J=12.8 Hz, 1H), 2.57 (t, J=12.8 Hz, 1H), 2.42-2.27 (m, 2H), 2.16 (tt, J=4.8, 8.8 Hz, 4H), 2.05-1.68 (m, 4H);

LRMS (ES) m/z 588.9 ($M^+$+1).

Example 31: Synthesis of Compound 4249, N-((7-(5-(difluoromethyl)-1,3,4-oxadiazol-2-yl)imidazo[1,2-a]pyridin-2-yl)methyl)-N-(3-fluorophenyl)-1-(oxetan-3-carbonyl)piperidine-4-sulfonamide

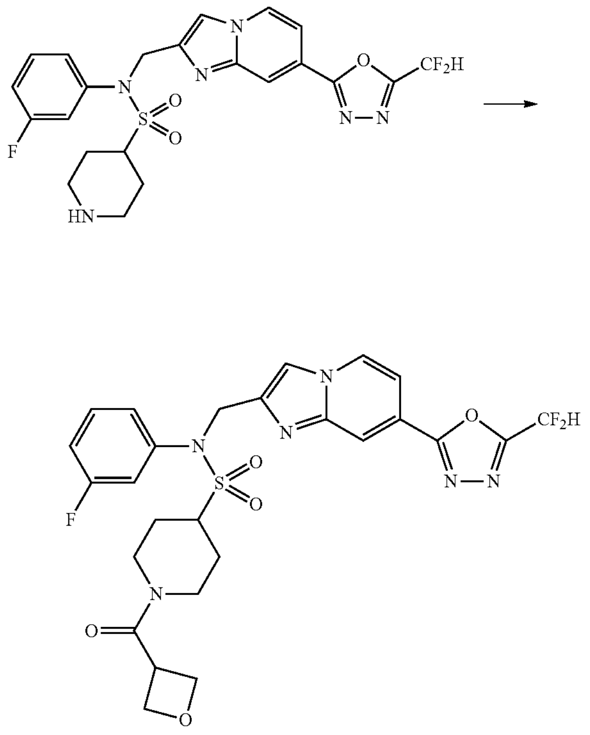

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step m 41 Example 18, oxetane-3-carboxylic acid (0.020 g, 0.197 mmol), 1-[bis(dimethylamino)methylene]-1H-1,2, 3-triazolo[4,5-b]pyridinium 3-oxide hexafluorophosphate (HATU, 0.056 g, 0.148 mmol), and triethylamine (0.028 mL, 0.197 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.013 g, 21.8%) as a yellow solid.

$^{1}$H NMR (400 MHZ, $CDCl_3$) δ 8.33-8.28 (m, 1H), 8.24 (dd, J=1.0, 7.1 Hz, 1H), 7.71 (s, 1H), 7.57 (dd, J=1.7, 7.1 Hz, 1H), 7.38-7.20 (m, 3H), 7.10-6.81 (m, 2H), 5.11 (s, 2H), 4.92 (ddd, J=5.8, 7.1, 16.4 Hz, 2H), 4.81 (dd, J=5.9, 8.7 Hz, 2H), 4.72 (d, J=13.8 Hz, 1H), 4.00 (tt, J=7.1, 8.7 Hz, 1H), 3.47 (d, J=13.8 Hz, 1H), 3.35 (tt, J=3.8, 11.6 Hz, 1H), 2.98 (ddd, J=2.8, 12.2, 14.2 Hz, 1H), 2.66 (td, J=2.9, 12.9, 13.7 Hz, 1H), 2.20 (d, J=13.0 Hz, 1H), 1.81 (dtt, J=6.1, 13.0, 20.0 Hz, 3H);

LRMS (ES) m/z 591.0 ($M^+$+1).

Example 32: Synthesis of Compound 4250, N-((7-(5-(difluoromethyl)-1,3,4-oxadiazol-2-yl)imidazo[1,2-a]pyridin-2-yl)methyl)-N-(3-fluorophenyl)-1-(2,2,2-trifluoroacetyl)piperidine-4-sulfonamide

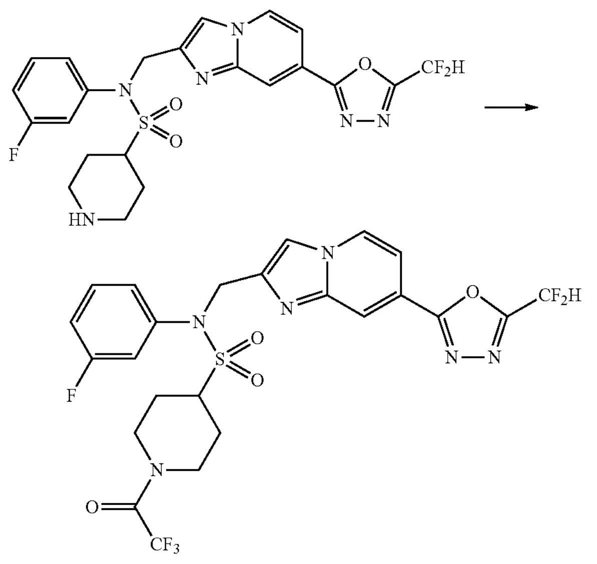

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, 2,2, 2-trifluoroacetic anhydride (0.041 g, 0.197 mmol), and triethylamine (0.041 mL, 0.296 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20x20x1 mm; methanol/dichloromethane=0% to 7%) and concentrated to obtain the title compound (0.025 g, 41.9%) as a yellow solid.

$^1H$ NMR (400 MHZ, $CDCl_3$) δ 8.30 (s, 1H), 8.27-8.21 (m, 1H), 7.71 (s, 1H), 7.57 (dd, J=1.7, 7.1 Hz, 1H), 7.38-7.19 (m, 3H), 7.11-6.81 (m, 2H), 5.11 (s, 2H), 4.60 (d, J=13.5 Hz, 1H), 4.13 (d, J=14.2 Hz, 1H), 3.45 (ddt, J=4.1, 7.3, 11.3 Hz, 1H), 3.20 (ddd, J=2.8, 11.8, 14.4 Hz, 1H), 2.93-2.81 (m, 1H), 2.27 (d, J=13.6 Hz, 2H), 2.04-1.88 (m, 2H);

LRMS (ES) m/z 602.7 ($M^+$+1).

Example 33: Synthesis of Compound 4251, N-((7-(5-(difluoromethyl)-1,3,4-oxadiazol-2-yl)imidazo[1,2-a]pyridin-2-yl)methyl)-N-(3-fluorophenyl)-1-(methylsulfonyl)piperidine-4-sulfonamide

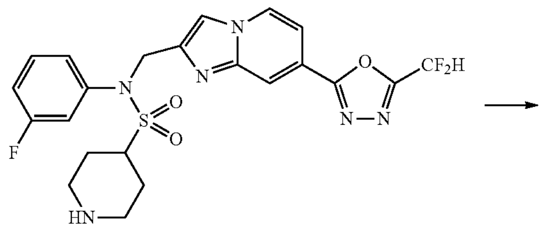

-continued

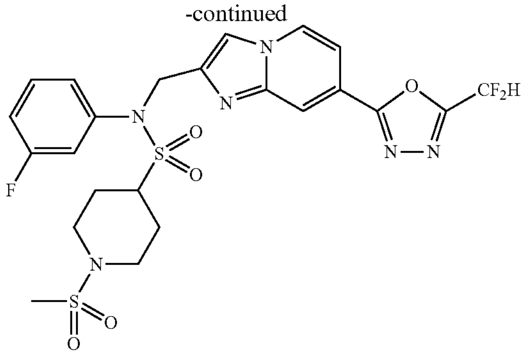

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, methanesulfonyl chloride (0.015 mL, 0.197 mmol), and triethylamine (0.041 mL, 0.296 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20x20x1 mm; methanol/dichloromethane=0% to 7%) and concentrated to obtain the title compound (0.004 g, 6.2%) as a white solid.

$^1H$ NMR (400 MHZ, $CDCl_3$) δ 8.29 (dt, J=0.8, 1.7 Hz, 1H), 8.24 (dd, J=1.0, 7.1 Hz, 1H), 7.75-7.71 (m, 1H), 7.56 (dd, J=1.7, 7.1 Hz, 1H), 7.38-7.21 (m, 3H), 7.09-6.80 (m, 2H), 5.12 (s, 2H), 3.89 (dt, J=4.2, 13.3 Hz, 2H), 3.24 (ddt, J=3.8, 7.7, 11.1 Hz, 1H), 2.85-2.73 (m, 5H), 2.30-2.17 (m, 2H), 2.07-1.95 (m, 2H);

LRMS (ES) m/z 584.7 ($M^+$+1).

Example 34: Synthesis of Compound 4252, methyl 4-(N-((7-(5-(difluoromethyl)-1,3,4-oxadiazol-2-yl)imidazo[1,2-a]pyridin-2-yl)methyl)-N-(3-fluorophenyl)sulfamoyl)piperidine-1-carboxylate

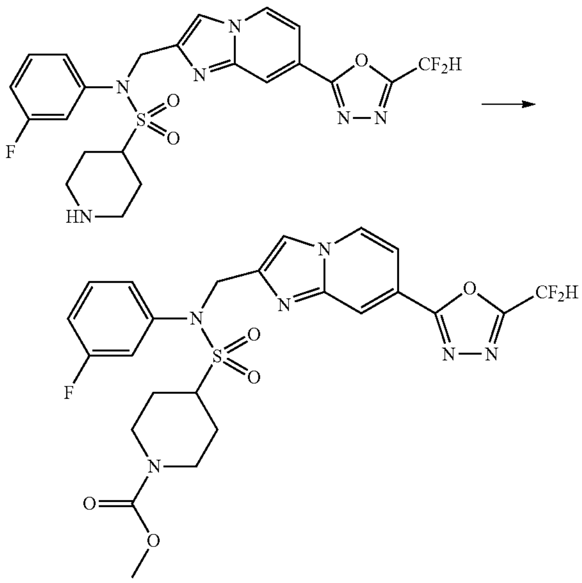

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, methyl carbonochloridate (0.019 g, 0.197 mmol), and triethylamine (0.041 mL, 0.296 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.025 g, 45.6%) as a yellow solid.

$^1$H NMR (400 MHZ, $CDCl_3$) 0 8.28 (dt, J=0.8, 1.7 Hz, 1H), 8.23 (dd, J=1.0, 7.1 Hz, 1H), 7.74 (s, 1H), 7.55 (dd, J=1.7, 7.2 Hz, 1H), 7.36-7.23 (m, 3H), 7.09-6.81 (m, 2H), 5.12 (s, 2H), 4.28 (s, 2H), 3.71 (s, 3H), 3.26 (ddd, J=3.7, 8.1, 11.8 Hz, 1H), 2.77 (s, 2H), 2.18-2.07 (m, 2H), 1.82 (qd, J=4.5, 12.4 Hz, 2H);

LRMS (ES) m/z 565.4 ($M^+$+1).

Example 35: Synthesis of Compound 4253,4—(N-((7-(5-(difluoromethyl)-1,3,4-oxadiazol-2-yl)imidazo[1,2-a]pyridin-2-yl)methyl)-N-(3-fluorophenyl)sulfamoyl)-N, N-dimethylpiperidine-1-carboxamide

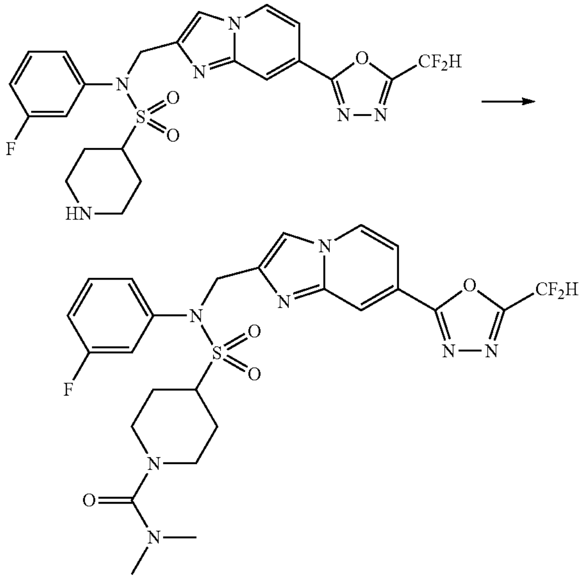

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, dimethylcarbamic chloride (0.021 g, 0.197 mmol), and triethylamine (0.041 mL, 0.296 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.022 g, 38.4%) as a white solid.

$^1$H NMR (400 MHZ, $CDCl_3$) δ 8.28 (dt, J=0.8, 1.7 Hz, 1H), 8.23 (dd, J=1.0, 7.2 Hz, 1H), 7.75 (s, 1H), 7.55 (dd, J=1.7, 7.2 Hz, 1H), 7.36-7.24 (m, 3H), 7.10-6.81 (m, 2H), 5.13 (s, 2H), 3.77 (dt, J=3.4, 13.9 Hz, 2H), 3.23 (tt, J=3.8, 11.9 Hz, 1H), 2.84 (s, 6H), 2.71 (td, J=2.5, 12.9, 13.4 Hz, 2H), 2.19-2.06 (m, 2H), 1.89 (qd, J=4.1, 12.4 Hz, 2H);

LRMS (ES) m/z 578.4 ($M^+$+1).

Example 36: Synthesis of Compound 4254, N-((7-(5-(difluoromethyl)-1,3,4-oxadiazol-2-yl)imidazo[1,2-a]pyridin-2-yl)methyl)-N-(3-fluorophenyl)-1-(pyridin-2-yl)piperidine-4-sulfonamide

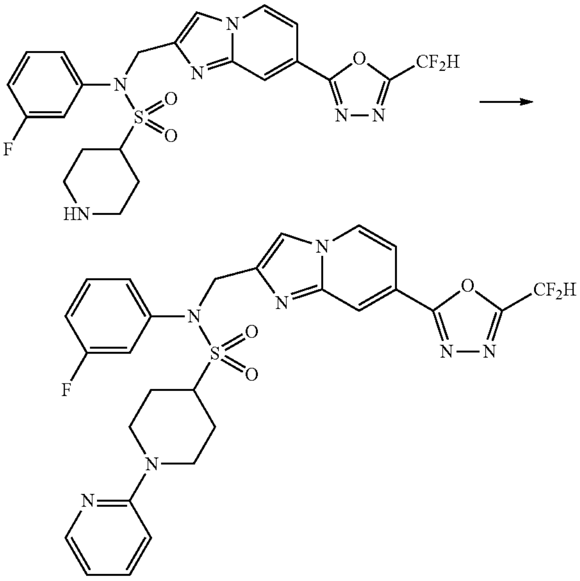

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, 2-bromopyridine (0.031 g, 0.197 mmol), RuPhos palladium G2 (0.004 g, 0.005 mmol) and cesium carbonate (0.064 g, 0.197 mmol) were dissolved in 1,4-dioxane (1 mL) at room temperature, and the resulting solution was stirred at 120° C. for 18 hours. Then, the temperature was lowered to room temperature to terminate the reaction. An aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated, and then the obtained product was again purified by chromatography ($SiO_2$ plate, 20×20×1 mm; methanol/1%-dichloromethane aqueous solution=0% to 7%) and concentrated to obtain the title compound (0.005 g, 8.0%) as a yellow solid.

$^1$H NMR (400 MHZ, $CDCl_3$) δ 8.30-8.26 (m, 1H), 8.23 (dd, J=1.0, 7.1 Hz, 1H), 8.20 (ddd, J=0.9, 2.0, 5.0 Hz, 1H), 7.76 (d, J=0.7 Hz, 1H), 7.55 (dd, J=1.7, 7.1 Hz, 1H), 7.51 (t, J=8.2 Hz, 1H), 7.37-7.24 (m, 3H), 7.10-6.81 (m, 2H), 6.67 (dd, J=7.3, 12.1 Hz, 2H), 5.16 (s, 2H), 4.46 (d, J=13.3 Hz, 2H), 3.35 (ddd, J=3.8, 8.2, 12.0 Hz, 1H), 2.86 (t, J=12.7 Hz, 2H), 2.21 (d, J=12.8 Hz, 2H), 1.95 (qd, J=4.2, 12.3 Hz, 2H);

LRMS (ES) m/z 584.1 ($M^{+}$+1).

Example 37: Synthesis of Compound 4255, N-((7-(5-(difluoromethyl)-1,3,4-oxadiazol-2-yl)imidazo[1,2-a]pyridin-2-yl)methyl)-N-(3-fluorophenyl)-1-(pyrimidin-2-yl)piperidine-4-sulfonamide

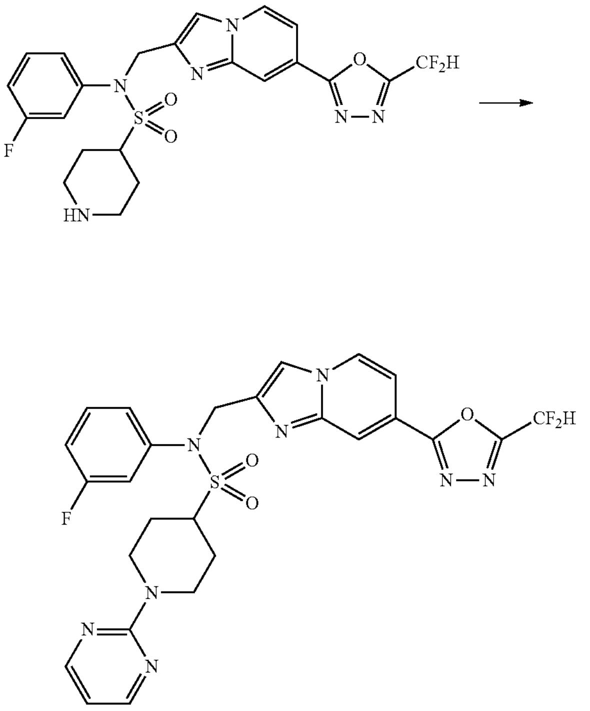

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 18, 2-chloropyrimidine (0.023 g, 0.197 mmol), and potassium carbonate (0.041 g, 0.296 mmol) were dissolved in N, N-dimethylformamide (0.5 mL)/acetonitrile (0.5 mL) at room temperature, and the resulting solution was stirred at the same temperature for 18 hours. An aqueous sodium hydrogen carbonate solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. Dichloromethane (3 mL) was added to the concentrate, followed by stirring, and the precipitated solid was filtered, washed with dichloromethane, and dried to obtain the title compound (0.012 g, 21.5%) as a yellow solid.

$^{1}$H NMR (400 MHZ, $CDCl_3$) δ 8.32 (d, J=4.7 Hz, 2H), 8.27 (dt, J=0.8, 1.7 Hz, 1H), 8.23 (dd, J=1.0, 7.1 Hz, 1H), 7.76 (d, J=0.7 Hz, 1H), 7.55 (dd, J=1.7, 7.1 Hz, 1H), 7.37-7.25 (m, 4H), 7.10-6.81 (m, 2H), 6.53 (t, J=4.7 Hz, 1H), 5.15 (s, 2H), 4.99-4.86 (m, 2H), 3.38 (ddt, J=3.7, 7.5, 11.9 Hz, 1H), 2.95-2.82 (m, 2H), 2.26-2.18 (m, 2H), 1.89 (qd, J=4.4, 12.4 Hz, 2H);

LRMS (ES) m/z 585.1 ($M^{+}$+1).

Example 38: Synthesis of Compound 4256, N-((7-(5-(difluoromethyl)-1,3,4-oxadiazol-2-yl)imidazo[1,2-a]pyridin-2-yl)methyl)-4-methyl-N-phenylpiperazine-1-sulfonamide

[Step 1] Synthesis of 1-((1H-imidazol-1-yl)sulfonyl)-3-methyl-1H-imidazol-3-ium trifluoromethanesulfonate

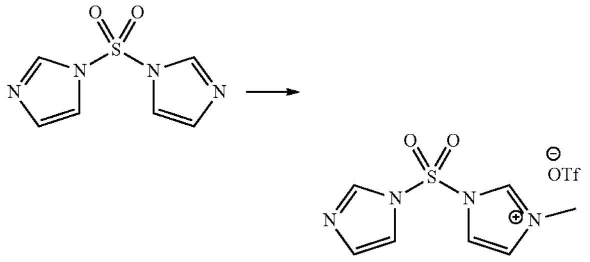

1, 1'-sulfonylbis(1H-imidazole, 10.000 g, 50.454 mmol) and methyl trifluoromethanesulfonate (4.981 mL, 45.409 mmol) were dissolved in dichloromethane (150 mL) at room temperature, and the resulting solution was stirred at the same temperature for 3 hours. After removing the solvent from the reaction mixture under reduced pressure, the title compound (18.280 g, 100.0%) was obtained as a white solid without further purification.

[Step 2] Synthesis of tert-butyl 4-((1H-imidazol-1-yl)sulfonyl)piperazine-1-carboxylate

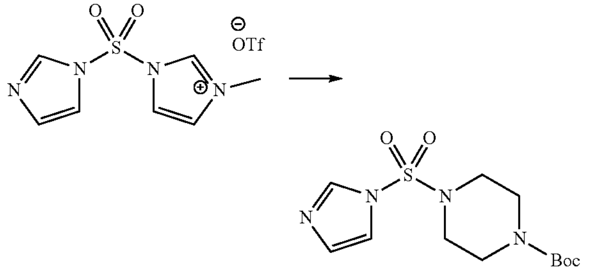

1-((1H-imidazol-1-yl)sulfonyl)-3-methyl-1H-imidazol-3-ium trifluoromethanesulfonate (18.000 g, 49.684 mmol) prepared in step 1 and tert-butyl piperazine-1-carboxylate (10.642 g, 57.137 mmol) were dissolved in acetonitrile (100 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with ethyl acetate. The organic layer was washed with a saturated aqueous water solution, dried over anhydrous magnesium sulfate, filtered, and concentrated under reduced pressure. The concentrate was purified by column chromatography ($SiO_2$, 80 g cartridge; hexane/ethyl acetate=0% to 100%) and concentrated to obtain the title compound (5.830 g, 37.1%) as a white solid.

[Step 3] Synthesis of 1-((4-(tert-butoxycarbonyl) piperazine-1-yl)sulfonyl)-3-methyl-1H-imidazol-3-ium trifluoromethanesulfonate

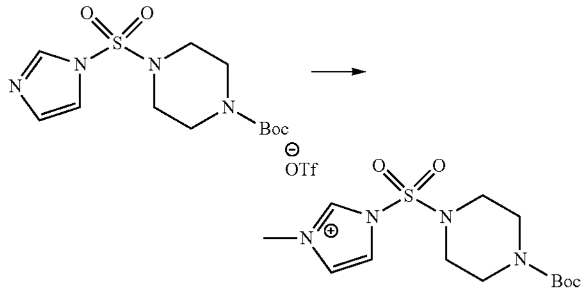

Tert-butyl 4-((1H-imidazol-1-yl)sulfonyl)piperazine-1-carboxylate (5.830 g, 18.427 mmol) prepared in step 2 and methyl trifluoromethanesulfonate (2.223 mL, 20.270 mmol) were dissolved in dichloromethane (150 mL) at 0° C., and the resulting solution was stirred at room temperature for 3 hours. After removing the solvent from the reaction mixture under reduced pressure, the title compound (8.850 g, 100.0%) was obtained as a white solid without further purification.

[Step 4] Synthesis of tert-butyl 4-(N-(phenylsulfamoyl)piperazine-1-carboxylate

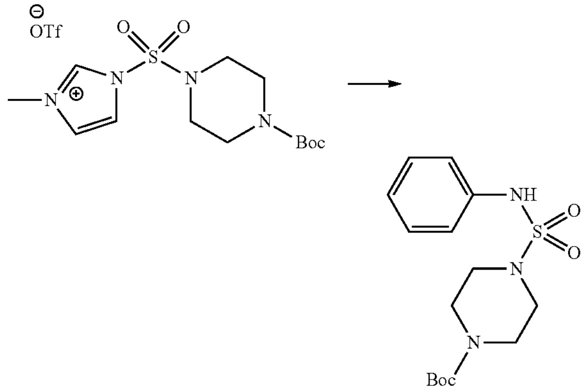

1-((4-(Tert-butoxycarbonyl)piperazine-1-yl)sulfonyl)-3-methyl-1H-imidazol-3-ium trifluoromethanesulfonate (4.400 g, 9.158 mmol) prepared in step 3 and aniline (1.003 mL, 10.989 mmol) were dissolved in acetonitrile (50 mL) at room temperature, and the resulting solution was heated to reflux for 18 hours. Then, the temperature was lowered to room temperature to terminate the reaction. A saturated aqueous ammonium chloride solution was poured into the concentrate obtained by removing the solvent from the reaction mixture under reduced pressure, followed by extraction with dichloromethane. The organic layer was washed with a saturated aqueous water solution, dried over anhydrous magnesium sulfate, filtered, and concentrated under reduced pressure. The concentrate was purified by column chromatography ($SiO_2$, 24 g cartridge; ethyl acetate/hexane=0% to 20%) and concentrated to obtain the title compound (1.200 9, 38.4%) as a beige solid.

[Step 5] Synthesis of tert-butyl 4-(N-((7-(5-(difluoromethyl)-1,3,4-oxadiazol-2-yl)imidazo[1,2-a]pyridin-2-yl)methyl)-N-phenylsulfamoyl)piperazine-1-carboxylate

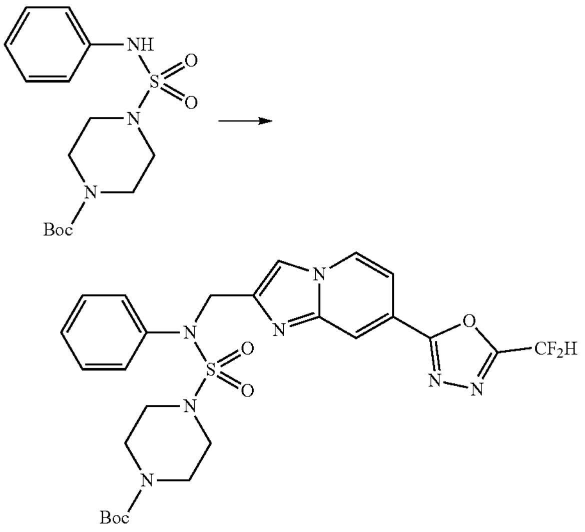

Tert-butyl 4-(N-phenylsulfamoyl)piperazine-1-carboxylate (0.300 g, 0.879 mmol) prepared in step 4, 2-(2-(chloromethyl)imidazo[1,2-a]pyridin-7-yl)-5-(difluoromethyl)-1,3,4-oxadiazole (0.300 g, 1.054 mmol) prepared in step 5 of Example 1, potassium carbonate (0.182 g, 1.318 mmol), and potassium iodide (0.073 g, 0.439 mmol) were dissolved in N, N-dimethylformamide (10 mL) at room temperature, and the resulting solution was stirred at the same temperature for 3 hours. A saturated aqueous ammonium chloride solution was poured into the concentrate obtained by removing the solvent from the reaction mixture under reduced pressure, followed by extraction with dichloromethane. The organic layer was washed with a saturated aqueous water solution, dried over anhydrous magnesium sulfate, filtered, and concentrated under reduced pressure. The concentrate was purified by column chromatography ($SiO_2$, 40 g cartridge; ethyl acetate/hexane=0% to 70%) and concentrated to obtain the title compound (0.450 g, 86.9%) as a white solid.

[Step 6] Synthesis of N-((7-(5-(difluoromethyl)-1,3,4-oxadiazol-2-yl)imidazo[1,2-a]pyridin-2-yl)methyl)-N-phenylpiperazine-1-sulfonamide

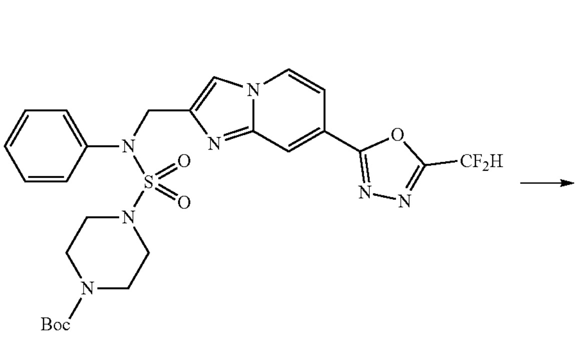

-continued

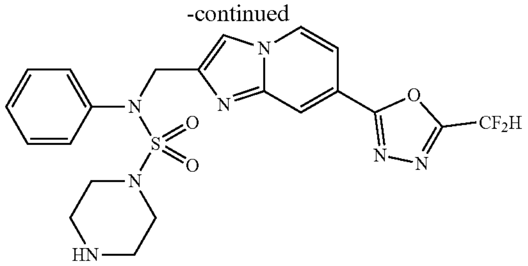

Tert-butyl 4-(N-((7-(5-(difluoromethyl)-1,3,4-oxadiazol-2-yl)imidazo[1,2-a]pyridin-2-yl)methyl)-N-phenylsulfamoyl)piperazine-1-carboxylate (0.470 g, 0.797 mmol) prepared in step 5, and trifluoroacetic acid (1.221 mL, 15.942 mmol) were dissolved in dichloromethane (10 mL) at room temperature, and the resulting solution was stirred at the same temperature for 3 hours. A saturated aqueous sodium hydrogen carbonate solution was poured into the reaction mixture, followed by extraction with dichloromethane. The organic layer was washed with a saturated aqueous water solution, dried over anhydrous magnesium sulfate, and filtered. After concentration under reduced pressure, the title compound (0.390 g, 100.0%) was obtained as a brown gel without further purification.

[Step 7] Synthesis of Compound 4256

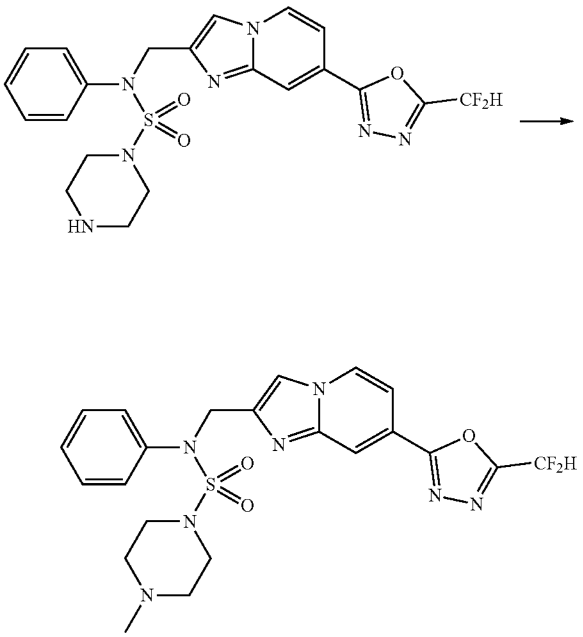

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6, formaldehyde (0.006 g, 0.204 mmol), acetic acid (0.006 mL, 0.102 mmol), and sodium triacetoxyborohydride (0.065 g, 0.306 mmol) were dissolved in dichloromethane (3 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.020 g, 38.9%) as a yellow solid.

$^1$H NMR (700 MHZ, $CDCl_3$) δ 8.30 (s, 1H), 8.23 (dd, J=7.1, 1.0 Hz, 1H), 7.76 (s, 1H), 7.54 (dd, J=7.1, 1.7 Hz, 1H), 7.48 (d, J=7.9 Hz, 2H), 7.36 (t, J=7.8 Hz, 2H), 7.30 (s, 1H), 6.95 (t, J=51.7 Hz, 1H), 5.11 (s, 2H), 3.39 (s, 4H), 2.71-2.28 (m, 7H);

LRMS (ES) m/z 504.3 ($M^+$+1).

Example 39: Synthesis of Compound 4257, N-((7-(5-(difluoromethyl)-1,3,4-oxadiazol-2-yl)imidazo[1,2-a]pyridin-2-yl)methyl)-4-ethyl-N-phenylpiperazine-1-sulfonamide

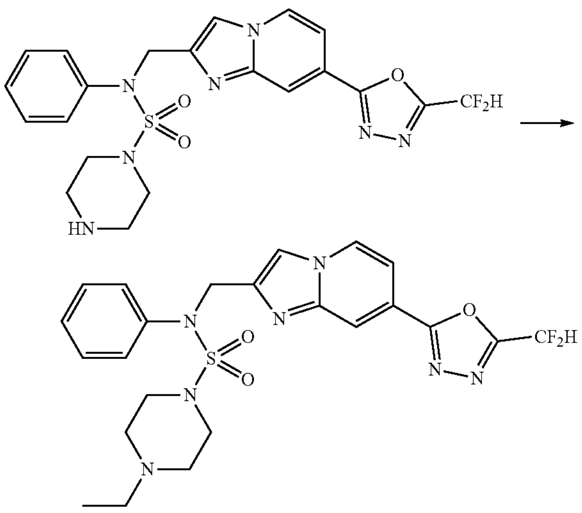

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, acetaldehyde (0.009 g, 0.204 mmol), acetic acid (0.006 mL, 0.102 mmol), and sodium triacetoxyborohydride (0.065 g, 0.306 mmol) were dissolved in dichloromethane (3 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.024 g, 45.4%) as a yellow solid.

$^1$H NMR (700 MHZ, $CDCl_3$) § 8.28 (d, J=1.7 Hz, 1H), 8.22 (dd, J=7.1, 1.0 Hz, 1H), 7.79 (s, 1H), 7.52 (dd, J=7.1, 1.7 Hz, 1H), 7.51-7.47 (m, 2H), 7.38-7.33 (m, 2H), 7.28-7.25 (m, 1H), 6.95 (t, J=51.7 Hz, 1H), 5.12 (s, 2H), 3.31 (s, 4H), 2.45 (s, 6H), 1.10 (s, 3H);

LRMS (ES) m/z 518.2 ($M^+$+1).

Example 40: Synthesis of Compound 4258, N-((7-(5-(difluoromethyl)-1,3,4-oxadiazol-2-yl)imidazo[1,2-a]pyridin-2-yl)methyl)-4-isopropyl-N-phenylpiperazine-1-sulfonamide

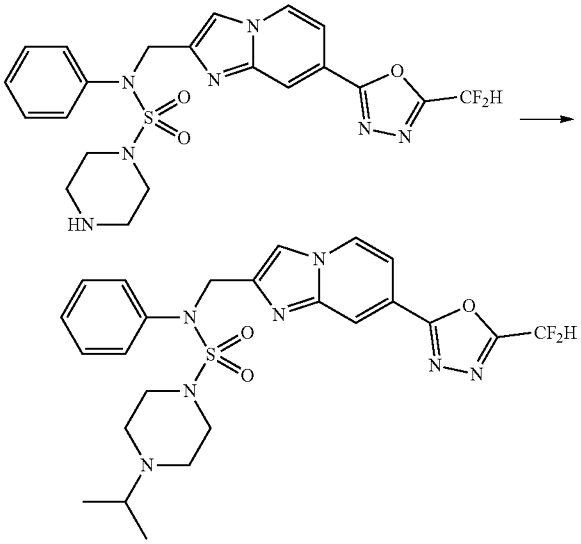

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, propan-2-one (0.012 g, 0.204 mmol), acetic acid (0.006 mL, 0.102 mmol), and sodium triacetoxyborohydride (0.065 g, 0.306 mmol) were dissolved in dichloromethane (3 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×mm; dichloromethane/methanol=0% to 10%) and concentrated to obtain the title compound (0.032 g, 58.9%) as a yellow solid.

$^1$H NMR (700 MHZ, $CDCl_3$) δ 8.28 (s, 1H), 8.22 (d, J=7.1 Hz, 1H), 7.80 (d, J=0.8 Hz, 1H), 7.52 (dd, J=7.1, 1.7 Hz, 1H), 7.51-7.48 (m, 2H), 7.35 (t, J=7.7 Hz, 2H), 7.28-7.25 (m, 1H), 7.03-6.86 (m, 1H), 5.12 (s, 2H), 3.27 (s, 4H), 2.70 (s, 1H), 2.48 (s, 4H), 1.02 (s, 6H);

LRMS (ES) m/z 532.3 ($M^+$+1).

Example 41: Synthesis of Compound 4259, N-((7-(5-(difluoromethyl)-1,3,4-oxadiazol-2-yl)imidazo[1,2-a]pyridin-2-yl)methyl)-4-(1-hydroxypropan-2-yl)-N-phenylpiperazine-1-sulfonamide

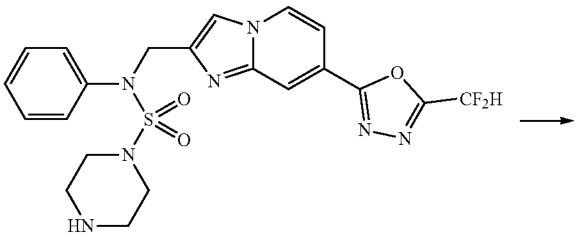

-continued

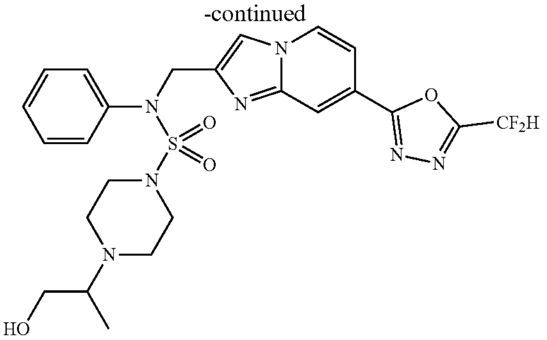

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, 1-hydroxypropan-2-one (0.015 g, 0.204 mmol), acetic acid (0.006 mL, 0.102 mmol), and sodium triacetoxyborohydride (0.065 g, 0.306 mmol) were dissolved in dichloromethane (3 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20:1 mm; dichloromethane/methanol=0% to 10%) and concentrated to obtain the title compound (0.019 g, 34.0%) as a yellow solid.

$^1$H NMR (400 MHz, $CDCl_3$) δ 8.28 (dt, J=1.7, 0.8 Hz, 1H), 8.21 (dd, J=7.1, 1.0 Hz, 1H), 7.76 (d, J=0.7 Hz, 1H), 7.52 (dd, J=7.1, 1.7 Hz, 1H), 7.51-7.46 (m, 2H), 7.39-7.32 (m, 2H), 7.30-7.25 (m, 1H), 6.95 (t, J=51.7 Hz, 1H), 5.11 (d, J=0.7 Hz, 2H), 3.45 (d, J=12.0 Hz, 1H), 3.41-3.20 (m, 5H), 2.85 (s, 1H), 2.66 (s, 2H), 2.44 (s, 2H), 0.92-0.87 (m, 3H);

LRMS (ES) m/z 548.3 ($M^+$+1).

Example 42: Synthesis of Compound 4260, 4-cyclobutyl-N-((7-(5-(difluoromethyl)-1,3,4-oxadiazol-2-yl)imidazo[1,2-a]pyridin-2-yl)methyl)-N-phenylpiperazine-1-sulfonamide

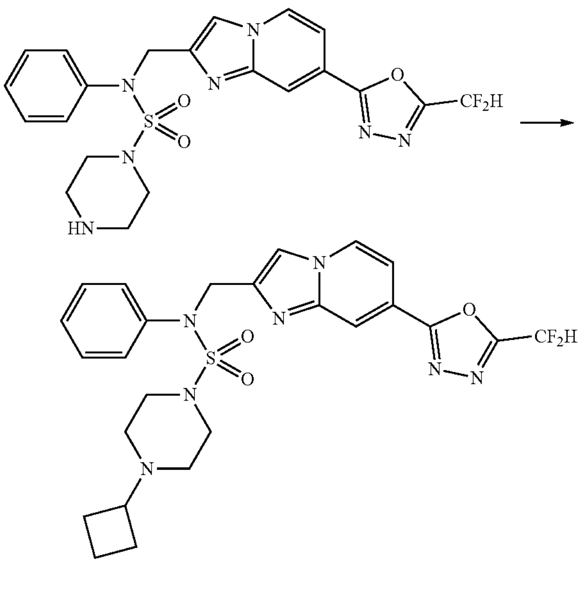

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, cyclobutanone (0.014 g, 0.204 mmol), acetic acid (0.006 mL, 0.102 mmol), and sodium triacetoxyborohydride (0.065 g, 0.306 mmol) were dissolved in dichloromethane (3 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then under reduced pressure. The concentrate was concentrated purified by chromatography ($SiO_2$ plate, 20×20×1 mm; dichloromethane/methanol=0% to 10%) and concentrated to obtain the title compound (0.022 g, 39.6%) as a yellow solid.

$^1$H NMR (700 MHZ, $CDCl_3$) δ 8.28 (s, 1H), 8.22 (d, J=7.1 Hz, 1H), 7.78 (s, 1H), 7.52 (dd, J=7.1, 1.7 Hz, 1H), 7.49 (d, J=7.9 Hz, 2H), 7.35 (t, J=7.7 Hz, 2H), 7.28-7.25 (m, 1H), 6.95 (t, J=51.7 Hz, 1H), 5.12 (s, 2H), 3.27 (s, 4H), 2.71 (s, 1H), 2.29 (s, 4H), 2.03 (s, 2H), 1.83 (s, 2H), 1.70 (s, 2H);

LRMS (ES) m/z 544.1 ($M^+$+1).

Example 43: Synthesis of Compound 4261, N-((7-(5-(difluoromethyl)-1,3,4-oxadiazol-2-yl)imidazo[1,2-a]pyridin-2-yl)methyl)-4-(oxetan-3-yl)-N-phenylpiperazine-1-sulfonamide

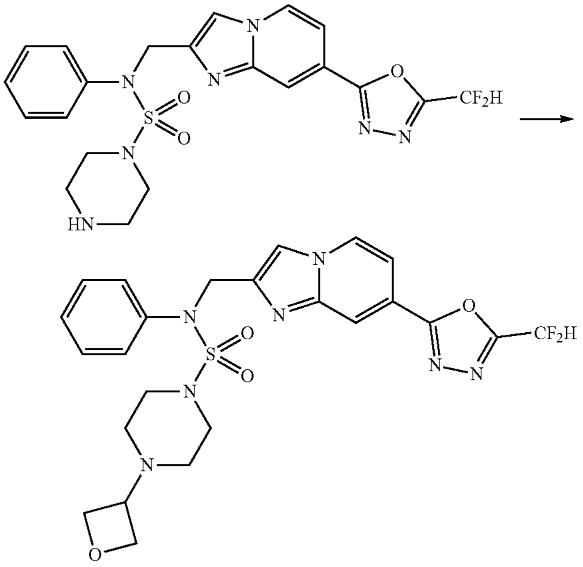

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, oxetan-3-one (0.015 g, 0.204 mmol), acetic acid (0.006 mL, 0.102 mmol), and sodium triacetoxyborohydride (0.065 g, 0.306 mmol) were dissolved in dichloromethane (3 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was 1 mm; purified by chromatography ($SiO_2$ plate, 20×20×dichloromethane/methanol=0% to 10%) and concentrated to obtain the title compound (0.022 g, 39.5%) as a yellow solid.

$^1$H NMR (700 MHZ, $CDCl_3$) δ 8.29 (s, 1H), 8.22 (dd, J=7.1, 1.0 Hz, 1H), 7.76 (s, 1H), 7.54 (dd, J=7.1, 1.7 Hz, 1H), 7.50-7.47 (m, 2H), 7.38-7.35 (m, 2H), 7.29 (s, 1H), 7.04-6.86 (m, 1H), 5.11 (s, 2H), 4.67 (t, J=6.5 Hz, 4H), 3.54 (s, 1H), 3.36 (s, 4H), 2.37 (s, 4H);

LRMS (ES) m/z 545.9 ($M^+$+1).

Example 44: Synthesis of Compound 4262, 4-cyclohexyl-N-((7-(5-(difluoromethyl)-1,3,4-oxadiazol-2-yl)imidazo[1,2-a]pyridin-2-yl)methyl)-N-phenylpiperazine-1-sulfonamide

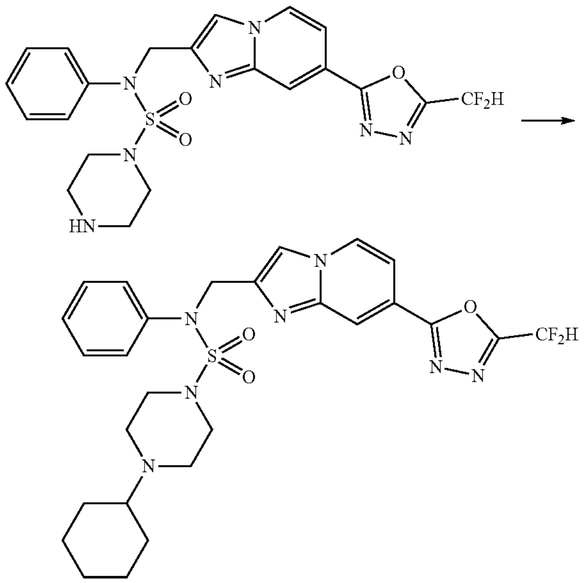

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, cyclohexanone (0.020 g, 0.204 mmol), acetic acid (0.006 mL, 0.102 mmol), and sodium triacetoxyborohydride (0.065 g, 0.306 mmol) were dissolved in dichloromethane (3 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography (SiOz plate, 20×20×1 mm; dichloromethane/methanol=0% to 10%) and concentrated to obtain the title compound (0.029 g, 49.7%) as a yellow solid.

$^1$H NMR (700 MHZ, $CDCl_3$) 0 8.28 (s, 1H), 8.24-8.20 (m, 1H), 7.80 (d, J=0.7 Hz, 1H), 7.53 (dd, J=7.1, 1.7 Hz, 1H), 7.49 (d, J=7.9 Hz, 2H), 7.35 (t, J=7.7 Hz, 2H), 7.28-7.24 (m, 1H), 6.95 (t, J=51.7 Hz, 1H), 5.12 (s, 2H), 3.25 (s, 4H), 2.53 (s, 4H), 2.31-2.20 (m, 1H), 1.80 (s, 4H), 1.17 (d, J=86.7 Hz, 6H);

LRMS (ES) m/z 572.2 ($M^+$+1).

Example 45: Synthesis of Compound 4263, N-((7-(5-(difluoromethyl)-1,3,4-oxadiazol-2-yl)imidazo[1,2-a]pyridin-2-yl)methyl)-N-phenyl-1-(tetrahydro-2H-pyran-4-yl)piperazine-1-sulfonamide

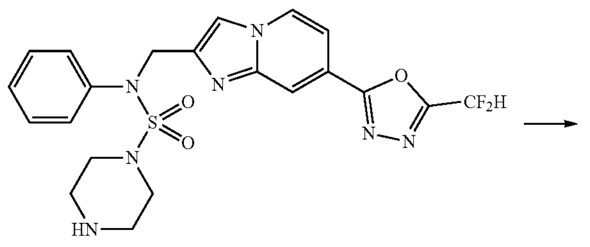

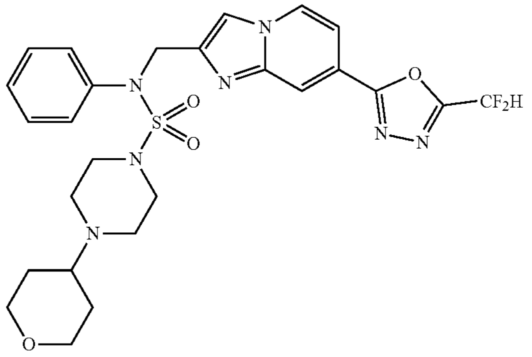

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, tetrahydro-4H-pyran-4-one (0.015 g, 0.153 mmol), acetic acid (0.006 mL, 0.102 mmol), sodium triacetoxyborohydride (0.065 g, 0.306 mmol), and triethylamine (0.014 mL, 0.102 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated, and then the obtained product was again purified by chromatography ($SiO_2$ plate, 20×20×1 mm; methanol/1%-dichloromethane aqueous solution=0% to 7%) and concentrated to obtain the title compound (0.017 g, 29.5%) as a white solid. $^1$H NMR (400 MHZ, $CDCl_3$) δ 8.27 (s, 1H), 8.21 (d, J=7.1 Hz, 1H), 7.77 (s, 1H), 7.55-7.45 (m, 3H), 7.35 (t, J=7.7 Hz, 2H), 7.26 (t, J=8.1 Hz, 1H), 6.95 (t, J=51.7 Hz, 1H), 5.12 (s, 2H), 4.02 (dd, J=4.3, 11.3 Hz, 2H), 3.36 (td, J=1.9, 11.9 Hz, 2H), 3.27 (t, J=4.9 Hz, 4H), 2.53 (t, J=4.9 Hz, 4H), 2.43 (d, J=12.9 Hz, 2H), 1.70 (d, J=12.7 Hz, 1H), 1.53 (qd, J=4.5, 12.0 Hz, 2H);

LRMS (ES) m/z 574.4 ($M^+$+1).

Example 46: Synthesis of Compound 4264, 4-14,4-difluorocyclohexyl)-N-((7-(5-(difluoromethyl)-1,3,4-oxadiazol-2-yl)imidazo[1,2-a]pyridin-2-yl)methyl)-N-phenylpiperazine-1-sulfonamide

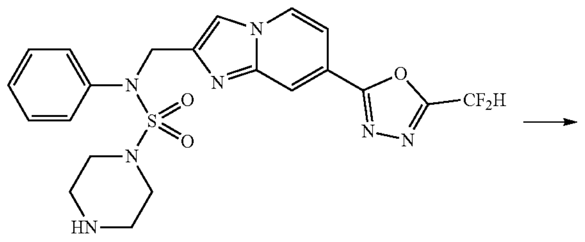

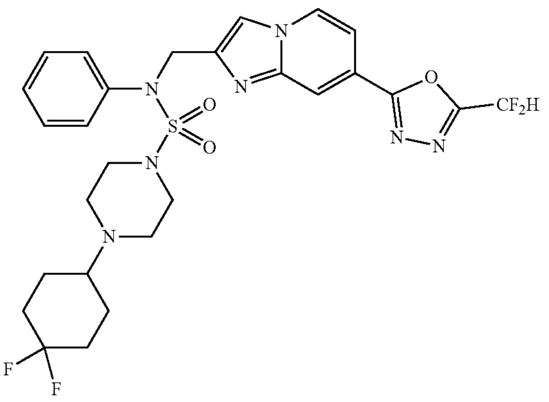

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, 4, 4-difluorocyclohexan-1-one (0.021 g, 0.153 mmol), acetic acid (0.006 mL, 0.102 mmol), sodium triacetoxyborohydride (0.065 g, 0.306 mmol), and triethylamine (0.014 mL, 0.102 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated, and then the obtained product was again purified by chromatography ($SiO_2$ plate, 20×20×1 mm; methanol/1%-dichloromethane aqueous solution=0% to 7%) and concentrated to obtain the title compound (0.011 g, 18.2%) as a white solid.

$^1$H NMR (400 MHZ, $CDCl_3$) δ 8.27 (s, 1H), 8.21 (d, J=7.1 Hz, 1H), 7.77 (s, 1H), 7.50 (ddd, J=1.7, 7.5, 13.0 Hz, 3H), 7.35 (dd, J=6.9, 8.6 Hz, 2H), 7.26 (d, J=7.4 Hz, 1H), 6.95 (t, J=51.7 Hz, 1H), 5.11 (s, 2H), 3.25 (s, 4H), 2.51 (s, 4H), 2.39 (s, 1H), 2.13 (d, J=10.7 Hz, 2H), 1.83-1.53 (m, 6H);

LRMS (ES) m/z 608.5 ($M^+$+1).

Example 47: Synthesis of Compound 4265, 4-acetyl-N-((7-(5-(difluoromethyl)-1,3,4-oxadiazol-2-yl)imidazo[1,2-a]pyridin-2-yl)methyl)-N-phenylpiperazine-1-sulfonamide

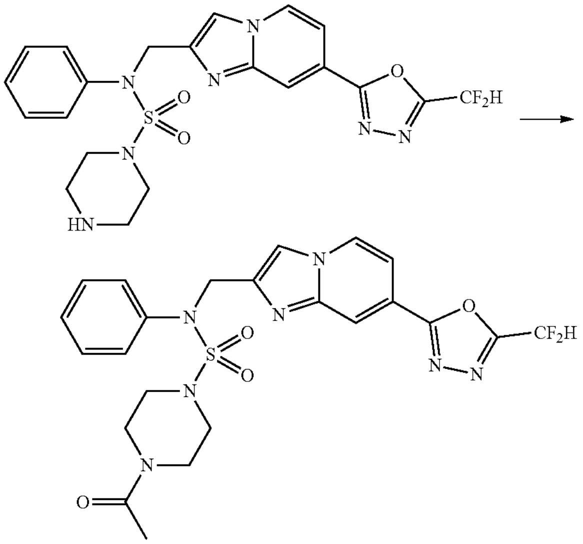

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, acetyl chloride (0.011 mL, 0.153 mmol), and triethylamine (0.043 mL, 0.306 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by column chromatography ($SiO_2$, 4 g cartridge; methanol/dichloromethane=0% to 5%) and concentrated to obtain the title compound (0.024 g, 43.5%) as a white solid.

$^1H$ NMR (400 MHZ, $CDCl_3$) 0 8.29 (dd, J=0.9, 1.8 Hz, 1H), 8.21 (dd, J=1.0, 7.1 Hz, 1H), 7.73 (s, 1H), 7.53 (dd, J=1.7, 7.1 Hz, 1H), 7.49-7.43 (m, 2H), 7.36 (ddd, J=1.4, 6.8, 7.8 Hz, 2H), 7.31-7.26 (m, 1H), 6.95 (t, J=51.7 Hz, 1H), 5.08 (s, 2H), 3.59 (t, J=5.2 Hz, 2H), 3.42 (t, J=5.1 Hz, 2H), 3.22 (dt, J=5.2, 10.9 Hz, 4H), 2.08 (s, 3H);

LRMS (ES) m/z 532.4 ($M^+$+1).

Example 48: Synthesis of Compound 4266, N-((7-(5-(difluoromethyl)-1,3,4-oxadiazol-2-yl)imidazo[1,2-a]pyridin-2-yl)methyl)-N-phenyl-4-propionylpiperazine-1-sulfonamide

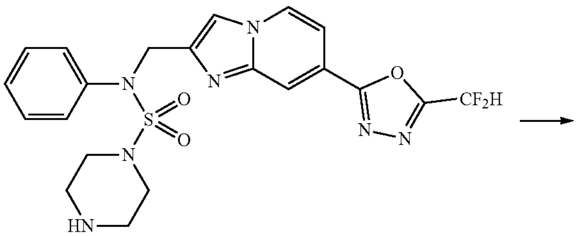

-continued

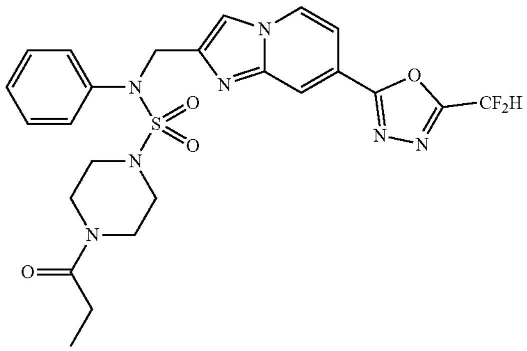

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, propionyl chloride (0.014 g, 0.153 mmol), and triethylamine (0.043 mL, 0.306 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then was concentrated under reduced pressure. The concentrate purified by chromatography ($SiO_2$ plate, 20x20x 1 mm; methanol/dichloromethane=0% to 7%) and concentrated to obtain the title compound (0.017 g, 30.9%) as a white solid.

$^1H$ NMR (400 MHZ, $CDCl_3$)>8.28 (dt, J=0.8, 1.7 Hz, 1H), 8.21 (dd, J=1.0, 7.1 Hz, 1H), 7.73 (d, J=0.7 Hz, 1H), 7.53 (dd, J=1.7, 7.2 Hz, 1H), 7.50-7.42 (m, 2H), 7.40-7.24 (m, 3H), 6.95 (t, J=51.7 Hz, 1H), 5.11-5.06 (m, 2H), 3.60 (t, J=5.2 Hz, 2H), 3.42 (t, J=5.1 Hz, 2H), 3.22 (q, J=5.6 Hz, 4H), 2.32 (q, J=7.4 Hz, 2H), 1.14 (t, J=7.4 Hz, 3H);

LRMS (ES) m/z 546.0 ($M^+$+1).

Example 49: Synthesis of Compound 4267, N-((7-(5-(difluoromethyl)-1,3,4-oxadiazol-2-yl)imidazo[1,2-a]pyridin-2-yl)methyl)-4-(2-hydroxyacetyl)-N-phenylpiperazine-1-sulfonamide

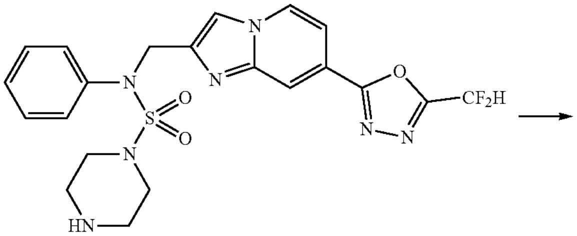

-continued

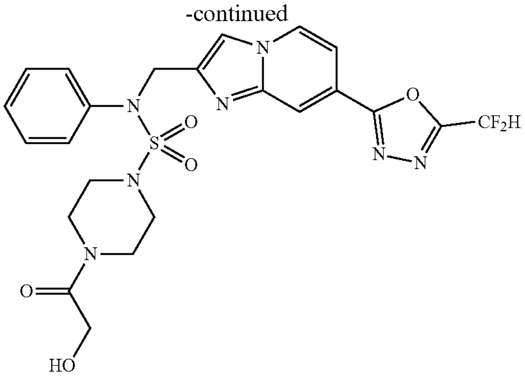

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, 2-hydroxyacetic acid (0.012 g, 0.153 mmol), 1-[bis(dimethylamino)methylene]-1H-1,2, 3-triazolo[4, 5-b]pyridinium 3-oxide hexafluorophosphate (HATU, 0.058 g, 0.153 mmol), and triethylamine (0.043 mL, 0.306 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.017 g, 30.9%) as a white solid.

$^1H$ NMR (400 MHZ, $CDCl_3$) δ 8.29 (dt, J=1.7, 0.8 Hz, 1H), 8.21 (dd, J=7.1, 1.0 Hz, 1H), 7.70 (s, 1H), 7.54 (dd, J=7.1, 1.7 Hz, 1H), 7.48-7.42 (m, 2H), 7.40-7.33 (m, 2H), 7.32-7.28 (m, 1H), 6.96 (t, J=51.7 Hz, 1H), 5.07 (s, 2H), 4.15 (s, 2H), 3.66 (t, J=5.2 Hz, 2H), 3.26 (d, J=6.5 Hz, 6H);

LRMS (ES) m/z 546.0 ($M^+$+1).

Example 50: Synthesis of Compound 4268, 4-(cyclobutanecarbonyl)-N-((7-(5-(difluoromethyl)-1,3,4-oxadiazol-2-yl)imidazo[1,2-a]pyridine-2-yl)methyl)-N-phenylpiperazine-1-sulfonamide -continued

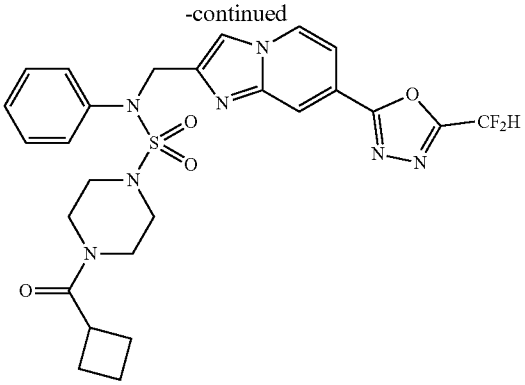

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, cyclobutanecarbonyl chloride (0.018 g, 0.153 mmol), and triethylamine (0.043 mL, 0.306 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated, and then the obtained product was again purified by chromatography ($SiO_2$ plate, 20×20×1 mm; methanol/1%-dichloromethane aqueous solution=0% to 7%) and concentrated to obtain the title compound (0.010 g, 17.6%) as a white solid.

$^1H$ NMR (400 MHZ, $CDCl_3$) 0 8.30 (s, 1H), 8.22 (dd, J=0.9, 7.1 Hz, 1H), 7.73 (s, 1H), 7.55 (dd, J=1.7, 7.2 Hz, 1H), 7.46 (dd, J=1.8, 7.5 Hz, 2H), 7.35 (t, J=7.7 Hz, 2H), 7.29 (d, J=7.6 Hz, 1H), 6.95 (t, J=51.7 Hz, 1H), 5.09 (s, 2H), 3.59 (t, J=5.1 Hz, 2H), 3.31 (t, J=5.0 Hz, 2H), 3.20 (ddd, J=3.1, 5.5, 10.8 Hz, 5H), 2.33 (dq, J=9.1, 11.5 Hz, 2H), 2.14 (qd, J=4.6, 8.8 Hz, 2H), 2.03-1.81 (m, 2H);

LRMS (ES) m/z 571.9 ($M^+$+1).

Example 51: Synthesis of Compound 4269, N-((7-(5-(difluoromethyl)-1,3,4-oxadiazol-2-yl)imidazo[1,2-a]pyridin-2-yl)methyl)-4-(oxetan-3-carbonyl)-N-phenylpiperazine-1-sulfonamide

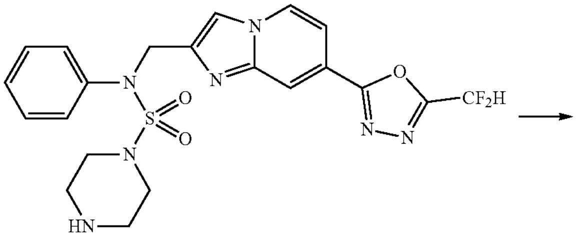

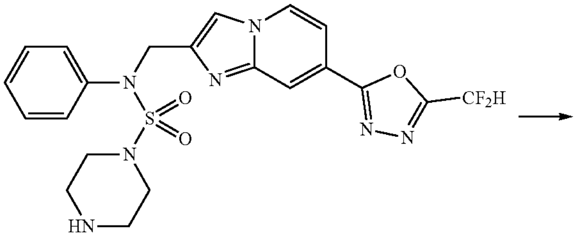

-continued

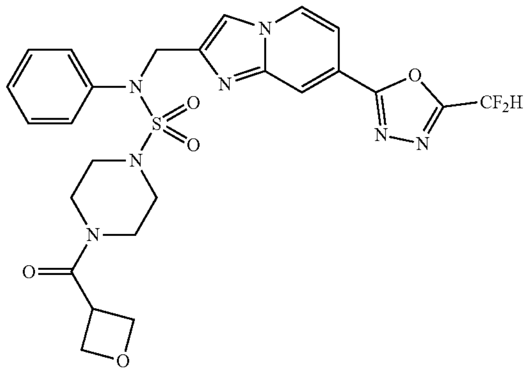

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, oxetane-3-carboxylic acid (0.016 g, 0.153 mmol), 1-[bis(dimethylamino)methylene]-1H-1,2, 3-triazolo[4, 5-b]pyridinium 3-oxide hexafluorophosphate (HATU, 0.058 g, 0.153 mmol), and triethylamine (0.043 mL, 0.306 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by column chromatography ($SiO_2$ plate, 4 g cartridge; methanol/dichloromethane=0% to 5%) and concentrated, and then the obtained product was again purified by chromatography ($SiO_2$ plate, 20×20×1 mm; methanol/1%-dichloromethane aqueous solution=0% to 7%) and concentrated to obtain the title compound (0.006 g, 10.2%) as a white solid. $^1H$ NMR (400 MHZ, $CDCl_3$) δ 8.32 (s, 1H), 8.22 (dd, J=0.9, 7.2 Hz, 1H), 7.71 (s, 1H), 7.56 (dd, J=1.7, 7.2 Hz, 1H), 7.49-7.42 (m, 2H), 7.40-7.33 (m, 2H), 7.35-7.27 (m, 1H), 6.96 (t, J=51.7 Hz, 1H), 5.08 (s, 2H), 4.89 (dd, J=5.9, 7.1 Hz, 2H), 4.79 (dd, J=5.9, 8.7 Hz, 2H), 3.97 (tt, J=7.0, 8.7 Hz, 1H), 3.64 (t, J=5.2 Hz, 2H), 3.28-3.10 (m, 6H);

LRMS (ES) m/z 574.1 ($M^+$+1).

Example 52: Synthesis of Compound 4270, N-((7-(5-(difluoromethyl)-1,3,4-oxadiazol-2-yl)imidazo[1,2-a]pyridin-2-yl)methyl)-N-phenyl-4-(2,2, 2-trifluoroacetyl)piperazine-1-sulfonamide

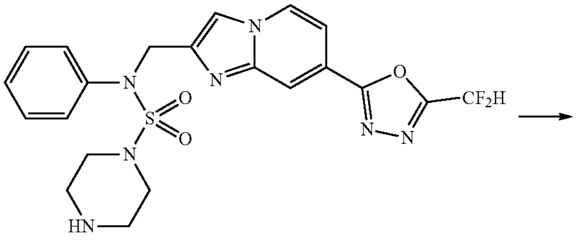

-continued

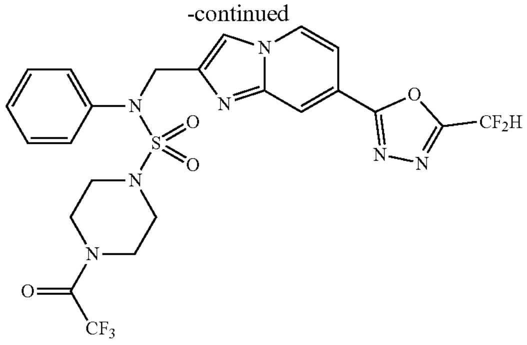

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, 2,2, 2-trifluoroacetic anhydride (0.026 g, 0.123 mmol), and triethylamine (0.043 mL, 0.306 mmol) were dissolved in dichloromethane (1 mL) at room temperature, and the resulting solution was stirred at the same temperature for 18 hours. An through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.021 g, 35.3%) as a yellow solid. $^1H$ NMR (400 MHZ, $CDCl_3$) δ 8.29 (dd, J=1.0, 1.9 Hz, 1H), 8.21 (dd, J=1.0, 7.1 Hz, 1H), 7.69 (s, 1H), 7.55 (dd, J=1.7, 7.1 Hz, 1H), 7.49-7.26 (m, 5H), 6.96 (t, J=51.7 Hz, 1H), 5.07 (s, 2H), 3.71-3.64 (m, 2H), 3.59 (t, J=5.0 Hz, 2H), 3.37-3.29 (m, 4H);

LRMS (ES) m/z 585.8 ($M^+$+1).

Example 53: Synthesis of Compound 4271, N-((7-(5-(difluoromethyl)-1,3,4-oxadiazol-2-yl)imidazo[1,2-a]pyridin-2-yl)methyl)-4-(methylsulfonyl)-N-phenylpiperazine-1-sulfonamide

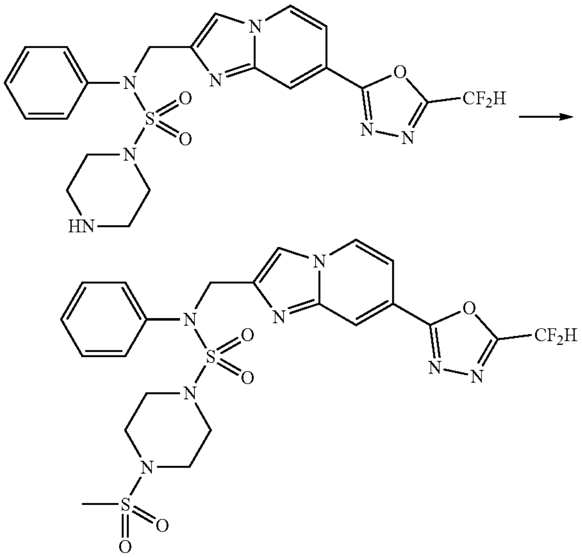

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, methanesulfonyl chloride (0.012 mL, 0.153 mmol), and triethylamine (0.043 mL, 0.306 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated, and then the obtained product was again purified by chromatography ($SiO_2$ plate, 20×20×1 mm; methanol/1%-dichloromethane aqueous solution=0% to 5%) and concentrated to obtain the title compound (0.002 g, 2.9%) as a yellow solid.

$^1$H NMR (400 MHZ, $CDCl_3$) δ 8.37 (s, 1H), 8.25 (d, J=7.0 Hz, 1H), 7.74 (s, 1H), 7.62 (d, J=6.9 Hz, 1H), 7.49 (d, J=7.8 Hz, 2H), 7.39 (t, J=7.6 Hz, 2H), 7.33 (d, J=7.2 Hz, 1H), 7.10-6.82 (m, 1H), 5.12 (s, 2H), 3.41-3.29 (m, 4H), 3.22 (t, J=5.0 Hz, 4H), 2.78 (s, 3H);

LRMS (ES) m/z 567.9 ($M^+$+1).

Example 54: Synthesis of Compound 4272, methyl 4-(N-((7-(5-(difluoromethyl)-1,3,4-oxadiazol-2-yl) imidazo[1,2-a]pyridin-2-yl)methyl)-N-phenylsulfamoyl)piperazine-1-carboxylate

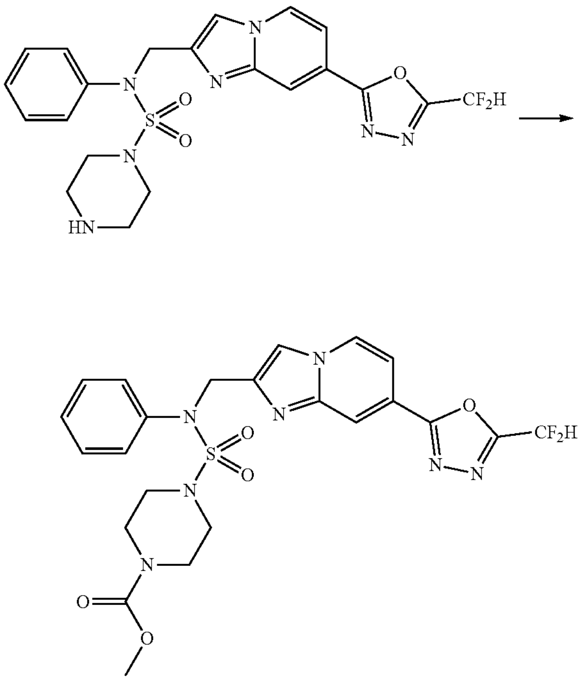

N-((7-(5-(difluoromethyl)-1,3,4-oxadiazol-2-yl)imidazo [1,2-a]pyridin-2-yl)methyl)-N-phenylpiperazine-1-sulfonamide (0.050 g, 0.102 mmol) prepared in step 6 of Example 38, methyl carbonochloridate (0.014 g, 0.153 mmol), and triethylamine (0.043 mL, 0.306 mmol) were dissolved in dichloromethane (1 mL) at room temperature, and the resulting solution was stirred at the same temperature for 18 hours. An through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.012 g, 21.8%) as a white solid. $^1$H NMR (400 MHZ, $CDCl_3$) δ 8.29 (dt, J=0.9, 1.8 Hz, 1H), 8.22 (dd, J=1.0, 7.2 Hz, 1H), 7.74 (d, J=0.7 Hz, 1H), 7.54 (dd, J=1.7, 7.1 Hz, 1H), 7.51-7.43 (m, 2H), 7.41-7.31 (m, 2H), 7.29 (d, J=7.1 Hz, 1H), 6.95 (t, J=51.7 Hz, 1H), 5.10 (d, J=0.7 Hz, 2H), 3.71 (s, 3H), 3.45 (t, J=5.1 Hz, 4H), 3.20 (t, J=5.1 Hz, 4H);

LRMS (ES) m/z 547.8 ($M^+$+1).

Example 55: Synthesis of Compound 4273,4—(N-((7-(5-(difluoromethyl)-1,3,4-oxadiazol-2-yl)imidazo[1,2-a]pyridin-2-yl)methyl)-N-phenylsulfamoyl)-N, N-dimethylpiperazine-1-carboxamide

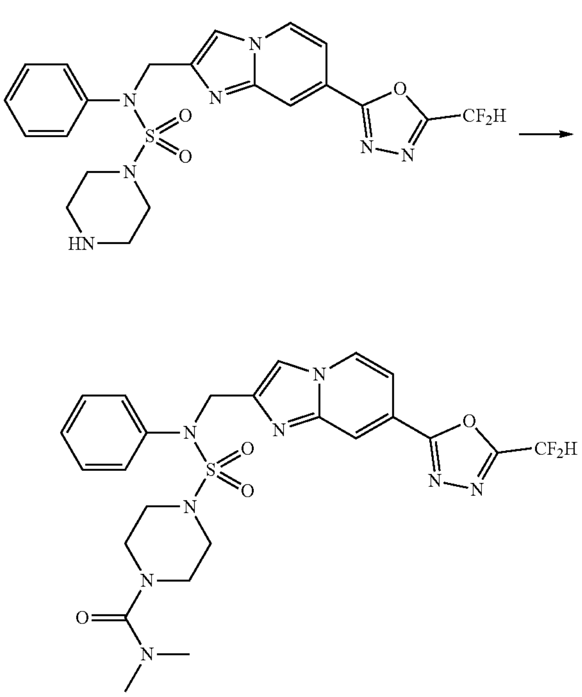

N-((7-(5-(difluoromethyl)-1,3,4-oxadiazol-2-yl)imidazo [1,2-a]pyridin-2-yl)methyl)-N-phenylpiperazine-1-sulfonamide (0.050 g, 0.102 mmol) prepared in step 6 of Example 38, dimethylcarbamic chloride (0.016 g, 0.153 mmol), and triethylamine (0.043 mL, 0.306 mmol) were dissolved in dichloromethane (1 mL) at room temperature, and the resulting solution was stirred at the same temperature for 18 hours. An through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.020 g, 35.3%) as a white solid. $^1$H NMR (400 MHZ, $CDCl_3$) δ 8.27 (dt, J=0.8, 1.7 Hz, 1H), 8.21 (dd, J=1.0, 7.2 Hz, 1H), 7.74 (s, 1H), 7.51 (dd, J=1.7, 7.2 Hz, 1H), 7.48-7.42 (m, 2H), 7.39-7.29 (m, 2H), 7.34-7.22 (m, 1H), 6.95 (t, J=51.7 Hz, 1H), 5.09 (s, 2H), 3.29-3.15 (m, 8H), 2.82 (s, 6H);

LRMS (ES) m/z 547.8 ($M^+$+1).

Example 56: Synthesis of Compound 4274, N-((7-(5-(difluoromethyl)-1,3,4-oxadiazol-2-yl)imidazo[1,2-a]pyridin-2-yl)methyl)-N-phenyl-4-(pyridin-2-yl)piperazine-1-sulfonamide

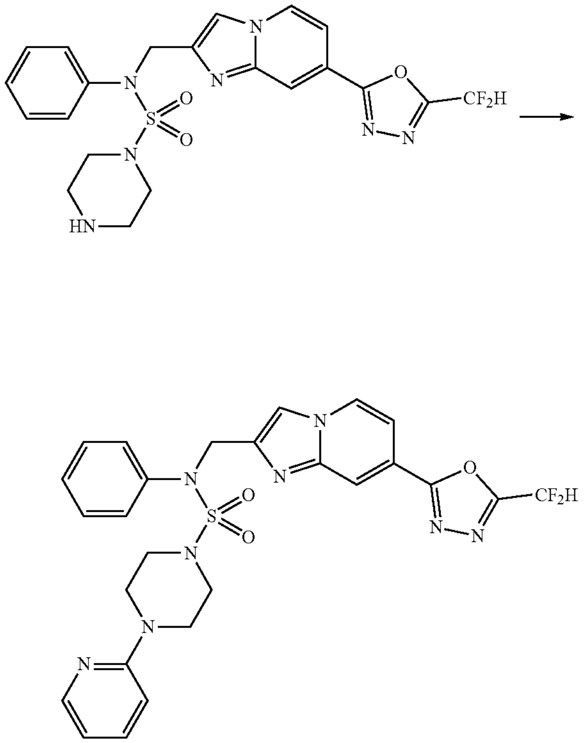

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, 2-chloropyridine (0.032 g, 0.204 mmol), RuPhos palladium G2 (0.004 g, 0.005 mmol), and cesium carbonate (0.067 g, 0.204 mmol) were dissolved in 1,4-dioxane (1 mL) at room temperature, and the resulting solution was stirred at 120° C. for 18 hours. Then, the temperature was lowered to room temperature to terminate the reaction. An aqueous sodium hydrogen carbonate solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.003 g, 5.7%) as a white solid.

$^1H$ NMR (400 MHZ, $CDCl_3$) δ 8.27 (dd, J=1.7, 0.9 Hz, 1H), 8.24-8.18 (m, 2H), 7.77 (d, J=0.7 Hz, 1H), 7.55-7.47 (m, 4H), 7.38-7.30 (m, 2H), 7.27-7.23 (m, 1H), 6.95 (t, J=51.7 Hz, 1H), 6.71-6.60 (m, 2H), 5.13 (s, 2H), 3.53 (q, J=4.6, 4.0 Hz, 4H), 3.35 (dd, J=6.4, 3.9 Hz, 4H);

LRMS (ES) m/z 567.5 ($M^+$+1).

Example 57: Synthesis of Compound 4275, N-((7-(5-(difluoromethyl)-1,3,4-oxadiazol-2-yl)imidazo[1,2-a]pyridin-2-yl)methyl)-N-phenyl-4-(pyrimidin-2-yl)piperazine-1-sulfonamide

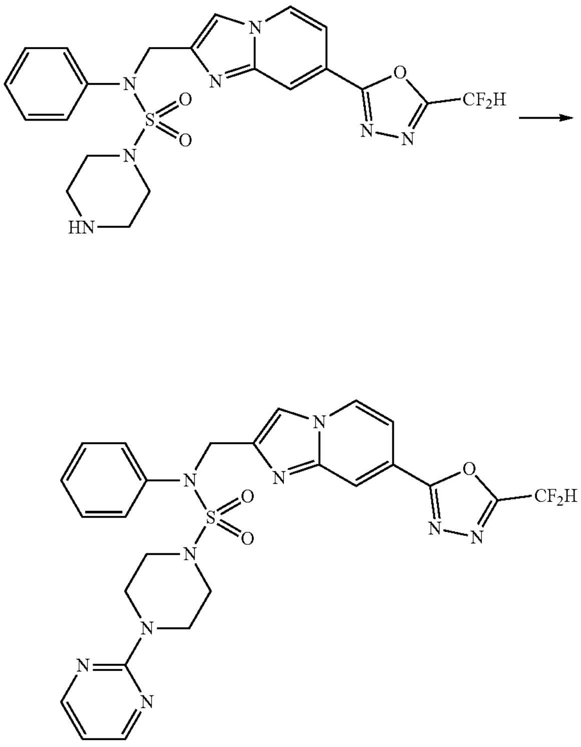

N-((7-(5-(difluoromethyl)-1,3,4-oxadiazol-2-yl)imidazo[1,2-a]pyridin-2-yl)methyl)-N-phenylpiperazine-1-sulfonamide (0.050 g, 0.102 mmol) prepared in step 6 of Example 38, 2-chloropyrimidine (0.023 g, 0.204 mmol), and potassium carbonate (0.042 g, 0.306 mmol) were dissolved in N,N-dimethylformamide (0.5 mL)/acetonitrile (0.5 mL) at room temperature, and the resulting solution was stirred at the same temperature for 18 hours. An aqueous sodium hydrogen carbonate solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.023 g, 39.2%) as a white solid. $^1H$ NMR (400 MHZ, $CDCl_3$) δ 8.31 (d, J=4.7 Hz, 2H), 8.28-8.25 (m, 1H), 8.21 (dd, J=1.0, 7.1 Hz, 1H), 7.77 (s, 1H), 7.55-7.47 (m, 3H), 7.37-7.31 (m, 2H), 7.28-7.23 (m, 1H), 6.95 (t, J=51.7 Hz, 1H), 6.54 (t, J=4.7 Hz, 1H), 5.12 (s, 2H), 3.83-3.77 (m, 4H), 3.32-3.23 (m, 4H);

LRMS (ES) m/z 568.0 ($M^+$+1).

Example 58: Synthesis of Compound 4297, N-((7-(5-(difluoromethyl)-1,3,4-oxadiazol-2-yl)imidazo[1,2-a]pyridin-2-yl)methyl)-N-(3-fluorophenyl)-4-methylpiperazine-1-sulfonamide

[Step 1] Synthesis of tert-butyl 4-(N-(3-fluorophenyl)sulfamoyl)piperazine-1-carboxylate

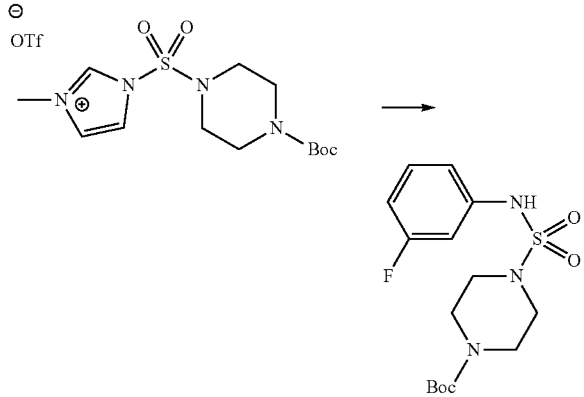

1-((4-(Tert-butoxycarbonyl)piperazine-1-yl)sulfonyl)-3-methyl-1H-imidazol-3-ium trifluoromethanesulfonate (4.400 g, 9.158 mmol) prepared in step 3 of Example 38 and 3-fluoroaniline (1.221 g, 10.989 mmol) were dissolved in acetonitrile (50 mL) at room temperature, and the resulting solution was heated to reflux for 18 hours. Then, the temperature was lowered to room temperature to terminate the reaction. A saturated aqueous ammonium chloride solution was poured into the concentrate obtained by removing the solvent from the reaction mixture under reduced pressure, followed by extraction with dichloromethane. The organic layer was washed with a saturated aqueous water solution, dried over anhydrous magnesium sulfate, filtered, and concentrated under reduced pressure. The concentrate was purified by column chromatography ($SiO_2$, 24 g cartridge; ethyl acetate/hexane=0% to 20%) and concentrated to obtain the title compound (2.400 g, 72.9%) as a beige solid.

[Step 2] Synthesis of tert-butyl 4-(N-((7-(5-(difluoromethyl)-1,3,4-oxadiazol-2-yl)imidazo[1,2-a]pyridin-2-yl)methyl)-N-(3-fluorophenyl)sulfamoyl)piperazine-1-carboxylate

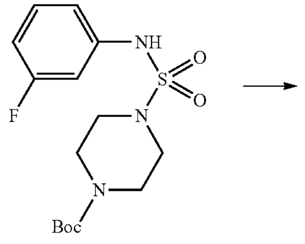

-continued

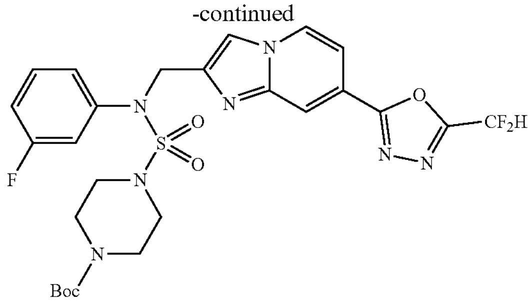

Tert-butyl 4-(N-(3-fluorophenyl)sulfamoyl)piperazine-1-carboxylate (0.300 g, 0.835 mmol) prepared in step 1,2-(2-(chloromethyl)imidazo[1,2-a]pyridin-7-yl)-5-(difluoromethyl)-1, 3,4-oxadiazole (0.285 g, 1.002 mmol) prepared in step 5 of Example 1, potassium carbonate (0.173 g, 1.252 mmol), and potassium iodide (0.069 g, 0.417 mmol) were dissolved in N, N-dimethylformamide (10 mL) at room temperature, and the resulting solution was stirred at the same temperature for 3 hours. A saturated aqueous ammonium chloride solution was poured into the concentrate obtained by removing the solvent from the reaction mixture under reduced pressure, followed by extraction with dichloromethane. The organic layer was washed with a saturated aqueous water solution, dried over anhydrous magnesium sulfate, filtered, and concentrated under reduced pressure. The concentrate was purified by column chromatography ($SiO_2$, 40 g cartridge; ethyl acetate/hexane=0% to 70%) and concentrated to obtain the title compound (0.400 g, 78.9%) as a white solid.

[Step 3] Synthesis of N-((7-(5-(difluoromethyl)-1,3,4-oxadiazol-2-yl)imidazo[1,2-a]pyridin-2-yl)methyl)-N-(3-fluorophenyl)piperazine-1-sulfonamide

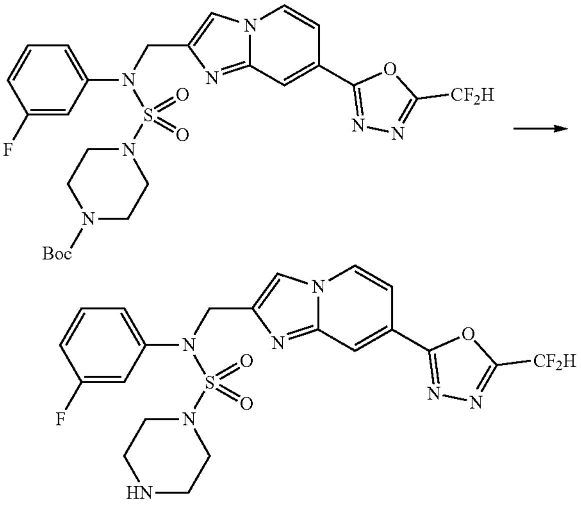

Tert-butyl 4-(N-((7-(5-(difluoromethyl)-1,3,4-oxadiazol-2-yl)imidazo[1,2-a]pyridin-2-yl)methyl)-N-(3-fluorophenyl)sulfamoyl)piperazine-1-carboxylate (0.450 g, 0.741 mmol) prepared in step 2 and trifluoroacetic acid (1.134 mL, 4.812 mmol) were dissolved in dichloromethane (10 mL) at room temperature, and the resulting solution was stirred at the same temperature for 3 hours. A saturated aqueous sodium hydrogen carbonate solution was poured into the reaction mixture, followed by extraction with dichloromethane. The organic layer was washed with a saturated aqueous water solution, dried over anhydrous magnesium sulfate, and filtered. After concentration under reduced pressure, the title compound (0.376 g, 100.0%) was obtained as a brown gel without further purification.

[Step 4] Synthesis of Compound 4297

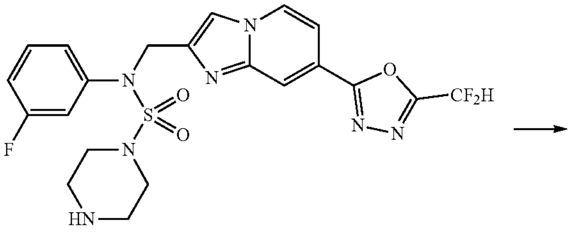

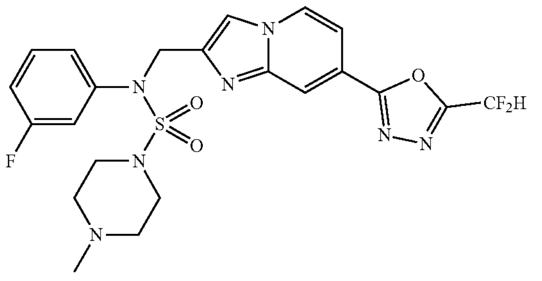

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3, formaldehyde (0.006 g, 0.197 mmol), acetic acid (0.006 mL, 0.099 mmol), and sodium triacetoxyborohydride (0.063 g, 0.296 mmol) were dissolved in dichloromethane (3 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20x20x1 mm; dichloromethane/methanol=0% to 10%) and concentrated to obtain the title compound (0.024 g, 46.7%) as a yellow solid.

$^1$H NMR (700 MHZ, $CDCl_3$) δ 8.31 (s, 1H), 8.24 (dd, J=7.1, 1.0 Hz, 1H), 7.77 (s, 1H), 7.55 (dd, J=7.1, 1.7 Hz, 1H), 7.35-7.28 (m, 3H), 7.05-6.84 (m, 2H), 5.09 (s, 2H), 3.38 (s, 4H), 2.39 (s, 7H);

LRMS (ES) m/z 523.1 ($M^+$+1).

Example 59: Synthesis of Compound 4298, N-((7-(5-(difluoromethyl)-1,3,4-oxadiazol-2-yl)imidazo[1,2-a]pyridin-2-yl)methyl)-4-ethyl-N-(3-fluorophenyl)-piperazine-1-sulfonamide

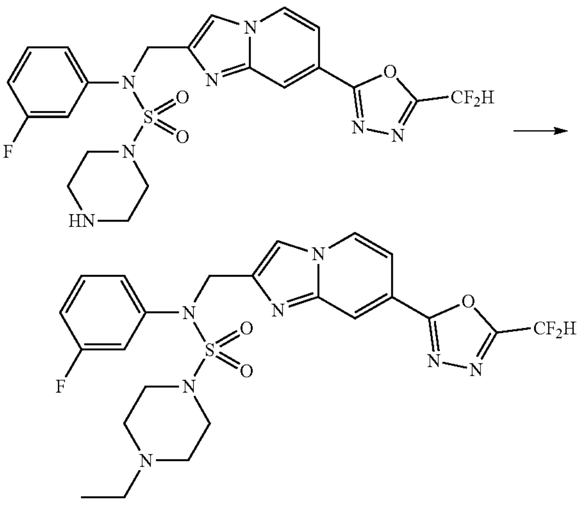

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, acetaldehyde (0.009 g, 0.197 mmol), acetic acid (0.006 mL, 0.099 mmol), and sodium triacetoxyborohydride (0.063 g, 0.296 mmol) were dissolved in dichloromethane (3 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20x20x1 mm; dichloromethane/methanol=0% to 10%) and concentrated to obtain the title compound (0.019 g, 36.0%) as a yellow solid.

$^1$H NMR (700 MHZ, $CDCl_3$) δ 8.30 (s, 1H), 8.26-8.22 (m, 1H), 7.79-7.76 (m, 1H), 7.55 (dd, J=7.1, 1.7 Hz, 1H), 7.34-7.29 (m, 3H), 7.06-6.84 (m, 2H), 5.10 (s, 2H), 3.32 (s, 4H), 2.46 (s, 6H), 1.12 (s, 3H);

LRMS (ES) m/z 536.3 ($M^+$+1).

Example 60: Synthesis of 41 Compound 4299, N-((7-(5-(difluoromethyl)-1,3,4-oxadiazol-2-yl)imidazo[1,2-a]pyridin-2-yl)methyl)-N-(3-fluorophenyl)-4-isopropylpiperazine-1-sulfonamide

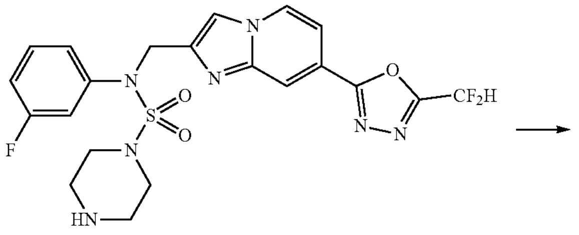

-continued

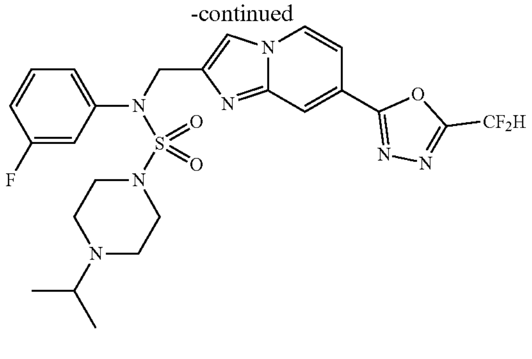

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, propan-2-one (0.011 g, 0.197 mmol), acetic acid (0.006 mL, 0.099 mmol), and sodium triacetoxyborohydride (0.063 g, 0.296 mmol) were dissolved in dichloromethane (3 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.024 g, 44.3%) as a yellow solid.

$^1$H NMR (700 MHZ, $CDCl_3$) δ 8.31-8.28 (m, 1H), 8.25-8.21 (m, 1H), 7.79 (d, J=0.8 Hz, 1H), 7.54 (dd, J=7.1, 1.7 Hz, 1H), 7.34-7.28 (m, 3H), 7.04-6.80 (m, 2H), 5.11 (s, 2H), 3.27 (s, 4H), 2.71 (s, 1H), 2.49 (s, 4H), 1.03 (s, 6H);

LRMS (ES) m/z 549.9 ($M^+$+1).

Example 61: Synthesis of Compound 4300, N-((7-(5-(difluoromethyl)-1,3,4-oxadiazol-2-yl)imidazo[1,2-a]pyridin-2-yl)methyl)-N-(3-fluorophenyl)-4-(1-hydroxypropan-2-yl)piperazine-1-sulfonamide

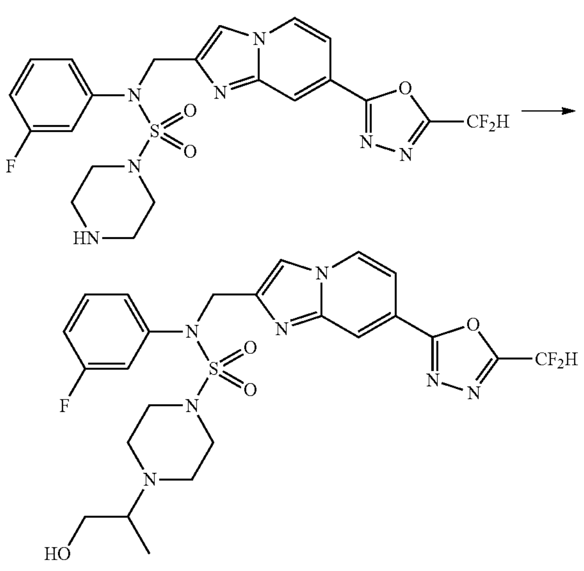

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, 1-hydroxypropan-2-one (0.015 g, 0.197 mmol), acetic acid (0.006 mL, 0.099 mmol), and sodium triacetoxyborohydride (0.063 g, 0.296 mmol) were dissolved in dichloromethane (3 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.032 g, 57.4%) as a yellow solid.

$^1$H NMR (400 MHZ, $CDCl_3$) δ 8.30 (dt, J=1.7, 0.9 Hz, 1H), 8.23 (dd, J=7.1, 1.0 Hz, 1H), 7.76 (d, J=0.7 Hz, 1H), 7.54 (dd, J=7.1, 1.7 Hz, 1H), 7.35-7.29 (m, 3H), 7.11-6.77 (m, 2H), 5.09 (d, J=0.7 Hz, 2H), 3.46 (d, J=11.5 Hz, 1H), 3.33 (d, J=18.2 Hz, 5H), 2.86 (s, 1H), 2.67 (s, 2H), 2.44 (s, 2H), 0.91 (d, J=6.6 Hz, 3H);

LRMS (ES) m/z 566.4 ($M^+$+1).

Example 62: Synthesis of Compound 4301, 4-cyclobutyl-N-((7-(5-(difluoromethyl)-1,3,4-oxadiazol-2-yl)imidazo[1,2-a]pyridin-2-yl)methyl)-N-(3-fluorophenyl)piperazine-1-sulfonamide

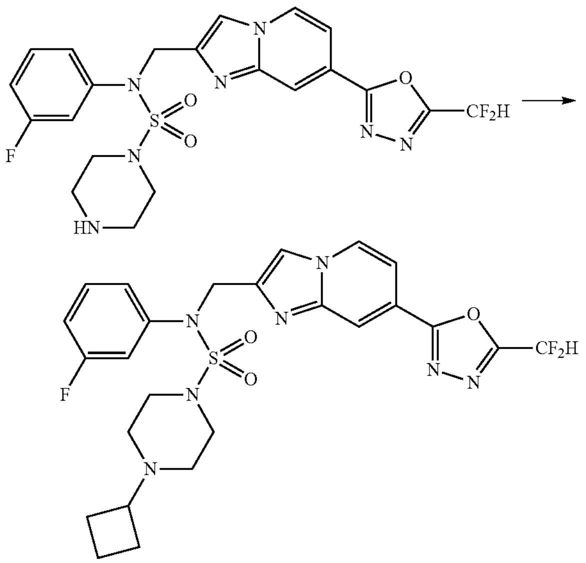

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, cyclobutanone (0.014 g, 0.197 mmol), acetic acid (0.006 mL, 0.099 mmol), and sodium triacetoxyborohydride (0.063 g, 0.296 mmol) were dissolved in dichloromethane (3 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.022 g, 39.8%) as a yellow solid.

$^1$H NMR (700 MHZ, $CDCl_3$) δ 8.29 (s, 1H), 8.23 (d, J=7.1 Hz, 1H), 7.78 (d, J=0.7 Hz, 1H), 7.54 (dd, J=7.1, 1.7 Hz, 1H), 7.33-7.29 (m, 3H), 7.05-6.86 (m, 2H), 5.10 (s, 2H), 3.27 (s, 4H), 2.71 (s, 1H), 2.29 (s, 4H), 2.03 (s, 2H), 1.83 (s, 2H), 1.70 (s, 2H);

LRMS (ES) m/z 562.2 ($M^+$+1).

Example 63: Synthesis of Compound 4302, N-((7-(5-(difluoromethyl)-1,3,4-oxadiazol-2-yl)imidazo[1,2-a]pyridin-2-yl)methyl)-N-(3-fluorophenyl)-4-oxetan-3-yl)piperazine-1-sulfonamide

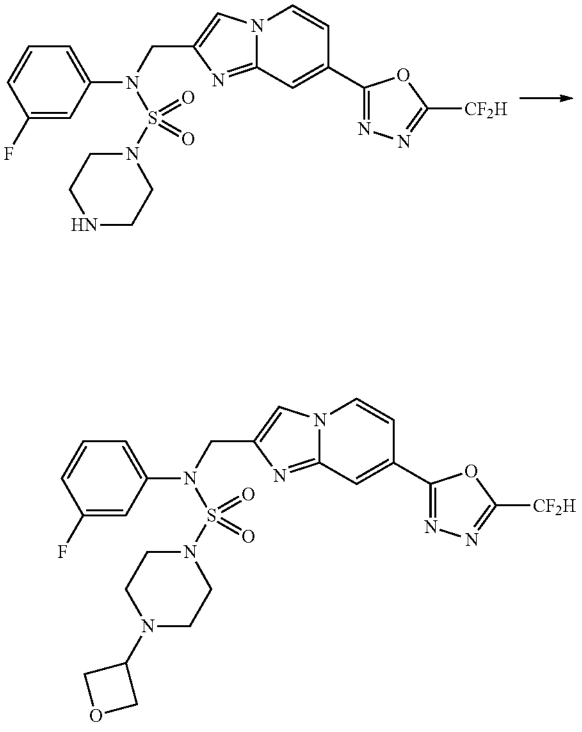

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, oxetan-3-one (0.014 g, 0.197 mmol), acetic acid (0.006 mL, 0.099 mmol), and sodium triacetoxyborohydride (0.063 g, 0.296 mmol) were dissolved in dichloromethane (3 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.017 g, 30.6%) as a yellow solid.

$^1$H NMR (700 MHZ, $CDCl_3$) 0 8.31 (dt, J=1.8, 0.8 Hz, 1H), 8.24 (dd, J=7.1, 1.0 Hz, 1H), 7.78-7.74 (m, 1H), 7.55 (dd, J=7.1, 1.7 Hz, 1H), 7.36-7.29 (m, 3H), 7.05-6.83 (m, 2H), 5.11-5.07 (m, 2H), 4.71-4.55 (m, 4H), 3.53 (s, 1H), 3.35 (s, 4H), 2.36 (s, 4H);

LRMS (ES) m/z 564.5 ($M^+$+1).

Example 64: Synthesis of Compound 4303,4-cyclohexyl-N-((7-(5-(difluoromethyl)-1,3,4-oxadiazol-2-yl)imidazo[1,2-a]pyridin-2-yl)methyl)-N-(3-fluorophenyl)piperazine-1-sulfonamide

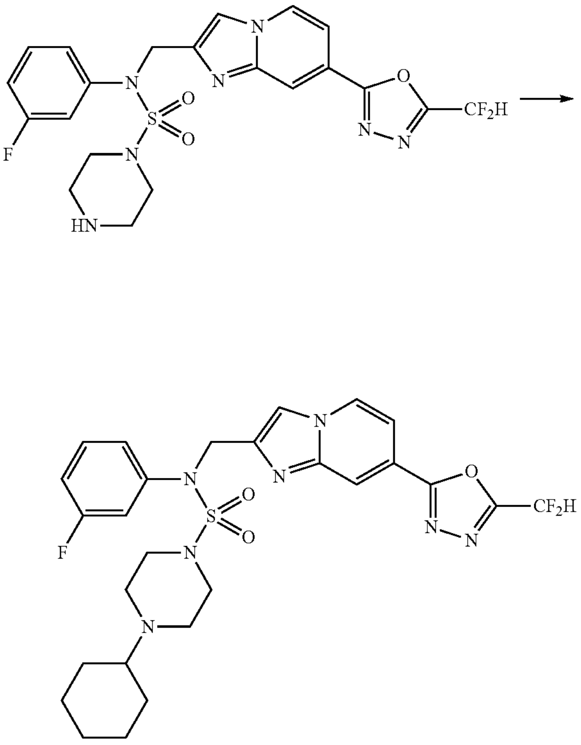

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, cyclohexanone (0.019 g, 0.197 mmol), acetic acid (0.006 mL, 0.099 0 mmol), and sodium triacetoxyborohydride (0.063 g, 0.296 mmol) were dissolved in dichloromethane (3 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.029 g, 49.9%) as a yellow solid.

$^1$H NMR (700 MHZ, $CDCl_3$) 0 8.29 (dt, J=1.8, 0.8 Hz, 1H), 8.23 (d, J=7.1 Hz, 1H), 7.80-7.78 (m, 1H), 7.54 (dd, J=7.1, 1.7 Hz, 1H), 7.33-7.29 (m, 3H), 7.05-6.86 (m, 2H), 5.10 (s, 2H), 3.25 (s, 4H), 2.53 (s, 4H), 2.31-2.18 (m, 1H), 1.80 (s, 4H), 1.25-1.06 (m, 6H);

LRMS (ES) m/z 590.0 ($M^+$+1).

Example 65: Synthesis of Compound 4304, N-((7-(5-(difluoromethyl)-1,3,4-oxadiazol-2-yl)imidazo[1,2-a]pyridin-2-yl)methyl)-N-(3-fluorophenyl)-4-(tetrahydro-2H-pyran-4-yl)piperazine-1-sulfonamide

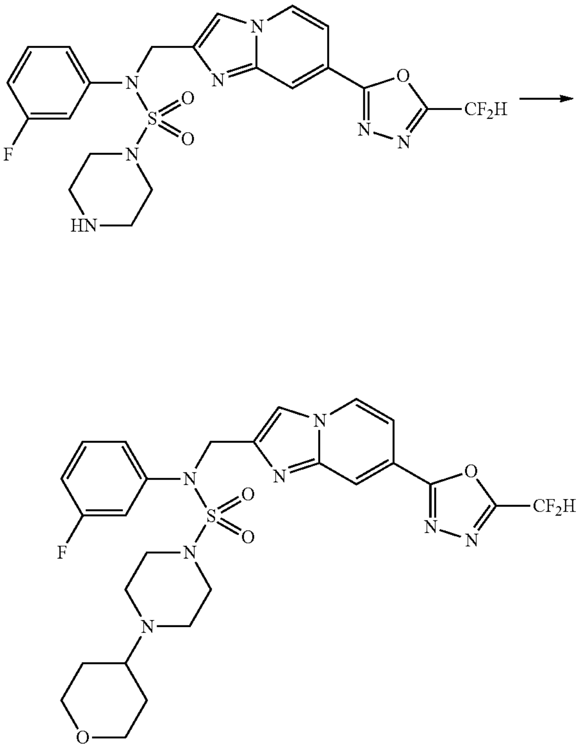

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, tetrahydro-4H-pyran-4-one (0.015 g, 0.148 mmol), acetic acid (0.006 mL, 0.099 mmol), sodium triacetoxyborohydride (0.063 g, 0.296 mmol), and triethylamine (0.014 mL, 0.099 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.021 g, 35.7%) as a white solid.

$^1H$ NMR (400 MHZ, $CDCl_3$) δ 8.30-8.27 (m, 1H), 8.22 (dd, J=1.0, 7.1 Hz, 1H), 7.77 (s, 1H), 7.53 (dd, J=1.7, 7.1 Hz, 1H), 7.33-7.25 (m, 4H), 7.10-6.80 (m, 2H), 5.10 (s, 2H), 4.06-3.97 (m, 2H), 3.36 (td, J=2.0, 11.8 Hz, 2H), 3.27 (t, J=4.9 Hz, 4H), 2.53 (t, J=4.8 Hz, 4H), 2.44 (s, 1H), 1.69 (d, J=12.0 Hz, 2H), 1.53 (qd, J=4.6, 12.0 Hz, 2H);

LRMS (ES) m/z 592.2 ($M^+$+1).

Example 66: Synthesis of Compound 4305, 4-(4,4-difluorocyclohexyl)-N-((7-(5-(difluoromethyl)-1,3,4-oxadiazol-2-yl)imidazo[1,2-a]pyridin-2-yl)methyl)-N-(3-fluorophenyl)piperazine-1-sulfonamide

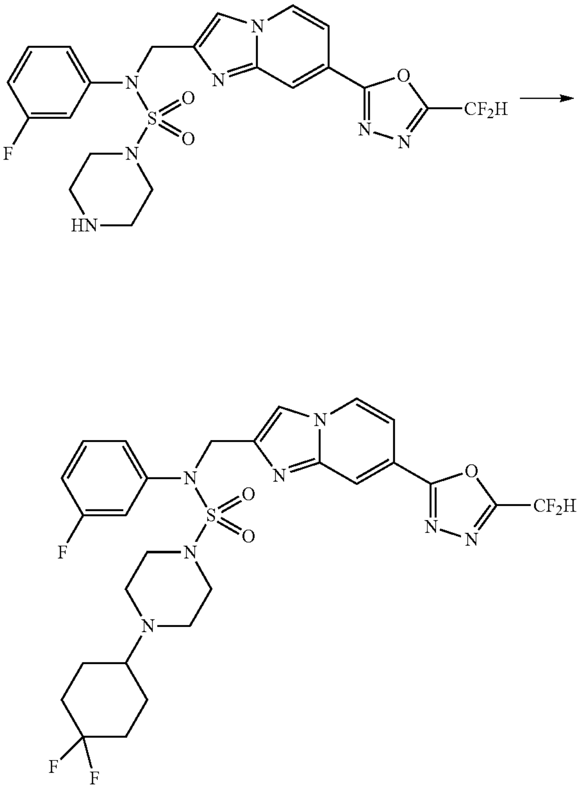

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, 4, 4-difluorocyclohexan-1-one (0.020 g, 0.148 mmol), acetic acid (0.006 mL, 0.099 mmol), sodium triacetoxyborohydride (0.063 g, 0.296 mmol), and triethylamine (0.014 mL, 0.099 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.020 g, 31.8%) as a white solid.

$^1H$ NMR (400 MHZ, $CDCl_3$) δ 8.31-8.27 (m, 1H), 8.23 (dd, J=1.0, 7.1 Hz, 1H), 7.77 (s, 1H), 7.54 (dd, J=1.7, 7.1 Hz, 1H), 7.33-7.25 (m, 3H), 7.09-6.81 (m, 2H), 5.10 (s, 2H), 3.25 (t, J=4.7 Hz, 4H), 2.51 (t, J=4.9 Hz, 4H), 2.38 (d, J=11.2 Hz, 1H), 2.13 (q, J=10.2, 10.8 Hz, 2H), 1.84-1.53 (m, 6H);

LRMS (ES) m/z 626.0 ($M^+$+1).

Example 67: Synthesis of Compound 4306, 4-acetyl-N-((7-(5-(difluoromethyl)-1,3,4-oxadiazol-2-yl)imidazo[1,2-a]pyridin-2-yl)methyl)-N-(3-fluorophenyl)piperazine-1-sulfonamide

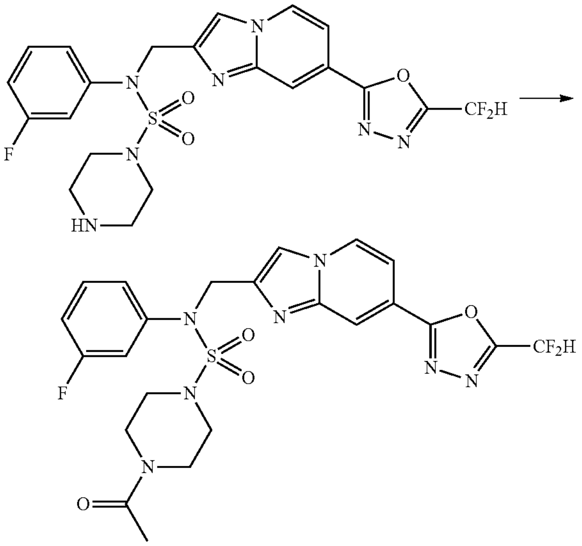

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, acetyl chloride (0.011 mL, 0.148 mmol), and triethylamine (0.041 mL, 0.296 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.020 g, 36.2%) as a white solid.

$^1$H NMR (400 MHZ, $CDCl_3$) § 8.30 (dt, J=0.8, 1.7 Hz, 1H), 8.23 (dd, J=1.0, 7.2 Hz, 1H), 7.73 (d, J=0.7 Hz, 1H), 7.55 (dd, J=1.7, 7.1 Hz, 1H), 7.38-7.22 (m, 3H), 7.11-6.80 (m, 2H), 5.07 (s, 2H), 3.59 (t, J=5.2 Hz, 2H), 3.43 (t, J=5.1 Hz, 2H), 3.29-3.17 (m, 4H), 2.09 (s, 3H);

LRMS (ES) m/z 550.4 ($M^+$+1).

Example 68: Synthesis of Compound 4307, N-((7-(5-(difluoromethyl)-1,3,4-oxadiazol-2-yl)imidazo[1,2-a]pyridin-2-yl)methyl)-N-(3-fluorophenyl)-4-propionylpiperazine-1-sulfonamide

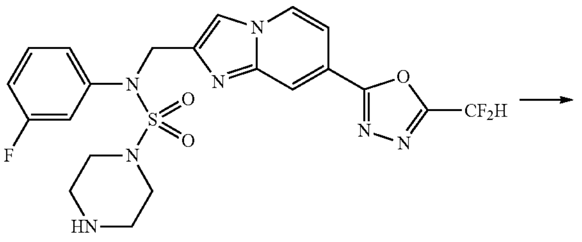

-continued

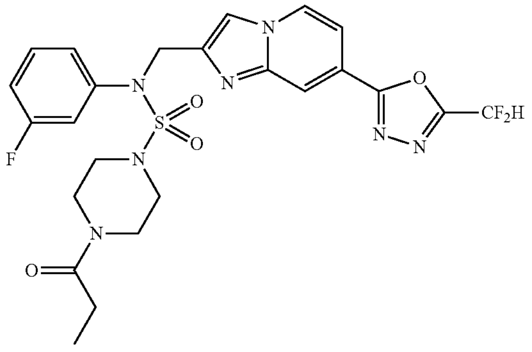

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, propionyl chloride (0.014 g, 0.148 mmol), and triethylamine (0.041 mL, 0.296 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.013 g, 23.8%) as a white solid.

$^1$H NMR (400 MHZ, $CDCl_3$) δ 8.34-8.28 (m, 1H), 8.23 (dd, J=1.0, 7.1 Hz, 1H), 7.74 (d, J=0.7 Hz, 1H), 7.56 (dd, J=1.7, 7.1 Hz, 1H), 7.38-7.23 (m, 3H), 7.11-6.80 (m, 2H), 5.07 (s, 2H), 3.61 (t, J=5.2 Hz, 2H), 3.48-3.40 (m, 2H), 3.23 (dt, J=5.1, 11.2 Hz, 4H), 2.33 (q, J=7.4 Hz, 2H), 1.15 (t, J=7.4 Hz, 3H);

LRMS (ES) m/z 563.9 ($M^+$+1).

Example 69: Synthesis of Compound 4308, N-((7-(5-(difluoromethyl)-1,3,4-oxadiazol-2-yl)imidazo[1,2-a]pyridin-2-yl)methyl)-N-(3-fluorophenyl)-4-(2-hydroxyacetyl)piperazine-1-sulfonamide

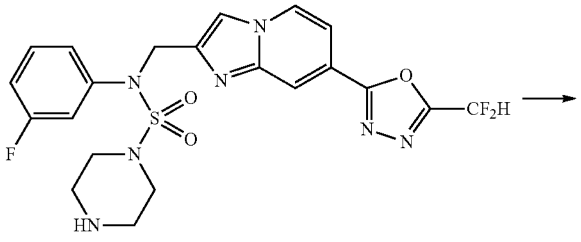

-continued

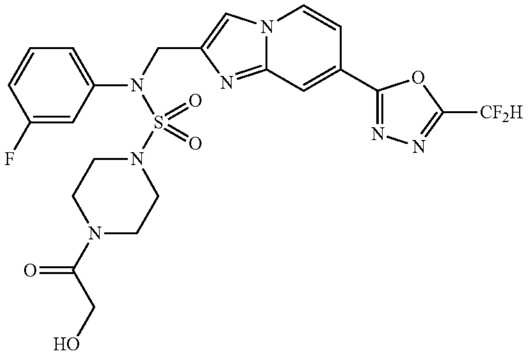

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, 2-hydroxyacetic acid (0.011 g, 0.148 mmol), triethylamine (0.041 mL, 0.296 mmol), and 1-[bis(dimethylamino)methylene]-1H-1,2, 3-triazolo[4,5-b]pyridinium 3-oxide hexafluorophosphate (HATU, 0.056 g, 0.148 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.019 g, 33.4%) as a white solid.

$^1H$ NMR (400 MHZ, $CDCl_3$) δ 8.33-8.28 (m, 1H), 8.23 (dd, J=1.0, 7.2 Hz, 1H), 7.71 (s, 1H), 7.56 (dd, J=1.7, 7.1 Hz, 1H), 7.39-7.22 (m, 3H), 7.12-6.81 (m, 2H), 5.05 (s, 2H), 4.15 (s, 2H), 3.66 (t, J=5.1 Hz, 2H), 3.28 (d, J=7.3 Hz, 6H);

LRMS (ES) m/z 566.3 ($M^+$+1).

Example 70: Synthesis of Compound 4309, 4-(cyclobutanecarbonyl)-N-((7-(5-(difluoromethyl)-1,3,4-oxadiazol-2-yl)imidazo[1,2-a]pyridine-2-yl)methyl)-N-(3-fluorophenyl)piperazine-1-sulfonamide

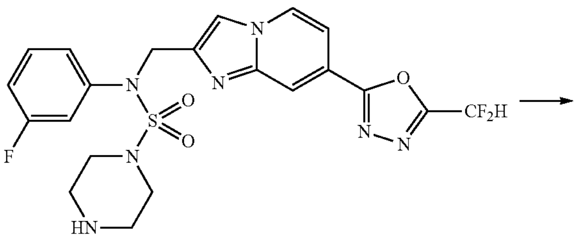

-continued

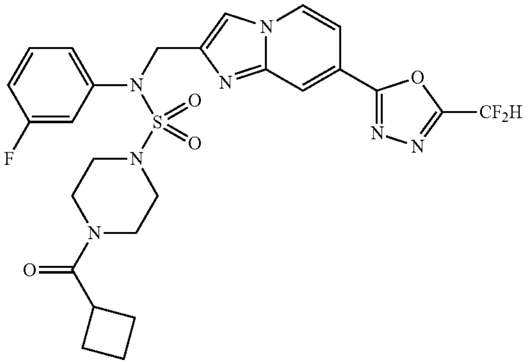

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, cyclobutanecarbonyl chloride (0.018 g, 0.148 mmol), and triethylamine (0.041 mL, 0.296 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.014 g, 23.4%) as a white solid.

$^1H$ NMR (400 MHZ, $CDCl_3$) δ 8.31 (s, 1H), 8.23 (d, J=7.1 Hz, 1H), 7.73 (s, 1H), 7.56 (dd, J=1.6, 7.1 Hz, 1H), 7.36-7.23 (m, 3H), 7.10-6.81 (m, 2H), 5.08 (s, 2H), 3.59 (t, J=5.2 Hz, 2H), 3.32 (t, J=5.0 Hz, 2H), 3.22-3.15 (m, 4H), 2.32 (td, J=2.7, 9.0 Hz, 3H), 2.18-2.09 (m, 2H), 2.03-1.84 (m, 2H);

LRMS (ES) m/z 590.0 ($M^+$+1).

Example 71: Synthesis of Compound 4310, N-((7-(5-(difluoromethyl)-1,3,4-oxadiazol-2-yl)imidazo[1,2-a]pyridin-2-yl)methyl)-N-(3-fluorophenyl)-4-(oxetane-3-carbonyl)piperazine-1-sulfonamide

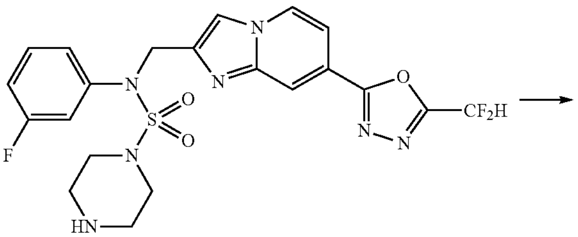

-continued

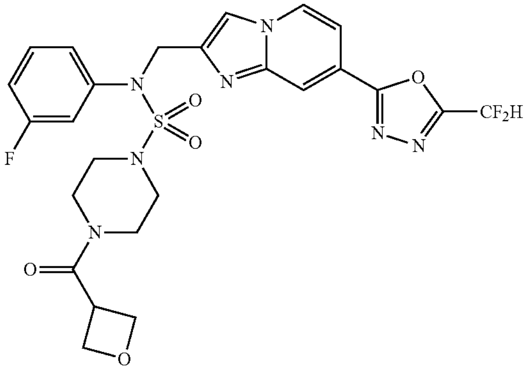

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, oxetane-3-carboxylic acid (0.015 g, 0.148 mmol), triethylamine (0.041 mL, 0.296 mmol), and 1-[bis(dimethylamino)methylene]-1H-1,2, 3-triazolo[4,5-b]pyridinium 3-oxide hexafluorophosphate (HATU, 0.056 g, 0.148 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.006 g, 10.8%) as a white solid.

$^1$H NMR (400 MHZ, $CDCl_3$) δ 8.32 (s, 1H), 8.23 (d, J=7.1 Hz, 1H), 7.71 (s, 1H), 7.57 (d, J=7.1 Hz, 1H), 7.36-7.22 (m, 3H), 7.11-6.81 (m, 2H), 5.06 (s, 2H), 4.89 (t, J=6.6 Hz, 2H), 4.79 (dd, J=6.2, 8.5 Hz, 2H), 3.97 (p, J=7.7, 8.2 Hz, 1H), 3.64 (t, J=5.0 Hz, 2H), 3.24 (dt, J=4.8, 10.2 Hz, 4H), 3.16 (d, J=5.4 Hz, 2H);

LRMS (ES) m/z 592.5 ($M^+$+1).

Example 72: Synthesis of Compound N-((7-(5-(difluoromethyl)-1,3,4-oxadiazol-2-yl)imidazo[1,2-a]pyridin-2-yl)methyl)-N-(3-fluorophenyl)-4-(2,2,2-trifluoroacetyl)piperazine-1-sulfonamide

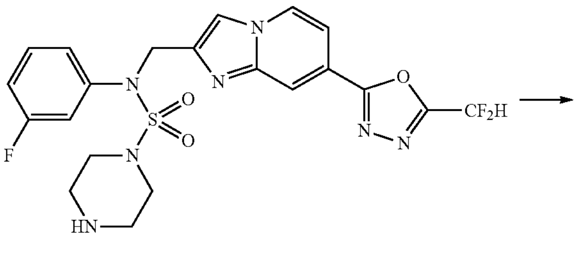

-continued

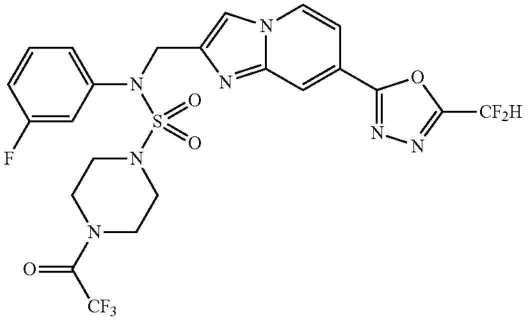

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, 2, 2,2-trifluoroacetic anhydride (0.031 g, 0.148 mmol), and triethylamine (0.041 mL, 0.296 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.016 g, 26.7%) as a white solid.

$^1$H NMR (400 MHZ, $CDCl_3$) δ 8.31 (s, 1H), 8.23 (dd, J=1.0, 7.1 Hz, 1H), 7.70 (s, 1H), 7.57 (dd, J=1.7, 7.1 Hz, 1H), 7.38-7.23 (m, 3H), 7.11-6.81 (m, 2H), 5.05 (s, 2H), 3.69 (t, J=5.2 Hz, 2H), 3.60 (t, J=5.0 Hz, 2H), 3.34 (dq, J=2.5, 7.8 Hz, 4H);

LRMS (ES) m/z 604.0 ($M^+$+1).

Example 73: Synthesis of Compound 4312, N-((7-(5-(difluoromethyl)-1,3,4-oxadiazol-2-yl)imidazo[1,2-a]pyridin-2-yl)methyl)-N-(3-fluorophenyl)-4-(methylsulfonyl)piperazine-1-sulfonamide

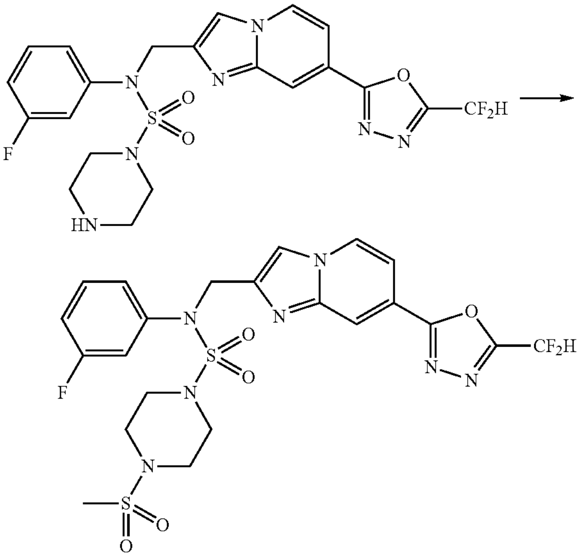

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.040 g, 0.079 mmol) prepared in step 3 of Example 58, methanesulfonyl chloride (0.009 mL, 0.118 mmol), and triethylamine (0.033 mL, 0.236 mmol) were dissolved in dichloromethane (1 mL) at 0° C., and the resulting solution was stirred at room temperature for 10 minutes. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.015 g, 33.1%) as a white solid.

$^1H$ NMR (400 MHz, $CDCl_3$) § 8.31 (dt, J=0.8, 1.7 Hz, 1H), 8.23 (dd, J=1.0, 7.2 Hz, 1H), 7.74-7.69 (m, 1H), 7.56 (dd, J=1.7, 7.1 Hz, 1H), 7.40-7.24 (m, 3H), 7.11-6.80 (m, 2H), 5.06 (s, 2H), 3.40-3.32 (m, 4H), 3.22 (dd, J=3.6, 6.3 Hz, 4H), 2.78 (s, 3H);

LRMS (ES) m/z 586.0 ($M^+$+1).

Example 74: Synthesis of Compound 4313, methyl 4-(N-((7-(5-(difluoromethyl)-1,3,4-oxadiazol-2-yl)imidazo[1,2-a]pyridin-2-yl)methyl)-N-(3-fluorophenyl)sulfamoyl)piperazine-1-carboxylate

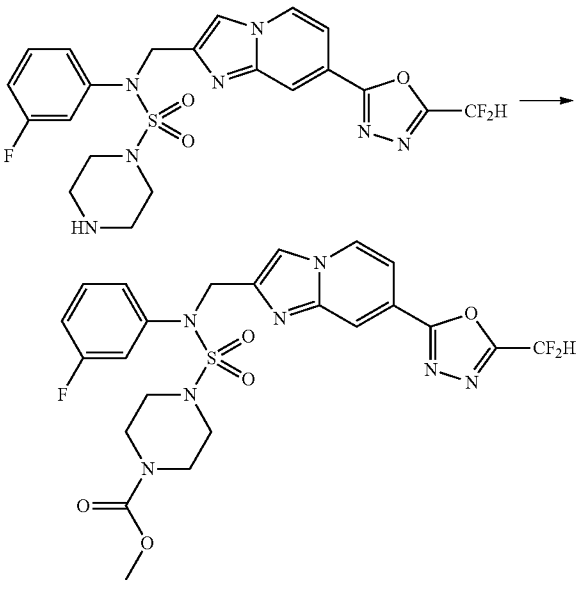

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, methyl carbonochloridate (0.014 g, 0.148 mmol), and triethylamine (0.041 mL, 0.296 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.014 g, 24.4%) as a white solid.

$^1H$ NMR (400 MHZ, $CDCl_3$) δ 8.33-8.27 (m, 1H), 8.23 (dd, J=1.0, 7.1 Hz, 1H), 7.77-7.72 (m, 1H), 7.55 (dd, J=1.7, 7.1 Hz, 1H), 7.38-7.24 (m, 3H), 7.11-6.80 (m, 2H), 5.07 (s, 2H), 3.71 (s, 3H), 3.45 (t, J=5.0 Hz, 4H), 3.21 (dd, J=4.0, 6.3 Hz, 4H);

LRMS (ES) m/z 566.4 ($M^+$+1).

Example 75: Synthesis of Compound 4314, 4—(N-((7-(5-(difluoromethyl)-1,3,4-oxadiazol-2-yl)imidazo[1,2-a]pyridin-2-yl)methyl)-N-(3-fluorophenyl)sulfamoyl)-N, N-dimethylpiperazine-1-carboxamide

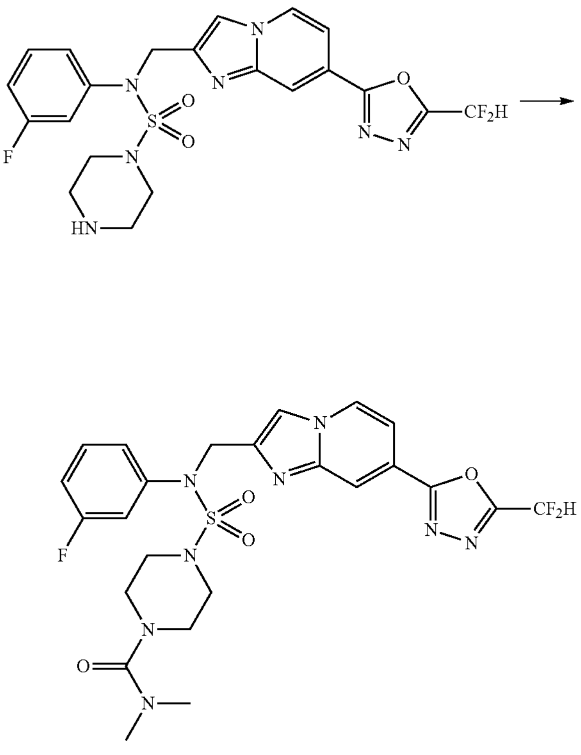

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, cyclobutanecarbonyl chloride (0.016 g, 0.148 mmol), and triethylamine (0.041 mL, 0.296 mmol) were dissolved in dichloromethane (1 mL) at room temperature, and the resulting solution was stirred at the same temperature for 18 hours. An aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.016 g, 27.5%) as a white solid.

$^1H$ NMR (400 MHZ, $CDCl_3$) δ 8.32-8.27 (m, 1H), 8.23 (dd, J=1.0, 7.2 Hz, 1H), 7.74 (s, 1H), 7.54 (dd, J=1.7, 7.2 Hz, 1H), 7.37-7.21 (m, 3H), 7.11-6.79 (m, 2H), 5.08 (s, 2H), 3.30-3.22 (m, 4H), 3.24-3.16 (m, 4H), 2.83 (s, 6H);

LRMS (ES) m/z 579.3 ($M^+$+1).

Example 76: Synthesis of Compound 4315, N-((7-(5-(difluoromethyl)-1,3,4-oxadiazol-2-yl)imidazo[1,2-a]pyridin-2-yl)methyl)-N-(3-fluorophenyl)-4-(pyrimidin-2-yl)piperazine-1-sulfonamide

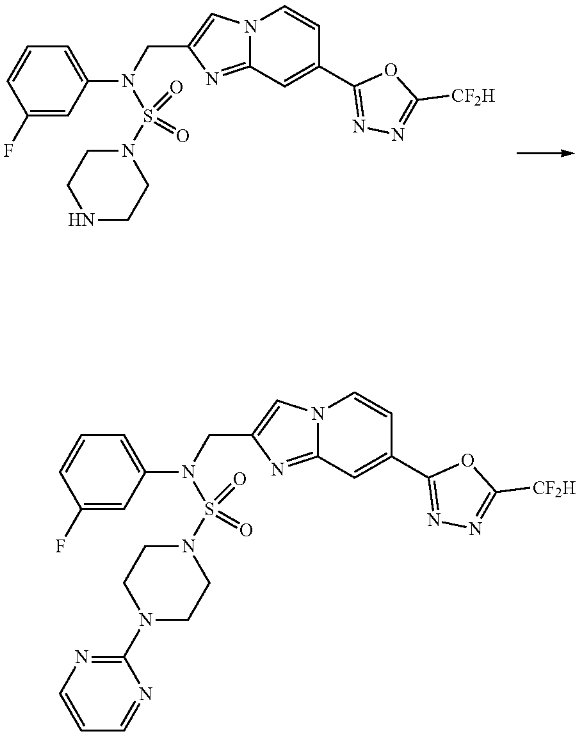

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.050 g, 0.099 mmol) prepared in step 3 of Example 58, 2-chloropyrimidine (0.023 g, 0.197 mmol), and potassium carbonate (0.041 g, 0.296 mmol) were dissolved in N, N-dimethylformamide (0.5 mL)/acetonitrile (0.5 mL) at room temperature, and the resulting solution was stirred at the same temperature for 18 hours. An aqueous sodium hydrogen carbonate solution was poured into the concentrate obtained by removing the solvent from the reaction mixture under reduced pressure, followed by extraction with dichloromethane. The organic layer was washed with a saturated aqueous sodium chloride solution, dried over anhydrous sodium sulfate, filtered, and concentrated under reduced pressure. The concentrate was purified by chromatography ($SiO_2$ plate, 20×20×1 mm; methanol/dichloromethane=0% to 7%) and concentrated to obtain the title compound (0.012 g, 20.3%) as a white solid.

$^1$H NMR (400 MHZ, $CDCl_3$) δ 8.32 (d, J=4.7 Hz, 2H), 8.28 (s, 1H), 8.23 (dd, J=0.9, 7.2 Hz, 1H), 7.77 (s, 1H), 7.55 (dd, J=1.7, 7.1 Hz, 1H), 7.37-7.25 (m, 3H), 7.11-6.80 (m, 2H), 6.55 (t, J=4.8 Hz, 1H), 5.11 (s, 2H), 3.86-3.78 (m, 4H), 3.30 (t, J=5.1 Hz, 4H);

LRMS (ES) m/z 586.5 ($M^+$+1).

Example 77: Synthesis of Compound 4616, N-((7-(5-(difluoromethyl)-1,3,4-oxadiazol-2-yl)imidazo[1,2-a]pyridin-2-yl)methyl)-N-(3-fluorophenyl)-1-(spiro[3.3]heptan-2-yl)piperidine-4-sulfonamide

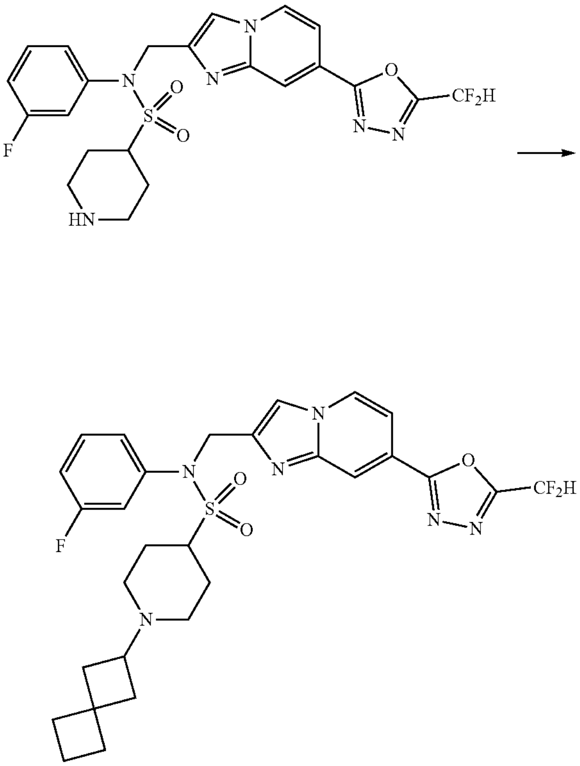

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.100 g, 0.197 mmol) prepared in step 3 of Example 18, spiro[3.3]heptan-2-one (0.043 g, 0.395 mmol), acetic acid (0.011 mL, 0.197 mmol), and sodium triacetoxyborohydride (0.126 g, 0.592 mmol) were dissolved in dichloromethane (5 mL) at room temperature, and the resulting solution was stirred at the same temperature for 3 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure.

The concentrate was purified by chromatography ($SiO_2$ plate, 20×20×1 mm; dichloromethane/methanol=0% to 10%) and concentrated to obtain the title compound (0.100 g, 84.3%) as a white solid.

$^1$H NMR (400 MHZ, $CDCl_3$) δ 8.28 (s, 1H), 8.23 (d, J=7.1 Hz, 1H), 7.78 (s, 1H), 7.54 (dd, J=7.1, 1.5 Hz, 1H), 7.36-7.23 (m, 3H), 7.10-6.79 (m, 2H), 5.14 (s, 2H), 3.12-2.87 (m, 3H), 2.49 (d, J=39.3 Hz, 1H), 2.41 (ddd, J=9.2,6.1,2.7 Hz, 1H), 2.19-2.04 (m, 4H), 2.04-1.61 (m, 11H);

LRMS (ES) m/z 601.1 ($M^+$+1).

Example 78: Synthesis of Compound 4617, N-((7-(5-(difluoromethyl)-1,3,4-oxadiazol-2-yl)imidazo[1,2-a]pyridin-2-yl)methyl)-N-(3-fluorophenyl)-1-(2-oxaspiro[3.3]heptan-6-yl)piperidine-4-sulfonamide

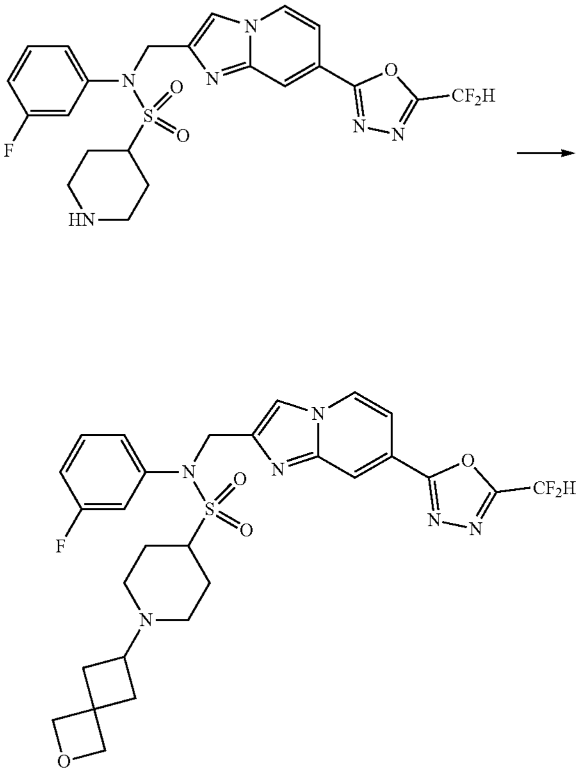

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.100 g, 0.197 mmol) prepared in step 3 of Example 18, 2-oxaspiro[3.3]heptan-6-one (0.044 g, 0.395 mmol), acetic acid (0.011 mL, 0.197 mmol), and sodium triacetoxyborohydride (0.126 g, 0.592 mmol) were dissolved in dichloromethane (5 mL) at room temperature, and the resulting solution was stirred at the same temperature for 3 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.100 g, 84.0%) as a white solid.

$^1$H NMR (400 MHz, $CDCl_3$) δ 8.28 (s, 1H), 8.23 (d, J=7.1 Hz, 1H), 7.77 (s, 1H), 7.54 (d, J=7.2 Hz, 1H), 7.36-7.21 (m, 3H), 7.11-6.79 (m, 2H), 5.14 (s, 2H), 4.75-4.64 (m, 2H), 4.61 (s, 2H), 3.13-2.88 (m, 3H), 2.59-2.31 (m, 3H), 2.08 (ddd, J=49.8, 24.9, 14.0 Hz, 4H), 1.89 (d, J=35.1 Hz, 2H), 1.70 (d, J=12.6 Hz, 2H);

LRMS (ES) m/z 603.3 ($M^+$+1).

Example 79: Synthesis of Compound 4622, N-((7-(5-(difluoromethyl)-1,3,4-oxadiazol-2-yl)imidazo[1,2-a]pyridin-2-yl)methyl)-N-(3-fluorophenyl)-4-(spiro[3.3]heptan-2-yl)piperazine-1-sulfonamide

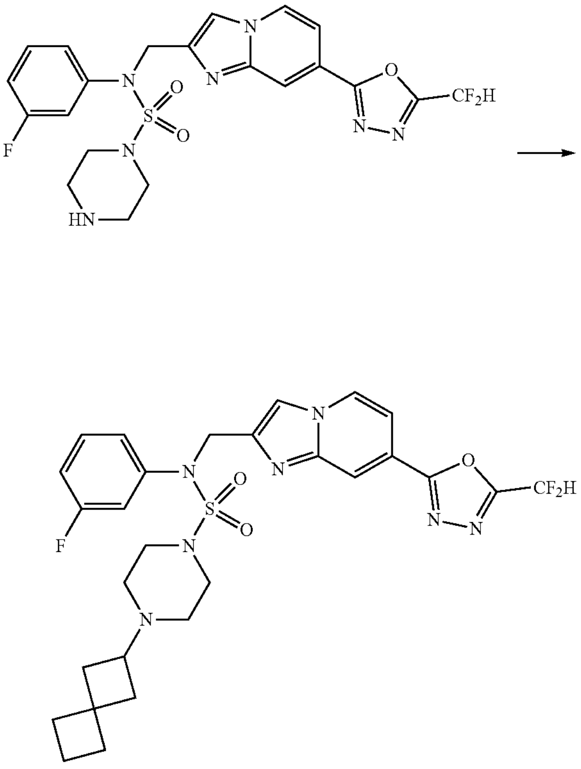

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.090 g, 0.177 mmol) prepared in step 3 of Example 58, spiro[3.3]heptan-2-one (0.039 g, 0.355 mmol), acetic acid (0.010 mL, 0.177 mmol), and sodium triacetoxyborohydride (0.113 g, 0.532 mmol) were dissolved in dichloromethane (5 mL) at room temperature, and the resulting solution was stirred at the same temperature for 3 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.050 g, 46.9%) as a white solid.

$^1$H NMR (400 MHZ, $CDCl_3$) δ 8.29 (s, 1H), 8.23 (d, J=7.1 Hz, 1H), 7.78 (s, 1H), 7.54 (dd, J=7.1, 1.7 Hz, 1H), 7.35-7.23 (m, 3H), 7.09-6.80 (m, 2H), 5.09 (s, 2H), 3.28 (s, 4H), 2.57 (s, 1H), 2.39-2.18 (m, 3H), 2.13 (s, 2H), 2.04-1.77 (m, 9H);

LRMS (ES) m/z 602.4 ($M^+$+1).

Example 80: Synthesis of Compound 4623, N-((7-(5-(difluoromethyl)-1,3,4-oxadiazol-2-yl)imidazo[1,2-a]pyridin-2-yl)methyl)-N-(3-fluorophenyl)-4-(2-oxaspiro[3.3]heptan-6-yl)piperazine-1-sulfonamide

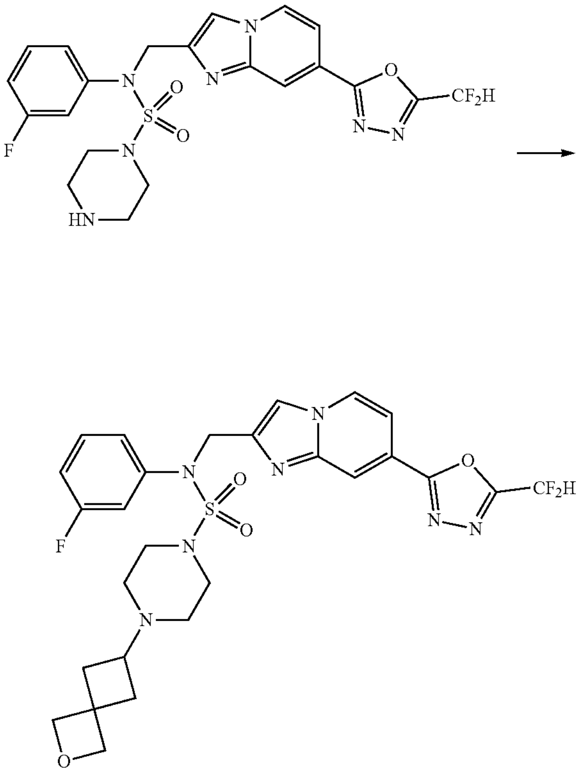

N-((7-(5-(difluoromethyl)-1,3,4-oxadiazol-2-yl)imidazo[1,2-a]pyridin-2-yl)methyl)-N-(3-fluorophenyl)piperazine-1-sulfonamide (0.090 g, 0.177 mmol) prepared in step 3 of Example 58, 2-oxaspiro[3.3]heptan-6-one (0.040 g, 0.355 mmol), acetic acid (0.010 mL, 0.177 mmol), and sodium triacetoxyborohydride (0.113 g, 0.532 mmol) were dissolved in dichloromethane (5 mL) at room temperature, and the resulting solution was stirred at the same temperature for 3 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.050 g, 46.7%) as a white solid.

$^1$H NMR (400 MHZ, $CDCl_3$) δ 8.29 (s, 1H), 8.23 (d, J=7.1 Hz, 1H), 7.76 (s, 1H), 7.54 (dd, J=7.1, 1.6 Hz, 1H), 7.36-7.23 (m, 3H), 7.10-6.81 (m, 2H), 5.08 (s, 2H), 4.71 (s, 2H), 4.60 (s, 2H), 3.24 (s, 4H), 2.50 (s, 1H), 2.39 (s, 2H), 2.26 (s, 4H), 1.99 (s, 2H);

LRMS (ES) m/z 604.2 ($M^+$+1).

Example 81: Synthesis of Compound 4624, N-((7-(5-(difluoromethyl)-1,3,4-oxadiazol-2-yl)imidazo[1,2-a]pyridin-2-yl)methyl)-6-methyl-N-phenyl-2,6-diazaspiro[3.3]heptan-2-sulfonamide

[Step 1] Synthesis of tert-butyl 6-((1H-imidazol-1-yl)sulfonyl)-2,6-diazaspiro[3.3]heptan-2-carboxylate

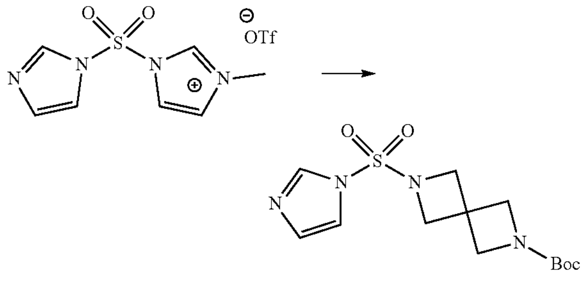

1-((1H-imidazol-1-yl)sulfonyl)-3-methyl-1H-imidazol-3-ium trifluoromethanesulfonate (3.600 g, 9.937 mmol) prepared in step 1 of Example 38 was dissolved in acetonitrile (25 mL). Then, tert-butyl 2,6-diazaspiro[3.3]heptan-2-carboxylate oxalate (2.659 g, 5.465 mmol) and N, N-diisopropylethylamine (8.654 mL, 49.683 mmol) were added at 0° C., stirred at the same temperature for 0.2 hours, and further stirred at room temperature for 3 hours. A saturated aqueous sodium hydrogen carbonate solution was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 24 g cartridge; ethyl acetate/hexane=10% to 80%) and concentrated to obtain the title compound (1.300 g, 39.8%) as a white solid.

[Step 2] Synthesis of (1-((6-(tert-butoxycarbonyl)-2,6-diazaspiro[3.3]heptan-2-yl)sulfonyl)-3-methyl-1H-imidazol-3-ium trifluoromethanesulfonate

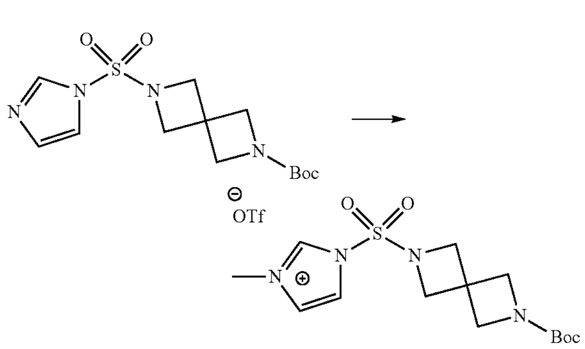

Tert-butyl 6-((1H-imidazol-1-yl)sulfonyl)-2,6-diazaspiro[3.3]heptan-2-carboxylate (1.300 g, 3.959 mmol) prepared in step 1 was dissolved in dichloromethane (20 mL). Then, methyl trifluoromethanesulfonate (0.499 mL, 4.553 mmol) was added at 0° C., stirred at the same temperature for 0.2 hours, and further stirred at room temperature for 3 hours. After removing the solvent from the reaction mixture under reduced pressure, the title compound (1.850 g, 94.9%) was obtained as a white solid without further purification.

[Step 3] Synthesis of tert-butyl 6-(N-(phenylsulfamoyl)-2,6-diazaspiro[3.3]heptan-2-carboxylate

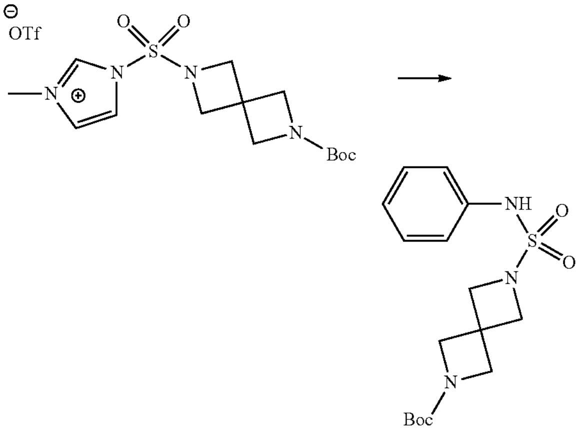

(1-((6-(Tert-butoxycarbonyl)-2,6-diazaspiro[3.3]heptan-2-yl)sulfonyl)-3-methyl-1H-imidazol-3-ium trifluoromethanesulfonate (1.140 g, 2.315 mmol) prepared in step 2 and aniline (0.254 mL, 2.778 mmol) were dissolved in acetonitrile (15 mL) at room temperature, and stirred at 85° C. for 18 hours. Then, the temperature was lowered to room temperature to terminate the reaction. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 24 g cartridge; ethyl acetate/hexane=0% to 30%) and concentrated to obtain the title compound (0.500 g, 61.1%) as a yellow solid.

[Step 4] Synthesis of tert-butyl 6-(N-((7-(5-(difluoromethyl)-1,3,4-oxadiazol-2-yl)imidazo[1,2-a]pyridin-2-yl)methyl)-N-phenylsulfamoyl)-2,6-diazaspiro[3.3]heptan-2-carboxylate

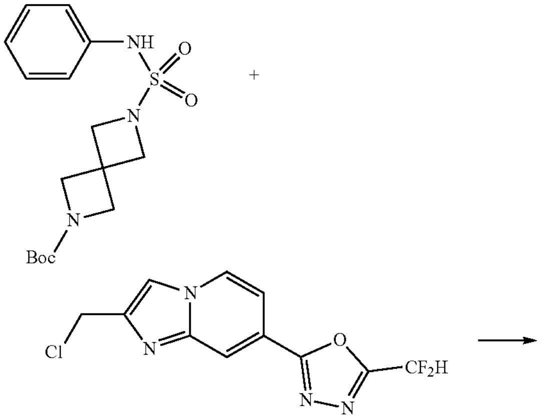

-continued

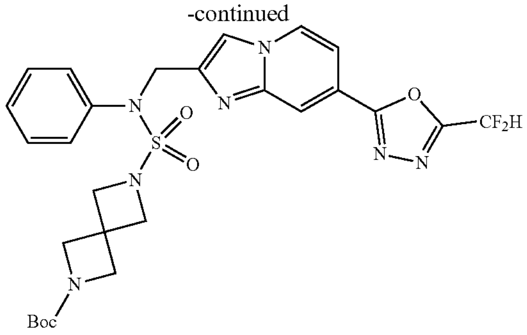

Tert-butyl 6-(N-phenylsulfamoyl)-2,6-diazaspiro[3.3]heptan-2-carboxylate (0.100 g, 0.283 mmol) prepared in step 3, 2-(2-(chloromethyl)imidazo[1,2-a]pyridin-7-yl)-5-(difluoromethyl)-1,3,4-oxadiazole (0.097 g, 0.340 mmol), potassium carbonate (0.059 g, 0.424 mmol), and potassium iodide (0.023 g, 0.141 mmol) were dissolved in N, N-dimethylformamide (5 mL) at room temperature, and the resulting solution was stirred at the same temperature for 3 hours. A saturated aqueous ammonium chloride solution was poured into the concentrate obtained by removing the solvent from the reaction mixture under reduced pressure, followed by extraction with dichloromethane. The organic layer was washed with a saturated aqueous water solution, dried over anhydrous magnesium sulfate, filtered, and concentrated under reduced pressure. The concentrate was purified by column chromatography ($SiO_2$, 40 g cartridge; ethyl acetate/hexane=0% to 70%) and concentrated to obtain the title compound (0.120 g, 70.5%) as a white solid.

[Step 5] Synthesis of N-((7-(5-(difluoromethyl)-1,3,4-oxadiazol-2-yl)imidazo[1,2-a]pyridin-2-yl)methyl)-N-phenyl-2,6-diazaspiro[3.3]heptan-2-sulfonamide

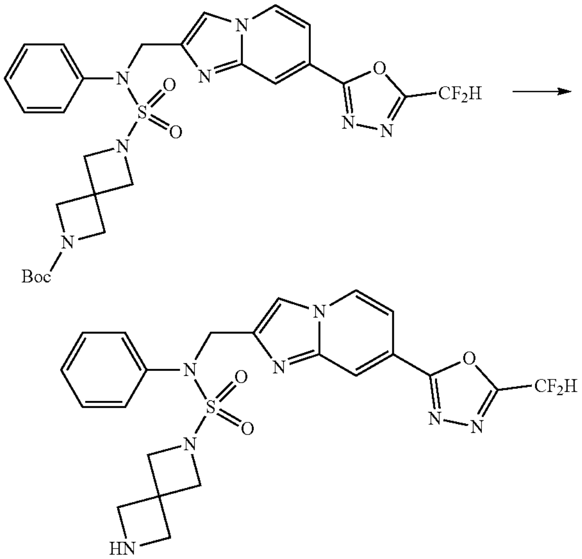

Tert-butyl 6-(N-((7-(5-(difluoromethyl)-1,3,4-oxadiazol-2-yl)imidazo[1,2-a]pyridin-2-yl)methyl)-N-phenylsulfamoyl)-2,6-diazaspiro[3.3]heptan-2-carboxylate (0.120 g, 0.199 mmol) prepared in step 4, and trifluoroacetic acid (0.305 mL, 3.989 mmol) were dissolved in dichloromethane (10 mL) at room temperature, and the resulting solution was stirred at the same temperature for 2 hours. A saturated aqueous sodium hydrogen carbonate solution was poured into the reaction mixture, followed by extraction with dichloromethane. The organic layer was washed with a saturated aqueous water solution, dried over anhydrous magnesium sulfate, and filtered. After concentration under reduced pressure, the title compound (0.100 g, 100.0%) was obtained as a yellow gel without further purification.

[Step 6] Synthesis of Compound 4624

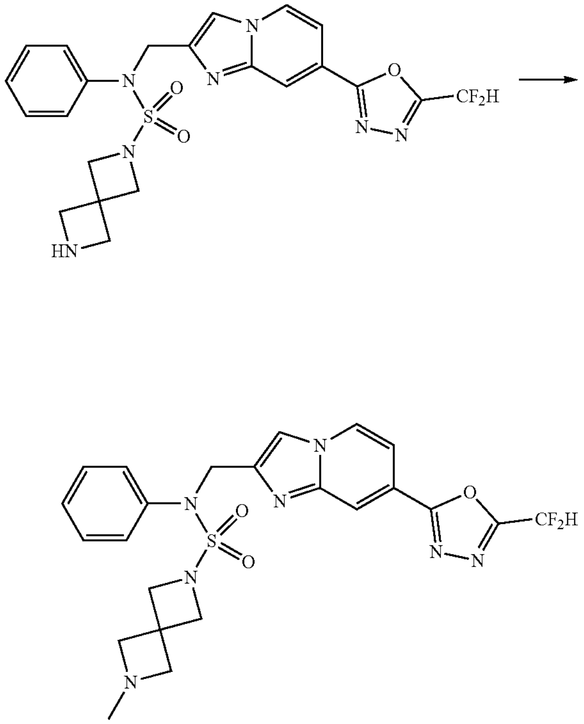

N-((7-(5-(difluoromethyl)-1,3,4-oxadiazol-2-yl)imidazo [1,2-a]pyridin-2-yl)methyl)-N-phenyl-2,6-diazaspiro[3.3] heptan-2-sulfonamide (0.100 g, 0.199 mmol) prepared in step 5, formaldehyde (0.012 g, 0.399 mmol), acetic acid (0.011 mL, 0.199 mmol), and sodium triacetoxyborohydride (0.127 g, 0.598 mmol) were dissolved in dichloromethane (5 mL) at room temperature, and the resulting solution was stirred at the same temperature for 3 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.080 g, 77.8%) as a white solid.

$^1$H NMR (400 MHZ, $CDCl_3$) δ 8.28 (s, 1H), 8.21 (d, J=7.1 Hz, 1H), 7.75 (s, 1H), 7.52 (dd, J=7.1, 1.7 Hz, 1H), 7.47-7.41 (m, 2H), 7.38-7.31 (m, 2H), 7.30-7.25 (m, 1H), 7.09-6.80 (m, 1H), 5.07 (s, 2H), 4.00 (s, 4H), 3.33 (s, 4H), 2.31 (s, 3H);

LRMS (ES) m/z 516.2 ($M^+$+1).

Example 82: Synthesis of Compound 6893, tert-butyl 4-(N-(3-fluorophenyl)-N-((7-(5-(trifluoromethyl)-1,3,4-oxadiazol-2-yl)imidazo[1,2-a]pyridin-2-yl)methyl)sulfamoyl)piperidine-1-carboxylate

[Step 1] Synthesis of tert-butyl (4-(5-(trifluoromethyl)-1, 3,4-oxadiazol-2-yl)pyridin-2-yl)carbamate

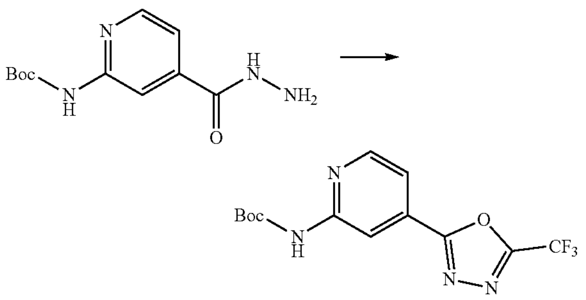

Tert-butyl (4-(hydrazinecarbonyl)pyridin-2-yl)carbamate (2.600 g, 10.306 mmol) prepared in step 2 of Example 1 and triethylamine (14.365 mL, 103.064 mmol) were dissolved in tetrahydrofuran (150 mL), and trifluoroacetic anhydride (7.279 mL, 51.532 mmol) was added at room temperature and heated to reflux for 16 hours. Then, the temperature was lowered to room temperature to terminate the reaction. A saturated aqueous ammonium chloride solution was added to the reaction mixture, followed by extraction with ethyl acetate. The organic layer was washed with a saturated aqueous sodium chloride solution, dried over anhydrous magnesium sulfate, filtered, and concentrated under reduced pressure. Ethyl acetate (30 mL) and hexane (100 mL) were poured into the concentrate, suspended, and filtered to obtain a solid, and the obtained solid was washed with hexane and dried to obtain the title compound (1.500 g, 44.1%) as a white solid.

[Step 2] Synthesis of 4-(5-(trifluoromethyl)-1,3,4-oxadiazol-2-yl)pyridin-2-amine

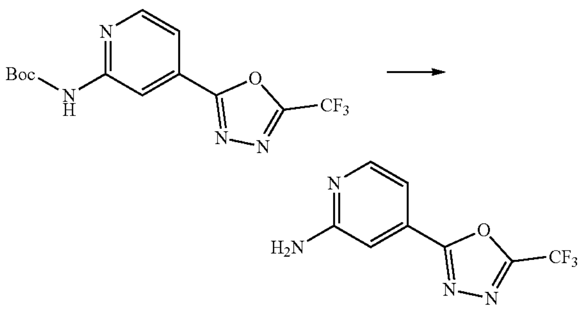

Tert-butyl (4-(5-(trifluoromethyl)-1,3,4-oxadiazol-2-yl) pyridin-2-yl)carbamate (1.500 g, 4.542 mmol) prepared in step 1 was dissolved in dichloromethane (70 mL). Then, trifluoroacetic acid (6.956 mL, 90.835 mmol) was added at 0° C., and the resulting solution was stirred at room temperature for 4 hours. After removing the solvent from the reaction mixture under reduced pressure, a saturated aqueous sodium hydrogen carbonate solution (50 mL) was poured into the concentrate and suspended, followed by filtration to obtain a solid. The obtained solid was washed with water and dried to obtain the title compound (1.030 g, 98.5%) as a yellow solid.

[Step 3] Synthesis of 2-(2-(chloromethyl)imidazo[1,2-a]pyridin-7-yl)-5-(trifluoromethyl)-1,3,4-oxadiazole

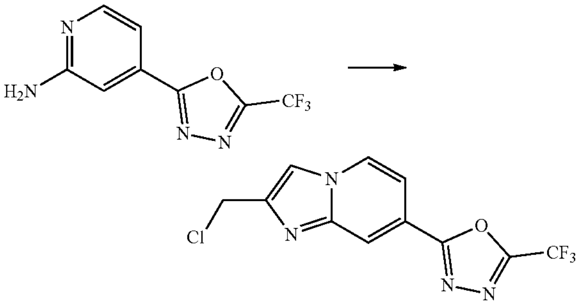

4-(5-(Trifluoromethyl)-1,3,4-oxadiazol-2-yl)pyridin-2-amine (1.100 g, 4.779 mmol) prepared in step 2, 1,3-dichloropropan-2-one (1.214 g, 9.559 mmol), and sodium hydrogen carbonate (2.008 g, 23.897 mmol) were dissolved in 1,4-dioxane (60 mL) at room temperature. The resulting solution was heated to reflux for 16 hours, and then the temperature was lowered to room temperature to terminate the reaction. The reaction mixture was filtered through a plastic filter to remove solids, and the filtrate was purified by column chromatography ($SiO_2$, 40 g cartridge; ethyl acetate/hexane=5% to 70%) and concentrated to obtain the title compound (0.850 g, 58.8%) as a beige solid.

[Step 4] Synthesis of Compound 6893

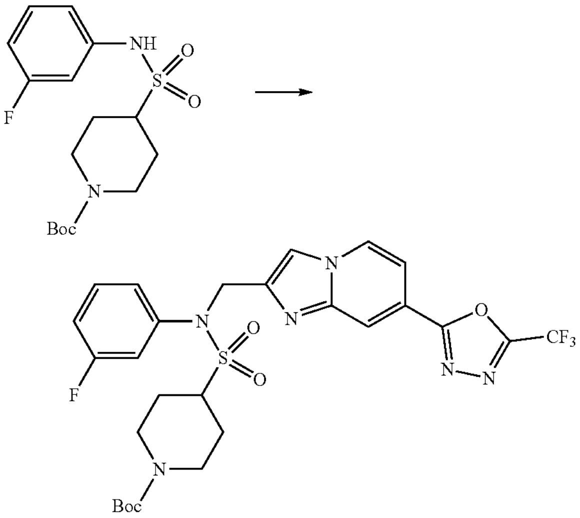

Tert-butyl 4-(N-(3-fluorophenyl)sulfamoyl)piperidine-1-carboxylate (0.250 g, 0.697 mmol) prepared in step 1 of Example 18, 2-(2-(chloromethyl)imidazo[1,2-a]pyridin-7-yl)-5-(trifluoromethyl)-1,3,4-oxadiazole (0.201 g, 0.663 mmol) prepared in step 3, potassium carbonate (0.193 g, 1.395 mmol), and potassium iodide (0.012 g, 0.070 mmol) were dissolved in N, N-dimethylformamide (6 mL) at room temperature, and the resulting solution was stirred at 60° C. for 16 hours. Then, the temperature was lowered to room temperature to terminate the reaction. Water was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by column chromatography ($SiO_2$, 24 g cartridge; ethyl acetate/hexane=10% to 90%) and concentrated to obtain the title compound (0.150 g, 34.4%) as a colorless oil.

$^1$H NMR (400 MHZ, $CDCl_3$) δ 8.08 (s, 1H), 7.98 (m, 1H), 7.59 (s, 1H), 7.28-7.15 (m, 4H), 6.87 (m, 1H), 5.11 (s, 2H), 4.19 (m, 2H), 3.21 (m, 1H), 2.67 (m, 2H), 2.05 (m, 2H), 1.75 (m, 2H), 1.41 (s, 9H).

Activity Measurement and Analysis Protocol of the Compounds of the Present Invention

<Experimental Example 1> In Vitro HDAC Enzyme Activity Inhibition Assay

In order to confirm the selectivity of the compounds represented by Chemical Formula I of the present invention to HDAC6 through HDAC1 and HDAC6 enzyme activity inhibition experiments, a comparison experiment was performed using the material that has already been developed as a control group.

HDAC enzyme activity was measured using the HDAC Fluorimetric Drug Discovery Kit (Enzo Life Sciences, Inc., BML-AK511, 516). For the HDAC1 enzyme activity test, human recombinant HDAC1 (BML-SE456) was used as an enzyme source and Fluor de Lys-SIRT1 (BNL-KI177) was used as a substrate. After dispensing 5-fold diluted compounds into a 96-well plate, 0.3 μg of enzyme and 10 μM substrate were added to each well of the plate and allowed to react at 30° C. for 60 minutes. Next, Fluor de Lys Developer II (BML-KI176) was added and reacted for 30 minutes to complete the reaction, and then the fluorescence values (Ex 360, Em 460) were measured using a multi-plate reader (Flexstation 3, Molecular Device). The HDAC6 enzymes were tested using human recombinant HDAC6 (382180) from Calbiochem Inc., according to the same protocol as the HDAC1 enzyme activity test method. With respect to the final result values, respective IC50 values were calculated using GraphPad Prism 4.0 program, and results thereof were summarized in Table 4 below.

TABLE 4

Results of HDAC enzyme activity inhibition assay

| Example | Compound | HDAC1 (nM) | HDAC6 (nM) | HDAC6 selectivity (fold) |
|---|---|---|---|---|
| 1 | 3778 | >50,000 | 91.0 | 549 |
| 2 | 3779 | >50,000 | 156.0 | 321 |
| 3 | 4214 | >50,000 | 179.8 | 278 |
| 4 | 4215 | >50,000 | 182.0 | 275 |
| 5 | 4216 | >50,000 | 119.0 | 420 |
| 6 | 4217 | >50,000 | 122.1 | 410 |
| 7 | 4218 | >50,000 | 115.6 | 433 |
| 8 | 4219 | >50,000 | 103.7 | 482 |
| 9 | 4220 | >50,000 | 156.3 | 320 |
| 10 | 4221 | >50,000 | 137.2 | 364 |

TABLE 4-continued

Results of HDAC enzyme activity inhibition assay

| Example | Compound | HDAC1 (nM) | HDAC6 (nM) | HDAC6 selectivity (fold) |
|---|---|---|---|---|
| 11 | 4222 | >50,000 | 218.0 | 229 |
| 12 | 4223 | >50,000 | 127.5 | 392 |
| 13 | 4224 | >50,000 | 141.3 | 354 |
| 14 | 4225 | >50,000 | 94.4 | 530 |
| 15 | 4226 | >50,000 | 115.7 | 432 |
| 16 | 4227 | >50,000 | 207.5 | 241 |
| 17 | 4228 | >50,000 | 102.9 | 486 |
| 18 | 4236 | >50,000 | 73.8 | 678 |
| 19 | 4237 | >50,000 | 60.9 | 821 |
| 20 | 4238 | >50,000 | 76.6 | 653 |
| 21 | 4239 | >50,000 | 78.8 | 635 |
| 22 | 4240 | >50,000 | 53.4 | 936 |
| 23 | 4241 | >50,000 | 69.9 | 715 |
| 24 | 4242 | >50,000 | 62.5 | 800 |
| 25 | 4243 | >50,000 | 94.3 | 530 |
| 26 | 4244 | >50,000 | 95.3 | 525 |
| 27 | 4245 | >50,000 | 47.4 | 1055 |
| 28 | 4246 | >50,000 | 75.8 | 660 |
| 29 | 4247 | >50,000 | 51.0 | 980 |
| 30 | 4248 | >50,000 | 92.2 | 542 |
| 31 | 4249 | >50,000 | 73.1 | 684 |
| 32 | 4250 | >50,000 | 115.9 | 431 |
| 33 | 4251 | >50,000 | 95.2 | 525 |
| 34 | 4252 | >50,000 | 109.8 | 455 |
| 35 | 4253 | >50,000 | 99.4 | 503 |
| 36 | 4254 | >50,000 | 116.2 | 430 |
| 37 | 4255 | >50,000 | 107.9 | 463 |
| 38 | 4256 | >50,000 | 79.4 | 630 |
| 39 | 4257 | >50,000 | 74.2 | 674 |
| 40 | 4258 | >50,000 | 100.1 | 500 |
| 41 | 4259 | >50,000 | 82.6 | 605 |
| 42 | 4260 | >50,000 | 87.3 | 573 |
| 43 | 4261 | >50,000 | 85.0 | 588 |
| 44 | 4262 | >50,000 | 299.3 | 167 |
| 45 | 4263 | >50,000 | 126.1 | 397 |
| 46 | 4264 | >50,000 | 203.0 | 246 |
| 47 | 4265 | >50,000 | 85.5 | 585 |
| 48 | 4266 | >50,000 | 116.0 | 431 |
| 49 | 4267 | >50,000 | 95.5 | 524 |
| 50 | 4268 | >50,000 | 128.7 | 389 |
| 51 | 4269 | >50,000 | 193.1 | 259 |
| 52 | 4270 | >50,000 | 152.7 | 327 |
| 53 | 4271 | >50,000 | 232.4 | 215 |
| 54 | 4272 | >50,000 | 168.0 | 298 |
| 55 | 4273 | >50,000 | 121.0 | 413 |
| 56 | 4274 | >50,000 | 150.0 | 333 |
| 57 | 4275 | >50,000 | 142.3 | 351 |
| 58 | 4297 | >50,000 | 89.2 | 561 |
| 59 | 4298 | >50,000 | 79.2 | 631 |
| 60 | 4299 | >50,000 | 102.4 | 488 |
| 61 | 4300 | >50,000 | 122.0 | 410 |
| 62 | 4301 | >50,000 | 84.1 | 595 |
| 63 | 4302 | >50,000 | 67.8 | 737 |
| 64 | 4303 | >50,000 | 167.4 | 299 |
| 65 | 4304 | >50,000 | 60.1 | 832 |
| 66 | 4305 | >50,000 | 114.5 | 437 |
| 67 | 4306 | >50,000 | 81.0 | 617 |
| 68 | 4307 | >50,000 | 136.8 | 365 |
| 69 | 4308 | >50,000 | 69.1 | 724 |
| 70 | 4309 | >50,000 | 114.5 | 437 |
| 71 | 4310 | >50,000 | 73.4 | 681 |
| 72 | 4311 | >50,000 | 98.0 | 510 |
| 73 | 4312 | >50,000 | 94.3 | 530 |
| 74 | 4313 | >50,000 | 134.9 | 371 |
| 75 | 4314 | >50,000 | 108.3 | 462 |
| 76 | 4315 | >50,000 | 162.0 | 309 |
| 77 | 4616 | >50,000 | 205 | 243 |
| 78 | 4617 | >50,000 | 75 | 666 |
| 79 | 4622 | >50,000 | 182 | 274 |
| 80 | 4623 | >50,000 | 62 | 806 |
| 81 | 4624 | >50,000 | 84 | 595 |
| 82 | 6893 | >50,000 | 3118 | 16 |

As shown in Table 4 above, it was found from the results of the activity inhibition assay for HDAC1 and HDAC6 that the 1,3,4-oxadiazole derivative compounds of the present invention, the optical isomers thereof, or the pharmaceutically acceptable salts thereof exhibited about 16 to about 1055 times higher selective HDAC6 inhibitory activity than that of HDAC1.

<Experimental Example 2> In vitro Analysis of Effect of HDAC6-Specific Inhibitors on Mitochondrial Axonal Transport The effects of the HDAC6-specific inhibitors on mitochondrial axonal transport were analyzed. Specifically, in order to confirm whether the compounds represented by Chemical Formula I of the present invention selectively inhibit the HDAC6 activity and increase the acetylation of tubulin, which is a major substrate of HDAC6, thereby improving the mitochondrial axonal transport rates reduced by amyloid-beta treatment in neuronal axons, a comparison experiment was performed using the material that has already been developed as a control group.

Hippocampal neurons from Sprague-Dawley (SD) rat embryos at embryonic day 17-18 (E17-18) were cultured for 7 days in an extracellular matrix-coated culture dish for imaging, and then treated with 1M of amyloid-beta peptide fragments. After 24 hours, the compound was treated on the 8th day of in vitro culture, and 3 hours later, treated with MitoTracker Red CMXRos (Life Technologies, NY, USA) for the last 5 minutes to stain the mitochondria. With regard to the axonal transport of the stained neuron mitochondria, the transport rates of each mitochondrion were determined using the IMARIS analysis software (BITPLANE, Zurich, Switzerland) by taking images using a confocal microscope (Leica 5P8; Leica Microsystems, UK) at 1-second intervals for 1 minute.

As a result, it was confirmed that the 1,3,4-oxadiazole derivative compounds of the present invention, the optical isomers thereof or the pharmaceutically acceptable salts thereof showed an improvement effect on the rates of mitochondrial axonal transport.

The invention claimed is:

1. A 1,3,4-oxadiazole derivative compound represented by Chemical Formula I below, an optical isomer thereof, or a pharmaceutically acceptable salt thereof:

[Chemical Formula I]

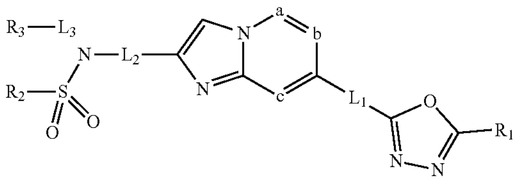

in the Chemical Formula I above, $L_1$, $L_2$ and $L_3$ are each independently —($C_0$-$C_2$alkyl)-;

a, b and c are each independently N or $CR^4$ {wherein a, b and c cannot be N at the same time, and $R^4$ is —H, —X or —O($C_1$-$C_4$alkyl)};

$R_1$ is —$CX_2H$ or —$CX_3$;

$R_2$ is —($C_1$-$C_4$alkyl), —($C_1$-$C_4$alkyl)-O—($C_1$-$C_4$alkyl), —$NR^AR^B$, aryl, heteroaryl,

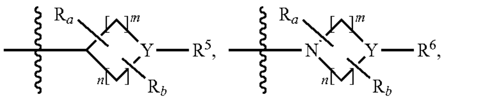

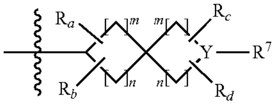

or

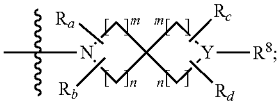

Y is —N—, —CH—, —O—or —$S(=O)_2$—;

when Y is —N—or —CH—, $R_5$, $R_6$, $R_7$ and $R_8$ are each independently —H, —X, —OH, —($C_1$-$C_4$alkyl), —($C_1$-$C_4$alkyl)-O($C_1$-$C_4$alkyl), —($C_3$-$C_7$cycloalkyl), —($C_2$-$C_6$heterocycloalkyl), —O($C_1$-$C_4$alkyl), —$NR^CR^D$, —$CF_3$, —$CF_2H$, —CN, —C(=O)—($C_1$-$C_4$alkyl), —C(=O)—($C_3$-$C_7$cycloalkyl), —C(=O)—($C_2$-$C_6$heterocycloalkyl), —C(=O)—O($C_1$-$C_4$alkyl), —($C_1$-$C_4$alkyl)-C(=O)—O($C_1$-$C_4$alkyl), —C(=O)—$NR^CR^D$, —C(=O)—($C_1$-$C_4$alkyl)-$NR^CR^D$, —$S(=O)_2$—($C_1$-$C_4$alkyl), -aryl, -heteroaryl, —($C_1$-$C_4$alkyl)-aryl, —($C_1$-$C_4$alkyl) heteroaryl, an amine protecting group or

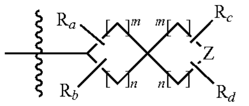

{wherein at least one H of —($C_1$-$C_4$alkyl), —(C=O)—($C_1$-$C_4$alkyl), —($C_3$-$C_7$cycloalkyl) and —C(=O)—($C_3$-$C_7$cycloalkyl) may be substituted with —X, —OH, —O($C_1$-$C_4$alkyl), —C(=O)—($C_1$-$C_4$alkyl), —C(=O)—O($C_1$-$C_4$alkyl), —$CF_3$ or —$CF_2H$; at least one H of -aryl, -heteroaryl, —($C_1$-$C_4$alkyl)-aryl and —($C_1$-$C_4$alkyl) heteroaryl may be substituted with —X, —OH, —($C_1$-$C_4$alkyl), —O($C_1$-$C_4$alkyl), —C(=O)—($C_1$-$C_4$alkyl), —C(=O)—O($C_1$-$C_4$alkyl), —$CF_3$ or —$CF_2H$; —($C_2$-$C_6$heterocycloalkyl), -heteroaryl or —($C_1$-$C_4$alkyl) heteroaryl may contain N, O or S atom in the ring; and Z is —NH—, —$CH_2$—or —O—};

when Y is —O—or —$S(=O)_2$—, $R_5$, $R_6$, $R_7$ and $R_8$ are nothing (null);

$R^A$ to $R^D$ are each independently —H, —($C_1$-$C_4$alkyl), —($C_3$-$C_7$cycloalkyl), —($C_2$-$C_6$heterocycloalkyl), —($C_1$-$C_4$alkyl)-($C_2$-$C_6$heterocycloalkyl), aryl, heteroaryl or —($C_1$-$C_4$alkyl)-aryl {wherein at least one H of —($C_3$-$C_7$cycloalkyl), —($C_2$-$C_6$heterocycloalkyl), —($C_1$-$C_4$alkyl)-($C_2$-$C_6$heterocycloalkyl), aryl, heteroaryl and —($C_1$-$C_4$alkyl)-aryl may be substituted with —($C_1$-$C_4$alkyl), —C(=O)—($C_1$-$C_4$alkyl), —$S(=O)_2$—($C_1$-$C_4$alkyl) or —($C_2$-$C_6$heterocycloalkyl)};

m and n are each independently an integer of 1,2 or 3;

$R_a$ to $R_d$ are each independently —H or —($C_1$-$C_4$alkyl);

$R^3$ is —H, —($C_1$-$C_4$alkyl), —($C_1$-$C_4$alkyl)-O($C_1$-$C_4$alkyl), —($C_1$-$C_4$alkyl)-C(=O)—O($C_1$-$C_4$alkyl), —C(=O)—O($C_1$-$C_4$alkyl), —($C_3$-$C_7$cycloalkyl), —($C_2$-$C_6$heterocycloalkyl), -aryl or -heteroaryl {wherein at least one H of —($C_1$-$C_4$alkyl), —($C_3$-$C_7$cycloalkyl), —($C_2$-$C_6$heterocycloalkyl), -aryl and -heteroaryl may each independently be substituted with —X, —OH, —O($C_1$-$C_4$alkyl), —C(=O)—O($C_1$-$C_4$alkyl), —C(=O)—($C_1$-$C_4$alkyl), —$CF_3$, —$CF_2H$, —$OCF_3$, —$S(=O)_2$—($C_1$-$C_4$alkyl), -aryl, —O-aryl, -heteroaryl or —$NR^ER_F$, and the $R_E$ and $R_F$ are each independently —H or —($C_1$-$C_4$alkyl)}; and X is F, Cl, Br or I.

2. The 1,3,4-oxadiazole derivative compound represented by Chemical Formula I, the optical isomer thereof, or the pharmaceutically acceptable salt thereof according to claim 1, wherein in the Chemical Formula I above, $L_1$ to $L_3$ are each independently —($C_0$-$C_1$alkyl)-;

a, b and c are each independently N or $CR^4$ {wherein a, b and c cannot be N at the same time, and $R_4$ is —H or —X};

$R_1$ is —$CX_2H$ or —$CX_3$;

$R_2$ is —($C_1$-$C_4$alkyl), —$NR^AR^B$,

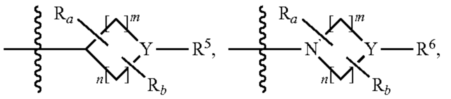

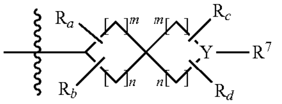

or

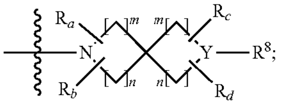

Y is —N—, —O—or —$S(=O)_2$—;

when Y is —N—, $R_5$, $R_6$, $R_7$ and $R_8$ are each independently —H, —($C_1$-$C_4$alkyl), —($C_3$-$C_7$cycloalkyl), —($C_2$-$C_6$heterocycloalkyl), —C(=O)—($C_1$-$C_4$alkyl), —C(=O)—($C_3$-$C_7$cycloalkyl), —C(=O)—($C_2$-$C_6$heterocycloalkyl), —C(=O)—O($C_1$-$C_4$alkyl), —C(=O)—$NR^CR^D$, —$S(=O)_2$—($C_1$-$C_4$alkyl), -heteroaryl or

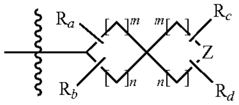

{wherein at least one-H of —($C_1$-$C_4$alkyl), —(C=O)—($C_1$-$C_4$alkyl) and —($C_3$-$C_7$cycloalkyl) may be substituted with —X or —OH; —($C_2$-$C_6$heterocycloalkyl) or -heteroaryl may contain N, O or S atoms in the ring; and Z is —NH—, —$CH_2$—or —O—};

when Y is —O—or —$S(=O)_2$—, $R_5$, $R_6$, $R_7$ and $R_8$ are nothing (null);

$R^A$ to $R^D$ are each independently —H or —($C_1$-$C_4$alkyl);

m and n are each independently an integer of 1 or 2;

$R_a$ to $R_d$ are each independently —H or —($C_1$-$C_4$alkyl);

$R^3$ is -aryl or -heteroaryl {wherein at least one H of -aryl and -heteroaryl may each independently be substituted with —X}; and X is F, $C_1$ or Br.

3. The 1,3,4-oxadiazole derivative compound represented by Chemical Formula I, the optical isomer thereof, or the pharmaceutically acceptable salt thereof according to claim 2, wherein in the Chemical Formula I above, $L_1$ and $L_3$ are each independently -($C_0$alkyl)-;

$L_2$ is -($C_1$alkyl)-;

a, b and c are each independently $CR^4$ {wherein $R_4$ is —H or —X};

$R_1$ is —$CX_2$H or —$CX_3$;

$R_2$ is

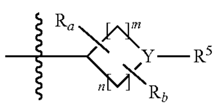 or 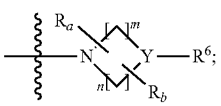;

Y is —N—, $R_5$ and $R_6$ are each independently —H, —($C_1$-$C_4$alkyl), —($C_3$-$C_7$cycloalkyl), —($C_2$-$C_6$heterocycloalkyl), —C(═O)—($C_1$-$C_4$alkyl), —C(═O)—($C_3$-$C_7$cycloalkyl), —C(═O)—($C_2$-$C_6$heterocycloalkyl), —C(═O)—O($C_1$-$C_4$alkyl), —C(—O)—$NR^CR^D$, —S(═O)$_2$—($C_1$-$C_4$alkyl), -heteroaryl or

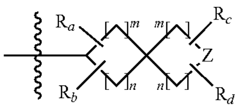

{wherein at least one-H of —($C_1$-$C_4$alkyl), —(C—O)—($C_1$-$C_4$alkyl) and —($C_3$-$C_7$cycloalkyl) may be substituted with —X or —OH; —($C_2$-$C_6$heterocycloalkyl) or -heteroaryl may contain N, O or S atoms in the ring; and Z is —$CH_2$—or —O—};

$R^C$ and $R^D$ are each independently —H or —($C_1$-$C_4$alkyl);

m and n are each independently an integer of 1 or 2;

$R_a$ and $R_b$ are each independently —H or —($C_1$-$C_4$alkyl);

$R^3$ is -aryl {wherein at least one H of -aryl may each independently be substituted with —X}; and X is F or $C_1$.

4. The 1,3,4-oxadiazole derivative compound represented by Chemical Formula I, the optical isomer thereof, or the pharmaceutically acceptable salt thereof according to claim 2, wherein in the Chemical Formula I above, $L_1$ to $L_3$ are each independently —($C_0$-$C_1$alkyl)-;

a, b and c are each independently N or $CR^4$ {wherein a, b and c cannot be N at the same time, and $R^4$ is —H or —X};

$R_1$ is —$CX_2$H or —$CX_3$;

$R_2$ is —($C_1$-$C_4$alkyl),

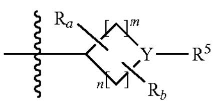 or 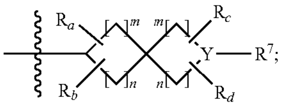;

Y is —N—, —O—or —S(═O)$_2$—;

when Y is —N—, $R_5$, $R_6$, $R_7$ and $R_8$ are each independently —H, —($C_1$-$C_4$alkyl), —($C_3$-$C_7$cycloalkyl), —($C_2$-$C_6$heterocycloalkyl), —C(═O)—($C_1$-$C_4$alkyl), —C(═O)—($C_3$-$C_7$cycloalkyl), —C(═O)—($C_2$-$C_6$heterocycloalkyl), —C(═O)—O($C_1$-$C_4$alkyl), —C(═O)—$NR^CR^D$, —S(═O)$_2$—($C_1$-$C_4$alkyl), -heteroaryl or

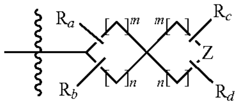

{wherein at least one-H of —($C_1$-$C_4$alkyl), —(C—O)—($C_1$-$C_4$alkyl) and —($C_3$-$C_7$cycloalkyl) may be substituted with —X or —OH; —($C_2$-$C_6$heterocycloalkyl) or -heteroaryl may contain N, O or S atoms in the ring; and Z is —NH—, —$CH_2$—or —O—};

when Y is —O—or —S(═O)$_2$—, $R_5$, $R_6$, $R_7$ and $R_8$ are nothing (null);

$R^C$ and $R^D$ are each independently —H or —($C_1$-$C_4$alkyl);

m and n are each independently an integer of 1 or 2;

$R_a$ to $R_d$ are each independently —H or —($C_1$-$C_4$alkyl);

$R^3$ is -aryl or -heteroaryl {wherein at least one H of -aryl and -heteroaryl may each independently be substituted with —X}; and X is F, $C_1$ or Br.

5. The 1,3,4-oxadiazole derivative compound represented by Chemical Formula I, the optical isomer thereof, or the pharmaceutically acceptable salt thereof according to claim 2, wherein in the Chemical Formula I above, $L_1$ to $L_3$ are each independently —($C_0$-$C_1$alkyl)-;

a, b and c are each independently N or $CR^4$ {wherein a, b and c cannot be N at the same time, and $R^4$ is —H or —X};

$R_1$ is —$CX_2$H or —$CX_3$;

$R_2$ is —$NR^AR^B$,

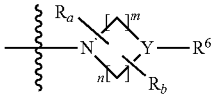 or 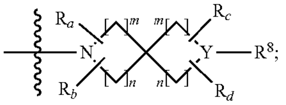;

Y is —N—, —O—or —S(═O)$_2$—;

when Y is —N—, $R_5$, $R_6$, $R_7$ and $R_8$ are each independently —H, —($C_1$-$C_4$alkyl), —($C_3$-$C_7$cycloalkyl), —($C_2$-$C_6$heterocycloalkyl), —C(═O)—($C_1$-$C_4$alkyl), —C(═O)—($C_3$-$C_7$cycloalkyl), —C(═O)—($C_2$-$C_6$heterocycloalkyl), —C(═O)—O($C_1$-$C_4$alkyl), —C(═O)—$NR^CR^D$, —S(═O)$_2$—($C_1$-$C_4$alkyl), -heteroaryl or

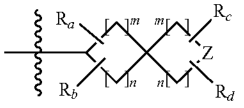

{wherein at least one-H of —($C_1$-$C_4$alkyl), —(C—O)—($C_1$-$C_4$alkyl) and —($C_3$-$C_7$cycloalkyl) may be substituted with —X or —OH; —($C_2$-$C_6$heterocycloalkyl) or -heteroaryl may contain N, O or S atoms in the ring; and Z is —NH—, —$CH_2$—or —O—};

when Y is —O—or —S(═O)$_2$—, $R_5$, $R_6$, $R_7$ and $R_8$ are nothing (null);

$R^A$ to $R^D$ are each independently —H or —($C_1$-$C_4$alkyl);

m and n are each independently an integer of 1 or 2;

$R_a$ to $R_d$ are each independently —H or —($C_1$-$C_4$alkyl);

$R^3$ is -aryl or -heteroaryl {wherein at least one H of -aryl and -heteroaryl may each independently be substituted with —X}; and X is F, $C_1$ or Br.

6. The 1,3,4-oxadiazole derivative compound, the optical isomer thereof or the pharmaceutically acceptable salt thereof according to claim 1, wherein it is any one of compounds listed in the following table:
| Ex | Comp | Structure |
|---|---|---|
| 1 | 3778 | 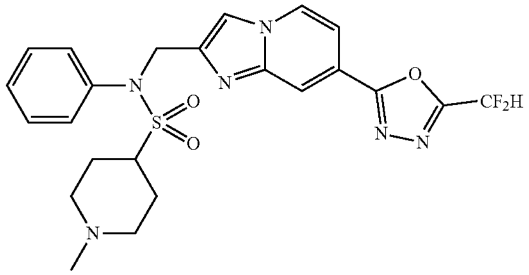 [SMILES: CN1CCC(S(=O)(=O)N(Cc2cn3ccc(-c4nnc(C(F)F)o4)cc3n2)c2ccccc2)CC1] |
| 2 | 3779 | 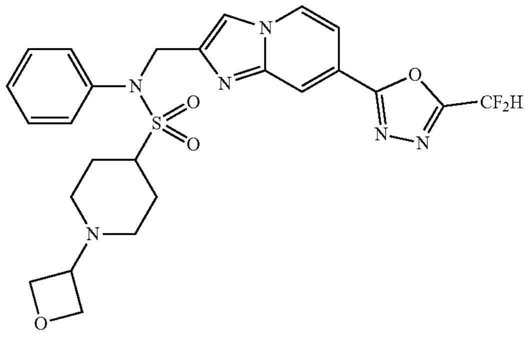 |
| 3 | 4214 | 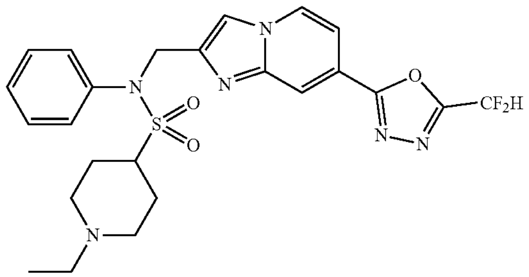 [SMILES: CCN1CCC(S(=O)(=O)N(Cc2cn3ccc(-c4nnc(C(F)F)o4)cc3n2)c2ccccc2)CC1] |
| 4 | 4215 | 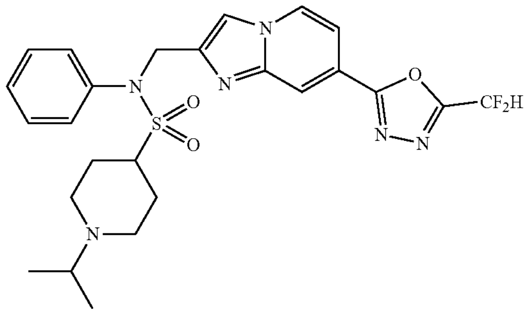 |
| 5 | 4216 | 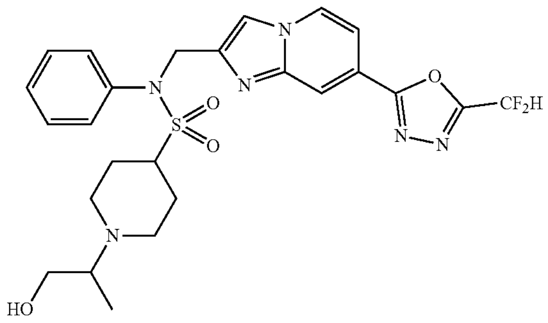 |

-continued
| Ex | Comp | Structure |
|---|---|---|
| 6 | 4217 | 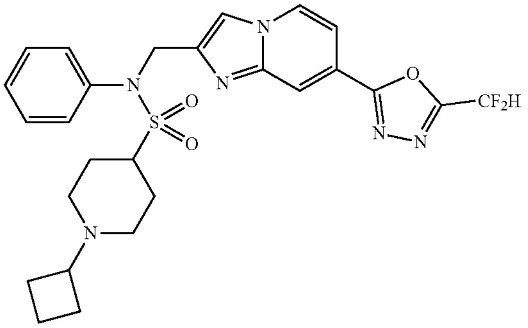 |
| 7 | 4218 | 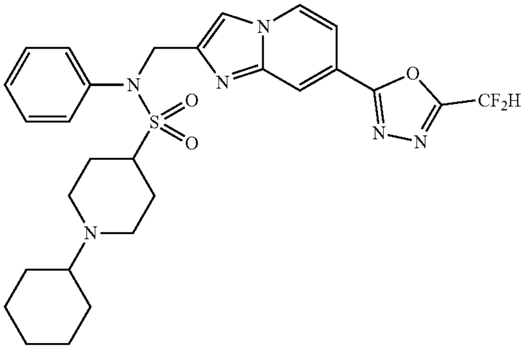 |
| 8 | 4219 | 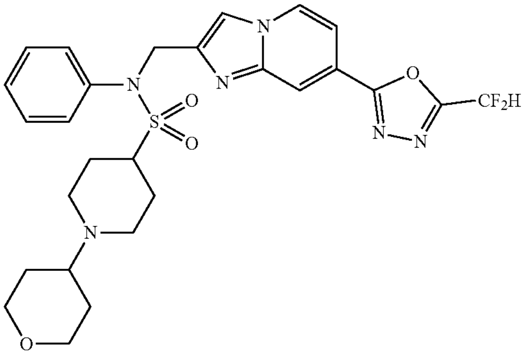 |
| 9 | 4220 | 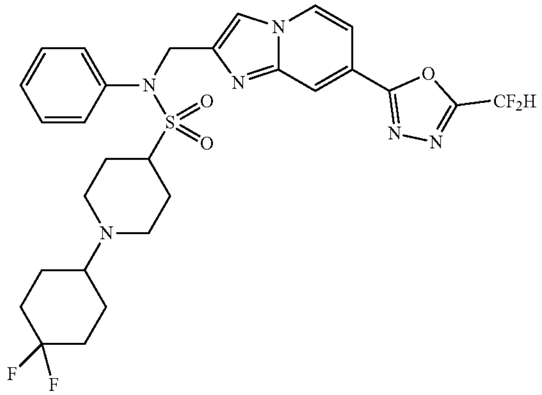 |

-continued
| Ex | Comp | Structure |
|---|---|---|
| 10 | 4221 | 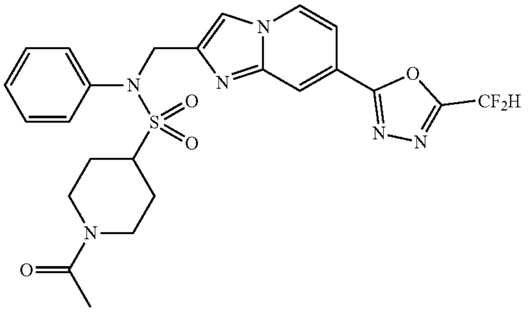 [SMILES: CC(=O)N1CCC(S(=O)(=O)N(Cc2cn3ccc(-c4nnc(C(F)F)o4)cc3n2)c2ccccc2)CC1] |
| 11 | 4222 | 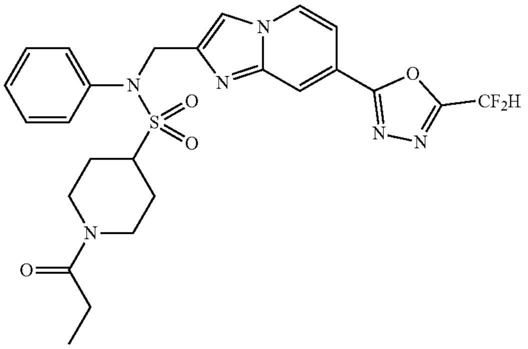 |
| 12 | 4223 | 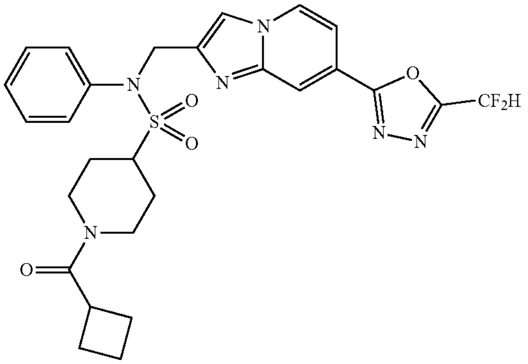 |
| 13 | 4224 | 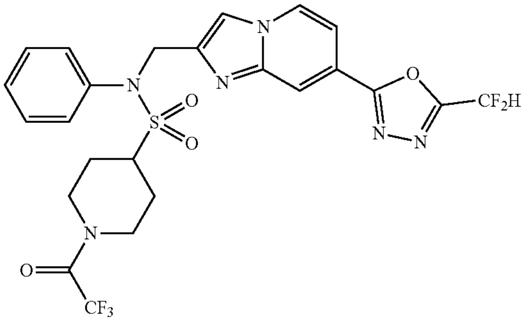 |

-continued
| Ex | Comp | Structure |
| --- | --- | --- |
| 14 | 4225 | 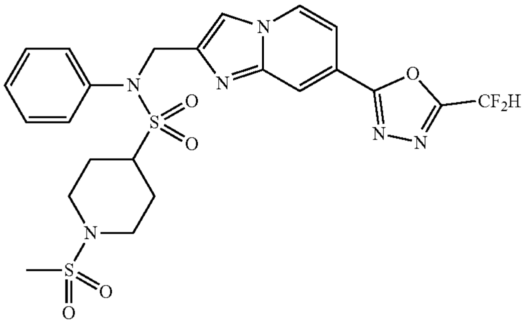 [SMILES: CS(=O)(=O)N1CCC(S(=O)(=O)N(Cc2cn3ccc(-c4nnc(C(F)F)o4)cc3n2)c2ccccc2)CC1] |
| 15 | 4226 | 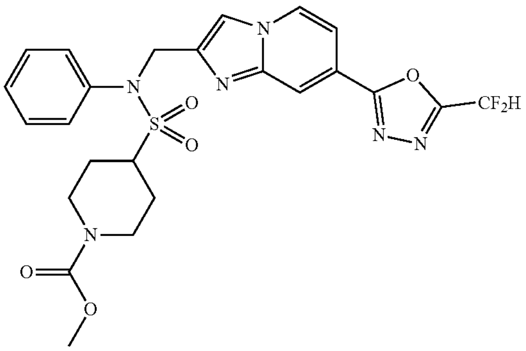 |
| 16 | 4227 | 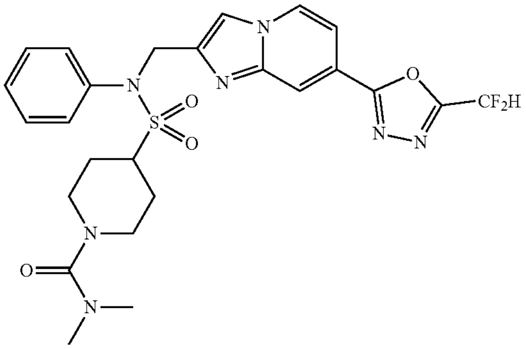 |
| 17 | 4228 | 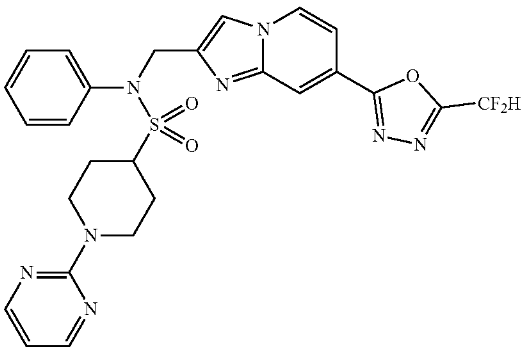 |

-continued
| Ex | Comp | Structure |
|---|---|---|
| 18 | 4236 | 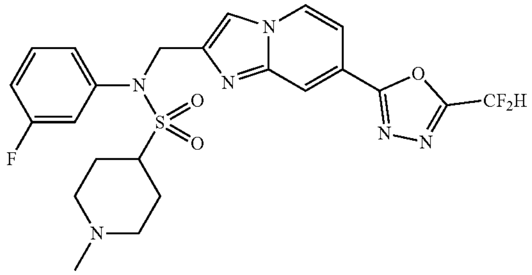 |
| 19 | 4237 | 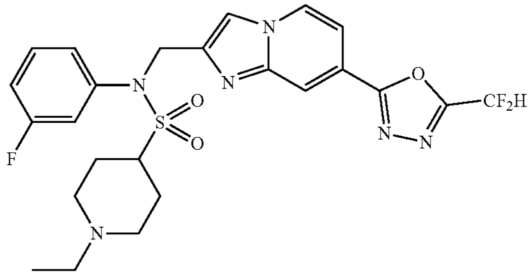 |
| 20 | 4238 | 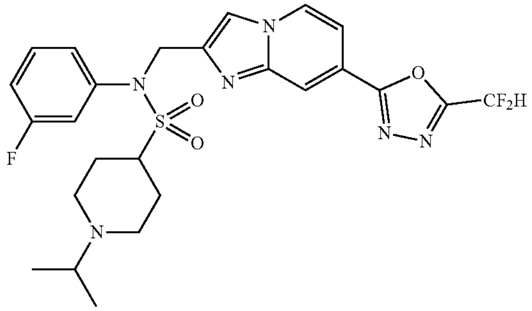 |
| 21 | 4239 | 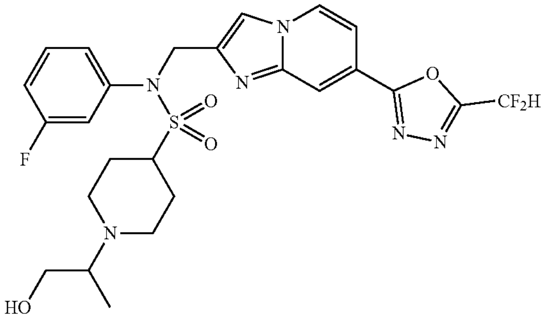 |
| 22 | 4240 | 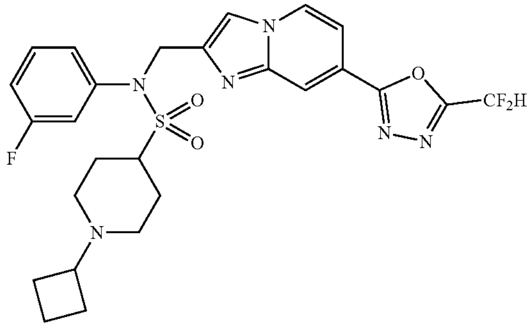 |

-continued
| Ex | Comp | Structure |
| --- | --- | --- |
| 23 | 4241 | 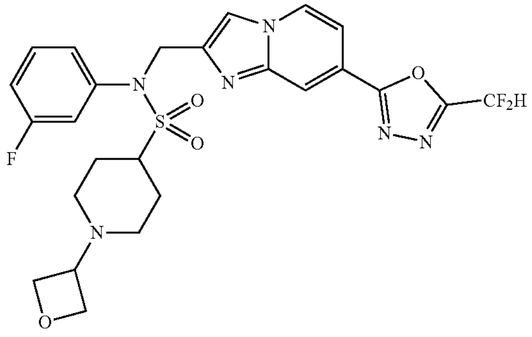 [SMILES: O=S(=O)(C1CCN(C2COC2)CC1)N(Cc1cn2ccc(-c3nnc(C(F)F)o3)cc2n1)c1cccc(F)c1] |
| 24 | 4242 | 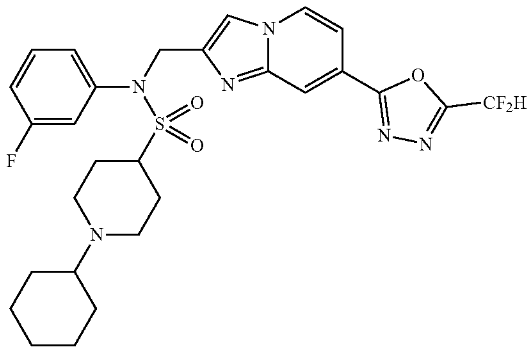 |
| 25 | 4243 | 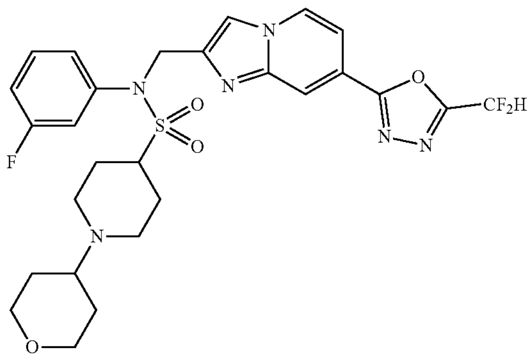 |
| 26 | 4244 | 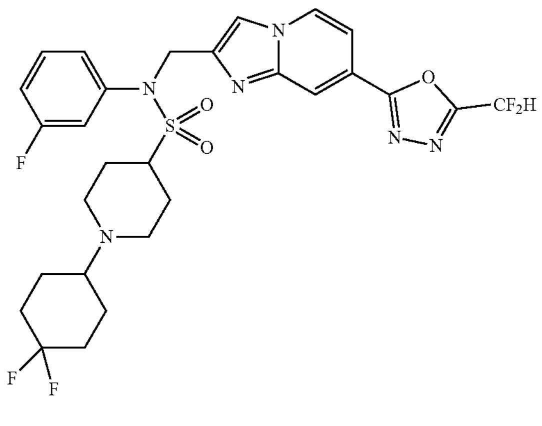 [SMILES: O=S(=O)(C1CCN(C2CCC(F)(F)CC2)CC1)N(Cc1cn2ccc(-c3nnc(C(F)F)o3)cc2n1)c1cccc(F)c1] |

-continued
| Ex | Comp | Structure |
| --- | --- | --- |
| 27 | 4245 | 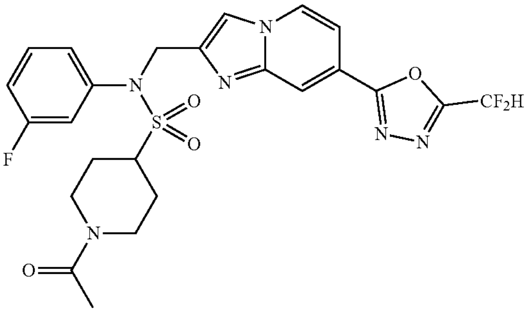 |
| 28 | 4246 | 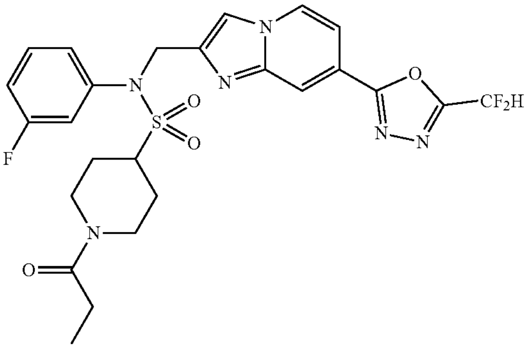 |
| 29 | 4247 | 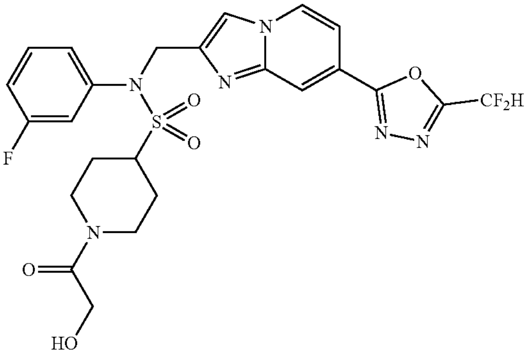 |
| 30 | 4248 | 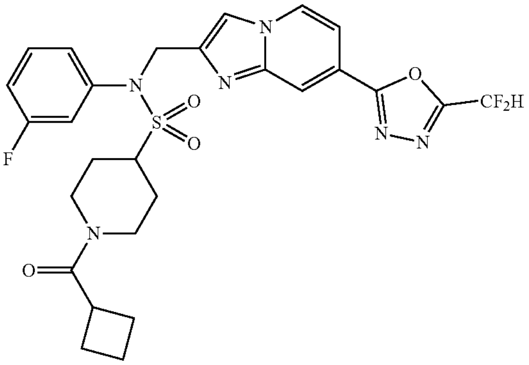 |

-continued
| Ex | Comp | Structure |
| --- | --- | --- |
| 31 | 4249 | 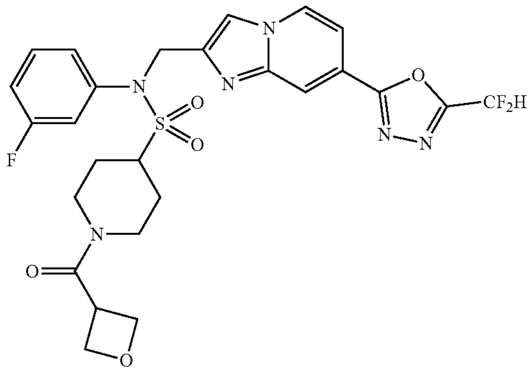 [SMILES: O=C(C1COC1)N1CCC(S(=O)(=O)N(Cc2cn3ccc(-c4nnc(C(F)F)o4)cc3n2)c2cccc(F)c2)CC1] |
| 32 | 4250 | 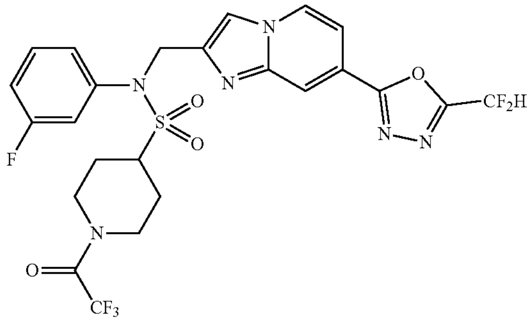 |
| 33 | 4251 | 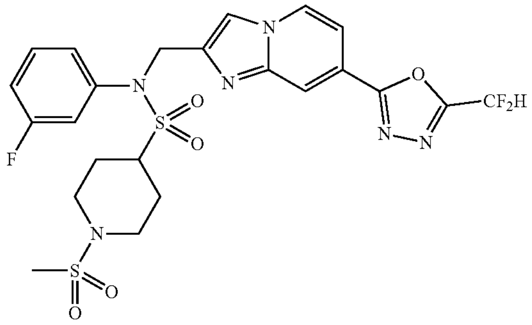 |
| 34 | 4252 | 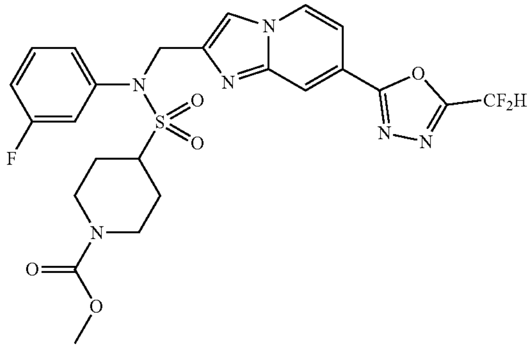 [SMILES: COC(=O)N1CCC(S(=O)(=O)N(Cc2cn3ccc(-c4nnc(C(F)F)o4)cc3n2)c2cccc(F)c2)CC1] |

-continued
| Ex | Comp | Structure |
|---|---|---|
| 35 | 4253 | 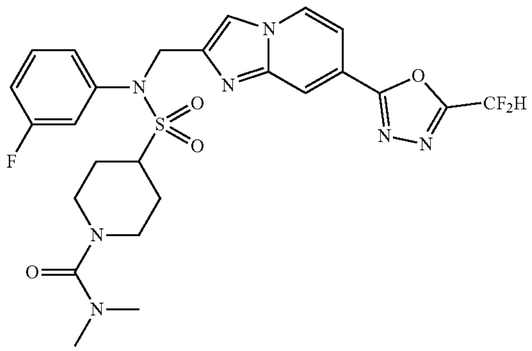 |
| 36 | 4254 | 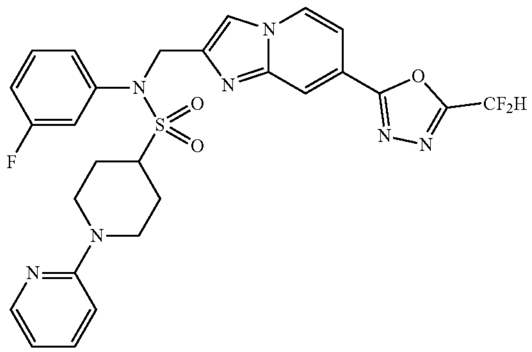 |
| 37 | 4255 | 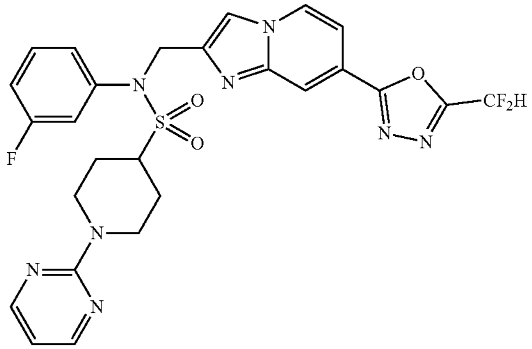 [SMILES: O=S(=O)(C1CCN(c2ncccn2)CC1)N(Cc1cn2ccc(-c3nnc(C(F)F)o3)cc2n1)c1cccc(F)c1] |
| 38 | 4256 | 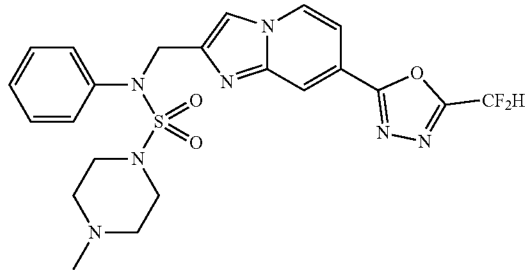 |

-continued
| Ex | Comp | Structure |
|---|---|---|
| 39 | 4257 | 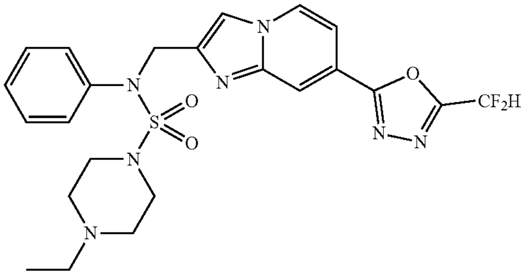 |
| 40 | 4258 | 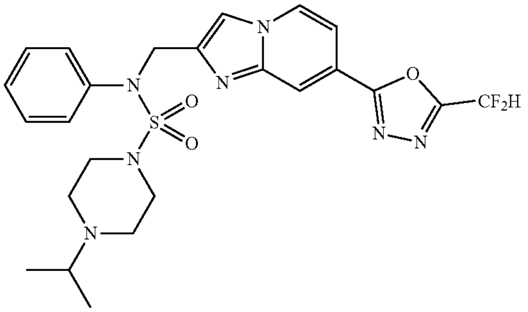 [SMILES: CC(C)N1CCN(S(=O)(=O)N(Cc2cn3ccc(-c4nnc(C(F)F)o4)cc3n2)c2ccccc2)CC1] |
| 41 | 4259 | 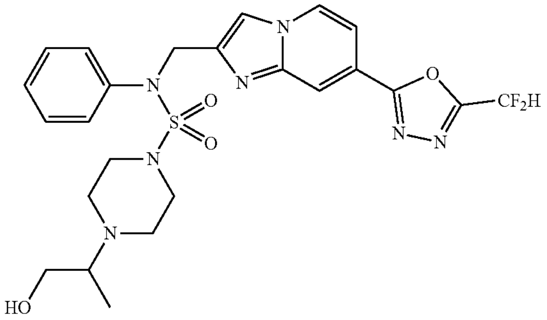 |
| 42 | 4260 | 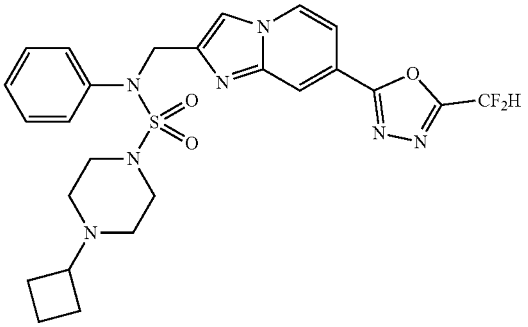 |
| 43 | 4261 | 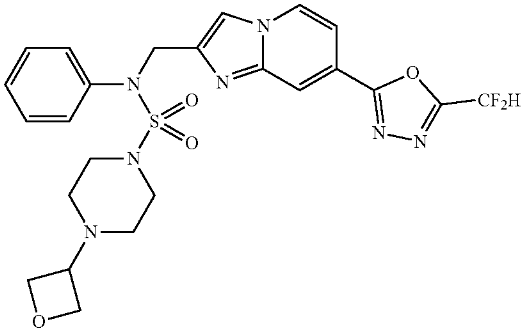 [SMILES: O=S(=O)(N1CCN(C2COC2)CC1)N(Cc1cn2ccc(-c3nnc(C(F)F)o3)cc2n1)c1ccccc1] |

-continued
| Ex | Comp | Structure |
| --- | --- | --- |
| 44 | 4262 | 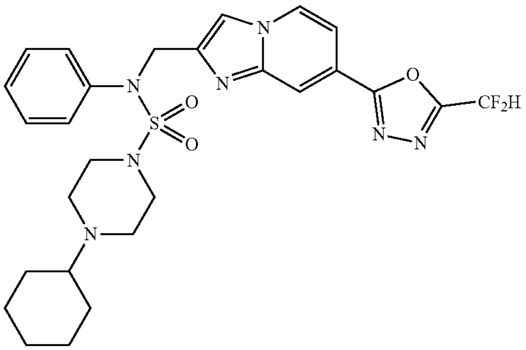 |
| 45 | 4263 | 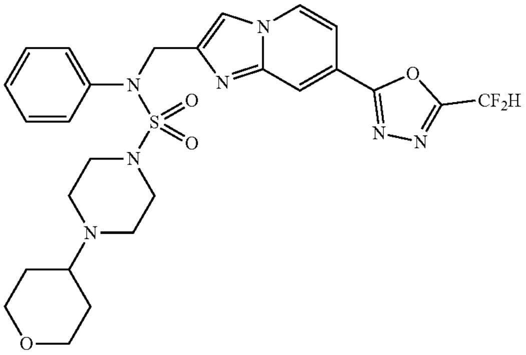 [SMILES: O=S(=O)(N1CCN(C2CCOCC2)CC1)N(Cc1cn2ccc(-c3nnc(C(F)F)o3)cc2n1)c1ccccc1] |
| 46 | 4264 | 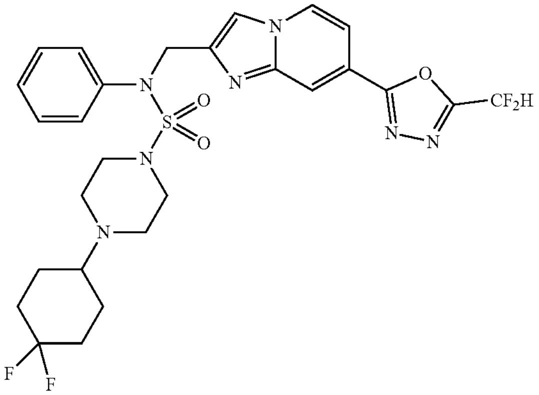 |
| 47 | 4265 | 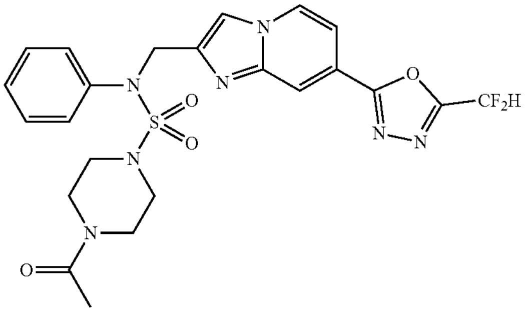 [SMILES: CC(=O)N1CCN(S(=O)(=O)N(Cc2cn3ccc(-c4nnc(C(F)F)o4)cc3n2)c2ccccc2)CC1] |

-continued
| Ex | Comp | Structure |
|---|---|---|
| 48 | 4266 | 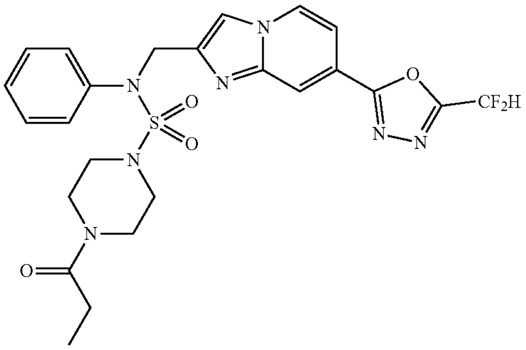 [SMILES: CCC(=O)N1CCN(S(=O)(=O)N(Cc2cn3ccc(-c4nnc(C(F)F)o4)cc3n2)c2ccccc2)CC1] |
| 49 | 4267 | 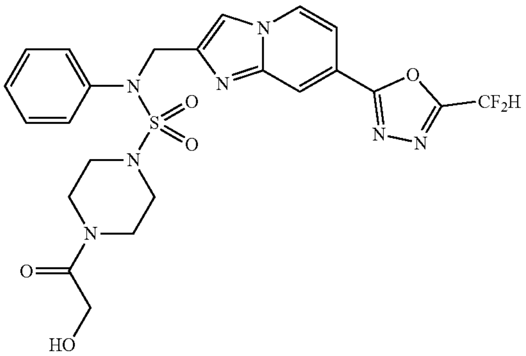 [SMILES: O=C(CO)N1CCN(S(=O)(=O)N(Cc2cn3ccc(-c4nnc(C(F)F)o4)cc3n2)c2ccccc2)CC1] |
| 50 | 4268 | 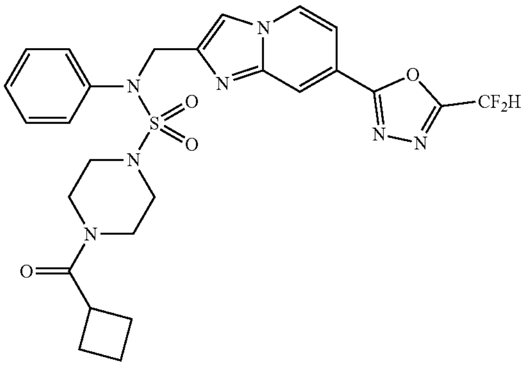 |
| 51 | 4269 | 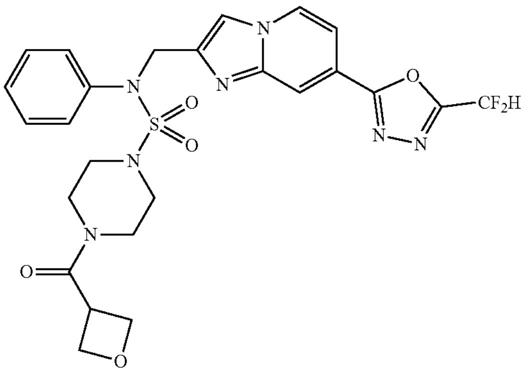 [SMILES: O=C(C1COC1)N1CCN(S(=O)(=O)N(Cc2cn3ccc(-c4nnc(C(F)F)o4)cc3n2)c2ccccc2)CC1] |

-continued
| Ex | Comp | Structure |
|---|---|---|
| 52 | 4270 | 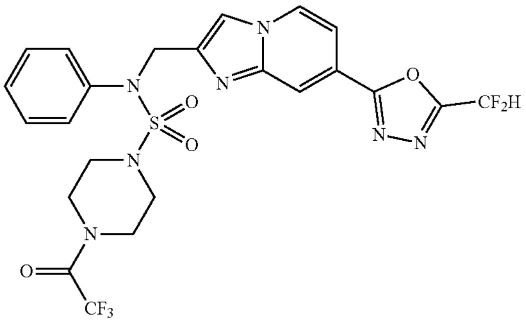 |
| 53 | 4271 | 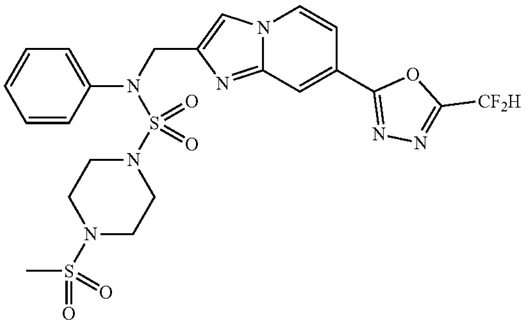 |
| 54 | 4272 | 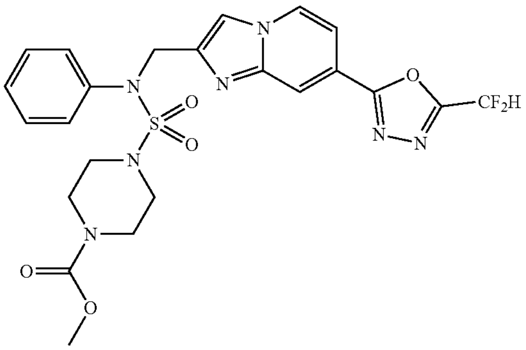 |
| 55 | 4273 | 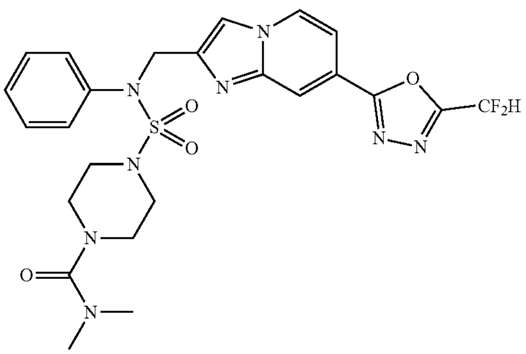 |

-continued
| Ex | Comp | Structure |
|---|---|---|
| 56 | 4274 | 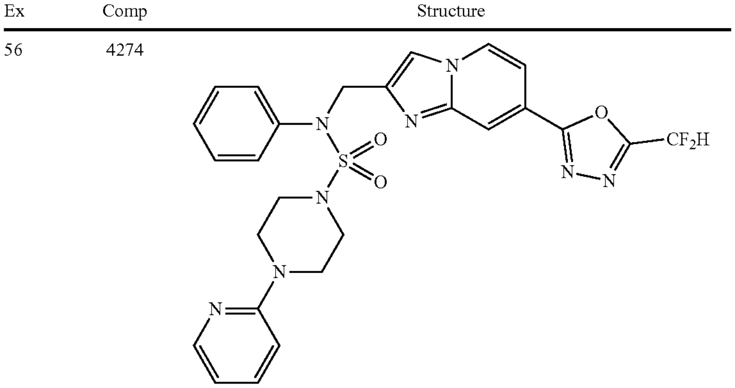 |
| 57 | 4275 | 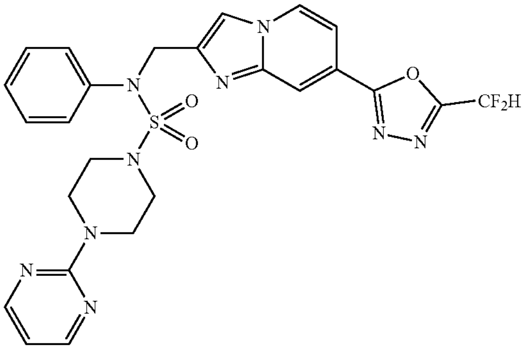 [SMILES: O=S(=O)(N1CCN(c2ncccn2)CC1)N(Cc1cn2ccc(-c3nnc(C(F)F)o3)cc2n1)c1ccccc1] |
| 58 | 4297 | 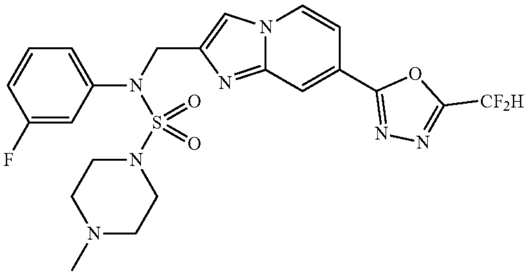 |
| 59 | 4298 | 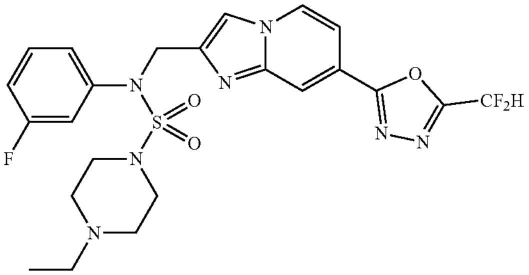 [SMILES: CCN1CCN(S(=O)(=O)N(Cc2cn3ccc(-c4nnc(C(F)F)o4)cc3n2)c2cccc(F)c2)CC1] |
| 60 | 4299 | 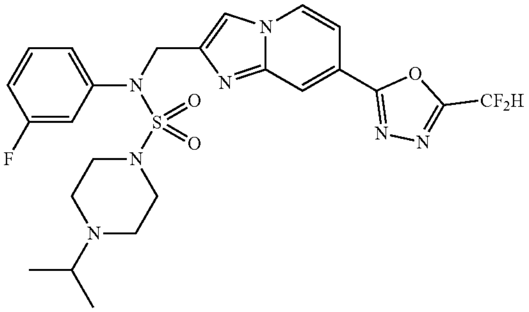 [SMILES: CC(C)N1CCN(S(=O)(=O)N(Cc2cn3ccc(-c4nnc(C(F)F)o4)cc3n2)c2cccc(F)c2)CC1] |

-continued
| Ex | Comp | Structure |
| --- | --- | --- |
| 61 | 4300 | 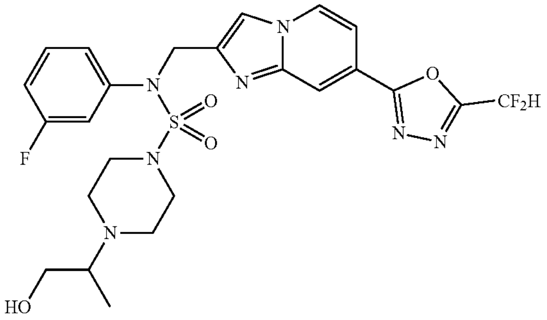 [SMILES: CC(CO)N1CCN(S(=O)(=O)N(Cc2cn3ccc(-c4nnc(C(F)F)o4)cc3n2)c2cccc(F)c2)CC1] |
| 62 | 4301 | 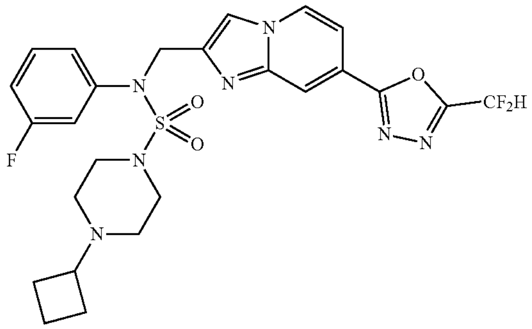 [SMILES: O=S(=O)(N1CCN(C2CCC2)CC1)N(Cc1cn2ccc(-c3nnc(C(F)F)o3)cc2n1)c1cccc(F)c1] |
| 63 | 4302 | 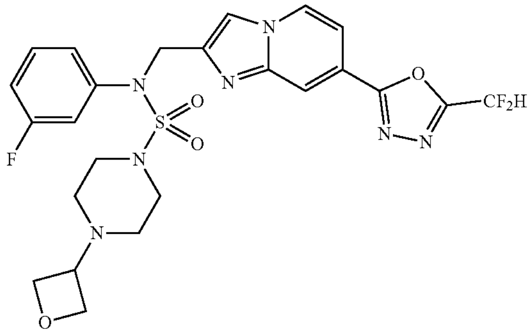 |
| 64 | 4303 | 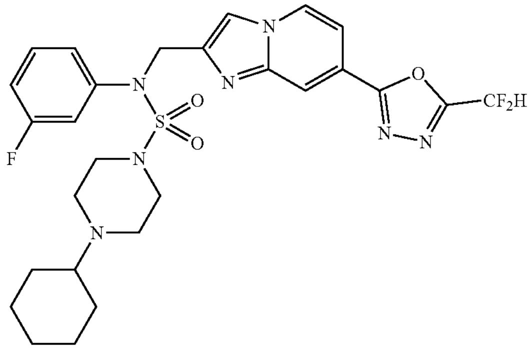 |

-continued
| Ex | Comp | Structure |
|---|---|---|
| 65 | 4304 | 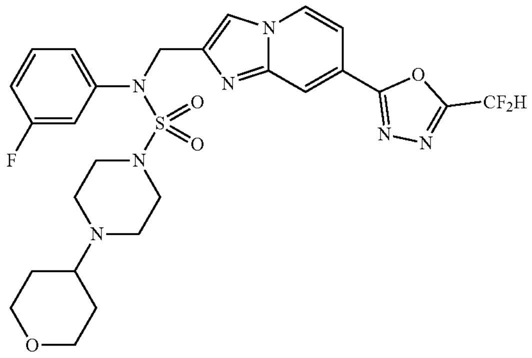 |
| 66 | 4305 | 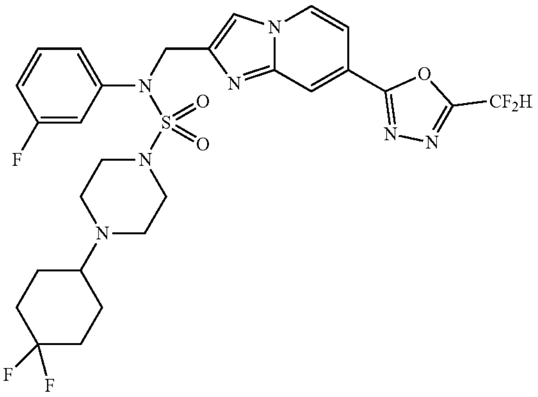 [SMILES: O=S(=O)(N1CCN(C2CCC(F)(F)CC2)CC1)N(Cc1cn2ccc(-c3nnc(C(F)F)o3)cc2n1)c1cccc(F)c1] |
| 67 | 4306 | 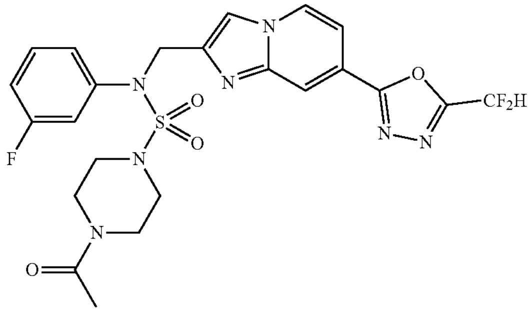 |
| 68 | 4307 | 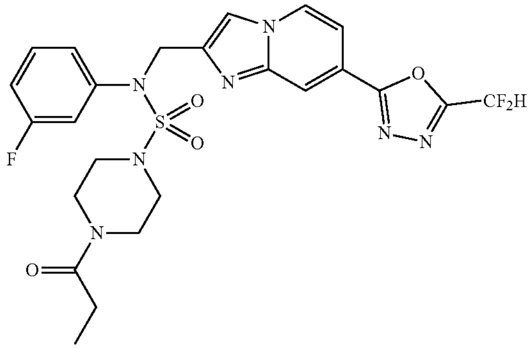 [SMILES: CCC(=O)N1CCN(S(=O)(=O)N(Cc2cn3ccc(-c4nnc(C(F)F)o4)cc3n2)c2cccc(F)c2)CC1] |

-continued
| Ex | Comp | Structure |
|---|---|---|
| 69 | 4308 | 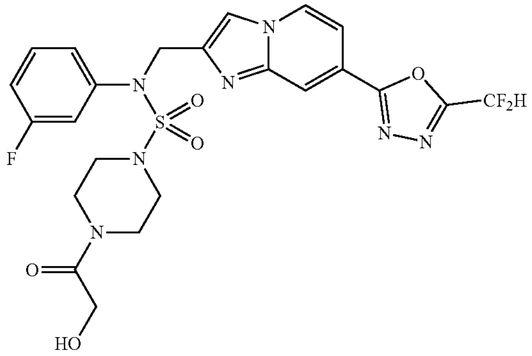 [SMILES: O=C(CO)N1CCN(S(=O)(=O)N(Cc2cn3ccc(-c4nnc(C(F)F)o4)cc3n2)c2cccc(F)c2)CC1] |
| 70 | 4309 | 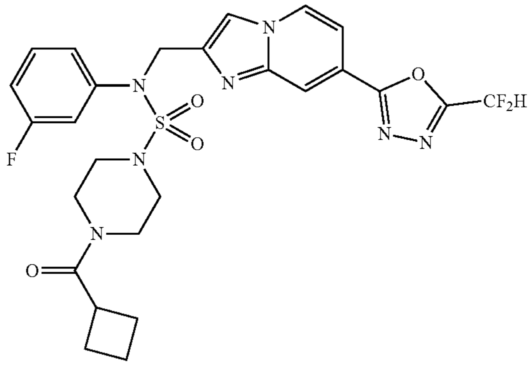 [SMILES: O=C(C1CCC1)N1CCN(S(=O)(=O)N(Cc2cn3ccc(-c4nnc(C(F)F)o4)cc3n2)c2cccc(F)c2)CC1] |
| 71 | 4310 | 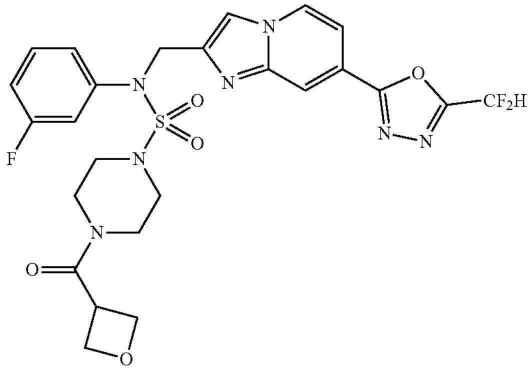 |
| 72 | 4311 | 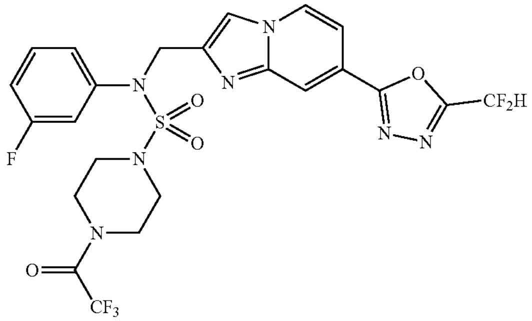 [SMILES: O=C(N1CCN(S(=O)(=O)N(Cc2cn3ccc(-c4nnc(C(F)F)o4)cc3n2)c2cccc(F)c2)CC1)C(F)(F)F] |

-continued
| Ex | Comp | Structure |
|---|---|---|
| 73 | 4312 | 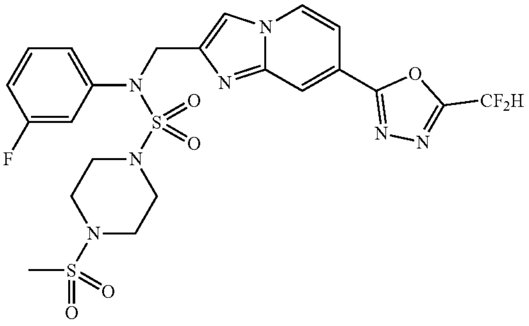 [SMILES: CS(=O)(=O)N1CCN(S(=O)(=O)N(Cc2cn3ccc(-c4nnc(C(F)F)o4)cc3n2)c2cccc(F)c2)CC1] |
| 74 | 4313 | 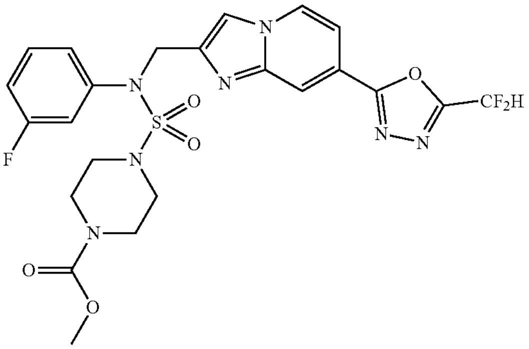 [SMILES: COC(=O)N1CCN(S(=O)(=O)N(Cc2cn3ccc(-c4nnc(C(F)F)o4)cc3n2)c2cccc(F)c2)CC1] |
| 75 | 4314 | 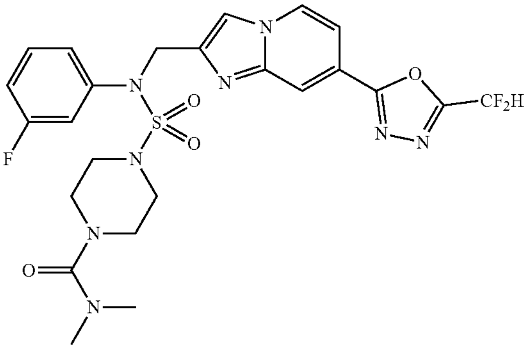 |
| 76 | 4315 | 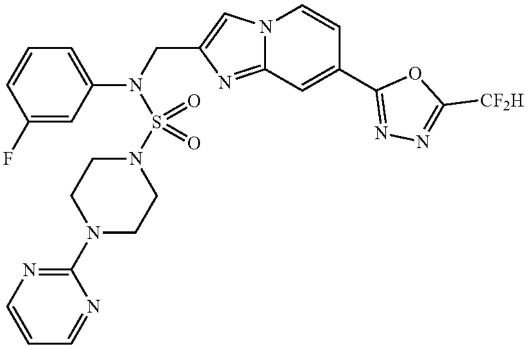 |

-continued
| Ex | Comp | Structure |
|---|---|---|
| 77 | 4616 | 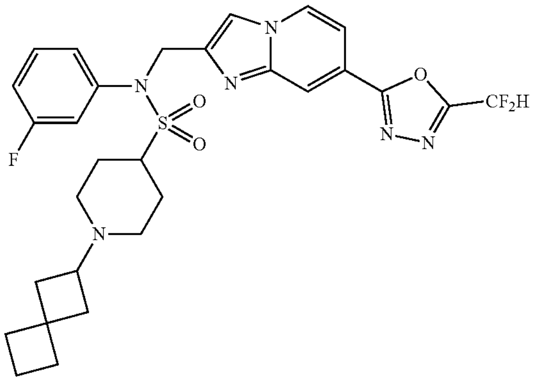 [SMILES: O=S(=O)(C1CCN(C2CC3(CCC3)C2)CC1)N(Cc1cn2ccc(-c3nnc(C(F)F)o3)cc2n1)c1cccc(F)c1] |
| 78 | 4617 | 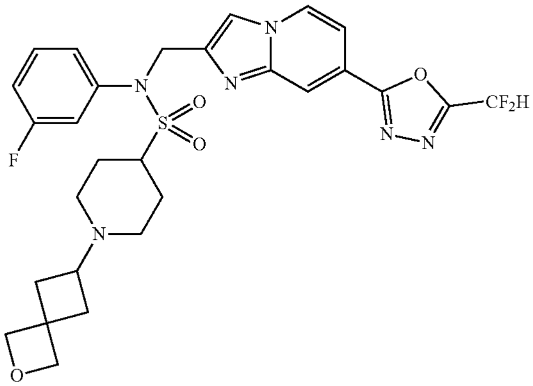 |
| 79 | 4622 | 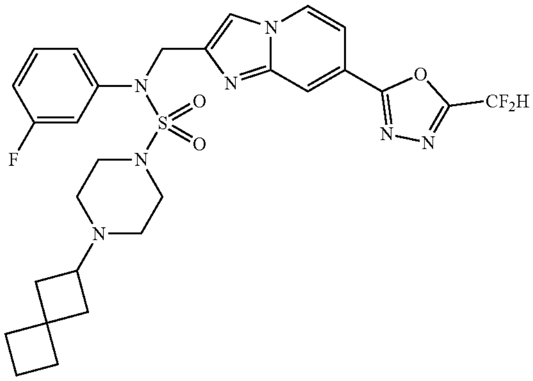 [SMILES: O=S(=O)(N1CCN(C2CC3(CCC3)C2)CC1)N(Cc1cn2ccc(-c3nnc(C(F)F)o3)cc2n1)c1cccc(F)c1] |
| 80 | 4623 | 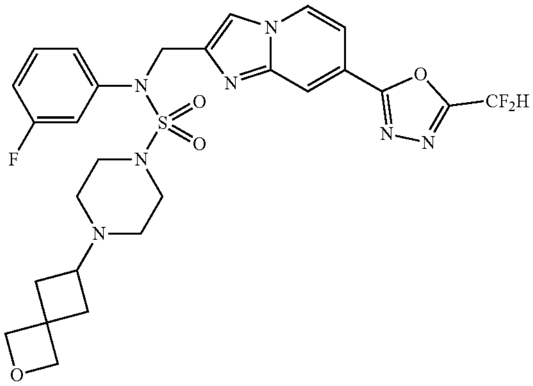 |

-continued
| Ex | Comp | Structure |
|---|---|---|
| 81 | 4624 | 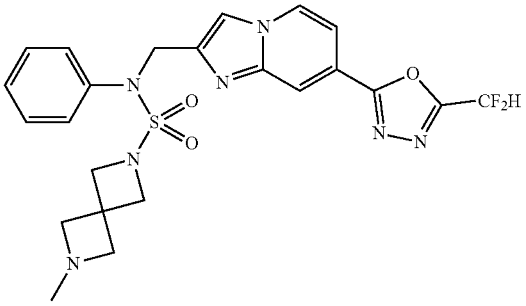 [SMILES: CN1CC2(C1)CN(S(=O)(=O)N(Cc1cn3ccc(-c4nnc(C(F)F)o4)cc3n1)c1ccccc1)C2] |
| 82 | 6893 | 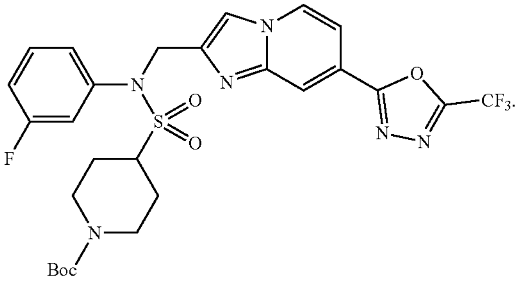 [SMILES: CC(C)(C)OC(=O)N1CCC(S(=O)(=O)N(Cc2cn3ccc(-c4nnc(C(F)(F)F)o4)cc3n2)c2cccc(F)c2)CC1] |
7. The 1,3,4-oxadiazole derivative compound, the optical isomer thereof or the pharmaceutically acceptable salt thereof according to claim 6, wherein it is any one of compounds listed in the following table:
| Ex | Comp | Structure |
|---|---|---|
| 1 | 3778 | 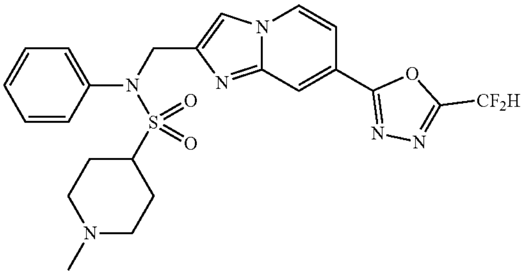 |
| 2 | 3779 | 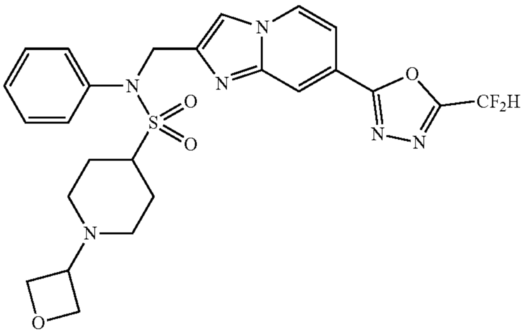 |

-continued
| Ex | Comp | Structure |
| --- | --- | --- |
| 3 | 4214 | 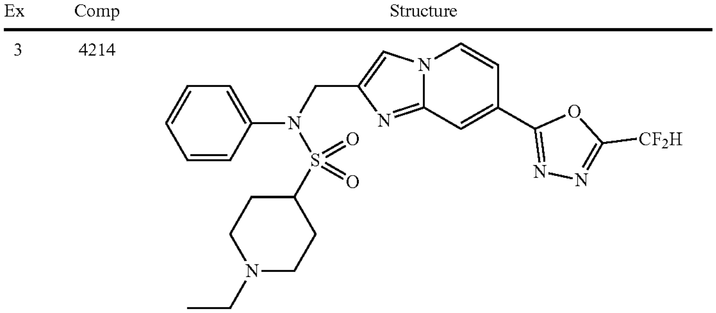 |
| 4 | 4215 | 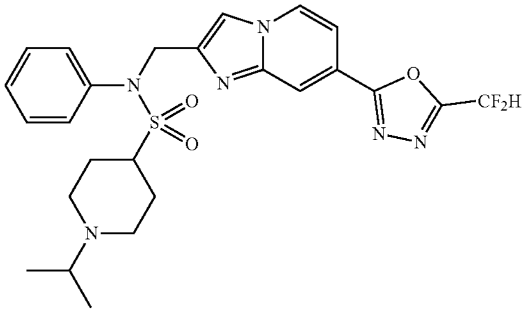 |
| 5 | 4216 | 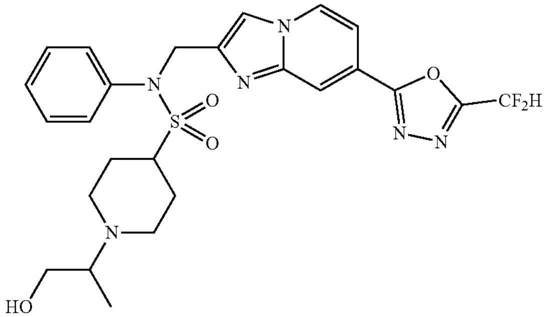 |
| 6 | 4217 | 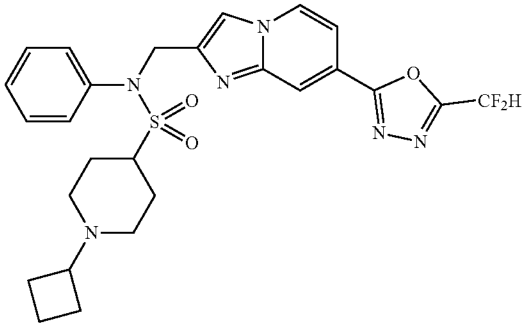 |
| 7 | 4218 | 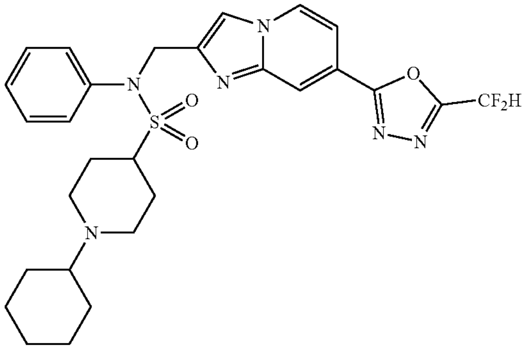 [SMILES: O=S(=O)(C1CCN(C2CCCCC2)CC1)N(Cc1cn2ccc(-c3nnc(C(F)F)o3)cc2n1)c1ccccc1] |

-continued
| Ex | Comp | Structure |
|---|---|---|
| 8 | 4219 | 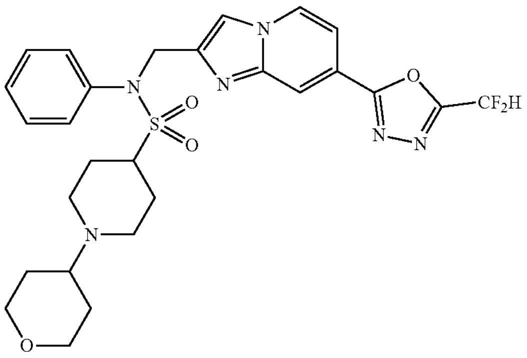 |
| 9 | 4220 | 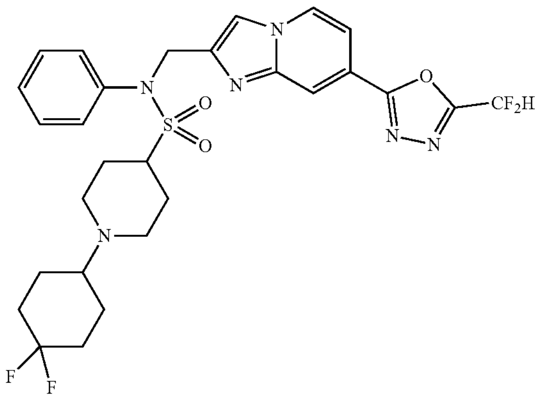 |
| 10 | 4221 | 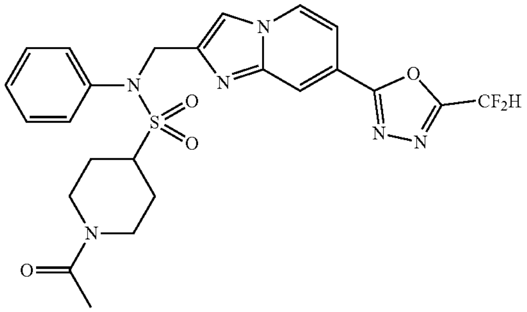 |
| 11 | 4222 | 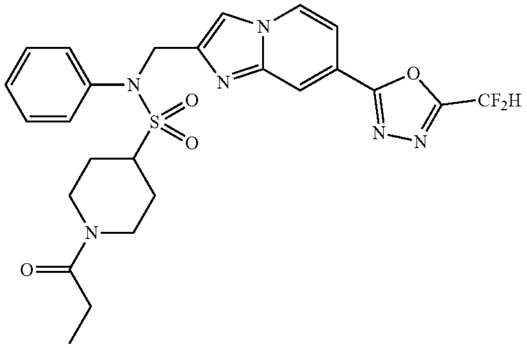 [SMILES: CCC(=O)N1CCC(S(=O)(=O)N(Cc2cn3ccc(-c4nnc(C(F)F)o4)cc3n2)c2ccccc2)CC1] |

-continued
| Ex | Comp | Structure |
|---|---|---|
| 12 | 4223 | 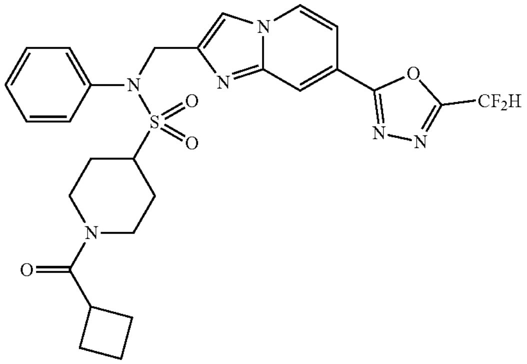 [SMILES: O=C(C1CCC1)N1CCC(S(=O)(=O)N(Cc2cn3ccc(-c4nnc(C(F)F)o4)cc3n2)c2ccccc2)CC1] |
| 13 | 4224 | 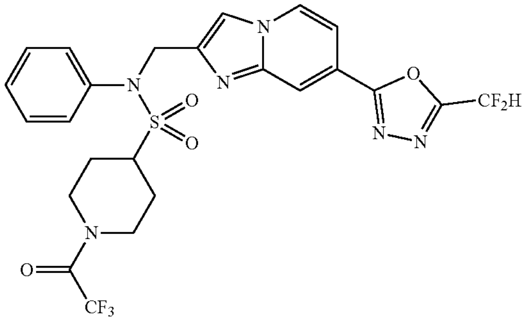 |
| 14 | 4225 | 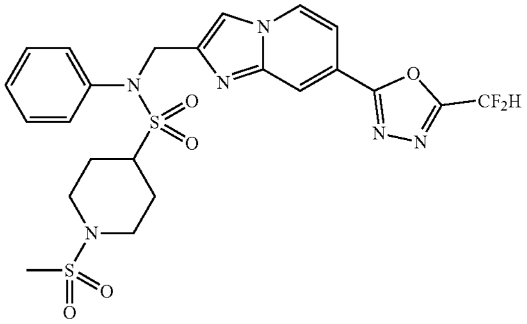 [SMILES: CS(=O)(=O)N1CCC(S(=O)(=O)N(Cc2cn3ccc(-c4nnc(C(F)F)o4)cc3n2)c2ccccc2)CC1] |
| 15 | 4226 | 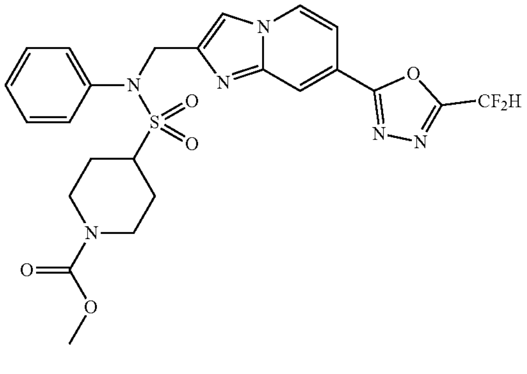 |

-continued
| Ex | Comp | Structure |
|---|---|---|
| 16 | 4227 | 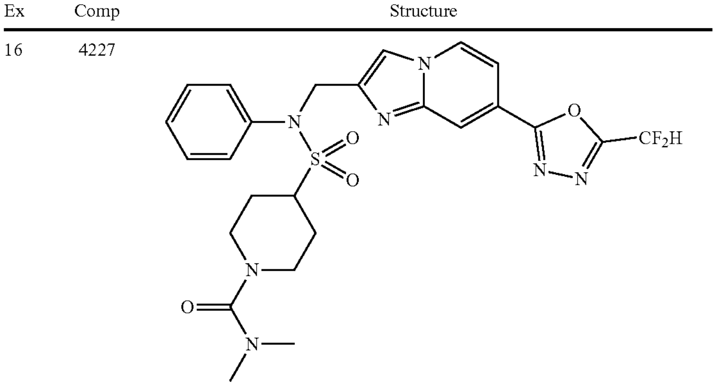 |
| 17 | 4228 | 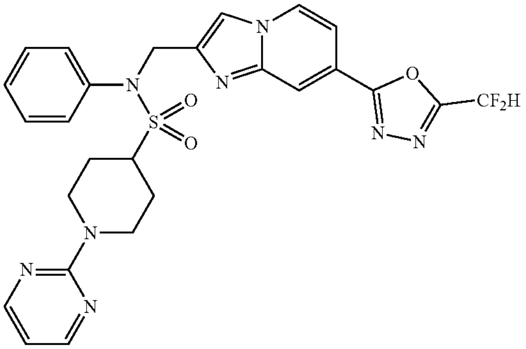 [SMILES: O=S(=O)(C1CCN(c2ncccn2)CC1)N(Cc1cn2ccc(-c3nnc(C(F)F)o3)cc2n1)c1ccccc1] |
| 18 | 4236 | 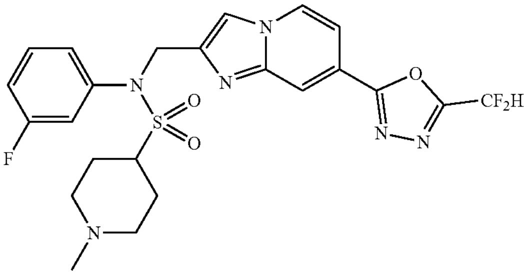 [SMILES: CN1CCC(S(=O)(=O)N(Cc2cn3ccc(-c4nnc(C(F)F)o4)cc3n2)c2cccc(F)c2)CC1] |
| 19 | 4237 | 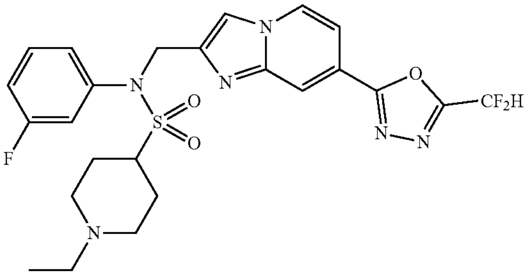 [SMILES: CCN1CCC(S(=O)(=O)N(Cc2cn3ccc(-c4nnc(C(F)F)o4)cc3n2)c2cccc(F)c2)CC1] |
| 20 | 4238 | 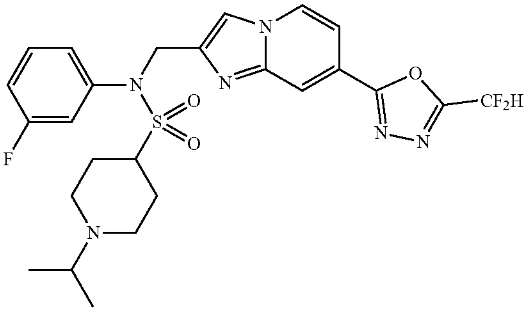 |

-continued
| Ex | Comp | Structure |
|---|---|---|
| 21 | 4239 | 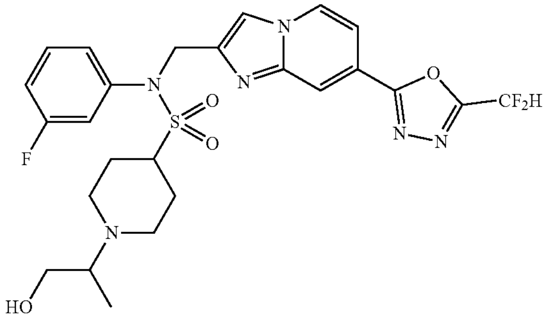 |
| 22 | 4240 | 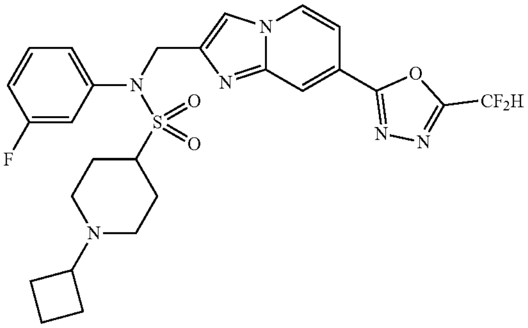 |
| 23 | 4241 | 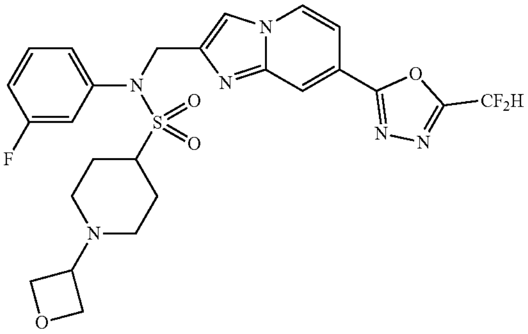 [SMILES: O=S(=O)(C1CCN(C2COC2)CC1)N(Cc1cn2ccc(-c3nnc(C(F)F)o3)cc2n1)c1cccc(F)c1] |
| 24 | 4242 | 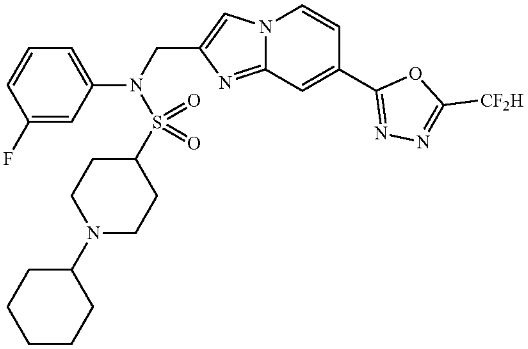 |

-continued
| Ex | Comp | Structure |
|---|---|---|
| 25 | 4243 | 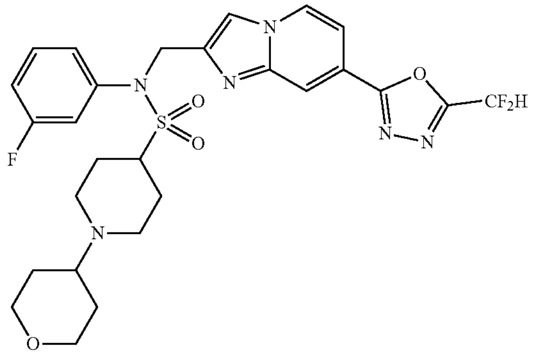 |
| 26 | 4244 | 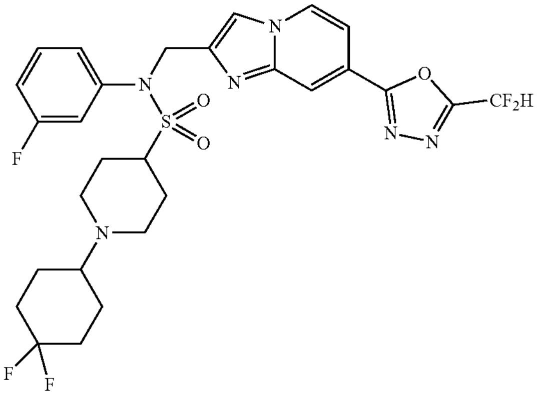 |
| 27 | 4245 | 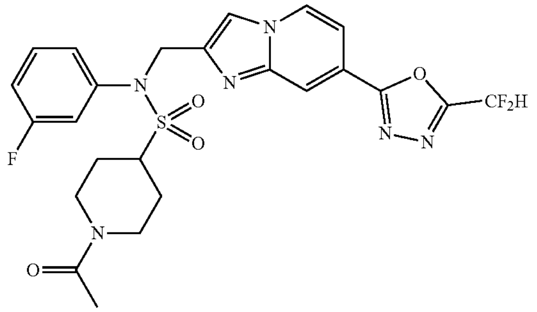 |
| 28 | 4246 | 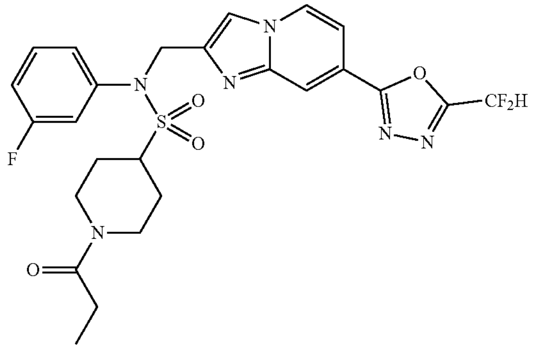 [SMILES: CCC(=O)N1CCC(S(=O)(=O)N(Cc2cn3ccc(-c4nnc(C(F)F)o4)cc3n2)c2cccc(F)c2)CC1] |

-continued
| Ex | Comp | Structure |
| --- | --- | --- |
| 29 | 4247 | 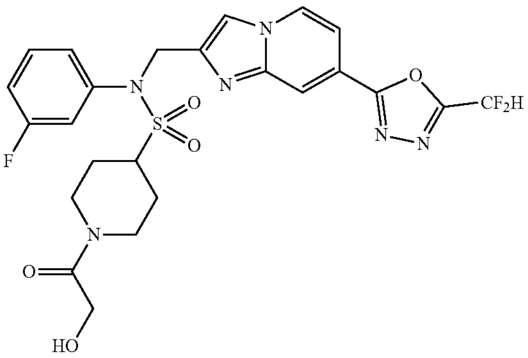 [SMILES: O=C(CO)N1CCC(S(=O)(=O)N(Cc2cn3ccc(-c4nnc(C(F)F)o4)cc3n2)c2cccc(F)c2)CC1] |
| 30 | 4248 | 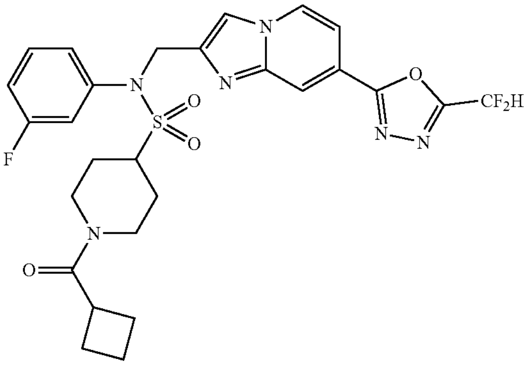 |
| 31 | 4249 | 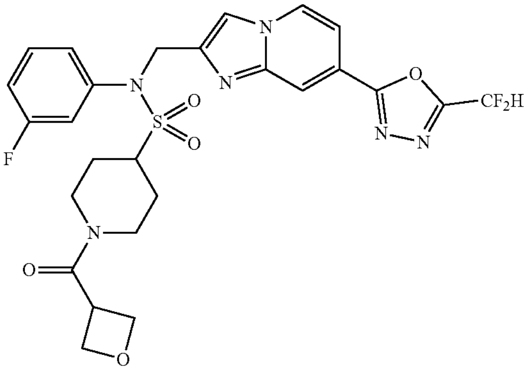 |
| 32 | 4250 | 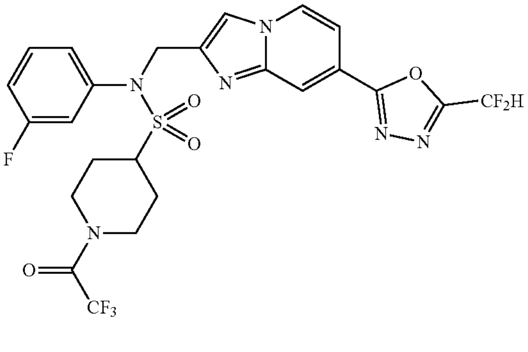 |

-continued
| Ex | Comp | Structure |
|---|---|---|
| 33 | 4251 | 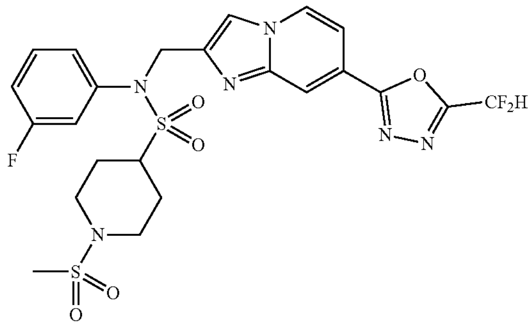 |
| 34 | 4252 | 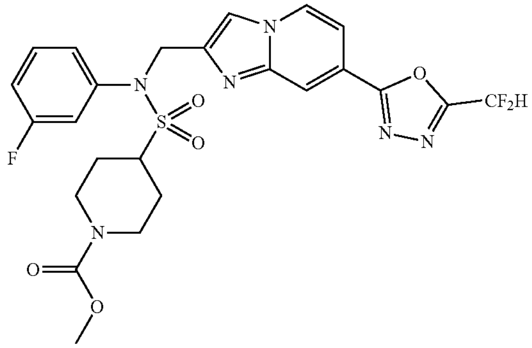 |
| 35 | 4253 | 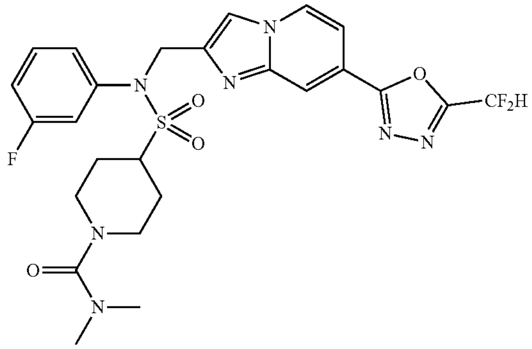 |
| 36 | 4254 | 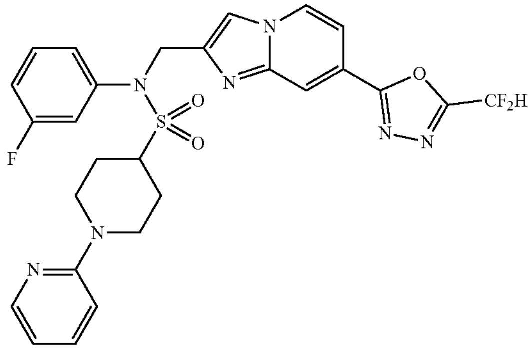 [SMILES: O=S(=O)(C1CCN(c2ccccn2)CC1)N(Cc1cn2ccc(-c3nnc(C(F)F)o3)cc2n1)c1cccc(F)c1] |

-continued
| Ex | Comp | Structure |
| --- | --- | --- |
| 37 | 4255 | 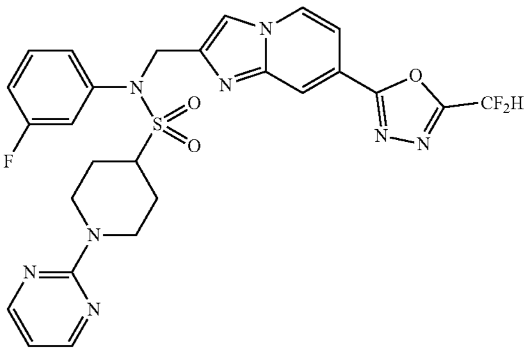 [SMILES: O=S(=O)(C1CCN(c2ncccn2)CC1)N(Cc1cn2ccc(-c3nnc(C(F)F)o3)cc2n1)c1cccc(F)c1] |
| 77 | 4616 | 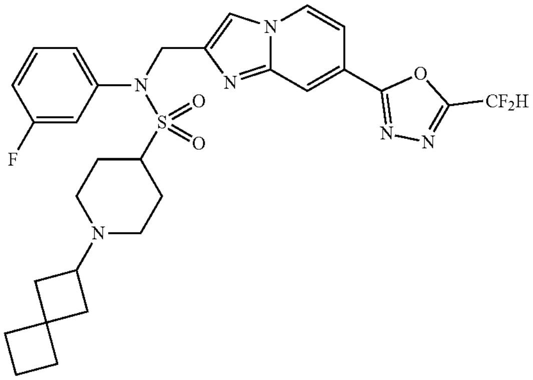 |
| 78 | 4617 | 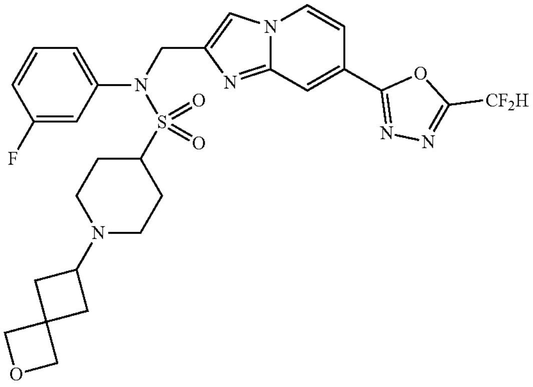 [SMILES: O=S(=O)(C1CCN(C2CC3(COC3)C2)CC1)N(Cc1cn2ccc(-c3nnc(C(F)F)o3)cc2n1)c1cccc(F)c1] |
| 82 | 6893 | 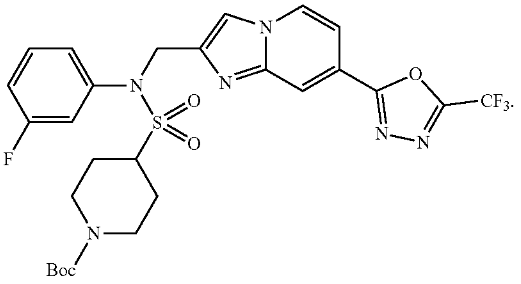 [SMILES: CC(C)(C)OC(=O)N1CCC(S(=O)(=O)N(Cc2cn3ccc(-c4nnc(C(F)(F)F)o4)cc3n2)c2cccc(F)c2)CC1] |

8. The 1,3,4-oxadiazole derivative compound, the optical isomer thereof or the pharmaceutically acceptable salt thereof according to claim 6, wherein it is any one of compounds listed in the following table:
| Ex | Comp | Structure |
|---|---|---|
| 38 | 4256 | 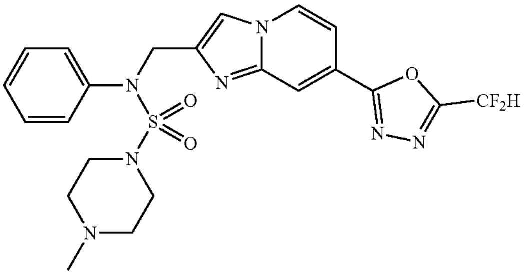 [SMILES: CN1CCN(S(=O)(=O)N(Cc2cn3ccc(-c4nnc(C(F)F)o4)cc3n2)c2ccccc2)CC1] |
| 39 | 4257 | 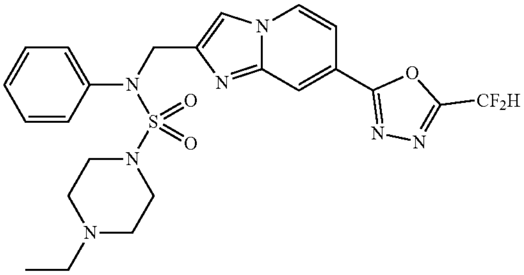 [SMILES: CCN1CCN(S(=O)(=O)N(Cc2cn3ccc(-c4nnc(C(F)F)o4)cc3n2)c2ccccc2)CC1] |
| 40 | 4258 | 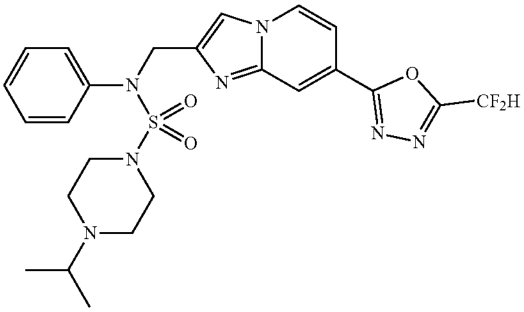 [SMILES: CC(C)N1CCN(S(=O)(=O)N(Cc2cn3ccc(-c4nnc(C(F)F)o4)cc3n2)c2ccccc2)CC1] |
| 41 | 4259 | 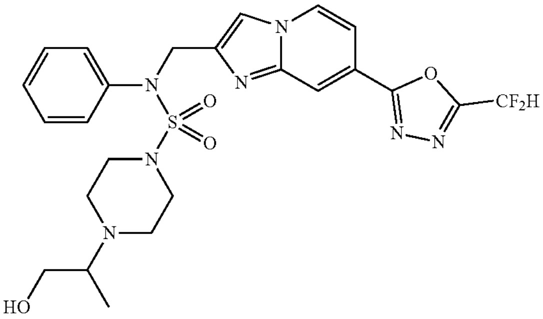 |
| 42 | 4260 | 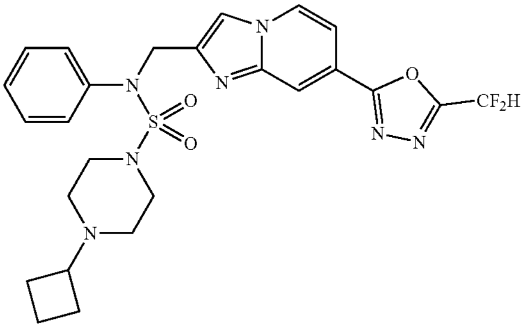 |

-continued
| Ex | Comp | Structure |
|---|---|---|
| 43 | 4261 | 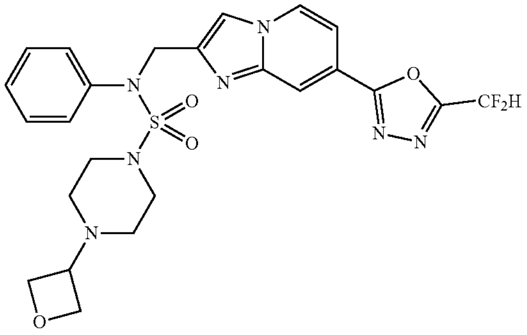 [SMILES: O=S(=O)(N1CCN(C2COC2)CC1)N(Cc1cn2ccc(-c3nnc(C(F)F)o3)cc2n1)c1ccccc1] |
| 44 | 4262 | 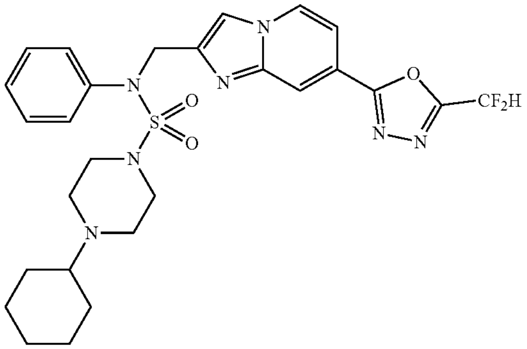 |
| 45 | 4263 | 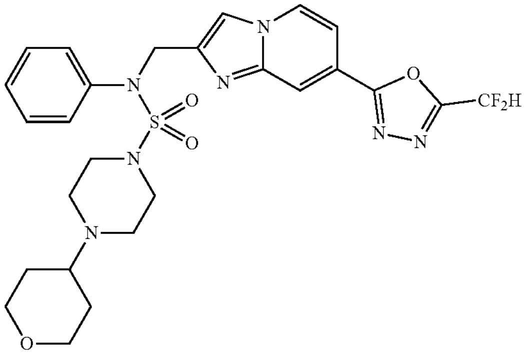 [SMILES: O=S(=O)(N1CCN(C2CCOCC2)CC1)N(Cc1cn2ccc(-c3nnc(C(F)F)o3)cc2n1)c1ccccc1] |
| 46 | 4264 | 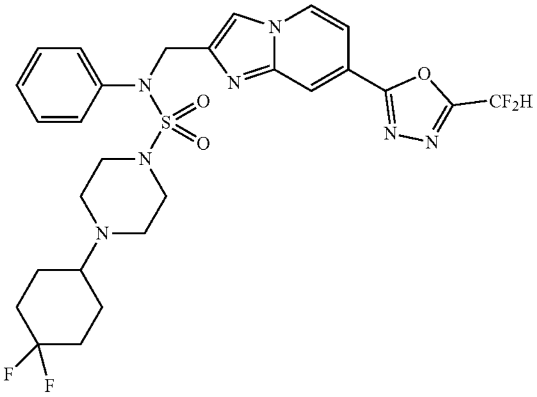 [SMILES: O=S(=O)(N1CCN(C2CCC(F)(F)CC2)CC1)N(Cc1cn2ccc(-c3nnc(C(F)F)o3)cc2n1)c1ccccc1] |

-continued
| Ex | Comp | Structure |
|---|---|---|
| 47 | 4265 | 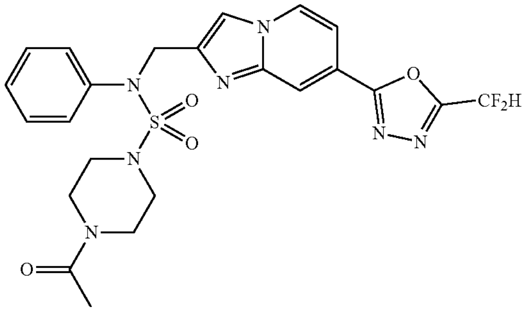 |
| 48 | 4266 | 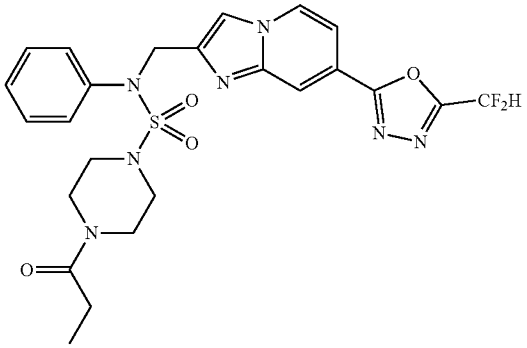 |
| 49 | 4267 | 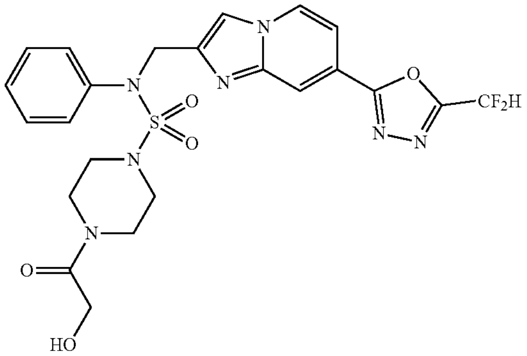 [SMILES: O=C(CO)N1CCN(S(=O)(=O)N(Cc2cn3ccc(-c4nnc(C(F)F)o4)cc3n2)c2ccccc2)CC1] |
| 50 | 4268 | 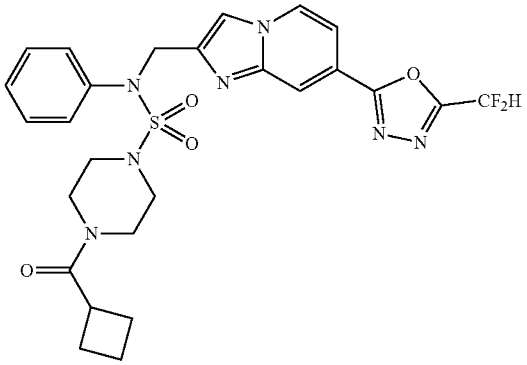 |

-continued
| Ex | Comp | Structure |
|---|---|---|
| 51 | 4269 | 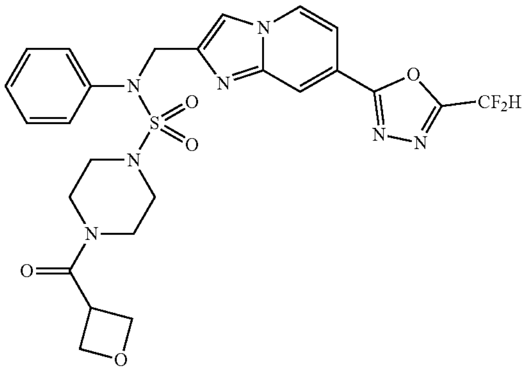 [SMILES: O=C(C1COC1)N1CCN(S(=O)(=O)N(Cc2cn3ccc(-c4nnc(C(F)F)o4)cc3n2)c2ccccc2)CC1] |
| 52 | 4270 | 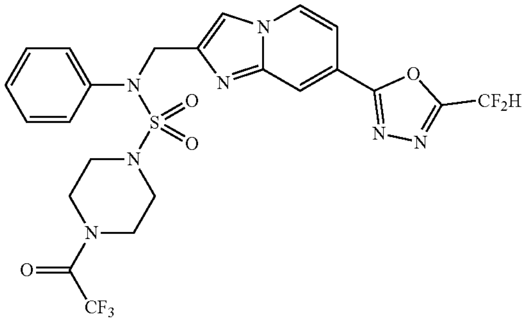 |
| 53 | 4271 | 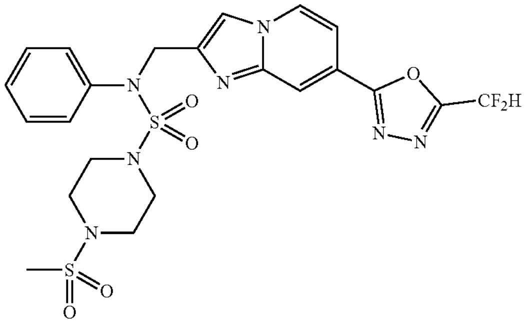 |
| 54 | 4272 | 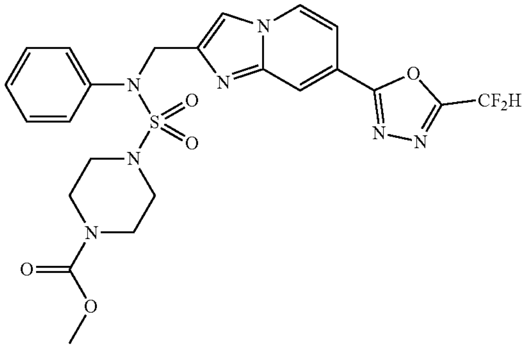 |

-continued
| Ex | Comp | Structure |
|---|---|---|
| 55 | 4273 | 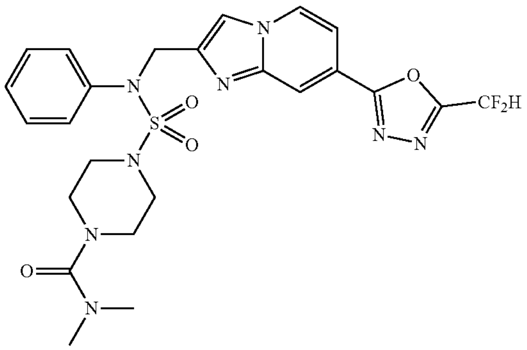 [SMILES: CN(C)C(=O)N1CCN(S(=O)(=O)N(Cc2cn3ccc(-c4nnc(C(F)F)o4)cc3n2)c2ccccc2)CC1] |
| 56 | 4274 | 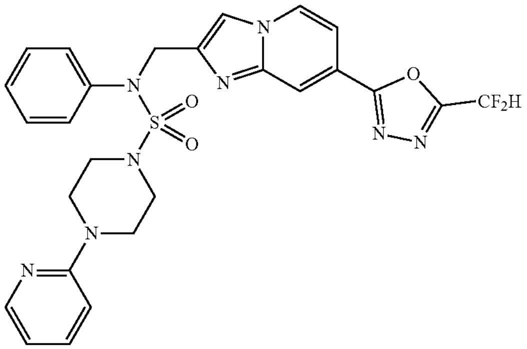 [SMILES: O=S(=O)(N1CCN(c2ccccn2)CC1)N(Cc1cn2ccc(-c3nnc(C(F)F)o3)cc2n1)c1ccccc1] |
| 57 | 4275 | 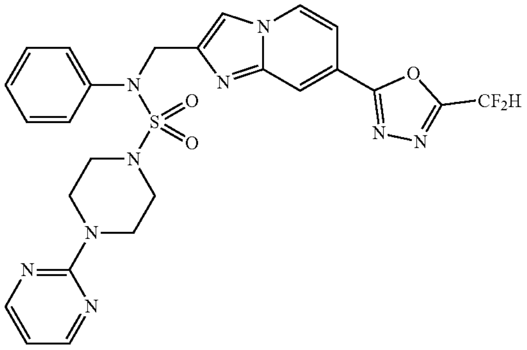 |
| 58 | 4297 | 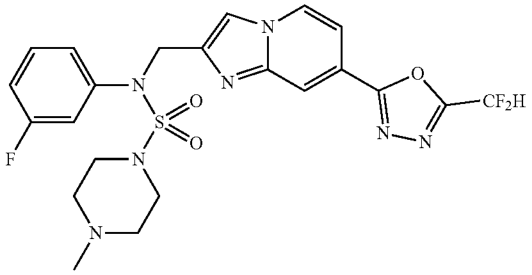 |

-continued
| Ex | Comp | Structure |
|---|---|---|
| 59 | 4298 | 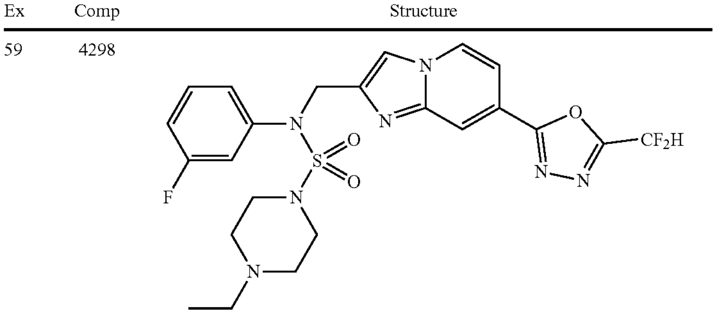 |
| 60 | 4299 | 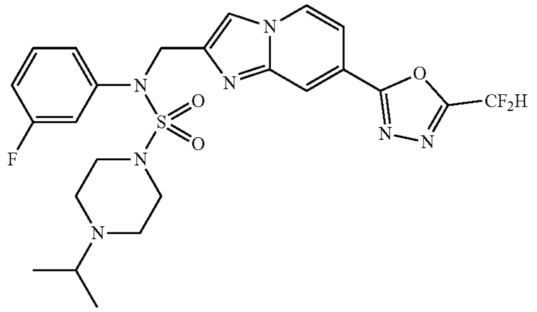 [SMILES: CC(C)N1CCN(S(=O)(=O)N(Cc2cn3ccc(-c4nnc(C(F)F)o4)cc3n2)c2cccc(F)c2)CC1] |
| 61 | 4300 | 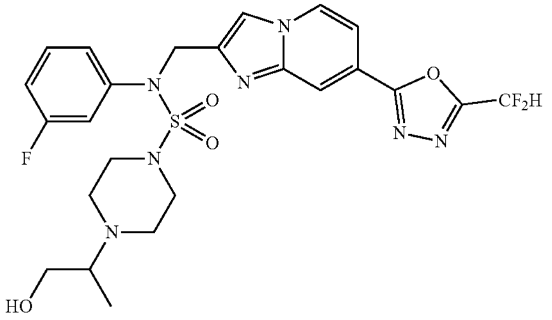 |
| 62 | 4301 | 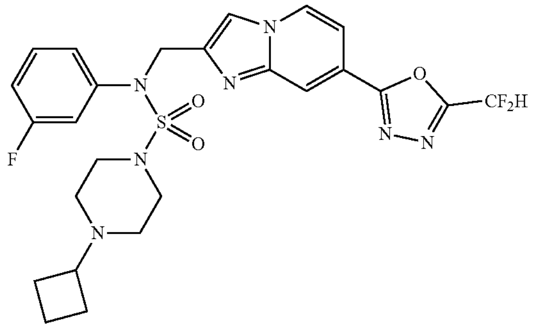 |
| 63 | 4302 | 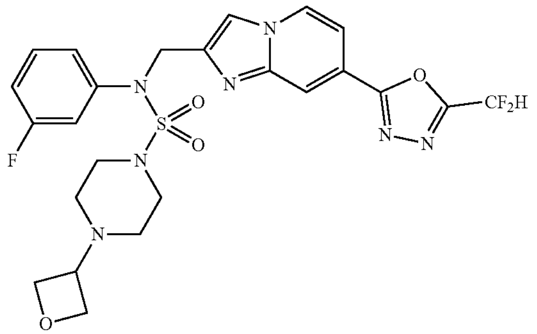 [SMILES: O=S(=O)(N1CCN(C2COC2)CC1)N(Cc1cn2ccc(-c3nnc(C(F)F)o3)cc2n1)c1cccc(F)c1] |

-continued
| Ex | Comp | Structure |
|---|---|---|
| 64 | 4303 | 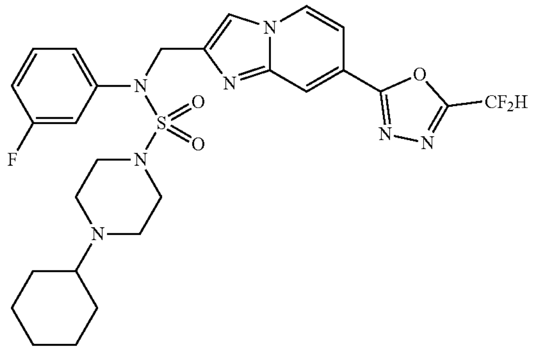 |
| 65 | 4304 | 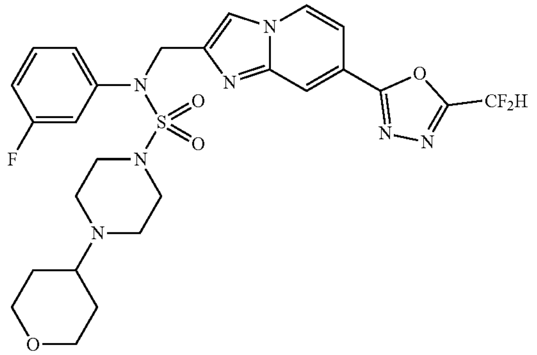 |
| 66 | 4305 | 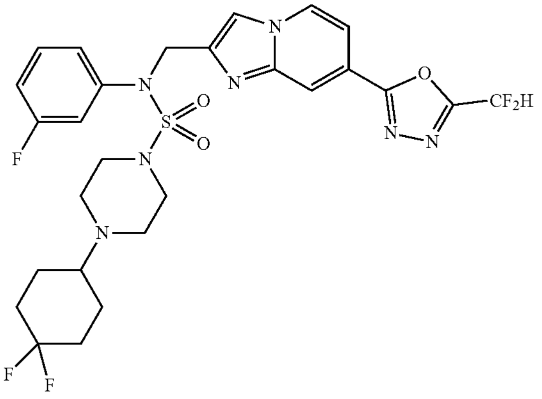 |
| 67 | 4306 | 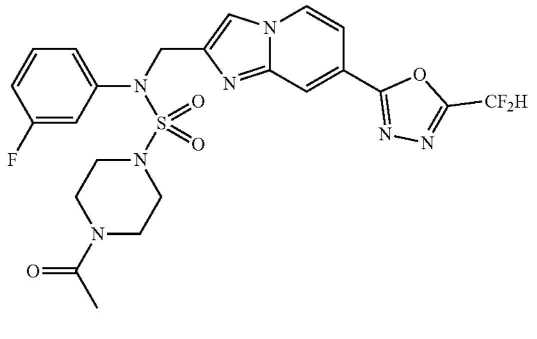 |

-continued
| Ex | Comp | Structure |
|---|---|---|
| 68 | 4307 | 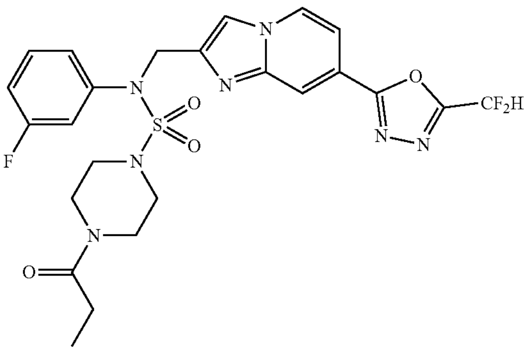 |
| 69 | 4308 | 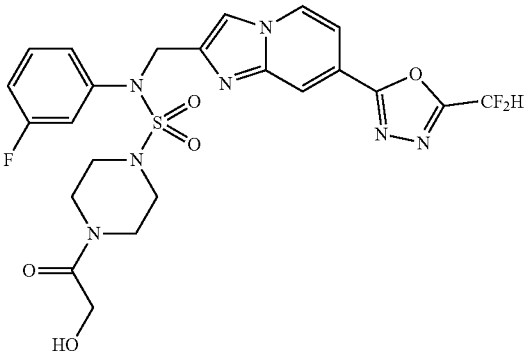 [SMILES: O=C(CO)N1CCN(S(=O)(=O)N(Cc2cn3ccc(-c4nnc(C(F)F)o4)cc3n2)c2cccc(F)c2)CC1] |
| 70 | 4309 | 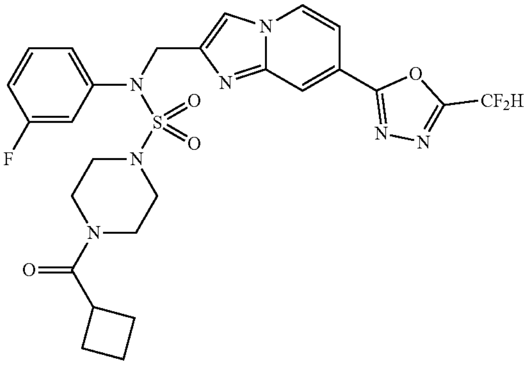 [SMILES: O=C(C1CCC1)N1CCN(S(=O)(=O)N(Cc2cn3ccc(-c4nnc(C(F)F)o4)cc3n2)c2cccc(F)c2)CC1] |
| 71 | 4310 | 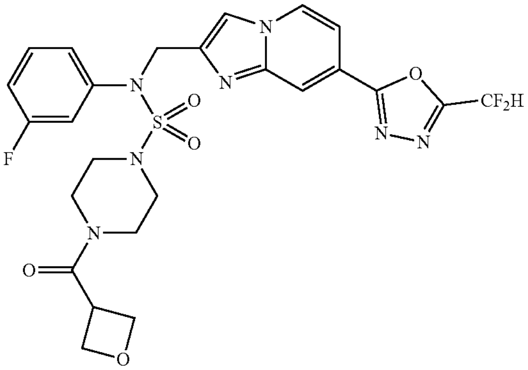 [SMILES: O=C(C1COC1)N1CCN(S(=O)(=O)N(Cc2cn3ccc(-c4nnc(C(F)F)o4)cc3n2)c2cccc(F)c2)CC1] |

-continued
| Ex | Comp | Structure |
|---|---|---|
| 72 | 4311 | 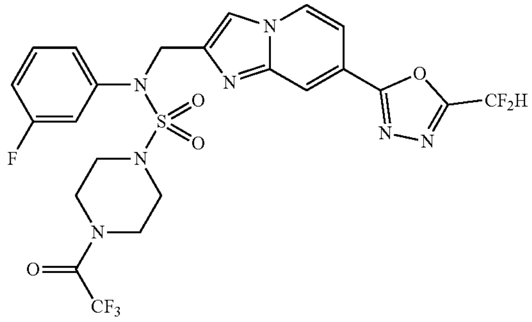 |
| 73 | 4312 | 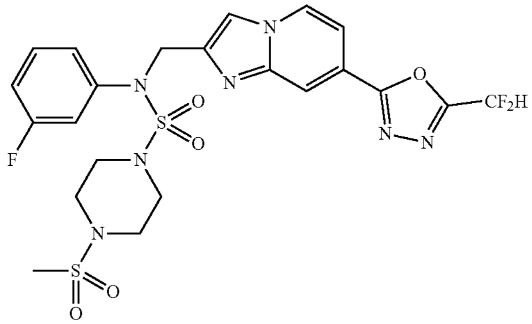 [SMILES: CS(=O)(=O)N1CCN(S(=O)(=O)N(Cc2cn3ccc(-c4nnc(C(F)F)o4)cc3n2)c2cccc(F)c2)CC1] |
| 74 | 4313 | 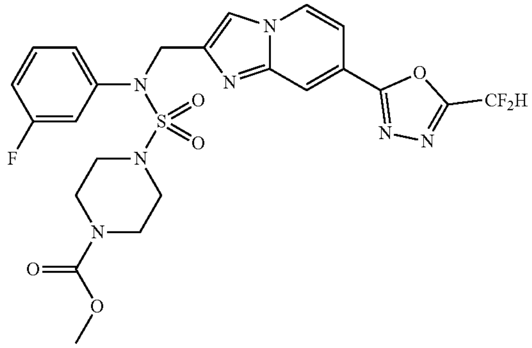 |
| 75 | 4314 | 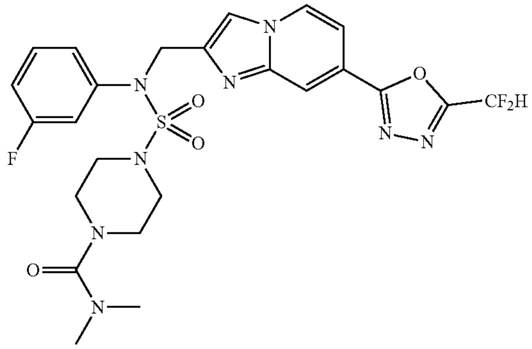 |

-continued
| Ex | Comp | Structure |
|---|---|---|
| 76 | 4315 | 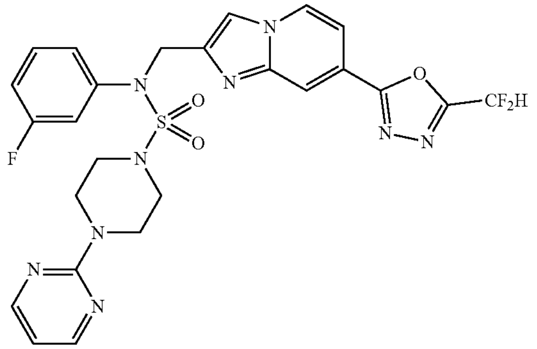 |
| 79 | 4622 | 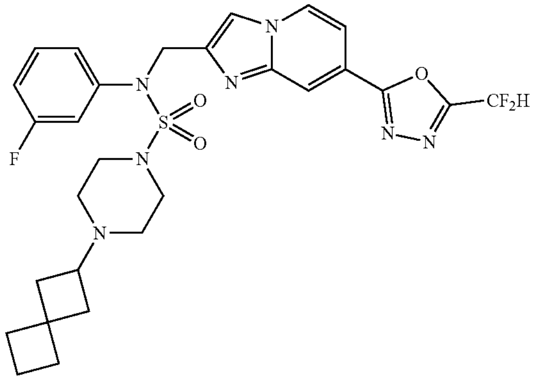 |
| 80 | 4623 | 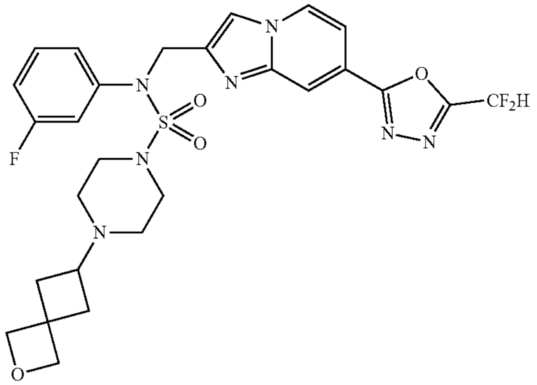 [SMILES: O=S(=O)(N1CCN(C2CC3(COC3)C2)CC1)N(Cc1cn2ccc(-c3nnc(C(F)F)o3)cc2n1)c1cccc(F)c1] |
| 81 | 4624 | 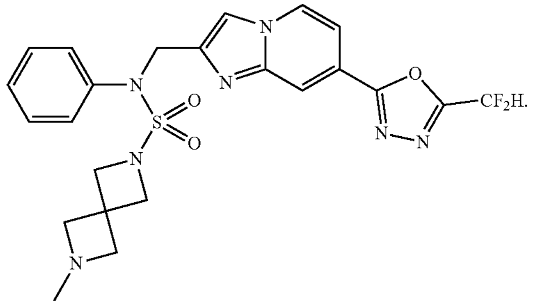 [SMILES: CN1CC2(C1)CN(S(=O)(=O)N(Cc1cn3ccc(-c4nnc(C(F)F)o4)cc3n1)c1ccccc1)C2] |

9. A pharmaceutical composition comprising the compound represented by Chemical Formula I, the optical isomer thereof, or the pharmaceutically acceptable salt thereof according to claim 1 as an active ingredient.

10. The pharmaceutical composition according to claim 9, further comprising a pharmaceutically acceptable carrier.

11. A method for treating a histone deacetylase 6-mediated disease comprising administering a therapeutically effective amount of the compound represented by Chemical Formula I, the optical isomer thereof, or the pharmaceutically acceptable salt thereof according to claim 1 as an active ingredient.

12. The method for treating the histone deacetylase 6-mediated disease according to claim 11, wherein the histone deacetylase 6-mediated disease is an infectious disease; a neoplasm disease; an endocrine disease; a nutritional and metabolic disease; a mental and behavioral disorder; a neurological disease; a diseases of an eye and an adnexal disease; a circulatory disease; a respiratory disease; a digestive disease; a skin and subcutaneous tissue disease; a musculoskeletal and connective tissue disease; or a congenital malformation, alteration, or chromosomal abnormality.

* * * * *